US012729246B2

(12) United States Patent
Santich et al.

(10) Patent No.: US 12,729,246 B2
(45) Date of Patent: Sep. 8, 2026

(54) ANTI-GPA33 MULTI-SPECIFIC ANTIBODIES AND USES THEREOF

(71) Applicant: MEMORIAL SLOAN KETTERING CANCER CENTER, New York, NY (US)

(72) Inventors: Brian H. Santich, New York, NY (US); Mao Wang, New York, NY (US); Nai-Kong V. Cheung, New York, NY (US); Steven Larson, New York, NY (US); Sarah Taldone, New York, NY (US); Darren Veach, New York, NY (US); Mahiuddin Ahmed, New York, NY (US); Hong Xu, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 542 days.

(21) Appl. No.: 18/253,319

(22) PCT Filed: Nov. 17, 2021

(86) PCT No.: PCT/US2021/059634

§ 371 (c)(1),
(2) Date: May 17, 2023

(87) PCT Pub. No.: WO2022/108976

PCT Pub. Date: May 27, 2022

(65) Prior Publication Data

US 2024/0026037 A1 Jan. 25, 2024

Related U.S. Application Data

(60) Provisional application No. 63/115,326, filed on Nov. 18, 2020.

(51) Int. Cl.

| | |
|---|---|
| ***C07K 16/46*** | (2006.01) |
| ***A61P 35/00*** | (2006.01) |
| ***G01N 33/575*** | (2026.01) |

(52) U.S. Cl.

CPC ............ *C07K 16/468* (2013.01); *A61P 35/00* (2018.01); *G01N 33/57557* (2026.01); *C07K 2317/14* (2013.01); *C07K 2317/31* (2013.01); *C07K 2317/52* (2013.01)

(58) Field of Classification Search

None

See application file for complete search history.

(56) References Cited

U.S. PATENT DOCUMENTS

| | | | | |
|---|---|---|---|---|
| 7,432,359 B2 * | 10/2008 | Kataoka | C07K 16/30 435/69.6 |
| 7,579,187 B2 * | 8/2009 | Kataoka | C07K 16/30 435/7.1 |
| 2018/0118824 A1 | 5/2018 | Moore et al. | |

FOREIGN PATENT DOCUMENTS

| | | |
|---|---|---|
| CN | 106414503 A | 2/2017 |
| CN | 111050808 A | 4/2020 |
| WO | WO-2014/106176 A1 | 7/2014 |
| WO | WO-2016/130539 A1 | 8/2016 |
| WO | WO-2018/131586 A1 | 7/2018 |
| WO | WO-2018/204873 A1 | 11/2018 |
| WO | WO-2019/060750 A2 | 3/2019 |
| WO | WO-2020/113164 A1 | 6/2020 |

OTHER PUBLICATIONS

International Search Report and Written Opinion for PCT PCT/US2021/059634 dated Aug. 1, 2022.

Jimenez-Gomez et al. "Modulated selection of IGHV gene somatic hypermutation during systemic maturation of human plasma cells", Genbenk entry (online), National Center for Biotechnology Information, Retrieved From The Internet: https://www.ncbi.nlm.nih.gov/protein/ACS96198.1, Jul. 24, 2016; pp. 1-2.

Sasaki et al. "Human monoclonal antibodies prepared with the peripheral blood lymphocytes of patients", Genbank entry (online), National Center for Biotechnology Information, Retrieved From The Internet: https://www.ncbi.nlm.nih.gov/protein/BAN63131.1, Jan. 17, 2013; pp. 1-3.

King et al., Preparation and preclinical evaluation of humanised A33 immunoconjugates for radioimmunotherapy British Journal of Cancer (1995) 72, 1364-1372.

Murer, et al., A novel human monoclonal antibody specific to the A33 glycoprotein recognizes colorectal cancer and inhibits metastasis, mAbs, 12:1, 1714371, DOI: 10.1080/19420862.2020.1714371.

* cited by examiner

*Primary Examiner* — Maher M Haddad
(74) *Attorney, Agent, or Firm* — Foley & Lardner LLP

(57) ABSTRACT

The present disclosure relates generally to immunoglobulin-related compositions (e.g., multi-specific antibodies or antigen binding fragments thereof) that can bind to the GPA33 protein. The multi-specific antibodies of the present technology are useful in methods for detecting and treating a GPA33-associated cancer in a subject in need thereof.

20 Claims, 74 Drawing Sheets

Specification includes a Sequence Listing.

FIG. 3A
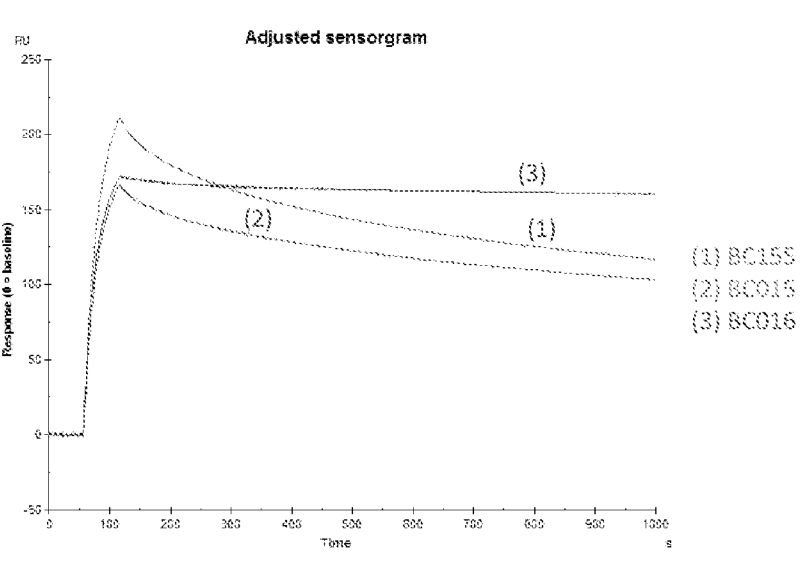
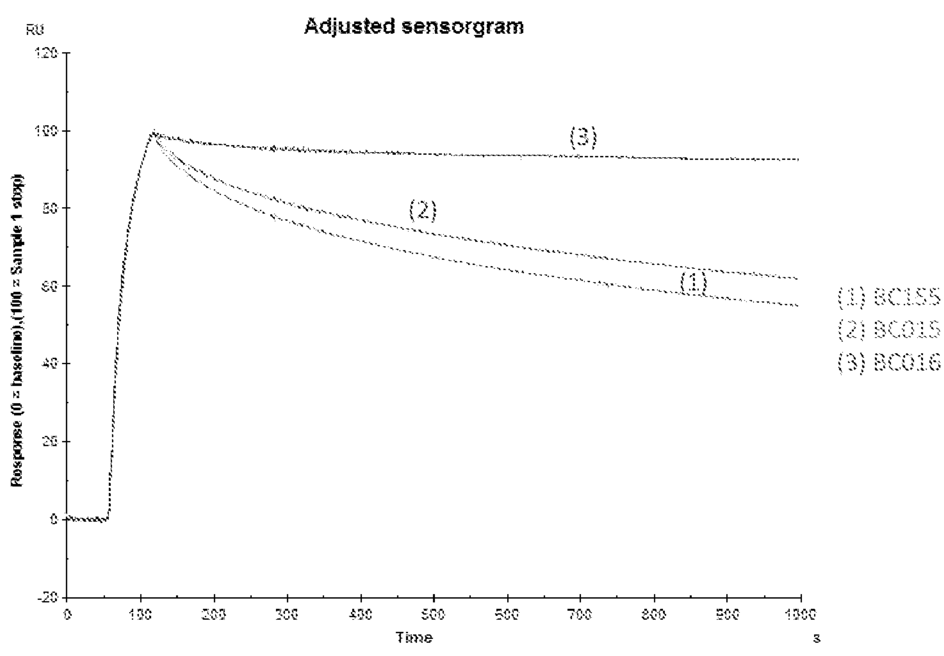
| Sample | ka1 (1/Ms) | kd1 (1/s) | ka2 (1/s) | kd2 (1/s) | KD (M) |
|---|---|---|---|---|---|
| BC155 | 4.13E+06 | 2.12E-03 | 3.28E-03 | 1.64E-03 | 1.71E-10 |
| BC015 | 4.36E+06 | 1.41E-03 | 3.07E-03 | 1.77E-03 | 1.18E-10 |
| BC016 | 5.50E+06 | 5.11E-04 | 5.41E-02 | 5.04E-03 | 7.92E-12 |

FIG. 3B
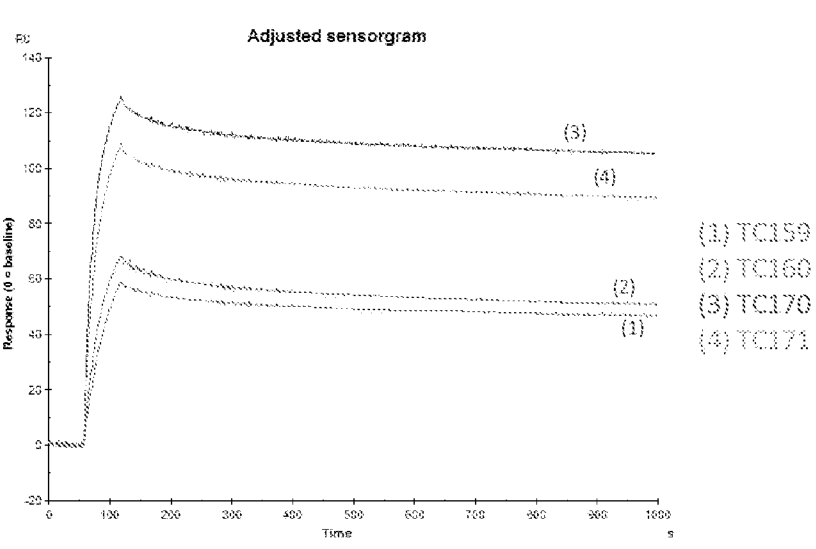
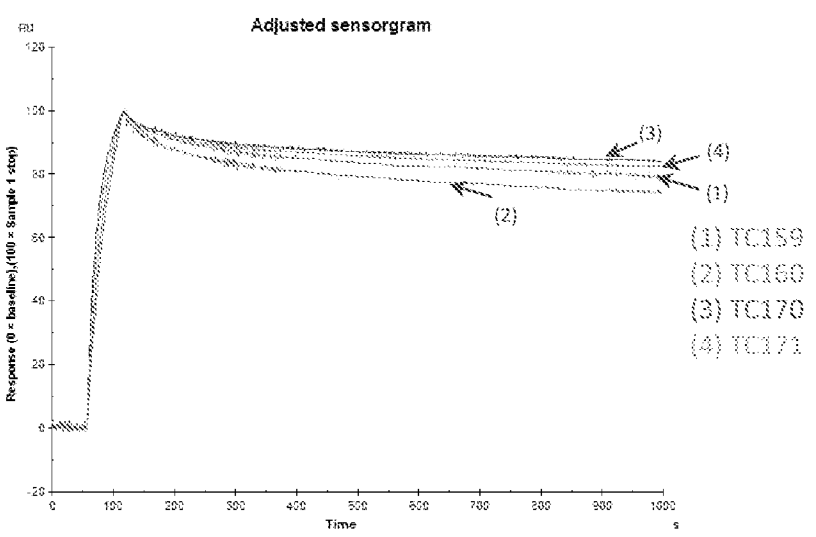
| Sample | ka1 (1/Ms) | kd1 (1/s) | ka2 (1/s) | kd2 (1/s) | KD (M) |
|---|---|---|---|---|---|
| TC159 | 4.09E+06 | 1.81E-03 | 6.13E-03 | 3.15E-04 | 2.16E-11 |
| TC160 | 3.43E+06 | 2.02E-03 | 6.78E-03 | 6.54E-04 | 5.18E-11 |
| TC170 | 3.54E+06 | 7.28E-04 | 6.46E-03 | 5.38E-04 | 1.58E-11 |
| TC171 | 3.34E+06 | 8.86E-04 | 6.63E-03 | 6.28E-04 | 2.30E-11 |

| Antibody | EC50 (nM) |
|---|---|
| TC170 | 0.73 |
| TC171 | 1.04 |
| TC213 | 0.55 |
| TC234 | 0.71 |
| TC235 | 0.53 |

| Antibody | EC50 (nM) |
|---|---|
| TC170 | 0.31 |
| TC171 | 0.56 |
| TC213 | 0.23 |
| TC234 | 0.21 |
| TC235 | 0.22 |

| Antibody | EC50 (nM) |
|---|---|
| TC170 | 1.65 |
| TC171 | 0.77 |
| TC213 | 1.05 |
| TC234 | 2.05 |
| TC235 | 1.03 |

| Antibody | EC50 (nM) |
|---|---|
| TC159 | 2.47 |
| TC160 | 1.20 |
| TC170 | 0.73 |
| TC171 | 1.04 |

FIG. 4B (contd.)
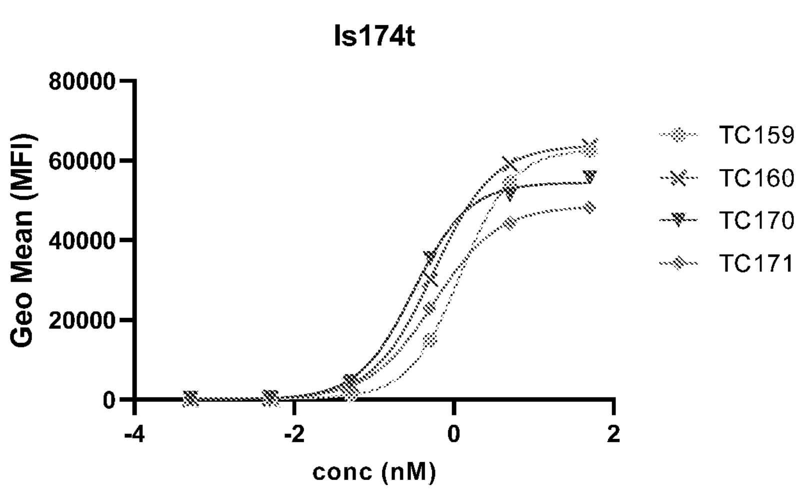
| Antibody | EC50 (nM) |
|---|---|
| TC159 | 1.22 |
| TC160 | 0.56 |
| TC170 | 0.31 |
| TC171 | 0.56 |

FIG. 4B (contd.)
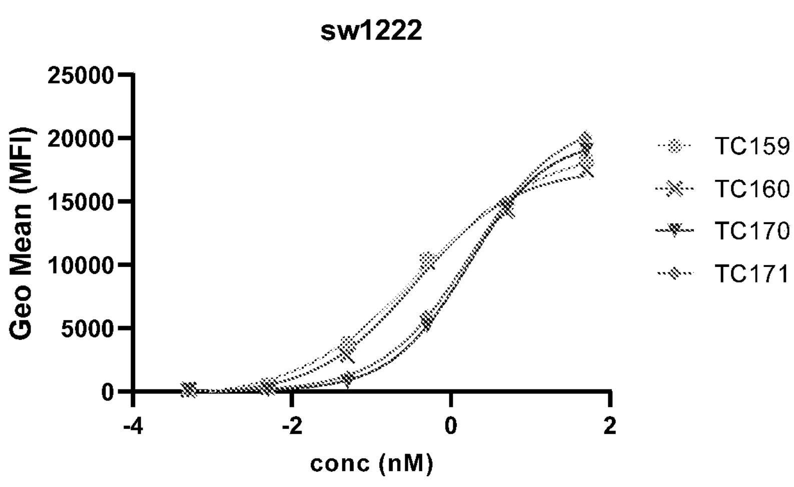
| Antibody | EC50 (nM) |
|---|---|
| TC159 | 0.40 |
| TC160 | 0.36 |
| TC170 | 1.65 |
| TC171 | 0.77 |

| Antibody | EC50 (nM) |
|---|---|
| BC015 | 1.04 |
| BC016 | 0.74 |

| Antibody | EC50 (nM) |
|---|---|
| BC015 | 0.39 |
| BC016 | 0.65 |

| Antibody | EC50 (nM) |
|---|---|
| BC015 | 0.71 |
| BC016 | 0.35 |

FIG. 5A (Cont.)

| | TC170 | BC015 |
|---|---|---|
| Blood | 0.052 ± 0.018 | 0.046 ± 0.005 |
| Tumor | 15.944 ± 9.349 | 10.078 ± 5.713 |
| Heart | 0.094 ± 0.027 | 0.058 ± 0.018 |
| Lungs | 0.104 ± 0.036 | 0.078 ± 0.019 |
| Liver | 0.116 ± 0.036 | 0.102 ± 0.026 |
| Spleen | 0.108 ± 0.033 | 0.076 ± 0.011 |
| Stomach | 0.07 ± 0.038 | 0.32 ± 0.521 |
| Small intestine | 0.06 ± 0.012 | 0.124 ± 0.160 |
| Large intestine | 2.456 ± 3.039 | 1.376 ± 1.956 |
| Kidneys | 1.074 ± 0.273 | 0.57 ± 0.196 |
| Muscle | 0.022 ± 0.004 | 0.018 ± 0.004 |
| Bone | 0.042 ± 0.004 | 0.038 ± 0.016 |
| Tail | 0.364 ± 0.262 | 0.25 ± 0.151 |

FIG. 5B (Cont.)

| | TC170 | BC015 |
|---|---|---|
| Blood | 2.000 ± 0.327 | 4.514 ± 1.214 |
| Tumor | 179.772 ± 99.753 | 175.754 ± 107.030 |
| Heart | 1.942 ± 0.757 | 2.538 ± 0.525 |
| Lungs | 2.428 ± 0.681 | 2.964 ± 0.929 |
| Liver | 2.018 ± 0.354 | 4.472 ± 1.292 |
| Spleen | 2.218 ± 0.557 | 3.090 ± 0.622 |
| Stomach | 0.606 ± 0.256 | 0.404 ± 0.266 |
| Small intestine | 0.788 ± 0.150 | 1.032 ± 0.283 |
| Large intestine | 0.772 ± 0.260 | 0.962 ± 0.200 |
| Kidneys | 15.448 ± 4.204 | 3.094 ± 0.616 |
| Muscle | 0.464 ± 0.284 | 0.704 ± 0.206 |
| Bone | 0.668 ± 0.337 | 0.818 ± 0.474 |
| Tail | 5.202 ± 1.722 | 1.5225 ± 0.675 |

FIG. 5C (Cont.)

| | TC170 IP | TC170 IV |
|---|---|---|
| Blood | 0.014 ± 0.005 | 0.008 ± 0.004 |
| Tumor | 0.432 ± 0.124 | 0.282 ± 0.234 |
| Heart | 0.032 ± 0.015 | 0.038 ± 0.019 |
| Lungs | 0.038 ± 0.011 | 0.048 ± 0.016 |
| Liver | 0.318 ± 0.072 | 0.216 ± 0.040 |
| Spleen | 0.290 ± 0.162 | 0.070 ± 0.055 |
| Stomach | 0.066 ± 0.036 | 0.058 ± 0.029 |
| Small intestine | 0.026 ± 0.024 | 0.076 ± 0.043 |
| Large intestine | 0.074 ± 0.035 | 0.494 ± 0.080 |
| Kidneys | 10108 ± 0.256 | 0.988 ± 0.062 |
| Muscle | 0.012 ± 0.018 | 0.006 ± 0.029 |
| Bone | 0.206 ± 0.278 | 0.090 ± 0.062 |
| Tail | 0.048 ± 0.008 | 0.976 ± 0.869 |

FIG. 6A
[$^{177}$Lu]BnDOTA only
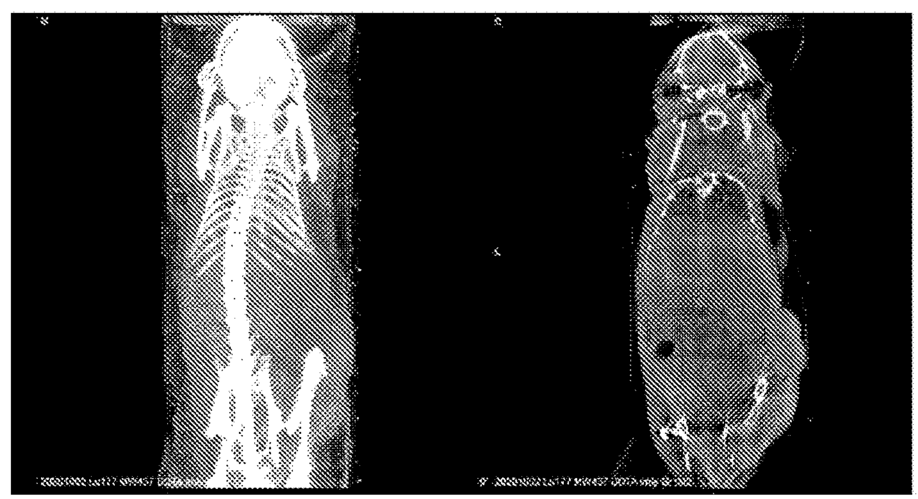
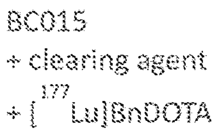
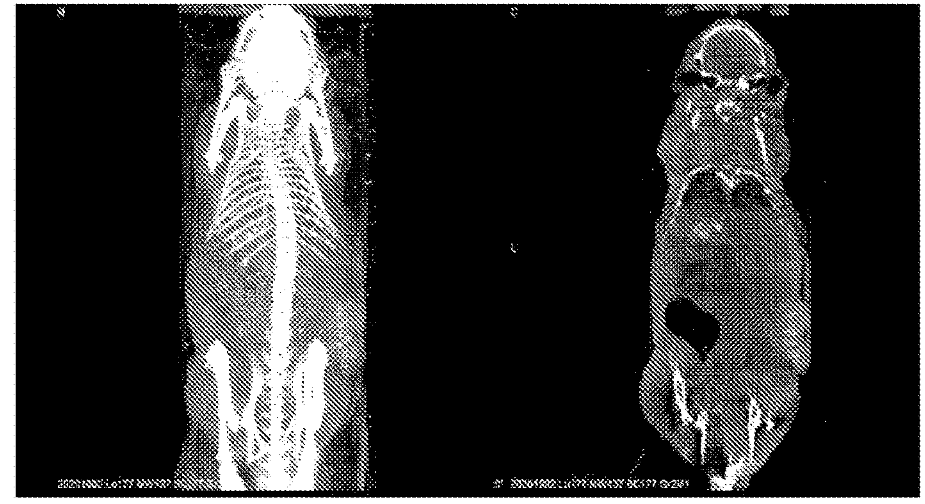
TC170
+ [$^{177}$Lu]BnDOTA

| | TC170 | SADA Control | [177Lu]BnDOTA |
|---|---|---|---|
| Volume (mm$^3$) | 1413.97 | -/- | 413.25 |
| Mean Signal | 0.171 | -/- | 0.075 |

FIG. 9

| Protein pairing | Yield (mg/50mL) | Purity (%) | Purity (%) post FT | Purity (%) on day32 |
|---|---|---|---|---|
| G3A_chimeric | 4.34 | 98 | 97 | 60 |
| G3A_VK1+VH1 | 17.41 | 99 | 96 | 65 |
| G3A_VK1+VH2 | 17.11 | 100 | 97 | 73 |
| G3A_VK1+VH3 | 14.91 | 100 | 98 | 75 |
| G3A_VK2+VH1 | 10.59 | 100 | 97 | 70 |
| G3A_VK2+VH2 | 6.66 | 100 | 99 | 70 |
| G3A_VK2+VH3 | 7.82 | 99 | 97 | 74 |
| G3A_VK3+VH1 | 18.30 | 99 | 97 | 72 |
| G3A_VK3+VH2 | 16.58 | 100 | 98 | 66 |
| G3A_VK3+VH3 | 15.01 | 99 | 97 | 71 |
| G3A_VK4+VH1 | 20.05 | 99 | 97 | 69 |
| G3A_VK4+VH2 | 14.67 | 99 | 97 | 59 |
| G3A_VK4+VH3 | 14.93 | 99 | 98 | 75 |
| G3A_VK5+VH1 | 19.89 | 99 | 97 | 74 |
| G3A_VK5+VH2 | 15.74 | 99 | 98 | 64 |
| G3A_VK5+VH3 | 16.20 | 99 | 98 | 69 |
| G3A_VK6+VH1 | 18.35 | 99 | 97 | 72 |
| G3A_VK6+VH2 | 14.16 | 100 | 98 | 67 |
| G3A_VK6+VH3 | 15.79 | 100 | 98 | 65 |
| G3A_VK7+VH1 | 17.59 | 100 | 98 | 69 |
| G3A_VK7+VH2 | 16.76 | 100 | 98 | 68 |
| G3A_VK7+VH3 | 15.76 | 99 | 98 | 64 |
| G3A_VK8+VH1 | 15.62 | 99 | 98 | 69 |
| G3A_VK8+VH2 | 17.72 | 100 | 98 | 72 |
| G3A_VK8+VH3 | 15.37 | 100 | 99 | 61 |

FIG. 10

| Protein pairing | Binding KD (M) to GPA33 by Biacore |
|---|---|
| G3A_chimeric | 1.96E-10 |
| G3A_VK1+VH1 | 8.70E-10 |
| G3A_VK1+VH2 | 1.73E-09 |
| G3A_VK1+VH3 | 1.49E-09 |
| G3A_VK2+VH1 | 5.80E-09 |
| G3A_VK2+VH2 | 9.54E-09 |
| G3A_VK2+VH3 | 8.39E-09 |
| G3A_VK3+VH1 | 1.90E-10 |
| G3A_VK3+VH2 | 2.41E-10 |
| G3A_VK3+VH3 | 2.41E-10 |
| G3A_VK4+VH1 | 1.68E-10 |
| G3A_VK4+VH2 | 2.29E-10 |
| G3A_VK4+VH3 | 2.36E-10 |
| G3A_VK5+VH1 | 1.71E-10 |
| G3A_VK5+VH2 | 2.30E-10 |
| G3A_VK5+VH3 | 2.38E-10 |
| G3A_VK6+VH1 | 8.84E-10 |
| G3A_VK6+VH2 | 1.74E-09 |
| G3A_VK6+VH3 | 1.45E-09 |
| G3A_VK7+VH1 | 8.88E-10 |
| G3A_VK7+VH2 | 1.75E-09 |
| G3A_VK7+VH3 | 1.62E-09 |
| G3A_VK8+VH1 | 9.75E-10 |
| G3A_VK8+VH2 | 1.85E-09 |
| G3A_VK8+VH3 | 1.89E-09 |

FIG. 11

| Protein pairing | Binding EC50 (mg/mL) to SW1222 Luc | Binding EC50 (mg/mL) to LS174T Luc |
|---|---|---|
| G3A_chimeric | 1.00E-03 | 2.48E-04 |
| G3A_VK1+VH1 | 1.51E-03 | 1.12E-03 |
| G3A_VK1+VH2 | 9.91E-04 | 6.54E-04 |
| G3A_VK1+VH3 | 1.32E-03 | 1.78E-03 |
| G3A_VK2+VH1 | | 1.20E-03 |
| G3A_VK2+VH2 | | |
| G3A_VK2+VH3 | 1.89E-03 | |
| G3A_VK3+VH1 | 3.38E-04 | 6.42E-04 |
| G3A_VK3+VH2 | 3.83E-04 | 3.81E-04 |
| G3A_VK3+VH3 | 3.91E-04 | 3.98E-04 |
| G3A_VK4+VH1 | 4.66E-04 | 5.03E-04 |
| G3A_VK4+VH2 | 3.14E-04 | 3.64E-04 |
| G3A_VK4+VH3 | 1.03E-03 | 2.79E-04 |
| G3A_VK5+VH1 | 4.96E-04 | 4.40E-04 |
| G3A_VK5+VH2 | 3.47E-04 | 4.78E-04 |
| G3A_VK5+VH3 | 3.87E-04 | 4.24E-04 |
| G3A_VK6+VH1 | 8.31E-04 | 4.02E-04 |
| G3A_VK6+VH2 | 1.07E-03 | |
| G3A_VK6+VH3 | 6.14E-04 | 8.47E-04 |
| G3A_VK7+VH1 | 1.14E-03 | 4.81E-04 |
| G3A_VK7+VH2 | 7.95E-04 | 5.76E-04 |
| G3A_VK7+VH3 | | 7.68E-04 |
| G3A_VK8+VH1 | 5.68E-04 | 4.54E-04 |
| G3A_VK8+VH2 | 9.93E-04 | 1.09E-03 |
| G3A_VK8+VH3 | 7.92E-04 | 4.33E-04 |

FIG. 12

*G3A-VH1 (humanness 90.8%, SEQ ID NO: 1):*

EVQLVESGGGLVKPGGSLRLSCAASGFAFSTYDMSWVRQAPGKGLEWVSTISSGGSYTYYADSVKGRFTISRDNAKNSLYLQMNSLRAEDTAVYYCAPTTVVPFAYWGQGTLVTVSA

*G3A-VH2 (humanness 80.8%, SEQ ID NO: 2):*

EVQLVESGGGLVKPGGSLRLSCAASGFAFSTYDMSWVRQAPGKGLEWVATISSGGSYTYYLDSVKGRFTISRDSAKNSLYLQMNSLRAEDTAVYYCAPTTVVPFAYWGQGTLVTVSA

*G3A-VH3 (humanness 88.8%, SEQ ID NO: 3):*

EVQLVESGGGLVKPGGSLRLSCAASGFAFSTYDMSWVRQAPGKGLEWVATISSGGSYTYYADSVKGRFTISRDSAKNSLYLQMNSLRAEDTAVYYCAPTTVVPFAYWGQGTLVTVSA

FIG. 13

*G3A-VK1 (humanness 85.3%, SEQ ID NO: 4):*

DIQMTQSPSSLSASVGDRVTITCKASQNVRTVVAWYQQKPGKAPKRLIYLASNRHTGVP
SRFSGSGSGTEFTLTISNLQPEDFATYYCLQHWSYPLTFGSGTKLEVK

*G3A-VK2 (humanness 86.3%, SEQ ID NO: 5):*

DIQMTQSPSSLSTSVGDRVTITCKASQNVRTVVAWYQQKPGKAPKTLIYLASSLQSGVPS
RFSGSGSGTEFTLTISNVQPEDFADYFCLQHWSYPLTFGSGTKLEVK

*G3A-VK3 (humanness 85.3%, SEQ ID NO: 6):*

DIQMTQSPSSLSTSVGDRVTITCKASQNVRTVVAWYQQKPGKAPKTLIYLASNRHSGVP
SRFSGSGSGTEFTLTISNLQPEDFATYYCLQHWSYPLTFGSGTKLEVK

*G3A-VK4/5 (humanness 85.3%, SEQ ID NO: 7):*

DIQMTQSPSSLSASVGDRVTITCKASQNVRTVVAWYQQKPGKAPKTLIYLASNRHTGVP
SRFSGSGSGTEFTLTISNLQPEDFATYYCLQHWSYPLTFGSGTKLEVK

*G3A-VK6 (humanness 85.3%, SEQ ID NO: 8):*

DIQMTQSPSSLSASVGDRVTITCKASQNVRTVVAWYQQKPGKAPKRLIYLASNRHTGVP
SRFSGSGSGTEFTLTISNLQPEDFATYFCLQHWSYPLTFGSGTKLEVK

*G3A-VK7 (humanness 85.3%, SEQ ID NO: 9):*

DIQMTQSPSSLSASVGDRVTITCKASQNVRTVVAWYQQKPGKAPKRLIYLASNRHTGVP
SRFSGSGSGTEFTLTISNVQPEDFATYYCLQHWSYPLTFGSGTKLEVK

*G3A-VK8 (humanness 85.3%, SEQ ID NO: 10):*

DIQMTQSPSSLSASVGDRVTITCKASQNVRTVVAWYQQKPGKAPKRLIYLASNRHTGVP
SRFSGSGSGTEFTLTISNLQPEDFADYYCLQHWSYPLTFGSGTKLEVK

FIG. 14

TC170 (G3A H1L4 huC825 SADA) full amino acid sequence (N to C terminal) [*G3A VH1*-linker-*G3A VL4*-linker-huC825-spacer-P53] (SEQ ID NO: 11)

*EVQLVESGGGLVKPGGSLRLSCAASGFAFSTYDMSWVRQAPGKGLEWVSTISSGGSYTYYADSVKGRFT*
*ISRDNAKNSLYLQMNSLRAEDTAVYYCAPTTVVPFAYWGQGTLVTVSA*GGGGSGGGGSGGGGSGG
GGSGGGGSGGGGS*DIQMTQSPSSLSASVGDRVTITCKASQNVRTVVAWYQQKPGKAPKTLIYLASNR*
*HTGVPSRFSGSGSGTEFTLTISNLQPEDFATYYCLQHWSYPLTFGSGTKLEVKR*GGGGSGGGGSGGG
GSGGGGS*HVQLVESGGGLVQPGGSLRLSCAASGFSLTDYGVHWVRQAPGKGLEWLGVIWSGGGTAY*
*NTALISRFTISRDNSKNTLYLQMNSLRAEDTAVYYCARRGSYPYNYFDAWGCGTLVTVSS*GGGGSGGG
GSGGGGSGGGGSGGGGSGGGGS*QAVVTQEPSLTVSPGGTVTLTCGSSTGAVTASNYANWVQQKP*
*GQCPRGLIGGHNNRPPGVPARFSGSLLGGKAALTLLGAQPEDEAEYYCALWYSDHWVIGGGTKLTVL*
*G*TPLGDTTHTSGKPLDGEYFTLQIRGRERFEMFRELNEALELKDAQAGKEPGGSGGAPHHHHH
H

TC170 (G3A H1L4 huC825 SADA) full nucleotide sequence (SEQ ID NO: 12)

GAGGTGCAGCTGGTGGAGAGCGGAGGAGGCCTGGTGAAGCCAGGAGGCAGCCTGAGGCTG
TCCTGCGCCGCCTCTGGATTCGCCTTTAGCACCTACGATATGTCCTGGGTGCGCCAGGCACCT
GGCAAGGGCCTGGAGTGGGTGTCTACCATCAGCTCCGGCGGCAGCTACACATACTATGCCG
ACTCCGTGAAGGGCCGGTTCACCATCAGCCGGGATAACGCCAAGAATAGCCTGTATCTGCA
GATGAACTCCCTGCGGGCCGAGGACACAGCCGTGTACTATTGTGCCCCAACCACAGTGGTGC
CCTTTGCCTATTGGGGCCAGGGCACCCTGGTGACAGTGAGCGCCGGCGGAGGAGGCTCTGG
AGGAGGAGGCAGCGGAGGCGGCGGCTCCGGCGGCGGCGGCTCTGGCGGCGGCGGCAGCGG
AGGAGGCGGCTCCGACATCCAGATGACCCAGAGCCCATCTAGCCTGTCCGCCTCTGTGGGCG
ATCGGGTGACCATCACATGCAAGGCCTCCCAGAATGTGAGAACAGTGGTGGCCTGGTACCA
GCAGAAGCCCGGCAAGGCCCCTAAGACCCTGATCTATCTGGCCTCCAACAGGCACACAGGA
GTGCCATCTCGCTTCAGCGGCTCCGGCTCTGGAACCGAGTTTACCCTGACAATCTCCAATCTG
CAGCCTGAGGATTTCGCCACATACTATTGTCTGCAGCACTGGTCTTACCCACTGACCTTTGGC
AGCGGCACAAAGCTGGAGGTGAAGCGGGGCGGAGGGGGATCCGGCGGCGGAGGATCTGGC
GGAGGTGGAAGTGGGGGAGGCGGATCTCATGTGCAGCTGGTGGAAAGCGGAGGCGGCCTG
GTGCAGCCTGGGGGATCTCTGAGACTGTCTTGTGCCGCCAGCGGCTTCTCCCTGACCGATTA
TGGCGTGCACTGGGTGCGACAGGCCCCTGGCAAAGGACTGGAATGGCTGGGAGTGATTTGG
AGTGGCGGAGGCACCGCCTACAACACCGCCCTGATCTCCCGGTTCACCATCAGCCGGGACA
ACTCCAAGAACACCCTGTACCTGCAGATGAACTCCCTGCGGGCCGAGGACACCGCTGTGTAC
TACTGCGCCAGACGGGGCTCCTACCCCTACAACTACTTCGACGCTTGGGGCTGCGGCACCCT
CGTGACAGTGTCTAGCGGAGGGGGAGGTTCTGGGGGCGGAGGTTCAGGTGGTGGTGGTTCC
GGGGGTGGTGGCTCTGGTGGCGGTGGTTCTGGCGGTGGCGGATCTCAGGCTGTCGTGACCCA
GGAACCCAGCCTGACTGTGTCTCCTGGCGGAACCGTGACCCTGACCTGCGGATCTTCTACCG
GCGCTGTGACCGCCAGCAACTACGCCAATTGGGTGCAGCAGAAACCTGGACAGTGCCCTAG
AGGCCTGATCGGCGGCCACAACAACAGACCTCCAGGCGTGCCAGCCCGGTTCTCTGGATCTC
TGCTGGGCGGAAAGGCCGCTCTGACACTGCTGGGTGCTCAGCCTGAGGACGAGGCCGAGTA
CTACTGTGCCCTGTGGTACTCCGACCACTGGGTCATCGGAGGCGGGACCAAGCTGACCGTGC
TGGGAACACCCCTGGGAGACACCACACATACTAGTGGGAAACCTCTGGATGGCGAGTACTT
TACCCTGCAGATTAGAGGCCGCGAACGATTCGAGATGTTTCGCGAACTGAATGAGGCCCTGG
AACTGAAGGATGCTCAGGCAGGCAAGGAGCCAGGAGGGTCAGGAGGAGCACCGCACCATC
ATCATCACCAT

FIG. 15

TC171 (G3A L4H1 huC825 SADA) full amino acid sequence (N to C terminal) [*G3A VL4*-linker-*G3A VH1*-linker-huC825-spacer-P53] (SEQ ID NO: 13)

DIQMTQSPSSLSASVGDRVTITCKASQNVRTVVAWYQQKPGKAPKTLIYLASNRHTGVPSRFSGSGSGTE
FTLTISNLQPEDFATYYCLQHWSYPLTFGSGTKLEVKRGGGGSGGGGSGGGGSGGGGSGGGGSG
GGGSEVQLVESGGGLVKPGGSLRLSCAASGFAFSTYDMSWVRQAPGKGLEWVSTISSGGSYTYYADSV
KGRFTISRDNAKNSLYLQMNSLRAEDTAVYYCAPTTVVPFAYWGQGTLVTVSAGGGGSGGGGSGGG
GSGGGGSHVQLVESGGGLVQPGGSLRLSCAASGFSLTDYGVHWVRQAPGKGLEWLGVIWSGGGTAY
NTALISRFTISRDNSKNTLYLQMNSLRAEDTAVYYCARRGSYPYNYFDAWGCGTLVTVSSGGGGSGGG
GSGGGGSGGGGSGGGGSGGGGSQAVVTQEPSLTVSPGGTVTLTCGSSTGAVTASNYANWVQQKP
GQCPRGLIGGHNNRPPGVPARFSGSLLGGKAALTLLGAQPEDEAEYYCALWYSDHWVIGGGTKLTVL
GTPLGDTTHTSGKPLDGEYFTLQIRGRERFEMFRELNEALELKDAQAGKEPGGSGGAPHHHHH
H

TC171 (G3A L4H1 huC825 SADA) full nucleotide sequence (SEQ ID NO: 14)

GACATCCAGATGACCCAGAGCCCAAGCTCCCTGTCCGCCTCTGTGGGCGATAGGGTGACCAT
CACATGCAAGGCCTCCCAGAACGTGAGAACAGTGGTGGCCTGGTACCAGCAGAAGCCCGGC
AAGGCCCCTAAGACCCTGATCTATCTGGCCTCCAACAGGCACACAGGAGTGCCATCTCGCTT
CAGCGGCTCCGGCTCTGGAACCGAGTTTACCCTGACAATCAGCAATCTGCAGCCTGAGGACT
TCGCCACATACTATTGTCTGCAGCACTGGTCTTACCCACTGACCTTTGGCAGCGGCACAAAG
CTGGAGGTGAAGAGGGGAGGAGGAGGCAGCGGCGGAGGAGGCTCCGGAGGCGGCGGCTCT
GGCGGCGGCGGCAGCGGCGGCGGCGGCTCCGGAGGAGGCGGCTCTGAGGTGCAGCTGGTGG
AGAGCGGAGGAGGCCTGGTGAAGCCAGGAGGCAGCCTGAGGCTGTCCTGCGCCGCCTCTGG
ATTCGCCTTTAGCACCTACGACATGTCCTGGGTGCGCCAGGCACCTGGCAAGGGCCTGGAGT
GGGTGTCCACCATCTCTAGCGGCGGCTCTTACACATACTATGCCGACAGCGTGAAGGGCCGG
TTCACCATCTCCAGAGATAACGCCAAGAATTCTCTGTATCTGCAGATGAATAGCCTGCGGGC
CGAGGATACAGCCGTGTACTATTGTGCCCCAACCACAGTGGTGCCCTTTGCCTATTGGGGCC
AGGGCACCCTGGTGACAGTGAGCGCCGGCGGAGGGGGATCCGGCGGCGGAGGATCTGGCG
GAGGTGGAAGTGGGGGAGGCGGATCTCATGTGCAGCTGGTGGAAAGCGGAGGCGGCCTGGT
GCAGCCTGGGGGATCTCTGAGACTGTCTTGTGCCGCCAGCGGCTTCTCCCTGACCGATTATG
GCGTGCACTGGGTGCGACAGGCCCCTGGCAAAGGACTGGAATGGCTGGGAGTGATTTGGAG
TGGCGGAGGCACCGCCTACAACACCGCCCTGATCTCCCGGTTCACCATCAGCCGGGACAACT
CCAAGAACACCCTGTACCTGCAGATGAACTCCCTGCGGGCCGAGGACACCGCTGTGTACTAC
TGCGCCAGACGGGGCTCCTACCCCTACAACTACTTCGACGCTTGGGGCTGCGGCACCCTCGT
GACAGTGTCTAGCGGAGGGGGAGGTTCTGGGGGCGGAGGTTCAGGTGGTGGTGGTTCCGGG
GGTGGTGGCTCTGGTGGCGGTGGTTCTGGCGGTGGCGGATCTCAGGCTGTCGTGACCCAGGA
ACCCAGCCTGACTGTGTCTCCTGGCGGAACCGTGACCCTGACCTGCGGATCTTCTACCGGCG
CTGTGACCGCCAGCAACTACGCCAATTGGGTGCAGCAGAAACCTGGACAGTGCCCTAGAGG
CCTGATCGGCGGCCACAACAACAGACCTCCAGGCGTGCCAGCCCGGTTCTCTGGATCTCTGC
TGGGCGGAAAGGCCGCTCTGACACTGCTGGGTGCTCAGCCTGAGGACGAGGCCGAGTACTA
CTGTGCCCTGTGGTACTCCGACCACTGGGTCATCGGAGGCGGGACCAAGCTGACCGTGCTGG
GAACACCCCTGGGAGACACCACACATACTAGTGGGAAACCTCTGGATGGCGAGTACTTTAC
CCTGCAGATTAGAGGCCGCGAACGATTCGAGATGTTTCGCGAACTGAATGAGGCCCTGGAA
CTGAAGGATGCTCAGGCAGGCAAGGAGCCAGGAGGGTCAGGAGGAGCACCGCACCATCATC
ATCACCAT

FIG. 16

TC213 (G3A H1L4 K13D K74A huC825 SADA) full amino acid sequence (N to C terminal) [*G3A VL4*-linker-*G3A VH1*-linker-huC825-spacer-P53] (SEQ ID NO: 15)

EVQLVESGGGLVDPGGSLRLSCAASGFAFSTYDMSWVRQAPGKGLEWVSTISSGGSYTYYADSVKGRF
TISRDNAANSLYLQMNSLRAEDTAVYYCAPTTVVPFAYWGQGTLVTVSAGGGGSGGGGSGGGGSGG
GGSGGGGSGGGGSDIQMTQSPSSLSASVGDRVTITCKASQNVRTVVAWYQQKPGKAPKTLIYLASNR
HTGVPSRFSGSGSGTEFTLTISNLQPEDFATYYCLQHWSYPLTFGSGTKLEVKRGGGGSGGGGSGGG
GSGGGGSHVQLVESGGGLVQPGGSLRLSCAASGFSLTDYGVHWVRQAPGKGLEWLGVIWSGGGTAY
NTALISRFTISRDNSKNTLYLQMNSLRAEDTAVYYCARRGSYPYNYFDAWGCGTLVTVSSGGGGSGGG
GSGGGGSGGGGSGGGGSGGGGSQAVVTQEPSLTVSPGGTVTLTCGSSTGAVTASNYANWVQQKP
GQCPRGLIGGHNNRPPGVPARFSGSLLGGKAALTLLGAQPEDEAEYYCALWYSDHWVIGGGTKLTVL
GTPLGDTTHTSGKPLDGEYFTLQIRGRERFEMFRELNEALELKDAQAGKEPGGSGGAPHHHHH
H

TC213 (G3A H1L4 K13D K74A huC825 SADA) full nucleotide sequence (SEQ ID NO: 16)

GAGGTGCAGCTGGTGGAGTCTGGTGGGGGTCTGGTCGATCCTGGTGGTAGTCTGAGGCTGAG
TTGTGCCGCTTCTGGGTTTGCCTTCAGCACCTACGACATGTCCTGGGTGAGACAGGCTCCAG
GCAAGGGCCTGGAGTGGGTGTCTACCATCAGCTCCGGCGGCAGCTACACATACTATGCTGAC
TCCGTGAAGGGCCGGTTCACCATCTCTAGGGATAACGCCGCTAATAGCCTGTATCTGCAGAT
GAACTCCCTGCGCGCCGAGGATACAGCCGTGTACTATTGCGCCCCAACCACAGTGGTGCCCT
TTGCTTATTGGGGCCAGGGCACCCTGGTGACAGTGTCCGCCGGCGGAGGAGGCTCTGGAGG
AGGAGGCAGCGGTGGCGGCGGCTCCGGCGGCGGCGGCTCTGGCGGCGGCGGCAGCGGTGGT
GGCGGCTCCGACATCCAGATGACCCAGTCCCCTTCTAGCCTGTCCGCTTCTGTGGGCGATCG
GGTGACCATCACATGCAAGGCCTCTCAGAATGTGAGGACAGTGGTGGCTTGGTACCAGCAG
AAGCCCGGCAAGGCCCCTAAGACCCTGATCTATCTGGCTTCTAACAGACACACAGGAGTGCC
TAGCCGCTTCAGCGGCTCCGGCTCTGGAACCGAGTTTACCCTGACAATCAGCAATCTGCAGC
CAGAGGACTTCGCCACATACTATTGTCTGCAGCACTGGTCTTACCCCCTGACTTTTGGGAGC
GGGACTAAACTGGAGGTGAAACGGGGCGGAGGGGGATCCGGCGGCGGAGGATCTGGCGGA
GGTGGAAGTGGGGGAGGCGGATCTCATGTGCAGCTGGTGGAAAGCGGAGGCGGCCTGGTGC
AGCCTGGGGGATCTCTGAGACTGTCTTGTGCCGCCAGCGGCTTCTCCCTGACCGATTATGGC
GTGCACTGGGTGCGACAGGCCCCTGGCAAAGGACTGGAATGGCTGGGAGTGATTTGGAGTG
GCGGAGGCACCGCCTACAACACCGCCCTGATCTCCCGGTTCACCATCAGCCGGGACAACTCC
AAGAACACCCTGTACCTGCAGATGAACTCCCTGCGGGCCGAGGACACCGCTGTGTACTACTG
CGCCAGACGGGGCTCCTACCCCTACAACTACTTCGACGCTTGGGGCTGCGGCACCCTCGTGA
CAGTGTCTAGCGGAGGGGGAGGTTCTGGGGGCGGAGGTTCAGGTGGTGGTGGTTCCGGGGG
TGGTGGCTCTGGTGGCGGTGGTTCTGGCGGTGGCGGATCTCAGGCTGTCGTGACCCAGGAAC
CCAGCCTGACTGTGTCTCCTGGCGGAACCGTGACCCTGACCTGCGGATCTTCTACCGGCGCT
GTGACCGCCAGCAACTACGCCAATTGGGTGCAGCAGAAACCTGGACAGTGCCCTAGAGGCC
TGATCGGCGGCCACAACAACAGACCTCCAGGCGTGCCAGCCCGGTTCTCTGGATCTCTGCTG
GGCGGAAAGGCCGCTCTGACACTGCTGGGTGCTCAGCCTGAGGACGAGGCCGAGTACTACT
GTGCCCTGTGGTACTCCGACCACTGGGTCATCGGAGGCGGGACCAAGCTGACCGTGCTGGG
AACACCCCTGGGAGACACCACACATACTAGTGGGAAACCTCTGGATGGCGAGTACTTTACCC
TGCAGATTAGAGGCCGCGAACGATTCGAGATGTTTCGCGAACTGAATGAGGCCCTGGAACT
GAAGGATGCTCAGGCAGGCAAGGAGCCAGGAGGGTCAGGAGGAGCACCGCACCATCATCA
TCACCAT

FIG. 17

TC234 (G3A H1L4 K13D huC825 SADA) full amino acid sequence (N to C terminal) [*G3A VL4*-linker-*G3A VH1*-linker-huC825-spacer-P53] (SEQ ID NO: 17)

*EVQLVESGGGLVDPGGSLRLSCAASGFAFSTYDMSWVRQAPGKGLEWVSTISSGGSYTYYADSVKGRF*
*TISRDNAKNSLYLQMNSLRAEDTAVYYCAPTTVVPFAYWGQGTLVTVSA*GGGGSGGGGSGGGGSGG
GGSGGGGSGGGGS*DIQMTQSPSSLSASVGDRVTITCKASQNVRTVVAWYQQKPGKAPKTLIYLASNR*
*HTGVPSRFSGSGSGTEFTLTISNLQPEDFATYYCLQHWSYPLTFGSGTKLEVKR*GGGGSGGGGSGGG
GSGGGGS*HVQLVESGGGLVQPGGSLRLSCAASGFSLTDYGVHWVRQAPGKGLEWLGVIWSGGGTAY*
*NTALISRFTISRDNSKNTLYLQMNSLRAEDTAVYYCARRGSYPYNYFDAWGCGTLVTVSS*GGGGSGGG
GSGGGGSGGGGSGGGGSGGGGS*QAVVTQEPSLTVSPGGTVTLTCGSSTGAVTASNYANWVQQKP*
*GQCPRGLIGGHNNRPPGVPARFSGSLLGGKAALTLLGAQPEDEAEYYCALWYSDHWVIGGGTKLTVL*
*G*TPLGDTTHTSGKPLDGEYFTLQIRGRERFEMFRELNEALELKDAQAGKEPGGSGGAPHHHHH
H

TC234 (G3A H1L4 K13D huC825 SADA) full nucleotide sequence (SEQ ID NO: 18)

GAGGTGCAGCTGGTGGAGAGCGGAGGAGGCCTGGTGGACCCCGGAGGCAGCCTGAGACTGT
CCTGCGCCGCTTCTGGCTTCGCCTTTAGCACCTACGATATGTCCTGGGTGCGCCAGGCTCCTG
GCAAGGGCCTGGAGTGGGTGTCTACCATCAGCTCCGGCGGCAGCTACACATACTATGCCGAC
TCCGTGAAGGGCCGGTTCACCATCTCTAGGGATAACGCTAAGAATAGCCTGTATCTGCAGAT
GAACTCCCTGCGGGCCGAGGACACAGCCGTGTACTATTGTGCCCCAACCACAGTGGTGCCCT
TTGCTTATTGGGGCCAGGGCACCCTGGTGACAGTGTCTGCCGGCGGAGGAGGCTCTGGAGG
AGGAGGCAGCGGTGGCGGCGGCTCCGGCGGCGGCGGCTCTGGCGGCGGCGGCAGCGGTGGT
GGCGGCTCCGACATCCAGATGACCCAGAGCCCATCTAGCCTGTCCGCTTCTGTGGGCGATCG
GGTGACCATCACATGCAAGGCCTCCCAGAATGTGAGGACAGTGGTGGCTTGGTACCAGCAG
AAGCCCGGCAAGGCCCCTAAGACCCTGATCTATCTGGCTTCCAACAGACACACAGGAGTGC
CCTCTCGCTTCAGCGGCTCCGGCTCTGGAACCGAGTTTACCCTGACAATCTCCAATCTGCAGC
CTGAGGATTTCGCCACATACTATTGTCTGCAGCACTGGTCTTACCCACTGACCTTTGGCAGCG
GCACAAAGCTGGAGGTGAAGCGGGGCGGAGGGGGATCCGGCGGCGGAGGATCTGGCGGAG
GTGGAAGTGGGGGAGGCGGATCTCATGTGCAGCTGGTGGAAAGCGGAGGCGGCCTGGTGCA
GCCTGGGGGATCTCTGAGACTGTCTTGTGCCGCCAGCGGCTTCTCCCTGACCGATTATGGCG
TGCACTGGGTGCGACAGGCCCCTGGCAAAGGACTGGAATGGCTGGGAGTGATTTGGAGTGG
CGGAGGCACCGCCTACAACACCGCCCTGATCTCCCGGTTCACCATCAGCCGGGACAACTCCA
AGAACACCCTGTACCTGCAGATGAACTCCCTGCGGGCCGAGGACACCGCTGTGTACTACTGC
GCCAGACGGGGCTCCTACCCCTACAACTACTTCGACGCTTGGGGCTGCGGCACCCTCGTGAC
AGTGTCTAGCGGAGGGGGAGGTTCTGGGGGCGGAGGTTCAGGTGGTGGTGGTTCCGGGGGT
GGTGGCTCTGGTGGCGGTGGTTCTGGCGGTGGCGGATCTCAGGCTGTCGTGACCCAGGAACC
CAGCCTGACTGTGTCTCCTGGCGGAACCGTGACCCTGACCTGCGGATCTTCTACCGGCGCTG
TGACCGCCAGCAACTACGCCAATTGGGTGCAGCAGAAACCTGGACAGTGCCCTAGAGGCCT
GATCGGCGGCCACAACAACAGACCTCCAGGCGTGCCAGCCCGGTTCTCTGGATCTCTGCTGG
GCGGAAAGGCCGCTCTGACACTGCTGGGTGCTCAGCCTGAGGACGAGGCCGAGTACTACTG
TGCCCTGTGGTACTCCGACCACTGGGTCATCGGAGGCGGGACCAAGCTGACCGTGCTGGGA
ACACCCCTGGGAGACACCACACATACTAGTGGGAAACCTCTGGATGGCGAGTACTTTACCCT
GCAGATTAGAGGCCGCGAACGATTCGAGATGTTTCGCGAACTGAATGAGGCCCTGGAACTG
AAGGATGCTCAGGCAGGCAAGGAGCCAGGAGGGTCAGGAGGAGCACCGCACCATCATCATC
ACCAT

FIG. 18

TC235 (G3A H1L4 K42Q K13D K74A huC825 SADA) full amino acid sequence (N to C terminal)
[*G3A VL4*-linker-*G3A VH1*-linker-huC825-spacer-P53] (SEQ ID NO: 19)

*EVQLVESGGGLVDPGGSLRLSCAASGFAFSTYDMSWVRQAPGKGLEWVSTISSGGSYTYYADSVKGRF*
*TISRDNAANSLYLQMNSLRAEDTAVYYCAPTTVVPFAYWGQGTLVTVSA*GGGGSGGGGSGGGGSGG
GGSGGGGSGGGGS*DIQMTQSPSSLSASVGDRVTITCKASQNVRTVVAWYQQKPGQAPKTLIYLASNR*
*HTGVPSRFSGSGSGTEFTLTISNLQPEDFATYYCLQHWSYPLTFGSGTKLEVKR*GGGGSGGGGSGGG
GSGGGGS*HVQLVESGGGLVQPGGSLRLSCAASGFSLTDYGVHWVRQAPGKGLEWLGVIWSGGGTAY*
*NTALISRFTISRDNSKNTLYLQMNSLRAEDTAVYYCARRGSYPYNYFDAWGCGTLVTVSS*GGGGSGGG
GSGGGGSGGGGSGGGGSGGGGS*QAVVTQEPSLTVSPGGTVTLTCGSSTGAVTASNYANWVQQKP*
*GQCPRGLIGGHNNRPPGVPARFSGSLLGGKAALTLLGAQPEDEAEYYCALWYSDHWVIGGGTKLTVL*
*G*TPLGDTTHTSGKPLDGEYFTLQIRGRERFEMFRELNEALELKDAQAGKEPGGSGGAPHHHHH
H

TC235 (G3A H1L4 K42Q K13D K74A huC825 SADA) full nucleotide sequence (SEQ ID NO: 20)

GAGGTGCAGCTGGTGGAGAGCGGAGGAGGCCTGGTGGACCCCGGAGGCAGCCTGAGACTGT
CCTGCGCCGCTTCTGGCTTCGCCTTTAGCACCTACGATATGTCCTGGGTGCGCCAGGCTCCTG
GCAAGGGCCTGGAGTGGGTGTCTACCATCAGCTCCGGCGGCAGCTACACATACTATGCCGAC
TCCGTGAAGGGCCGGTTCACCATCTCTAGGGATAACGCCGCTAATAGCCTGTATCTGCAGAT
GAACTCCCTGCGGGCCGAGGACACAGCCGTGTACTATTGTGCCCCAACCACAGTGGTGCCCT
TTGCTTATTGGGGCCAGGGCACCCTGGTGACAGTGTCTGCCGGCGGAGGAGGCTCTGGAGG
AGGAGGCAGCGGTGGCGGCGGCTCCGGCGGCGGCGGCTCTGGCGGCGGCGGCAGCGGTGGT
GGCGGCTCCGACATCCAGATGACCCAGAGCCCATCTAGCCTGTCCGCTTCTGTGGGCGATCG
GGTGACCATCACATGCAAGGCCTCCCAGAATGTGAGGACAGTGGTGGCTTGGTACCAGCAG
AAGCCCGGCCAGGCCCCTAAGACCCTGATCTATCTGGCTTCCAACAGACACACAGGAGTGCC
CTCTCGCTTCAGCGGCTCCGGCTCTGGAACCGAGTTTACCCTGACAATCTCCAATCTGCAGCC
TGAGGATTTCGCCACATACTATTGTCTGCAGCACTGGTCTTACCCACTGACCTTTGGCAGCGG
CACAAAGCTGGAGGTGAAGCGGGCGGAGGGGGATCCGGCGGCGGAGGATCTGGCGGAGGT
GGAAGTGGGGGAGGCGGATCTCATGTGCAGCTGGTGGAAAGCGGAGGCGGCCTGGTGCAGC
CTGGGGGATCTCTGAGACTGTCTTGTGCCGCCAGCGGCTTCTCCCTGACCGATTATGGCGTG
CACTGGGTGCGACAGGCCCCTGGCAAAGGACTGGAATGGCTGGGAGTGATTTGGAGTGGCG
GAGGCACCGCCTACAACACCGCCCTGATCTCCCGGTTCACCATCAGCCGGGACAACTCCAAG
AACACCCTGTACCTGCAGATGAACTCCCTGCGGGCCGAGGACACCGCTGTGTACTACTGCGC
CAGACGGGGCTCCTACCCCTACAACTACTTCGACGCTTGGGGCTGCGGCACCCTCGTGACAG
TGTCTAGCGGAGGGGGAGGTTCTGGGGGCGGAGGTTCAGGTGGTGGTGGTTCCGGGGGTGG
TGGCTCTGGTGGCGGTGGTTCTGGCGGTGGCGGATCTCAGGCTGTCGTGACCCAGGAACCCA
GCCTGACTGTGTCTCCTGGCGGAACCGTGACCCTGACCTGCGGATCTTCTACCGGCGCTGTG
ACCGCCAGCAACTACGCCAATTGGGTGCAGCAGAAACCTGGACAGTGCCCTAGAGGCCTGA
TCGGCGGCCACAACAACAGACCTCCAGGCGTGCCAGCCCGGTTCTCTGGATCTCTGCTGGGC
GGAAAGGCCGCTCTGACACTGCTGGGTGCTCAGCCTGAGGACGAGGCCGAGTACTACTGTG
CCCTGTGGTACTCCGACCACTGGGTCATCGGAGGCGGGACCAAGCTGACCGTGCTGGGAAC
ACCCCTGGGAGACACCACACATACTAGTGGGAAACCTCTGGATGGCGAGTACTTTACCCTGC
AGATTAGAGGCCGCGAACGATTCGAGATGTTTCGCGAACTGAATGAGGCCCTGGAACTGAA
GGATGCTCAGGCAGGCAAGGAGCCAGGAGGGTCAGGAGGAGCACCGCACCATCATCATCAC
CAT

FIG. 19

BC015 (G3A H1L4) light chain full amino acid sequence (N to C terminal) [*G3A L4*-CL-linker-huC825 scFv] (SEQ ID NO: 21)

*DIQMTQSPSSLSASVGDRVTITCKASQNVRTVVAWYQQKPGKAPKTLIYLASNRHTGVPSRFSG SGSGTEFTLTISNLQPEDFATYYCLQHWSYPLTFGSGTKLEVK*RTVAAPSVFIFPPSDEQLKS GTASVVCLLNNFYPREAKVQWKVDNALQSGNSQEkSVTEQDSKDSTYSLSSTLTLSKAD YEKHKVYACEVTHQGLSSPVTKSFNRGECTSGGGGSGGGGSGGGGS*HVQLVESGGGL VQPGGSLRLSCAASGFSLTDYGVHWVRQAPGKGLEWLGVIWSGGGTAYNTALISRFTISRDNS KNTLYLQMNSLRAEDTAVYYCARRGSYPYNYFDAWGCGTLVTVSS*GGGGSGGGGSGGGGS GGGGSGGGGSGGGGS*QAVVTQEPSLTVSPGGTVTLTCGSSTGAVTASNYANWVQQKPGQ CPRGLIGGHNNRPPGVPARFSGSLLGGKAALTLLGAQPEDEAEYYCALWYSDHWVIGGGTKL TVLG*

BC015 (G3A H1L4) light chain full nucleotide sequence (SEQ ID NO: 22)

GACATCCAGATGACCCAGAGCCCATCTAGCCTGTCCGCCTCTGTGGGCGATCGGGTG
ACCATCACATGCAAGGCCTCCCAGAATGTGAGAACAGTGGTGGCCTGGTACCAGCA
GAAGCCCGGCAAGGCCCCTAAGACCCTGATCTATCTGGCCTCCAACAGGCACACAG
GAGTGCCATCTCGCTTCAGCGGCTCCGGCTCTGGAACCGAGTTTACCCTGACAATCT
CCAATCTGCAGCCTGAGGATTTCGCCACATACTATTGTCTGCAGCACTGGTCTTACC
CACTGACCTTTGGCAGCGGCACAAAGCTGGAGGTGAAGAGAACCGTGGCCGCTCCC
TCCGTGTTCATCTTCCCACCTTCCGACGAGCAGCTGAAGTCCGGCACCGCTTCTGTC
GTGTGCCTGCTGAACAACTTCTACCCCCGCGAGGCCAAGGTGCAGTGGAAGGTGGA
CAACGCCCTGCAGTCCGGCAACTCCCAGGAATCCGTGACCGAGCAGGACTCCAAGG
ACAGCACCTACAGCCTGTCCTCTACCCTGACCCTGTCCAAGGCCGACTACGAGAAGC
ACAAGGTGTACGCCTGCGAAGTGACCCACCAGGGCCTGTCTAGCCCCGTGACCAAG
TCTTTCAACCGGGGCGAGTGCACTAGTGGCGGCGGAGGATCTGGCGGAGGTGGAAG
TGGGGGAGGCGGATCTCATGTGCAGCTGGTGGAAAGCGGAGGCGGCCTGGTGCAGC
CTGGGGGATCTCTGAGACTGTCTTGTGCCGCCAGCGGCTTCTCCCTGACCGATTATG
GCGTGCACTGGGTGCGACAGGCCCCTGGCAAAGGACTGGAATGGCTGGGAGTGATT
TGGAGTGGCGGAGGCACCGCCTACAACACCGCCCTGATCTCCCGGTTCACCATCAGC
CGGGACAACTCCAAGAACACCCTGTACCTGCAGATGAACTCCCTGCGGGCCGAGGA
CACCGCTGTGTACTACTGCGCCAGACGGGGCTCCTACCCCTACAACTACTTCGACGC
TTGGGGCTGCGGCACCCTCGTGACAGTGTCTAGCGGAGGGGGAGGTTCTGGGGGCG
GAGGTTCAGGTGGTGGTGGTTCCGGGGGTGGTGGCTCTGGTGGCGGTGGTTCTGGCG
GTGGCGGATCTCAGGCTGTCGTGACCCAGGAACCCAGCCTGACTGTGTCTCCTGGCG
GAACCGTGACCCTGACCTGCGGATCTTCTACCGGCGCTGTGACCGCCAGCAACTACG
CCAATTGGGTGCAGCAGAAACCTGGACAGTGCCCTAGAGGCCTGATCGGCGGCCAC
AACAACAGACCTCCAGGCGTGCCAGCCCGGTTCTCTGGATCTCTGCTGGGCGGAAA
GGCCGCTCTGACACTGCTGGGTGCTCAGCCTGAGGACGAGGCCGAGTACTACTGTG
CCCTGTGGTACTCCGACCACTGGGTCATCGGAGGCGGGACCAAGCTGACCGTGCTG
GGA

FIG. 20

BC015 (G3A H1L4) heavy chain full amino acid sequence (N to C terminal) [*G3A* VH1-CH1-CH2-CH3] (SEQ ID NO: 23)

*EVQLVESGGGLVKPGGSLRLSCAASGFAFSTYDMSWVRQAPGKGLEWVSTISSGGSYTYYADS VKGRFTISRDNAKNSLYLQMNSLRAEDTAVYYCAPTTVVPFAYWGQGTLVTVSA*ASTKGPSVF
PLAPSSKSTSGGTAALGCLVKDYFPEPVTVSWNSGALTSGVHTFPAVLQSSGLYSLSSVV
TVPSSSLGTQTYICNVNHKPSNTKVDKRVEPKSCDKTHTCPPCPAPELLGGPSVFLFPPKP
KDTLMISRTPEVTCVVVDVSHEDPEVKFNWYVDGVEVHNAKTKPREEQYASTYRVVS
VLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNV
FSCSVMHEALHNHYTQKSLSLSPGK

BC015 (G3A H1L4) heavy chain full nucleotide sequence (SEQ ID NO: 24)

GAGGTGCAGCTGGTGGAATCTGGCGGCGGACTCGTGAAGCCTGGCGGCTCTCTGAG
ACTGTCTTGTGCCGCCTCTGGCTTCGCCTTCTCCACCTACGACATGTCCTGGGTGCGA
CAGGCCCCTGGCAAGAGACTGGAATGGGTGGCCACAATCTCCTCCGGCGGCTCCTA
CACCTACTACCTGGACTCTGTGAAGGGCCGGTTCACCATCTCCCGGGACAACGCCAA
GAACTCCCTGTACCTGCAGATGAACAGCCTGCGGGCCGAGGACACCGCCGTGTACT
ATTGTGCTCCCACCACCGTGGTGCCCTTCGCCTATTGGGGACAGGGCACCCTCGTGA
CCGTGTCCTCTGCTTCTACCAAGGGCCCATCGGTCTTCCCCCTGGCACCCTCCTCCAA
GAGCACCTCTGGGGGCACAGCGGCCCTGGGCTGCCTGGTCAAGGACTACTTCCCCG
AACCGGTGACGGTGTCGTGGAACTCAGGCGCCCTGACCAGCGGCGTGCACACCTTC
CCGGCCGTCCTACAGTCCTCAGGACTCTACTCCCTCAGCAGCGTGGTGACCGTGCCC
TCCAGCAGCTTGGGCACCCAGACCTACATCTGCAACGTGAATCACAAGCCCAGCAA
CACCAAGGTGGACAAGAGAGTTGAGCCCAAATCTTGTGACAAAACTCACACATGCC
CACCGTGCCCAGCACCTGAACTCCTGGGGGGACCGTCAGTCTTCCTCTTCCCCCCAA
AACCCAAGGACACCCTCATGATCTCCCGGACCCCTGAGGTCACATGCGTGGTGGTG
GACGTGAGCCACGAAGACCCTGAGGTCAAGTTCAACTGGTACGTGGACGGCGTGGA
GGTGCATAATGCCAAGACAAAGCCGCGGGAGGAGCAGTACGCCAGCACGTACCGTG
TGGTCAGCGTCCTCACCGTCCTGCACCAGGACTGGCTGAATGGCAAGGAGTACAAG
TGCAAGGTCTCCAACAAAGCCCTCCCAGCCCCCATCGAGAAAACCATCTCCAAAGC
CAAAGGGCAGCCCCGAGAACCACAGGTGTACACCCTGCCCCCATCCCGGGATGAGC
TGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGC
CTCCCGTGCTGGACTCCGACGGCTCCTTCTTCCTCTACAGCAAGCTCACCGTGGACA
AGAGCAGGTGGCAGCAGGGGAACGTCTTCTCATGCTCCGTGATGCATGAGGCTCTG
CACAACCACTACACGCAGAAGAGCCTCTCCCTGTCTCCGGGTAAA

FIG. 21

BC016 (G3A H3L3) light chain full amino acid sequence (N to C terminal) [*G3A L3*-CL-linker-huC825 scFv] (SEQ ID NO: 25)

*DIQMTQSPSSLSTSVGDRVTITCKASQNVRTVVAWYQQKPGKAPKTLIYLASNRHSGVPSRFSG*
*SGSGTEFTLTISNLQPEDFATYYCLQHWSYPLTFGSGTKLEVKR*TVAAPSVFIFPPSDEQLKS
GTASVVCLLNNFYPREAKVQWKVDNALQSGNSQESVTEQDSKDSTYSLSSTLTLSKAD
YEKHKVYACEVTHQGLSSPVTKSFNRGECTSGGGGSGGGGSGGGGS*HVQLVESGGGL*
*VQPGGSLRLSCAASGFSLTDYGVHWVRQAPGKGLEWLGVIWSGGGTAYNTALISRFTISRDNS*
*KNTLYLQMNSLRAEDTAVYYCARRGSYPYNYFDAWGCGTLVTVSS*GGGGSGGGGSGGGGS
GGGGSGGGGSGGGGS*QAVVTQEPSLTVSPGGTVTLTCGSSTGAVTASNYANWVQQKPGQ*
*CPRGLIGGHNNRPPGVPARFSGSLLGGKAALTLLGAQPEDEAEYYCALWYSDHWVIGGGTKL*
*TVLG*

BC016 (G3A H3L3) light chain full nucleotide sequence (SEQ ID NO: 26)

GACATCCAGATGACCCAGAGCCCTAGCTCCCTGTCTACAAGCGTGGGCGATAGGGT
GACCATCACATGCAAGGCCTCCCAGAACGTGAGAACCGTGGTGGCCTGGTACCAGC
AGAAGCCCGGCAAGGCCCCTAAGACACTGATCTATCTGGCCTCCAACAGGCACTCT
GGAGTGCCCAGCAGATTCTCCGGCTCTGGCAGCGGCACCGAGTTTACCCTGACAATC
TCTAATCTGCAGCCAGAGGACTTCGCCACATACTATTGTCTGCAGCACTGGTCCTAC
CCCCTGACCTTTGGCTCTGGCACAAAGCTGGAGGTGAAGAGAACCGTGGCCGCTCC
CTCCGTGTTCATCTTCCCACCTTCCGACGAGCAGCTGAAGTCCGGCACCGCTTCTGTC
GTGTGCCTGCTGAACAACTTCTACCCCCGCGAGGCCAAGGTGCAGTGGAAGGTGGA
CAACGCCCTGCAGTCCGGCAACTCCCAGGAATCCGTGACCGAGCAGGACTCCAAGG
ACAGCACCTACAGCCTGTCCTCTACCCTGACCCTGTCCAAGGCCGACTACGAGAAGC
ACAAGGTGTACGCCTGCGAAGTGACCCACCAGGGCCTGTCTAGCCCCGTGACCAAG
TCTTTCAACCGGGGCGAGTGCACTAGTGGCGGCGGAGGATCTGGCGGAGGTGGAAG
TGGGGGAGGCGGATCTCATGTGCAGCTGGTGGAAAGCGGAGGCGGCCTGGTGCAGC
CTGGGGGATCTCTGAGACTGTCTTGTGCCGCCAGCGGCTTCTCCCTGACCGATTATG
GCGTGCACTGGGTGCGACAGGCCCCTGGCAAAGGACTGGAATGGCTGGGAGTGATT
TGGAGTGGCGGAGGCACCGCCTACAACACCGCCCTGATCTCCCGGTTCACCATCAGC
CGGGACAACTCCAAGAACACCCTGTACCTGCAGATGAACTCCCTGCGGGCCGAGGA
CACCGCTGTGTACTACTGCGCCAGACGGGGCTCCTACCCCTACAACTACTTCGACGC
TTGGGGCTGCGGCACCCTCGTGACAGTGTCTAGCGGAGGGGGAGGTTCTGGGGGCG
GAGGTTCAGGTGGTGGTGGTTCCGGGGGTGGTGGCTCTGGTGGCGGTGGTTCTGGCG
GTGGCGGATCTCAGGCTGTCGTGACCCAGGAACCCAGCCTGACTGTGTCTCCTGGCG
GAACCGTGACCCTGACCTGCGGATCTTCTACCGGCGCTGTGACCGCCAGCAACTACG
CCAATTGGGTGCAGCAGAAACCTGGACAGTGCCCTAGAGGCCTGATCGGCGGCCAC
AACAACAGACCTCCAGGCGTGCCAGCCCGGTTCTCTGGATCTCTGCTGGGCGGAAA
GGCCGCTCTGACACTGCTGGGTGCTCAGCCTGAGGACGAGGCCGAGTACTACTGTG
CCCTGTGGTACTCCGACCACTGGGTCATCGGAGGCGGGACCAAGCTGACCGTGCTG
GGA

FIG. 22

BC016 (G3A H3L3) heavy chain full amino acid sequence (N to C terminal) [*G3A H3*-CH1-CH2-CH3] (SEQ ID NO: 27)

*EVQLVESGGGLVKPGGSLRLSCAASGFAFSTYDMSWVRQAPGKGLEWVATISSGGSYTYYADS VKGRFTISRDSAKNSLYLQMNSLRAEDTAVYYCAPTTVVPFAYWGQGTLVTVSA*ASTKGPSVF PLAPSSKSTSGGTAALGCLVKDYFPEPVTVSWNSGALTSGVHTFPAVLQSSGLYSLSSVV TVPSSSLGTQTYICNVNHKPSNTKVDKRVEPKSCDKTHTCPPCPAPELLGGPSVFLFPPKP KDTLMISRTPEVTCVVVDVSHEDPEVKFNWYVDGVEVHNAKTKPREEQYASTYRVVS VLTVLHQDWLNGKEYKCKVSNKALPAPIEKTISKAKGQPREPQVYTLPPSRDELTKNQV SLTCLVKGFYPSDIAVEWESNGQPENNYKTTPPVLDSDGSFFLYSKLTVDKSRWQQGNV FSCSVMHEALHNHYTQKSLSLSPGK

*BC016 (G3A H3L3) heavy chain full nucleotide sequence* (SEQ ID NO: 28)

GAGGTGCAGCTGGTGGAGTCCGGAGGAGGCCTGGTGAAGCCAGGAGGCTCCCTGAG
GCTGTCTTGCGCCGCCAGCGGATTCGCCTTTTCCACCTACGACATGTCTTGGGTGCG
CCAGGCACCAGGCAAGGGCCTGGAGTGGGTGGCAACCATCAGCTCCGGAGGCAGCT
ACACATACTATGCCGACTCCGTGAAGGGCCGGTTCACCATCAGCCGGGACAGCGCC
AAGAACTCTCTGTATCTGCAGATGAATAGCCTGCGGGCCGAGGATACAGCCGTGTA
CTATTGTGCCCCCACCACAGTGGTGCCTTTTGCCTATTGGGGCCAGGGCACCCTGGT
GACAGTGTCTGCCGCTTCTACCAAGGGCCCATCGGTCTTCCCCCTGGCACCCTCCTC
CAAGAGCACCTCTGGGGGCACAGCGGCCCTGGGCTGCCTGGTCAAGGACTACTTCC
CCGAACCGGTGACGGTGTCGTGGAACTCAGGCGCCCTGACCAGCGGCGTGCACACC
TTCCCGGCCGTCCTACAGTCCTCAGGACTCTACTCCCTCAGCAGCGTGGTGACCGTG
CCCTCCAGCAGCTTGGGCACCCAGACCTACATCTGCAACGTGAATCACAAGCCCAG
CAACACCAAGGTGGACAAGAGAGTTGAGCCCAAATCTTGTGACAAAACTCACACAT
GCCCACCGTGCCCAGCACCTGAACTCCTGGGGGGACCGTCAGTCTTCCTCTTCCCCC
CAAAACCCAAGGACACCCTCATGATCTCCCGGACCCCTGAGGTCACATGCGTGGTG
GTGGACGTGAGCCACGAAGACCCTGAGGTCAAGTTCAACTGGTACGTGGACGGCGT
GGAGGTGCATAATGCCAAGACAAAGCCGCGGGAGGAGCAGTACGCCAGCACGTAC
CGTGTGGTCAGCGTCCTCACCGTCCTGCACCAGGACTGGCTGAATGGCAAGGAGTA
CAAGTGCAAGGTCTCCAACAAAGCCCTCCCAGCCCCCATCGAGAAAACCATCTCCA
AAGCCAAAGGGCAGCCCCGAGAACCACAGGTGTACACCCTGCCCCCATCCCGGGAT
GAGCTGACCAAGAACCAGGTCAGCCTGACCTGCCTGGTCAAAGGCTTCTATCCCAG
CGACATCGCCGTGGAGTGGGAGAGCAATGGGCAGCCGGAGAACAACTACAAGACC
ACGCCTCCCGTGCTGGACTCCGACGGCTCCTTCTTCCTCTACAGCAAGCTCACCGTG
GACAAGAGCAGGTGGCAGCAGGGGAACGTCTTCTCATGCTCCGTGATGCATGAGGC
TCTGCACAACCACTACACGCAGAAGAGCCTCTCCCTGTCTCCGGGTAAA

FIG. 23

TC252 (G3A H1L4 huOKT3 SADA) full amino acid sequence (N to C terminal) [*G3A VH1*-linker-*G3A VL4*-linker-OKT3-spacer-P53] (SEQ ID NO: 29)

*EVQLVESGGGLVKPGGSLRLSCAASGFAFSTYDMSWVRQAPGKGLEWVSTISSGGSYTYYADSVKGRFTISRDNAKNSLYLQMNSLRAEDTAVYYCAPTTVVPFAYWGQGTLVTVSA*GGGGSGGGGSGGGGSGGGGSGGGGSGGGGS*DIQMTQSPSSLSASVGDRVTITCKASQNVRTVVAWYQQKPGKAPKTLIYLASNRHTGVPSRFSGSGSGTEFTLTISNLQPEDFATYYCLQHWSYPLTFGSGTKLEVKR*GGGGSGGGGSGGGGSGGGGS*QVQLVQSGGGVVQPGRSLRLSCKASGYTFTRYTMHWVRQAPGKCLEWIGYINPSRGYTNYNQKFKDRFTISRDNSKNTAFLQMDSLRPEDTGVYFCARYYDDHYSLDYWGQGTPVTVSS*GGGGSGGGGSGGGGSGGGGSGGGGSGGGGS*DIQMTQSPSSLSASVGDRVTITCSASSSVSYMNWYQQTPGKAPKRWIYDTSKLASGVPSRFSGSGSGTDYTFTISSLQPEDIATYYCQQWSSNPFTFGCGTKLQITR*TPLGDTTHTSGKPLDGEYFTLQIRGRERFEMFRELNEALELKDAQAGKEPGGSGGAPHHHHHH

TC253 (G3A H1L4 K13D OKT3 SADA) full amino acid sequence (N to C terminal) [*G3A VH1*-linker-*G3A VL4*-linker-OKT3-spacer-P53] (SEQ ID NO: 30)

*EVQLVESGGGLVDPGGSLRLSCAASGFAFSTYDMSWVRQAPGKGLEWVSTISSGGSYTYYADSVKGRFTISRDNAKNSLYLQMNSLRAEDTAVYYCAPTTVVPFAYWGQGTLVTVSA*GGGGSGGGGSGGGGSGGGGSGGGGSGGGGS*DIQMTQSPSSLSASVGDRVTITCKASQNVRTVVAWYQQKPGKAPKTLIYLASNRHTGVPSRFSGSGSGTEFTLTISNLQPEDFATYYCLQHWSYPLTFGSGTKLEVKR*GGGGSGGGGSGGGGSGGGGS*QVQLVQSGGGVVQPGRSLRLSCKASGYTFTRYTMHWVRQAPGKCLEWIGYINPSRGYTNYNQKFKDRFTISRDNSKNTAFLQMDSLRPEDTGVYFCARYYDDHYSLDYWGQGTPVTVSS*GGGGSGGGGSGGGGSGGGGSGGGGSGGGGS*DIQMTQSPSSLSASVGDRVTITCSASSSVSYMNWYQQTPGKAPKRWIYDTSKLASGVPSRFSGSGSGTDYTFTISSLQPEDIATYYCQQWSSNPFTFGCGTKLQITR*TPLGDTTHTSGKPLDGEYFTLQIRGRERFEMFRELNEALELKDAQAGKEPGGSGGAPHHHHHH

TC254 (G3A H1L4 K13D K74A OKT3 SADA) full amino acid sequence (N to C terminal) [*G3A VH1*-linker-*G3A VL4*-linker-OKT3-spacer-P53] (SEQ ID NO: 31)

*EVQLVESGGGLVDPGGSLRLSCAASGFAFSTYDMSWVRQAPGKGLEWVSTISSGGSYTYYADSVKGRFTISRDNAANSLYLQMNSLRAEDTAVYYCAPTTVVPFAYWGQGTLVTVSA*GGGGSGGGGSGGGGSGGGGSGGGGSGGGGS*DIQMTQSPSSLSASVGDRVTITCKASQNVRTVVAWYQQKPGKAPKTLIYLASNRHTGVPSRFSGSGSGTEFTLTISNLQPEDFATYYCLQHWSYPLTFGSGTKLEVKR*GGGGSGGGGSGGGGSGGGGS*QVQLVQSGGGVVQPGRSLRLSCKASGYTFTRYTMHWVRQAPGKCLEWIGYINPSRGYTNYNQKFKDRFTISRDNSKNTAFLQMDSLRPEDTGVYFCARYYDDHYSLDYWGQGTPVTVSS*GGGGSGGGGSGGGGSGGGGSGGGGSGGGGS*DIQMTQSPSSLSASVGDRVTITCSASSSVSYMNWYQQTPGKAPKRWIYDTSKLASGVPSRFSGSGSGTDYTFTISSLQPEDIATYYCQQWSSNPFTFGCGTKLQITR*TPLGDTTHTSGKPLDGEYFTLQIRGRERFEMFRELNEALELKDAQAGKEPGGSGGAPHHHHHH

FIG. 23 (Cont.)

TC255 (G3A H1L4 K13D K42Q K74A OKT3 SADA) full amino acid sequence (N to C terminal) [*G3A VH1*-linker-*G3A VL4*-linker-OKT3-spacer-P53] (SEQ ID NO: 32)

*EVQLVESGGGLVDPGGSLRLSCAASGFAFSTYDMSWVRQAPGKGLEWVSTISSGGSYTYYADSVKGRF*
*TISRDNAANSLYLQMNSLRAEDTAVYYCAPTTVVPFAYWGQGTLVTVSA* GGGGSGGGGSGGGGSGG
GGSGGGGSGGGGS *DIQMTQSPSSLSASVGDRVTITCKASQNVRTVVAWYQQKPGQAPKTLIYLASNR*
*HTGVPSRFSGSGSGTEFTLTISNLQPEDFATYYCLQHWSYPLTFGSGTKLEVKR* GGGGSGGGGSGGG
GSGGGGS *QVQLVQSGGGVVQPGRSLRLSCKASGYTFTRYTMHWVRQAPGKCLEWIGYINPSRGYTNY*
*NQKFKDRFTISRDNSKNTAFLQMDSLRPEDTGVYFCARYYDDHYSLDYWGQGTPVTVSS* GGGGSGG
GGSGGGGSGGGGSGGGGSGGGGS *DIQMTQSPSSLSASVGDRVTITCSASSSVSYMNWYQQTPGKA*
*PKRWIYDTSKLASGVPSRFSGSGSGTDYTFTISSLQPEDIATYYCQQWSSNPFTFGCGTKLQITR* TPLGD
TTHTSG KPLDGEYFTLQIRGRERFEMFRELNEALELKDAQAGKEPGGSGGAPHHHHHH

TC256 (G3A H1L4 OT3 H2L2 SADA) full amino acid sequence (N to C terminal) [*G3A VH1*-linker-*G3A VL4*-linker-OKT3-spacer-P53] (SEQ ID NO: 33)

*EVQLVESGGGLVKPGGSLRLSCAASGFAFSTYDMSWVRQAPGKGLEWVSTISSGGSYTYYADSVKGRFT*
*ISRDNAKNSLYLQMNSLRAEDTAVYYCAPTTVVPFAYWGQGTLVTVSA* GGGGSGGGGSGGGGSGG
GGSGGGGSGGGGS *DIQMTQSPSSLSASVGDRVTITCKASQNVRTVVAWYQQKPGKAPKTLIYLASNR*
*HTGVPSRFSGSGSGTEFTLTISNLQPEDFATYYCLQHWSYPLTFGSGTKLEVKR* GGGGSGGGGSGGG
GSGGGGS *QVQLQQSGAEVAKPGASVKVSCKASGYTFTRYTMHWVRQAPGQGLEWMGYINPSRGYTN*
*YNQKFKDRATLTRDKSISTAYMELSRLRSDDTAVYYCARYYDDHYSLDYWGQGTTLTVSS* GGGGSGG
GGSGGGGSGGGGSGGGGSGGGGS *DIQMTQSPSSLSASVGDRVTMTCSASSSVSYMNWYQQKPGK*
*APKLLIYDTSKLASGVPSRFSGSGSGTDFTLTISSMQPEDFATYYCQQWSSNPFTFGSGTKLEINR* TPLG
DTTHTSG KPLDGEYFTLQIRGRERFEMFRELNEALELKDAQAGKEPGGSGGAPHHHHHH

TC257 (G3A H1L4 K13D OT3 H2L2 SADA) full amino acid sequence (N to C terminal) [*G3A VH1*-linker-*G3A VL4*-linker-OKT3-spacer-P53] (SEQ ID NO: 34)

*EVQLVESGGGLVDPGGSLRLSCAASGFAFSTYDMSWVRQAPGKGLEWVSTISSGGSYTYYADSVKGRF*
*TISRDNAKNSLYLQMNSLRAEDTAVYYCAPTTVVPFAYWGQGTLVTVSA* GGGGSGGGGSGGGGSGG
GGSGGGGSGGGGS *DIQMTQSPSSLSASVGDRVTITCKASQNVRTVVAWYQQKPGKAPKTLIYLASNR*
*HTGVPSRFSGSGSGTEFTLTISNLQPEDFATYYCLQHWSYPLTFGSGTKLEVKR* GGGGSGGGGSGGG
GSGGGGS *QVQLQQSGAEVAKPGASVKVSCKASGYTFTRYTMHWVRQAPGQGLEWMGYINPSRGYTN*
*YNQKFKDRATLTRDKSISTAYMELSRLRSDDTAVYYCARYYDDHYSLDYWGQGTTLTVSS* GGGGSGG
GGSGGGGSGGGGSGGGGSGGGGS *DIQMTQSPSSLSASVGDRVTMTCSASSSVSYMNWYQQKPGK*
*APKLLIYDTSKLASGVPSRFSGSGSGTDFTLTISSMQPEDFATYYCQQWSSNPFTFGSGTKLEINR* TPLG
DTTHTSG KPLDGEYFTLQIRGRERFEMFRELNEALELKDAQAGKEPGGSGGAPHHHHHH

FIG. 23 (Cont.)

TC258 (G3A H1L4 K13D K74A OT3 H2L2 SADA) full amino acid sequence (N to C terminal) [*G3A VH1*-linker-*G3A VL4*-linker-OKT3-spacer-P53] (SEQ ID NO: 35)

*EVQLVESGGGLVDPGGSLRLSCAASGFAFSTYDMSWVRQAPGKGLEWVSTISSGGSYTYYADSVKGRF*
*TISRDNAANSLYLQMNSLRAEDTAVYYCAPTTVVPFAYWGQGTLVTVSA*GGGGSGGGGSGGGGSGG
GGSGGGGSGGGGS*DIQMTQSPSSLSASVGDRVTITCKASQNVRTVVAWYQQKPGKAPKTLIYLASNR*
*HTGVPSRFSGSGSGTEFTLTISNLQPEDFATYYCLQHWSYPLTFGSGTKLEVKR*GGGGSGGGGSGGG
GSGGGGS*QVQLQQSGAEVAKPGASVKVSCKASGYTFTRYTMHWVRQAPGQGLEWMGYINPSRGYTN*
*YNQKFKDRATLTRDKSISTAYMELSRLRSDDTAVYYCARYYDDHYSLDYWGQGTTLTVSS*GGGGSGG
GGSGGGGSGGGGSGGGGSGGGGS*DIQMTQSPSSLSASVGDRVTMTCSASSSVSYMNWYQQKPGK*
*APKLLIYDTSKLASGVPSRFSGSGSGTDFTLTISSMQPEDFATYYCQQWSSNPFTFGSGTKLEINR*TPLG
DTTHTSGKPLDGEYFTLQIRGRERFEMFRELNEALELKDAQAGKEPGGSGGAPHHHHHH

TC259 (G3A H1L4 K13D K42Q K74A OT3 H2L2 SADA) full amino acid sequence (N to C terminal) [*G3A VH1*-linker-*G3A VL4*-linker-OKT3-spacer-P53] (SEQ ID NO: 36)

*EVQLVESGGGLVDPGGSLRLSCAASGFAFSTYDMSWVRQAPGKGLEWVSTISSGGSYTYYADSVKGRF*
*TISRDNAANSLYLQMNSLRAEDTAVYYCAPTTVVPFAYWGQGTLVTVSA*GGGGSGGGGSGGGGSGG
GGSGGGGSGGGGS*DIQMTQSPSSLSASVGDRVTITCKASQNVRTVVAWYQQKPGQAPKTLIYLASNR*
*HTGVPSRFSGSGSGTEFTLTISNLQPEDFATYYCLQHWSYPLTFGSGTKLEVKR*GGGGSGGGGSGGG
GSGGGGS*QVQLQQSGAEVAKPGASVKVSCKASGYTFTRYTMHWVRQAPGQGLEWMGYINPSRGYTN*
*YNQKFKDRATLTRDKSISTAYMELSRLRSDDTAVYYCARYYDDHYSLDYWGQGTTLTVSS*GGGGSGG
GGSGGGGSGGGGSGGGGSGGGGS*DIQMTQSPSSLSASVGDRVTMTCSASSSVSYMNWYQQKPGK*
*APKLLIYDTSKLASGVPSRFSGSGSGTDFTLTISSMQPEDFATYYCQQWSSNPFTFGSGTKLEINR*TPLG
DTTHTSGKPLDGEYFTLQIRGRERFEMFRELNEALELKDAQAGKEPGGSGGAPHHHHHH

TC260 (G3A H1L4 OT3 H2L5 SADA) full amino acid sequence (N to C terminal) [*G3A VH1*-linker-*G3A VL4*-linker-OKT3-spacer-P53] (SEQ ID NO: 37)

*EVQLVESGGGLVKPGGSLRLSCAASGFAFSTYDMSWVRQAPGKGLEWVSTISSGGSYTYYADSVKGRFT*
*ISRDNAKNSLYLQMNSLRAEDTAVYYCAPTTVVPFAYWGQGTLVTVSA*GGGGSGGGGSGGGGSGG
GGSGGGGSGGGGS*DIQMTQSPSSLSASVGDRVTITCKASQNVRTVVAWYQQKPGKAPKTLIYLASNR*
*HTGVPSRFSGSGSGTEFTLTISNLQPEDFATYYCLQHWSYPLTFGSGTKLEVKR*GGGGSGGGGSGGG
GSGGGGS*QVQLQQSGAEVAKPGASVKVSCKASGYTFTRYTMHWVRQAPGQGLEWMGYINPSRGYTN*
*YNQKFKDRATLTRDKSISTAYMELSRLRSDDTAVYYCARYYDDHYSLDYWGQGTTLTVSS*GGGGSGG
GGSGGGGSGGGGSGGGGSGGGGS*DIQMTQSPSSLSASVGDRVTITCSASSSVSYMNWYQQKPGKA*
*PKRWIYDTSKLASGVPSRFSGSGSGTDFTLTISSLQPEDFATYYCQQWSSNPFTFGSGTKLEINR*TPLGD
TTHTSGKPLDGEYFTLQIRGRERFEMFRELNEALELKDAQAGKEPGGSGGAPHHHHHH

FIG. 23 (Cont.)

TC261 (G3A H1L4 K13D OT3 H2L5 SADA) full amino acid sequence (N to C terminal) [*G3A VH1*-linker-*G3A VL4*-linker-OKT3-spacer-P53] (SEQ ID NO: 38)

*EVQLVESGGGLVDPGGSLRLSCAASGFAFSTYDMSWVRQAPGKGLEWVSTISSGGSYTYYADSVKGRFTISRDNAKNSLYLQMNSLRAEDTAVYYCAPTTVVPFAYWGQGTLVTVSA*GGGGSGGGGSGGGGSGGGGSGGGGSGGGGS*DIQMTQSPSSLSASVGDRVTITCKASQNVRTVVAWYQQKPGKAPKTLIYLASNRHTGVPSRFSGSGSGTEFTLTISNLQPEDFATYYCLQHWSYPLTFGSGTKLEVKR*GGGGSGGGGSGGGGSGGGGS*QVQLQQSGAEVAKPGASVKVSCKASGYTFTRYTMHWVRQAPGQGLEWMGYINPSRGYTNYNQKFKDRATLTRDKSISTAYMELSRLRSDDTAVYYCARYYDDHYSLDYWGQGTTLTVSS*GGGGSGGGGSGGGGSGGGGSGGGGSGGGGS*DIQMTQSPSSLSASVGDRVTITCSASSSVSYMNWYQQKPGKAPKRWIYDTSKLASGVPSRFSGSGSGTDFTLTISSLQPEDFATYYCQQWSSNPFTFGSGTKLEINR*TPLGDTTHTSGKPLDGEYFTLQIRGRERFEMFRELNEALELKDAQAGKEPGGSGGAPHHHHHH

TC262 (G3A H1L4 K13D K74A OT3 H2L5 SADA) full amino acid sequence (N to C terminal) [*G3A VH1*-linker-*G3A VL4*-linker-OKT3-spacer-P53] (SEQ ID NO: 39)

*EVQLVESGGGLVDPGGSLRLSCAASGFAFSTYDMSWVRQAPGKGLEWVSTISSGGSYTYYADSVKGRFTISRDNAANSLYLQMNSLRAEDTAVYYCAPTTVVPFAYWGQGTLVTVSA*GGGGSGGGGSGGGGSGGGGSGGGGSGGGGS*DIQMTQSPSSLSASVGDRVTITCKASQNVRTVVAWYQQKPGKAPKTLIYLASNRHTGVPSRFSGSGSGTEFTLTISNLQPEDFATYYCLQHWSYPLTFGSGTKLEVKR*GGGGSGGGGSGGGGSGGGGS*QVQLQQSGAEVAKPGASVKVSCKASGYTFTRYTMHWVRQAPGQGLEWMGYINPSRGYTNYNQKFKDRATLTRDKSISTAYMELSRLRSDDTAVYYCARYYDDHYSLDYWGQGTTLTVSS*GGGGSGGGGSGGGGSGGGGSGGGGSGGGGS*DIQMTQSPSSLSASVGDRVTITCSASSSVSYMNWYQQKPGKAPKRWIYDTSKLASGVPSRFSGSGSGTDFTLTISSLQPEDFATYYCQQWSSNPFTFGSGTKLEINR*TPLGDTTHTSGKPLDGEYFTLQIRGRERFEMFRELNEALELKDAQAGKEPGGSGGAPHHHHHH

TC263 (G3A H1L4 K13D K42Q K74A OT3 H2L5 SADA) full amino acid sequence (N to C terminal) [*G3A VH1*-linker-*G3A VL4*-linker-OKT3-spacer-P53] (SEQ ID NO: 40)

*EVQLVESGGGLVDPGGSLRLSCAASGFAFSTYDMSWVRQAPGKGLEWVSTISSGGSYTYYADSVKGRFTISRDNAANSLYLQMNSLRAEDTAVYYCAPTTVVPFAYWGQGTLVTVSA*GGGGSGGGGSGGGGSGGGGSGGGGSGGGGS*DIQMTQSPSSLSASVGDRVTITCKASQNVRTVVAWYQQKPGQAPKTLIYLASNRHTGVPSRFSGSGSGTEFTLTISNLQPEDFATYYCLQHWSYPLTFGSGTKLEVKR*GGGGSGGGGSGGGGSGGGGS*QVQLQQSGAEVAKPGASVKVSCKASGYTFTRYTMHWVRQAPGQGLEWMGYINPSRGYTNYNQKFKDRATLTRDKSISTAYMELSRLRSDDTAVYYCARYYDDHYSLDYWGQGTTLTVSS*GGGGSGGGGSGGGGSGGGGSGGGGSGGGGS*DIQMTQSPSSLSASVGDRVTITCSASSSVSYMNWYQQKPGKAPKRWIYDTSKLASGVPSRFSGSGSGTDFTLTISSLQPEDFATYYCQQWSSNPFTFGSGTKLEINR*TPLGDTTHTSGKPLDGEYFTLQIRGRERFEMFRELNEALELKDAQAGKEPGGSGGAPHHHHHH

FIG. 24

TC264 (G3A H1L4 HER2 LH DOTA SADA) full amino acid sequence (N to C terminal) [*G3A VH1*-linker *G3A VL4*-linker-*HER2 VL*-linker-*HER2 VH*-linker-huC825-spacer-P53]
(SEQ ID NO: 41)

*EVQLVESGGGLVKPGGSLRLSCAASGFAFSTYDMSWVRQAPGKGLEWVSTISSGGSYTYYADSVKGRFT*
*ISRDNAKNSLYLQMNSLRAEDTAVYYCAPTTVVPFAYWGQGTLVTVSA*GGGGSGGGGSGGGGSGG
GGSGGGGSGGGGS*DIQMTQSPSSLSASVGDRVTITCKASQNVRTVVAWYQQKPGKAPKTLIYLASNR*
*HTGVPSRFSGSGSGTEFTLTISNLQPEDFATYYCLQHWSYPLTFGSGTKLEVKR*GGGGSGGGGSGGG
GSGGGGS*DIQMTQSPSSLSASVGDRVTITCRASQDVNTAVAWYQQKPGKAPKLLIYSASFLYSGVPSRF*
*SGSRSGTDFTLTISSLQPEDFATYYCQQHYTTPPTFGQGTKVEIKR*GGGGSGGGGSGGGGSGGGGS
GGGGSGGGGS*EVQLVESGGGLVQPGGSLRLSCAASGFNIKDTYIHWVRQAPGKGLEWVARIYPTNG*
*YTRYADSVKGRFTISADTSKNTAYLQMNSLRAEDTAVYYCSRWGGDGFYAMDYWGQGTLVTVSS*GGG
GSGGGGSGGGGSGGGGS*HVQLVESGGGLVQPGGSLRLSCAASGFSLTDYGVHWVRQAPGKGLEW*
*LGVIWSGGGTAYNTALISRFTISRDNSKNTLYLQMNSLRAEDTAVYYCARRGSYPYNYFDAWGCGTLVTV*
*SS*GGGGSGGGGSGGGGSGGGGSGGGGSGGGGS*QAVVTQEPSLTVSPGGTVTLTCGSSTGAVTAS*
*NYANWVQQKPGQCPRGLIGGHNNRPPGVPARFSGSLLGGKAALTLLGAQPEDEAEYYCALWYSDHW*
*VIGGGTKLTVLG*TPLGDTTHTSGKPLDGEYFTLQIRGRERFEMFRELNEALELKDAQAGKEPGGS
GGAPHHHHHH

TC265 (G3A H1L4 K13D HER2 LH DOTA SADA) full amino acid sequence (N to C terminal)
[*G3A VL4*-linker-*G3A VH1*-linker- *HER2 VL*-linker-*HER2 VH*-linker-huC825-spacer-P53] (SEQ ID NO: 42)

*EVQLVESGGGLVDPGGSLRLSCAASGFAFSTYDMSWVRQAPGKGLEWVSTISSGGSYTYYADSVKGRF*
*TISRDNAKNSLYLQMNSLRAEDTAVYYCAPTTVVPFAYWGQGTLVTVSA*GGGGSGGGGSGGGGSGG
GGSGGGGSGGGGS*DIQMTQSPSSLSASVGDRVTITCKASQNVRTVVAWYQQKPGKAPKTLIYLASNR*
*HTGVPSRFSGSGSGTEFTLTISNLQPEDFATYYCLQHWSYPLTFGSGTKLEVKR*GGGGSGGGGSGGG
GSGGGGS*DIQMTQSPSSLSASVGDRVTITCRASQDVNTAVAWYQQKPGKAPKLLIYSASFLYSGVPSRF*
*SGSRSGTDFTLTISSLQPEDFATYYCQQHYTTPPTFGQGTKVEIKR*GGGGSGGGGSGGGGSGGGGS
GGGGSGGGGS*EVQLVESGGGLVQPGGSLRLSCAASGFNIKDTYIHWVRQAPGKGLEWVARIYPTNG*
*YTRYADSVKGRFTISADTSKNTAYLQMNSLRAEDTAVYYCSRWGGDGFYAMDYWGQGTLVTVSS*GGG
GSGGGGSGGGGSGGGGS*HVQLVESGGGLVQPGGSLRLSCAASGFSLTDYGVHWVRQAPGKGLEW*
*LGVIWSGGGTAYNTALISRFTISRDNSKNTLYLQMNSLRAEDTAVYYCARRGSYPYNYFDAWGCGTLVTV*
*SS*GGGGSGGGGSGGGGSGGGGSGGGGSGGGGS*QAVVTQEPSLTVSPGGTVTLTCGSSTGAVTAS*
*NYANWVQQKPGQCPRGLIGGHNNRPPGVPARFSGSLLGGKAALTLLGAQPEDEAEYYCALWYSDHW*
*VIGGGTKLTVLG*TPLGDTTHTSGKPLDGEYFTLQIRGRERFEMFRELNEALELKDAQAGKEPGGS
GGAPHHHHHH

FIG. 24 (Cont.)

TC266 (G3A H1L4 K13D K74A HER2 LH DOTA SADA) full amino acid sequence (N to C terminal) [*G3A VL4*-linker-*G3A VH1*-linker- *HER2 VL*-linker-*HER2 VH*-linker-huC825-spacer-P53] (SEQ ID NO: 43)

*EVQLVESGGGLVDPGGSLRLSCAASGFAFSTYDMSWVRQAPGKGLEWVSTISSGGSYTYYADSVKGRFTISRDNAANSLYLQMNSLRAEDTAVYYCAPTTVVPFAYWGQGTLVTVSA*GGGGSGGGGSGGGGSGGGGSGGGGSGGGGS*DIQMTQSPSSLSASVGDRVTITCKASQNVRTVVAWYQQKPGKAPKTLIYLASNRHTGVPSRFSGSGSGTEFTLTISNLQPEDFATYYCLQHWSYPLTFGSGTKLEVKR*GGGGSGGGGSGGGGSGGGGS*DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKR*GGGGSGGGGSGGGGSGGGGSGGGGSGGGGS*EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSS*GGGGSGGGGSGGGGSGGGGS*HVQLVESGGGLVQPGGSLRLSCAASGFSLTDYGVHWVRQAPGKGLEWLGVIWSGGGTAYNTALISRFTISRDNSKNTLYLQMNSLRAEDTAVYYCARRGSYPYNYFDAWGCGTLVTVSS*GGGGSGGGGSGGGGSGGGGSGGGGSGGGGS*QAVVTQEPSLTVSPGGTVTLTCGSSTGAVTASNYANWVQQKPGQCPRGLIGGHNNRPPGVPARFSGSLLGGKAALTLLGAQPEDEAEYYCALWYSDHWVIGGGTKLTVLG*TPLGDTTHTSGKPLDGEYFTLQIRGRERFEMFRELNEALELKDAQAGKEPGGSGGAPHHHHHH

TC267 (G3A H1L4 K42Q K13D K74A HER2 LH DOTA SADA) full amino acid sequence (N to C terminal) [*G3A VL4*-linker-*G3A VH1*-linker- *HER2 VL*-linker-*HER2 VH*-linker-huC825-spacer-P53] (SEQ ID NO: 44)

*EVQLVESGGGLVDPGGSLRLSCAASGFAFSTYDMSWVRQAPGKGLEWVSTISSGGSYTYYADSVKGRFTISRDNAANSLYLQMNSLRAEDTAVYYCAPTTVVPFAYWGQGTLVTVSA*GGGGSGGGGSGGGGSGGGGSGGGGSGGGGS*DIQMTQSPSSLSASVGDRVTITCKASQNVRTVVAWYQQKPGQAPKTLIYLASNRHTGVPSRFSGSGSGTEFTLTISNLQPEDFATYYCLQHWSYPLTFGSGTKLEVKR*GGGGSGGGGSGGGGSGGGGS*DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKR*GGGGSGGGGSGGGGSGGGGSGGGGSGGGGS*EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSS*GGGGSGGGGSGGGGSGGGGS*HVQLVESGGGLVQPGGSLRLSCAASGFSLTDYGVHWVRQAPGKGLEWLGVIWSGGGTAYNTALISRFTISRDNSKNTLYLQMNSLRAEDTAVYYCARRGSYPYNYFDAWGCGTLVTVSS*GGGGSGGGGSGGGGSGGGGSGGGGSGGGGS*QAVVTQEPSLTVSPGGTVTLTCGSSTGAVTASNYANWVQQKPGQCPRGLIGGHNNRPPGVPARFSGSLLGGKAALTLLGAQPEDEAEYYCALWYSDHWVIGGGTKLTVLG*TPLGDTTHTSGKPLDGEYFTLQIRGRERFEMFRELNEALELKDAQAGKEPGGSGGAPHHHHHH

FIG. 25

TC268 (G3A H1L4 HER2 LH OKT3 SADA) full amino acid sequence (N to C terminal) [*G3A VH1*-linker-*G3A VL4*-linker- *HER2 VL*-linker-*HER2 VH*-linker-OKT3-spacer-P53] (SEQ ID NO: 45)

*EVQLVESGGGLVKPGGSLRLSCAASGFAFSTYDMSWVRQAPGKGLEWVSTISSGGSYTYYADSVKGRFT*
*ISRDNAKNSLYLQMNSLRAEDTAVYYCAPTTVVPFAYWGQGTLVTVSA*GGGGSGGGGSGGGGSGG
GGSGGGGSGGGGS*DIQMTQSPSSLSASVGDRVTITCKASQNVRTVVAWYQQKPGKAPKTLIYLASNR*
*HTGVPSRFSGSGSGTEFTLTISNLQPEDFATYYCLQHWSYPLTFGSGTKLEVKR*GGGGSGGGGSGGG
GSGGGGS*DIQMTQSPSSLSASVGDRVTITCRASQDVNTAVAWYQQKPGKAPKLLIYSASFLYSGVPSRF*
*SGSRSGTDFTLTISSLQPEDFATYYCQQHYTTPPTFGQGTKVEIKR*GGGGSGGGGSGGGGSGGGGS
GGGGSGGGGS*EVQLVESGGGLVQPGGSLRLSCAASGFNIKDTYIHWVRQAPGKGLEWVARIYPTNG*
*YTRYADSVKGRFTISADTSKNTAYLQMNSLRAEDTAVYYCSRWGGDGFYAMDYWGQGTLVTVSS*GGG
GSGGGGSGGGGSGGGGS*QVQLVQSGGGVVQPGRSLRLSCKASGYTFTRYTMHWVRQAPGKCLEW*
*IGYINPSRGYTNYNQKFKDRFTISRDNSKNTAFLQMDSLRPEDTGVYFCARYYDDHYSLDYWGQGTPV*
*TVSS*GGGGSGGGGSGGGGSGGGGSGGGGSGGGGS*DIQMTQSPSSLSASVGDRVTITCSASSSVSY*
*MNWYQQTPGKAPKRWIYDTSKLASGVPSRFSGSGSGTDYTFTISSLQPEDIATYYCQQWSSNPFTFGCG*
*TKLQITR*TPLGDTTHTSGKPLDGEYFTLQIRGRERFEMFRELNEALELKDAQAGKEPGGSGGAPH
HHHHH

TC269 (G3A H1L4 K13D OKT3 SADA) full amino acid sequence (N to C terminal) [*G3A VH1*-linker-*G3A VL4*-linker- *HER2 VL*-linker-*HER2 VH*-linker-OKT3-spacer-P53] (SEQ ID NO: 46)

*EVQLVESGGGLVDPGGSLRLSCAASGFAFSTYDMSWVRQAPGKGLEWVSTISSGGSYTYYADSVKGRF*
*TISRDNAKNSLYLQMNSLRAEDTAVYYCAPTTVVPFAYWGQGTLVTVSA*GGGGSGGGGSGGGGSGG
GGSGGGGSGGGGS*DIQMTQSPSSLSASVGDRVTITCKASQNVRTVVAWYQQKPGKAPKTLIYLASNR*
*HTGVPSRFSGSGSGTEFTLTISNLQPEDFATYYCLQHWSYPLTFGSGTKLEVKR*GGGGSGGGGSGGG
GSGGGGS*DIQMTQSPSSLSASVGDRVTITCRASQDVNTAVAWYQQKPGKAPKLLIYSASFLYSGVPSRF*
*SGSRSGTDFTLTISSLQPEDFATYYCQQHYTTPPTFGQGTKVEIKR*GGGGSGGGGSGGGGSGGGGS
GGGGSGGGGS*EVQLVESGGGLVQPGGSLRLSCAASGFNIKDTYIHWVRQAPGKGLEWVARIYPTNG*
*YTRYADSVKGRFTISADTSKNTAYLQMNSLRAEDTAVYYCSRWGGDGFYAMDYWGQGTLVTVSS*GGG
GSGGGGSGGGGSGGGGS*QVQLVQSGGGVVQPGRSLRLSCKASGYTFTRYTMHWVRQAPGKCLEW*
*IGYINPSRGYTNYNQKFKDRFTISRDNSKNTAFLQMDSLRPEDTGVYFCARYYDDHYSLDYWGQGTPV*
*TVSS*GGGGSGGGGSGGGGSGGGGSGGGGSGGGGS*DIQMTQSPSSLSASVGDRVTITCSASSSVSY*
*MNWYQQTPGKAPKRWIYDTSKLASGVPSRFSGSGSGTDYTFTISSLQPEDIATYYCQQWSSNPFTFGCG*
*TKLQITR*TPLGDTTHTSGKPLDGEYFTLQIRGRERFEMFRELNEALELKDAQAGKEPGGSGGAPH
HHHHH

FIG. 25 (Cont.)

TC270 (G3A H1L4 K13D K74A HER2 LH OKT3 SADA) full amino acid sequence (N to C terminal) [*G3A VH1*-linker-*G3A VL4*-linker- *HER2 VL*-linker-*HER2 VH*-linker-OKT3-spacer-P53] (SEQ ID NO: 47)

EVQLVESGGGLVDPGGSLRLSCAASGFAFSTYDMSWVRQAPGKGLEWVSTISSGGSYTYYADSVKGRF
TISRDNAANSLYLQMNSLRAEDTAVYYCAPTTVVPFAYWGQGTLVTVSAGGGGSGGGGSGGGGSGG
GGSGGGGSGGGGSDIQMTQSPSSLSASVGDRVTITCKASQNVRTVVAWYQQKPGKAPKTLIYLASNR
HTGVPSRFSGSGSGTEFTLTISNLQPEDFATYYCLQHWSYPLTFGSGTKLEVKRGGGGSGGGGSGGG
GSGGGGSQVQLVQSGGGVVQPGRSLRLSCKASGYTFTRYTMHWVRQAPGKCLEWIGYINPSRGYTNY
NQKFKDRFTISRDNSKNTAFLQMDSLRPEDTGVYFCARYYDDHYSLDYWGQGTPVTVSSGGGGSGG
GGSGGGGSGGGGSGGGGSGGGGSDIQMTQSPSSLSASVGDRVTITCSASSSVSYMNWYQQTPGKA
PKRWIYDTSKLASGVPSRFSGSGSGTDYTFTISSLQPEDIATYYCQQWSSNPFTFGCGTKLQITRTPLGD
TTHTSGKPLDGEYFTLQIRGRERFEMFRELNEALELKDAQAGKEPGGSGGAPHHHHHH

TC271 (G3A H1L4 K13D K42Q K74A HER2 LH OKT3 SADA) full amino acid sequence (N to C terminal) [*G3A VH1*-linker-*G3A VL4*-linker- *HER2 VL*-linker-*HER2 VH*-linker-OKT3-spacer-P53] (SEQ ID NO: 48)

EVQLVESGGGLVDPGGSLRLSCAASGFAFSTYDMSWVRQAPGKGLEWVSTISSGGSYTYYADSVKGRF
TISRDNAANSLYLQMNSLRAEDTAVYYCAPTTVVPFAYWGQGTLVTVSAGGGGSGGGGSGGGGSGG
GGSGGGGSGGGGSDIQMTQSPSSLSASVGDRVTITCKASQNVRTVVAWYQQKPGQAPKTLIYLASNR
HTGVPSRFSGSGSGTEFTLTISNLQPEDFATYYCLQHWSYPLTFGSGTKLEVKRGGGGSGGGGSGGG
GSGGGGSDIQMTQSPSSLSASVGDRVTITCRASQDVNTAVAWYQQKPGKAPKLLIYSASFLYSGVPSRF
SGSRSGTDFTLTISSLQPEDFATYYCQQHYTTPPTFGQGTKVEIKRGGGGSGGGGSGGGGSGGGGS
GGGGSGGGGSEVQLVESGGGLVQPGGSLRLSCAASGFNIKDTYIHWVRQAPGKGLEWVARIYPTNG
YTRYADSVKGRFTISADTSKNTAYLQMNSLRAEDTAVYYCSRWGGDGFYAMDYWGQGTLVTVSSGGG
GSGGGGSGGGGSGGGGSQVQLVQSGGGVVQPGRSLRLSCKASGYTFTRYTMHWVRQAPGKCLEW
IGYINPSRGYTNYNQKFKDRFTISRDNSKNTAFLQMDSLRPEDTGVYFCARYYDDHYSLDYWGQGTPV
TVSSGGGGSGGGGSGGGGSGGGGSGGGGSGGGGSDIQMTQSPSSLSASVGDRVTITCSASSSVSY
MNWYQQTPGKAPKRWIYDTSKLASGVPSRFSGSGSGTDYTFTISSLQPEDIATYYCQQWSSNPFTFGCG
TKLQITRTPLGDTTHTSGKPLDGEYFTLQIRGRERFEMFRELNEALELKDAQAGKEPGGSGGAPH
HHHHH

FIG. 25 (Cont.)

TC272 (G3A H1L4 HER2 LH OT3 H2L2 SADA) full amino acid sequence (N to C terminal) [*G3A VH1*-linker-*G3A VL4*-linker- *HER2 VL*-linker-*HER2 VH*-linker-OKT3-spacer-P53] (SEQ ID NO: 49)

*EVQLVESGGGLVKPGGSLRLSCAASGFAFSTYDMSWVRQAPGKGLEWVSTISSGGSYTYYADSVKGRFT*
*ISRDNAKNSLYLQMNSLRAEDTAVYYCAPTTVVPFAYWGQGTLVTVSA*GGGGSGGGGSGGGGSGG
GGSGGGGSGGGGS*DIQMTQSPSSLSASVGDRVTITCKASQNVRTVVAWYQQKPGKAPKTLIYLASNR*
*HTGVPSRFSGSGSGTEFTLTISNLQPEDFATYYCLQHWSYPLTFGSGTKLEVKR*GGGGSGGGGSGGG
GSGGGGS*DIQMTQSPSSLSASVGDRVTITCRASQDVNTAVAWYQQKPGKAPKLLIYSASFLYSGVPSRF*
*SGSRSGTDFTLTISSLQPEDFATYYCQQHYTTPPTFGQGTKVEIKR*GGGGSGGGGSGGGGSGGGGS
GGGGSGGGGS*EVQLVESGGGLVQPGGSLRLSCAASGFNIKDTYIHWVRQAPGKGLEWVARIYPTNG*
*YTRYADSVKGRFTISADTSKNTAYLQMNSLRAEDTAVYYCSRWGGDGFYAMDYWGQGTLVTVSS*GGG
GSGGGGSGGGGSGGGGS*QVQLQQSGAEVAKPGASVKVSCKASGYTFTRYTMHWVRQAPGQGLEW*
*MGYINPSRGYTNYNQKFKDRATLTRDKSISTAYMELSRLRSDDTAVYYCARYYDDHYSLDYWGQGTTLT*
*VSS*GGGGSGGGGSGGGGSGGGGSGGGGSGGGGS*DIQMTQSPSSLSASVGDRVTMTCSASSSVSY*
*MNWYQQKPGKAPKLLIYDTSKLASGVPSRFSGSGSGTDFTLTISSMQPEDFATYYCQQWSSNPFTFGS*
*GTKLEINR*TPLGDTTHTSGKPLDGEYFTLQIRGRERFEMFRELNEALELKDAQAGKEPGGSGGAP
HHHHHH

TC273 (G3A H1L4 K13D HER2 LH OT3 H2L2 SADA) full amino acid sequence (N to C terminal) [*G3A VH1*-linker-*G3A VL4*-linker- *HER2 VL*-linker-*HER2 VH*-linker-OKT3-spacer-P53] (SEQ ID NO: 50)

*EVQLVESGGGLVDPGGSLRLSCAASGFAFSTYDMSWVRQAPGKGLEWVSTISSGGSYTYYADSVKGRF*
*TISRDNAKNSLYLQMNSLRAEDTAVYYCAPTTVVPFAYWGQGTLVTVSA*GGGGSGGGGSGGGGSGG
GGSGGGGSGGGGS*DIQMTQSPSSLSASVGDRVTITCKASQNVRTVVAWYQQKPGKAPKTLIYLASNR*
*HTGVPSRFSGSGSGTEFTLTISNLQPEDFATYYCLQHWSYPLTFGSGTKLEVKR*GGGGSGGGGSGGG
GSGGGGS*DIQMTQSPSSLSASVGDRVTITCRASQDVNTAVAWYQQKPGKAPKLLIYSASFLYSGVPSRF*
*SGSRSGTDFTLTISSLQPEDFATYYCQQHYTTPPTFGQGTKVEIKR*GGGGSGGGGSGGGGSGGGGS
GGGGSGGGGS*EVQLVESGGGLVQPGGSLRLSCAASGFNIKDTYIHWVRQAPGKGLEWVARIYPTNG*
*YTRYADSVKGRFTISADTSKNTAYLQMNSLRAEDTAVYYCSRWGGDGFYAMDYWGQGTLVTVSS*GGG
GSGGGGSGGGGSGGGGS*QVQLQQSGAEVAKPGASVKVSCKASGYTFTRYTMHWVRQAPGQGLEW*
*MGYINPSRGYTNYNQKFKDRATLTRDKSISTAYMELSRLRSDDTAVYYCARYYDDHYSLDYWGQGTTLT*
*VSS*GGGGSGGGGSGGGGSGGGGSGGGGSGGGGS*DIQMTQSPSSLSASVGDRVTMTCSASSSVSY*
*MNWYQQKPGKAPKLLIYDTSKLASGVPSRFSGSGSGTDFTLTISSMQPEDFATYYCQQWSSNPFTFGS*
*GTKLEINR*TPLGDTTHTSGKPLDGEYFTLQIRGRERFEMFRELNEALELKDAQAGKEPGGSGGAP
HHHHHH

FIG. 25 (Cont.)

TC274 (G3A H1L4 K13D K74A HER2 LH OT3 H2L2 SADA) full amino acid sequence (N to C terminal) [*G3A VH1*-linker-*G3A VL4*-linker- *HER2 VL*-linker-*HER2 VH*-linker-OKT3-spacer-P53] (SEQ ID NO: 51)

*EVQLVESGGGLVDPGGSLRLSCAASGFAFSTYDMSWVRQAPGKGLEWVSTISSGGSYTYYADSVKGRFTISRDNAANSLYLQMNSLRAEDTAVYYCAPTTVVPFAYWGQGTLVTVSA*GGGGSGGGGSGGGGSGGGGSGGGGSGGGGS*DIQMTQSPSSLSASVGDRVTITCKASQNVRTVVAWYQQKPGKAPKTLIYLASNRHTGVPSRFSGSGSGTEFTLTISNLQPEDFATYYCLQHWSYPLTFGSGTKLEVKR*GGGGSGGGGSGGGGSGGGGS*DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKR*GGGGSGGGGSGGGGSGGGGSGGGGSGGGGS*EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSS*GGGGSGGGGSGGGGSGGGGS*QVQLQQSGAEVAKPGASVKVSCKASGYTFTRYTMHWVRQAPGQGLEWMGYINPSRGYTNYNQKFKDRATLTRDKSISTAYMELSRLRSDDTAVYYCARYYDDHYSLDYWGQGTTLTVSS*GGGGSGGGGSGGGGSGGGGSGGGGSGGGGS*DIQMTQSPSSLSASVGDRVTMTCSASSSVSYMNWYQQKPGKAPKLLIYDTSKLASGVPSRFSGSGSGTDFTLTISSMQPEDFATYYCQQWSSNPFTFGSGTKLEINR*TPLGDTTHTSGKPLDGEYFTLQIRGRERFEMFRELNEALELKDAQAGKEPGGSGGAPHHHHHH

TC275 (G3A H1L4 K13D K42Q K74A HER2 LH OT3 H2L2 SADA) full amino acid sequence (N to C terminal) [*G3A VH1*-linker-*G3A VL4*-linker- *HER2 VL*-linker-*HER2 VH*-linker-OKT3-spacer-P53] (SEQ ID NO: 52)

*EVQLVESGGGLVDPGGSLRLSCAASGFAFSTYDMSWVRQAPGKGLEWVSTISSGGSYTYYADSVKGRFTISRDNAANSLYLQMNSLRAEDTAVYYCAPTTVVPFAYWGQGTLVTVSA*GGGGSGGGGSGGGGSGGGGSGGGGSGGGGS*DIQMTQSPSSLSASVGDRVTITCKASQNVRTVVAWYQQKPGQAPKTLIYLASNRHTGVPSRFSGSGSGTEFTLTISNLQPEDFATYYCLQHWSYPLTFGSGTKLEVKR*GGGGSGGGGSGGGGSGGGGS*DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKR*GGGGSGGGGSGGGGSGGGGSGGGGSGGGGS*EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSS*GGGGSGGGGSGGGGSGGGGS*QVQLQQSGAEVAKPGASVKVSCKASGYTFTRYTMHWVRQAPGQGLEWMGYINPSRGYTNYNQKFKDRATLTRDKSISTAYMELSRLRSDDTAVYYCARYYDDHYSLDYWGQGTTLTVSS*GGGGSGGGGSGGGGSGGGGSGGGGSGGGGS*DIQMTQSPSSLSASVGDRVTMTCSASSSVSYMNWYQQKPGKAPKLLIYDTSKLASGVPSRFSGSGSGTDFTLTISSMQPEDFATYYCQQWSSNPFTFGSGTKLEINR*TPLGDTTHTSGKPLDGEYFTLQIRGRERFEMFRELNEALELKDAQAGKEPGGSGGAPHHHHHH

FIG. 25 (Cont.)

TC276 (G3A H1L4 HER2 LH OT3 H2L5 SADA) full amino acid sequence (N to C terminal) [*G3A VH1*-linker-*G3A VL4*-linker- *HER2 VL*-linker-*HER2 VH*-linker-OKT3-spacer-P53] (SEQ ID NO: 53)

*EVQLVESGGGLVKPGGSLRLSCAASGFAFSTYDMSWVRQAPGKGLEWVSTISSGGSYTYYADSVKGRFTISRDNAKNSLYLQMNSLRAEDTAVYYCAPTTVVPFAYWGQGTLVTVSA*GGGGSGGGGSGGGGSGGGGSGGGGSGGGGS*DIQMTQSPSSLSASVGDRVTITCKASQNVRTVVAWYQQKPGKAPKTLIYLASNRHTGVPSRFSGSGSGTEFTLTISNLQPEDFATYYCLQHWSYPLTFGSGTKLEVKR*GGGGSGGGGSGGGGSGGGGS*DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKR*GGGGSGGGGSGGGGSGGGGSGGGGSGGGGS*EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSS*GGGGSGGGGSGGGGSGGGGS*QVQLQQSGAEVAKPGASVKVSCKASGYTFTRYTMHWVRQAPGQGLEWMGYINPSRGYTNYNQKFKDRATLTRDKSISTAYMELSRLRSDDTAVYYCARYYDDHYSLDYWGQGTTLTVSS*GGGGSGGGGSGGGGSGGGGSGGGGSGGGGS*DIQMTQSPSSLSASVGDRVTITCSASSSVSYMNWYQQKPGKAPKRWIYDTSKLASGVPSRFSGSGSGTDFTLTISSLQPEDFATYYCQQWSSNPFTFGSGTKLEINR*TPLGDTTHTSGKPLDGEYFTLQIRGRERFEMFRELNEALELKDAQAGKEPGGSGGAPHHHHHH

TC277 (G3A H1L4 K13D HER2 LH OT3 H2L5 SADA) full amino acid sequence (N to C terminal) [*G3A VH1*-linker-*G3A VL4*-linker- *HER2 VL*-linker-*HER2 VH*-linker-OKT3-spacer-P53] (SEQ ID NO: 54)

*EVQLVESGGGLVDPGGSLRLSCAASGFAFSTYDMSWVRQAPGKGLEWVSTISSGGSYTYYADSVKGRFTISRDNAKNSLYLQMNSLRAEDTAVYYCAPTTVVPFAYWGQGTLVTVSA*GGGGSGGGGSGGGGSGGGGSGGGGSGGGGS*DIQMTQSPSSLSASVGDRVTITCKASQNVRTVVAWYQQKPGKAPKTLIYLASNRHTGVPSRFSGSGSGTEFTLTISNLQPEDFATYYCLQHWSYPLTFGSGTKLEVKR*GGGGSGGGGSGGGGSGGGGS*DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKR*GGGGSGGGGSGGGGSGGGGSGGGGSGGGGS*EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSS*GGGGSGGGGSGGGGSGGGGS*QVQLQQSGAEVAKPGASVKVSCKASGYTFTRYTMHWVRQAPGQGLEWMGYINPSRGYTNYNQKFKDRATLTRDKSISTAYMELSRLRSDDTAVYYCARYYDDHYSLDYWGQGTTLTVSS*GGGGSGGGGSGGGGSGGGGSGGGGSGGGGS*DIQMTQSPSSLSASVGDRVTITCSASSSVSYMNWYQQKPGKAPKRWIYDTSKLASGVPSRFSGSGSGTDFTLTISSLQPEDFATYYCQQWSSNPFTFGSGTKLEINR*TPLGDTTHTSGKPLDGEYFTLQIRGRERFEMFRELNEALELKDAQAGKEPGGSGGAPHHHHHH

FIG. 25 (Cont.)

TC278 (G3A H1L4 K13D K74A HER2 LH OT3 H2L5 SADA) full amino acid sequence (N to C terminal) [*G3A VH1*-linker-*G3A VL4*-linker- *HER2 VL*-linker-*HER2 VH*-linker-OKT3-spacer-P53] (SEQ ID NO: 55)

EVQLVESGGGLVDPGGSLRLSCAASGFAFSTYDMSWVRQAPGKGLEWVSTISSGGSYTYYADSVKGRF
TISRDNAANSLYLQMNSLRAEDTAVYYCAPTTVVPFAYWGQGTLVTVSAGGGGSGGGGSGGGGSGG
GGSGGGGSGGGGSDIQMTQSPSSLSASVGDRVTITCKASQNVRTVVAWYQQKPGKAPKTLIYLASNR
HTGVPSRFSGSGSGTEFTLTISNLQPEDFATYYCLQHWSYPLTFGSGTKLEVKRGGGGSGGGGSGGG
GSGGGGSDIQMTQSPSSLSASVGDRVTITCRASQDVNTAVAWYQQKPGKAPKLLIYSASFLYSGVPSRF
SGSRSGTDFTLTISSLQPEDFATYYCQQHYTTPPTFGQGTKVEIKRGGGGSGGGGSGGGGSGGGGS
GGGGSGGGGSEVQLVESGGGLVQPGGSLRLSCAASGFNIKDTYIHWVRQAPGKGLEWVARIYPTNG
YTRYADSVKGRFTISADTSKNTAYLQMNSLRAEDTAVYYCSRWGGDGFYAMDYWGQGTLVTVSSGGG
GSGGGGSGGGGSGGGGSQVQLQQSGAEVAKPGASVKVSCKASGYTFTRYTMHWVRQAPGQGLEW
MGYINPSRGYTNYNQKFKDRATLTRDKSISTAYMELSRLRSDDTAVYYCARYYDDHYSLDYWGQGTTLT
VSSGGGGSGGGGSGGGGSGGGGSGGGGSGGGGSDIQMTQSPSSLSASVGDRVTITCSASSSVSYM
NWYQQKPGKAPKRWIYDTSKLASGVPSRFSGSGSGTDFTLTISSLQPEDFATYYCQQWSSNPFTFGSGT
KLEINRTPLGDTTHTSGKPLDGEYFTLQIRGRERFEMFRELNEALELKDAQAGKEPGGSGGAPH
HHHHH

TC279 (G3A H1L4 K13D K42Q K74A HER2 LH OT3 H2L5 SADA) full amino acid sequence (N to C terminal) [*G3A VH1*-linker-*G3A VL4*-linker-*HER2 VL*-linker-*HER2 VH*-linker-OKT3-spacer-P53] (SEQ ID NO: 56)

EVQLVESGGGLVDPGGSLRLSCAASGFAFSTYDMSWVRQAPGKGLEWVSTISSGGSYTYYADSVKGRF
TISRDNAANSLYLQMNSLRAEDTAVYYCAPTTVVPFAYWGQGTLVTVSAGGGGSGGGGSGGGGSGG
GGSGGGGSGGGGSDIQMTQSPSSLSASVGDRVTITCKASQNVRTVVAWYQQKPGQAPKTLIYLASNR
HTGVPSRFSGSGSGTEFTLTISNLQPEDFATYYCLQHWSYPLTFGSGTKLEVKRGGGGSGGGGSGGG
GSGGGGSDIQMTQSPSSLSASVGDRVTITCRASQDVNTAVAWYQQKPGKAPKLLIYSASFLYSGVPSRF
SGSRSGTDFTLTISSLQPEDFATYYCQQHYTTPPTFGQGTKVEIKRGGGGSGGGGSGGGGSGGGGS
GGGGSGGGGSEVQLVESGGGLVQPGGSLRLSCAASGFNIKDTYIHWVRQAPGKGLEWVARIYPTNG
YTRYADSVKGRFTISADTSKNTAYLQMNSLRAEDTAVYYCSRWGGDGFYAMDYWGQGTLVTVSSGGG
GSGGGGSGGGGSGGGGSQVQLQQSGAEVAKPGASVKVSCKASGYTFTRYTMHWVRQAPGQGLEW
MGYINPSRGYTNYNQKFKDRATLTRDKSISTAYMELSRLRSDDTAVYYCARYYDDHYSLDYWGQGTTLT
VSSGGGGSGGGGSGGGGSGGGGSGGGGSGGGGSDIQMTQSPSSLSASVGDRVTITCSASSSVSYM
NWYQQKPGKAPKRWIYDTSKLASGVPSRFSGSGSGTDFTLTISSLQPEDFATYYCQQWSSNPFTFGSGT
KLEINRTPLGDTTHTSGKPLDGEYFTLQIRGRERFEMFRELNEALELKDAQAGKEPGGSGGAPH
HHHHH

FIG. 26

TC280 (G3A H1L4 hu8H9 LH huC825 HL SADA
full amino acid sequence (N to C terminal) [*G3A VH1*-linker-*G3A VL4*-linker-*hu8H9 VL*-linker-*hu8H9 VH*-linker-huC825-spacer-P53] (SEQ ID NO: 57)

EVQLVESGGGLVKPGGSLRLSCAASGFAFSTYDMSWVRQAPGKGLEWVSTISSGGSYTYYADSVKGRFT
ISRDNAKNSLYLQMNSLRAEDTAVYYCAPTTVVPFAYWGQGTLVTVSAGGGGSGGGGSGGGGSGG
GGSGGGGSGGGGSDIQMTQSPSSLSASVGDRVTITCKASQNVRTVVAWYQQKPGKAPKTLIYLASNR
HTGVPSRFSGSGSGTEFTLTISNLQPEDFATYYCLQHWSYPLTFGSGTKLEVKRGGGGSGGGGSGGG
GSGGGGSEIVMTQSPATLSVSPGERVTLSCRASQSISDYLYWYQQKSHESPRLLIKYASQSISGIPARFSG
SGSGSEFTLTINSVEPEDVGVYYCQNGHSFPLTFGQGTKLELKRGGGGSGGGGSGGGGSGGGGSG
GGGSGGGGSQVQLVQSGAEVVKPGASVKLSCKTSGYTFTNYDINWVRQRPGQGLEWIGWIFPGDDS
TQYNEKFKGKATLTTDTSTSTAYMELSSLRSEDTAVYFCARQTTGTWFAYWGQGTLVTVSSGGGGSGG
GGSGGGGSGGGGSHVQLVESGGGLVQPGGSLRLSCAASGFSLTDYGVHWVRQAPGKGLEWLGVIW
SGGGTAYNTALISRFTISRDNSKNTLYLQMNSLRAEDTAVYYCARRGSYPYNYFDAWGCGTLVTVSSGG
GGSGGGGSGGGGSGGGGSGGGGSGGGGSQAVVTQEPSLTVSPGGTVTLTCGSSTGAVTASNYAN
WVQQKPGQCPRGLIGGHNNRPPGVPARFSGSLLGGKAALTLLGAQPEDEAEYYCALWYSDHWVIGG
GTKLTVLGTPLGDTTHTSGKPLDGEYFTLQIRGRERFEMFRELNEALELKDAQAGKEPGGSGGA
PHHHHHH

FIG. 27

TC281 (G3A H1L4 hu8H9 LH huOKT3 HL SADA
full amino acid sequence (N to C terminal) [*G3A VH1*-linker-*G3A VL4*-linker-*hu8H9 VL*-linker-*hu8H9 VH*-linker-huOKT3-spacer-P53] (SEQ ID NO: 58)

EVQLVESGGGLVKPGGSLRLSCAASGFAFSTYDMSWVRQAPGKGLEWVSTISSGGSYTYYADSVKGRFT
ISRDNAKNSLYLQMNSLRAEDTAVYYCAPTTVVPFAYWGQGTLVTVSAGGGGSGGGGSGGGGSGG
GGSGGGGSGGGGSDIQMTQSPSSLSASVGDRVTITCKASQNVRTVVAWYQQKPGKAPKTLIYLASNR
HTGVPSRFSGSGSGTEFTLTISNLQPEDFATYYCLQHWSYPLTFGSGTKLEVKRGGGGSGGGGSGGG
GSGGGGSEIVMTQSPATLSVSPGERVTLSCRASQSISDYLYWYQQKSHESPRLLIKYASQSISGIPARFSG
SGSGSEFTLTINSVEPEDVGVYYCQNGHSFPLTFGQGTKLELKRGGGGSGGGGSGGGGSGGGGSG
GGGSGGGGSQVQLVQSGAEVVKPGASVKLSCKTSGYTFTNYDINWVRQRPGQGLEWIGWIFPGDDS
TQYNEKFKGKATLTTDTSTSTAYMELSSLRSEDTAVYFCARQTTGTWFAYWGQGTLVTVSSGGGGSGG
GGSGGGGSGGGGSQVQLQQSGAEVAKPGASVKVSCKASGYTFTRYTMHWVRQAPGQGLEWMGYI
NPSRGYTNYNQKFKDRATLTRDKSISTAYMELSRLRSDDTAVYYCARYYDDHYSLDYWGQGTTLTVSSG
GGGSGGGGSGGGGSGGGGSGGGGSGGGGSDIQMTQSPSSLSASVGDRVTITCSASSSVSYMNWY
QQKPGKAPKRWIYDTSKLASGVPSRFSGSGSGTDFTLTISSLQPEDFATYYCQQWSSNPFTFGSGTKLEI
NRTPLGDTTHTSGKPLDGEYFTLQIRGRERFEMFRELNEALELKDAQAGKEPGGSGGAPHHHH
HH

FIG. 28

BC369 (G3A H1L4 huOKT3) light chain full amino acid sequence (N to C terminal) [*G3A L4*-CL-linker-huOKT3 scFv] (SEQ ID NO: 59)

*DIQMTQSPSSLSASVGDRVTITCKASQNVRTVVAWYQQKPGKAPKTLIYLASNRHTGVPSRFSGSGSGTE FTLTISNLQPEDFATYYCLQHWSYPLTFGSGTKLEVK*RTVAAPSVFIFPPSDEQLKSGTASVVCLLNN FYPREAKVQWKVDNALQSGNSQEkSVTEQDSKDSTYSLSSTLTLSKADYEKHKVYACEVTHQG LSSPVTKSFNRGECTSGGGGSGGGGSGGGGS*QVQLVQSGGGVVQPGRSLRLSCKASGYTFTRYTM HWVRQAPGKCLEWIGYINPSRGYTNYNQKFKDRFTISRDNSKNTAFLQMDSLRPEDTGVYFCARYYDD HYSLDYWGQGTPVTVSS*GGGGSGGGGSGGGGSGGGGSGGGGSGGGGS*DIQMTQSPSSLSASVG DRVTITCSASSSVSYMNWYQQTPGKAPKRWIYDTSKLASGVPSRFSGSGSGTDYTFTISSLQPEDIATYYC QQWSSNPFTFGCGTKLQITR*

BC369 (G3A H1L4 huOKT3) heavy chain full amino acid sequence (N to C terminal) [*G3A* VH1-CH1-CH2-CH3] (SEQ ID NO: 60)

*EVQLVESGGGLVKPGGSLRLSCAASGFAFSTYDMSWVRQAPGKGLEWVSTISSGGSYTYYADSVKGRFT ISRDNAKNSLYLQMNSLRAEDTAVYYCAPTTVVPFAYWGQGTLVTVSA*ASTKGPSVFPLAPSSKSTSGG TAALGCLVKDYFPEPVTVSWNSGALTSGVHTFPAVLQSSGLYSLSSVVTVPSSSLGTQTYICNVN HKPSNTKVDKRVEPKSCDKTHTCPPCPAPELLGGPSVFLFPPKPKDTLMISRTPEVTCVVVDVSH EDPEVKFNWYVDGVEVHNAKTKPREEQYASTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSPGK

FIG. 28 (Cont.)

BC373 (G3A H1L4 huOT3 H2L2) light chain full amino acid sequence (N to C terminal) [*G3A L4*-CL-linker-huOT3 scFv] (SEQ ID NO: 61)

*DIQMTQSPSSLSASVGDRVTITCKASQNVRTVVAWYQQKPGKAPKTLIYLASNRHTGVPSRFSGSGSGTEFTLTISNLQPEDFATYYCLQHWSYPLTFGSGTKLEVK*RTVAAPSVFIFPPSDEQLKSGTASVVCLLNNFYPREAKVQWKVDNALQSGNSQEkSVTEQDSKDSTYSLSSTLTLSKADYEKHKVYACEVTHQGLSSPVTKSFNRGECTSGGGGSGGGGSGGGGS*QVQLQQSGAEVAKPGASVKVSCKASGYTFTRYTMHWVRQAPGQGLEWMGYINPSRGYTNYNQKFKDRATLTRDKSISTAYMELSRLRSDDTAVYYCARYYDDHYSLDYWGQGTTLTVSS*GGGGSGGGGSGGGGSGGGGSGGGGSGGGGS*DIQMTQSPSSLSASVGDRVTMTCSASSSVSYMNWYQQKPGKAPKLLIYDTSKLASGVPSRFSGSGSGTDFTLTISSMQPEDFATYYCQQWSSNPFTFGSGTKLEINR*

BC373 (G3A H1L4 huOT3 H2L2) heavy chain full amino acid sequence (N to C terminal) [*G3A* VH1-CH1-CH2-CH3] (SEQ ID NO: 62)

*EVQLVESGGGLVKPGGSLRLSCAASGFAFSTYDMSWVRQAPGKGLEWVSTISSGGSYTYYADSVKGRFTISRDNAKNSLYLQMNSLRAEDTAVYYCAPTTVVPFAYWGQGTLVTVSA*ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

BC377 (G3A H1L4 huOT3 H2L4) light chain full amino acid sequence (N to C terminal) [*G3A L4*-CL-linker-huOT3 scFv] (SEQ ID NO: 63)

*DIQMTQSPSSLSASVGDRVTITCKASQNVRTVVAWYQQKPGKAPKTLIYLASNRHTGVPSRFSGSGSGTEFTLTISNLQPEDFATYYCLQHWSYPLTFGSGTKLEVK*RTVAAPSVFIFPPSDEQLKSGTASVVCLLNNFYPREAKVQWKVDNALQSGNSQEkSVTEQDSKDSTYSLSSTLTLSKADYEKHKVYACEVTHQGLSSPVTKSFNRGECTSGGGGSGGGGSGGGGS*QVQLQQSGAEVAKPGASVKVSCKASGYTFTRYTMHWVRQAPGQGLEWMGYINPSRGYTNYNQKFKDRATLTRDKSISTAYMELSRLRSDDTAVYYCARYYDDHYSLDYWGQGTTLTVSS*GGGGSGGGGSGGGGSGGGGSGGGGSGGGGS*DIQMTQSPSSLSASVGDRVTITCSASSSVSYMNWYQQKPGKAPKRWIYDTSKLASGVPSRFSGSGSGTDFTLTISSLQPEDFATYYCQQWSSNPFTFGSGTKLEINR*

BC377 (G3A H1L4 huOT3 H2L4) heavy chain full amino acid sequence (N to C terminal) [*G3A* VH1-CH1-CH2-CH3] (SEQ ID NO: 64)

*EVQLVESGGGLVKPGGSLRLSCAASGFAFSTYDMSWVRQAPGKGLEWVSTISSGGSYTYYADSVKGRFTISRDNAKNSLYLQMNSLRAEDTAVYYCAPTTVVPFAYWGQGTLVTVSA*ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

(G3A H1L4) light chain full amino acid sequence (N to C terminal) [*G3A L4*-CL-linker-huC825 scFv] (First polypeptide chain, SEQ ID NO: 65)
*DIQMTQSPSSLSASVGDRVTITCKASQNVRTVVAWYQQKPGKAPKTLIYLASNRHTGVPSRFSGSGSGTE*
*FTLTISNLQPEDFATYYCLQHWSYPLTFGSGTKLEVK*RTVAAPSVFIFPPSDEQLKSGTASVVCLLNN
FYPREAKVQWKVDNALQSGNSQEkSVTEQDSKDSTYSLSSTLTLSKADYEKHKVYACEVTHQG
LSSPVTKSFNRGECTSGGGGSGGGGSGGGGS*HVQLVESGGGLVQPGGSLRLSCAASGFSLTDYGV*
*HWVRQAPGKGLEWLGVIWSGGGTAYNTALISRFTISRDNSKNTLYLQMNSLRAEDTAVYYCARRGSYPY*
*NYFDAWGCGTLVTVSS*GGGGSGGGGSGGGGSGGGGSGGGGSGGGGS*QAVVTQEPSLTVSPGGT*
*VTLTCGSSTGAVTASNYANWVQQKPGQCPRGLIGGHNNRPPGVPARFSGSLLGGKAALTLLGAQPED*
*EAEYYCALWYSDHWVIGGGTKLTVLG*

(HER2 LH) light chain full amino acid sequence (N to C terminal) [*HER2 VL*-CL-linker-huC825 scFv] (Fourth polypeptide chain, SEQ ID NO: 66)
*DIQMTQSPSSLSASVGDRVTITCRASQDVNTAVAWYQQKPGKAPKLLIYSASFLYSGVPSRFSGSRSGTD*
*FTLTISSLQPEDFATYYCQQHYTTPPTFGQGTKVEIKRTVAAPSVFIFPPSDEQLKSGTASVVCLLNNFYP*
*REAKVQWKVDNALQSGNSQESVTEQDSKDSTYSLSSTLTLSKADYEKHKVYACEVTHQGLSSPVTKSFN*
*RGECTS*GGGGSGGGGSGGGGS*HVQLVESGGGLVQPGGSLRLSCAASGFSLTDYGVHWVRQAPGK*
*GLEWLGVIWSGGGTAYNTALISRFTISRDNSKNTLYLQMNSLRAEDTAVYYCARRGSYPYNYFDAWGCG*
*TLVTVSS*GGGGSGGGGSGGGGSGGGGSGGGGSGGGGS*QAVVTQEPSLTVSPGGTVTLTCGSSTG*
*AVTASNYANWVQQKPGQCPRGLIGGHNNRPPGVPARFSGSLLGGKAALTLLGAQPEDEAEYYCALWY*
*SDHWVIGGGTKLTVLG*

(G3A H1L4 F405L) heavy chain full amino acid sequence (N to C terminal) [*G3A* VH1-CH1-CH2-CH3] (Second polypeptide chain, SEQ ID NO: 67)
*EVQLVESGGGLVKPGGSLRLSCAASGFAFSTYDMSWVRQAPGKGLEWVSTISSGGSYTYYADSVKGRFT*
*ISRDNAKNSLYLQMNSLRAEDTAVYYCAPTTVVPFAYWGQGTLVTVSA*ASTKGPSVFPLAPSSKSTSGG
TAALGCLVKDYFPEPVTVSWNSGALTSGVHTFPAVLQSSGLYSLSSVVTVPSSSLGTQTYICNVN
HKPSNTKVDKRVEPKSCDKTHTCPPCPAPELLGGPSVFLFPPKPKDTLMISRTPEVTCVVVDVSH
EDPEVKFNWYVDGVEVHNAKTKPREEQYASTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTTPP
VLDSDGSFLLYSKLTVDKSRWQQGNVFSCSVMHEALHNHYTQKSLSLSPGK

(HER2 LH K409R) heavy chain full amino acid sequence (N to C terminal) [*HER2 VH*-CH1-CH2-CH3] (Third polypeptide chain, SEQ ID NO: 68)
*EVQLVESGGGLVQPGGSLRLSCAASGFNIKDTYIHWVRQAPGKGLEWVARIYPTNGYTRYADSVKGRF*
*TISADTSKNTAYLQMNSLRAEDTAVYYCSRWGGDGFYAMDYWGQGTLVTVSS*ASTKGPSVFPLAPSSK
STSGGTAALGCLVKDYFPEPVTVSWNSGALTSGVHTFPAVLQSSGLYSLSSVVTVPSSSLGTQTYI
CNVNHKPSNTKVDKRVEPKSCDKTHTCPPCPAPELLGGPSVFLFPPKPKDTLMISRTPEVTCVVV
DVSHEDPEVKFNWYVDGVEVHNAKTKPREEQYASTYRVVSVLTVLHQDWLNGKEYKCAVSN
KALPAPIEKTISKAKGQPREPQVYTLPPSRDELTKNQVSLTCLVKGFYPSDIAVEWESNGQPENN
YKTTPPVLDSDGSFFLYSRLTVDKSRWQQGNVFSCSVMHEALHNHYTQKSLSLSPGK

(G3A H1L4 huOKT3) light chain full amino acid sequence (N to C terminal) [*G3A L4*-CL-linker-huOKT3 scFv] (First polypeptide chain, SEQ ID NO: 69)
*DIQMTQSPSSLSASVGDRVTITCKASQNVRTVVAWYQQKPGKAPKTLIYLASNRHTGVPSRFSGSGSGTE FTLTISNLQPEDFATYYCLQHWSYPLTFGSGTKLEVK*RTVAAPSVFIFPPSDEQLKSGTASVVCLLNN FYPREAKVQWKVDNALQSGNSQEkSVTEQDSKDSTYSLSSTLTLSKADYEKHKVYACEVTHQG LSSPVTKSFNRGECTSGGGGSGGGGSGGGGS*QVQLVQSGGGVVQPGRSLRLSCKASGYTFTRYTM HWVRQAPGKCLEWIGYINPSRGYTNYNQKFKDRFTISRDNSKNTAFLQMDSLRPEDTGVYFCARYYDD HYSLDYWGQGTPVTVSS*GGGGSGGGGSGGGGSGGGGSGGGGSGGGGS*DIQMTQSPSSLSASVG DRVTITCSASSSVSYMNWYQQTPGKAPKRWIYDTSKLASGVPSRFSGSGSGTDYTFTISSLQPEDIATYYC QQWSSNPFTFGCGTKLQITR*

(HER2 LH) light chain full amino acid sequence (N to C terminal) [*HER2 VL*-CL-linker-huOKT3 scFv] (Fourth polypeptide chain, SEQ ID NO: 70)
*DIQMTQSPSSLSASVGDRVTITCRASQDVNTAVAWYQQKPGKAPKLLIYSASFLYSGVPSRFSGSRSGTD FTLTISSLQPEDFATYYCQQHYTTPPTFGQGTKVEIK*RTVAAPSVFIFPPSDEQLKSGTASVVCLLNNF YPREAKVQWKVDNALQSGNSQESVTEQDSKDSTYSLSSTLTLSKADYEKHKVYACEVTHQGLS SPVTKSFNRGECTSGGGGSGGGGSGGGGS*QVQLVQSGGGVVQPGRSLRLSCKASGYTFTRYTMH WVRQAPGKCLEWIGYINPSRGYTNYNQKFKDRFTISRDNSKNTAFLQMDSLRPEDTGVYFCARYYDDH YSLDYWGQGTPVTVSS*GGGGSGGGGSGGGGSGGGGSGGGGSGGGGS*DIQMTQSPSSLSASVGD RVTITCSASSSVSYMNWYQQTPGKAPKRWIYDTSKLASGVPSRFSGSGSGTDYTFTISSLQPEDIATYYCQ QWSSNPFTFGCGTKLQITR*

(G3A H1L4 huOKT3 F405L) heavy chain full amino acid sequence (N to C terminal) [*G3A* VH1-CH1-CH2-CH3] (Second polypeptide chain, SEQ ID NO: 71)
*EVQLVESGGGLVKPGGSLRLSCAASGFAFSTYDMSWVRQAPGKGLEWVSTISSGGSYTYYADSVKGRFT ISRDNAKNSLYLQMNSLRAEDTAVYYCAPTTVVPFAYWGQGTLVTVSA*ASTKGPSVFPLAPSSKSTSGG TAALGCLVKDYFPEPVTVSWNSGALTSGVHTFPAVLQSSGLYSLSSVVTVPSSSLGTQTYICNVN HKPSNTKVDKRVEPKSCDKTHTCPPCPAPELLGGPSVFLFPPKPKDTLMISRTPEVTCVVVDVSH EDPEVKFNWYVDGVEVHNAKTKPREEQYASTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPP VLDSDGSFLLYSKLTVDKSRWQQGNVFSCSVMHEALHNHYTQKSLSLSPGK

(HER2 LH K409R) heavy chain full amino acid sequence (N to C terminal) [*HER2 VH*-CH1-CH2-CH3] (Third polypeptide chain, SEQ ID NO: 72)
*EVQLVESGGGLVQPGGSLRLSCAASGFNIKDTYIHWVRQAPGKGLEWVARIYPTNGYTRYADSVKGRF TISADTSKNTAYLQMNSLRAEDTAVYYCSRWGGDGFYAMDYWGQGTLVTVSS*ASTKGPSVFPLAPSSK STSGGTAALGCLVKDYFPEPVTVSWNSGALTSGVHTFPAVLQSSGLYSLSSVVTVPSSSLGTQTYI CNVNHKPSNTKVDKRVEPKSCDKTHTCPPCPAPELLGGPSVFLFPPKPKDTLMISRTPEVTCVVV DVSHEDPEVKFNWYVDGVEVHNAKTKPREEQYASTYRVVSVLTVLHQDWLNGKEYKCAVSN KALPAPIEKTISKAKGQPREPQVYTLPPSRDELTKNQVSLTCLVKGFYPSDIAVEWESNGQPENN YKTTPPVLDSDGSFFLYSRLTVDKSRWQQGNVFSCSVMHEALHNHYTQKSLSLSPGK

(G3A H1L4 huOT3 H2L2) light chain full amino acid sequence (N to C terminal) [*G3A L4*-CL-linker-huOT3 scFv] (First polypeptide chain, SEQ ID NO: 73)
*DIQMTQSPSSLSASVGDRVTITCKASQNVRTVVAWYQQKPGKAPKTLIYLASNRHTGVPSRFSGSGSGTE*
*FTLTISNLQPEDFATYYCLQHWSYPLTFGSGTKLEVK*RTVAAPSVFIFPPSDEQLKSGTASVVCLLNN
FYPREAKVQWKVDNALQSGNSQEkSVTEQDSKDSTYSLSSTLTLSKADYEKHKVYACEVTHQG
LSSPVTKSFNRGECTSGGGGSGGGGSGGGGS*QVQLQQSGAEVAKPGASVKVSCKASGYTFTRYTM*
*HWVRQAPGQGLEWMGYINPSRGYTNYNQKFKDRATLTRDKSISTAYMELSRLRSDDTAVYYCARYYDD*
*HYSLDYWGQGTTLTVSS*GGGGSGGGGSGGGGSGGGGSGGGGSGGGGS*DIQMTQSPSSLSASVG*
*DRVTMTCSASSSVSYMNWYQQKPGKAPKLLIYDTSKLASGVPSRFSGSGSGTDFTLTISSMQPEDFATYY*
*CQQWSSNPFTFGSGTKLEINR*

(HER2 LH) light chain full amino acid sequence (N to C terminal) [*HER2 VL*-CL-linker-huOKT3 scFv] (Fourth polypeptide chain, SEQ ID NO: 74)
*DIQMTQSPSSLSASVGDRVTITCRASQDVNTAVAWYQQKPGKAPKLLIYSASFLYSGVPSRFSGSRSGTD*
*FTLTISSLQPEDFATYYCQQHYTTPPTFGQGTKVEIK*RTVAAPSVFIFPPSDEQLKSGTASVVCLLNNF
YPREAKVQWKVDNALQSGNSQESVTEQDSKDSTYSLSSTLTLSKADYEKHKVYACEVTHQGLS
SPVTKSFNRGECTSGGGGSGGGGSGGGGS*QVQLVQSGGGVVQPGRSLRLSCKASGYTFTRYTMH*
*WVRQAPGKCLEWIGYINPSRGYTNYNQKFKDRFTISRDNSKNTAFLQMDSLRPEDTGVYFCARYYDDH*
*YSLDYWGQGTPVTVSS*GGGGSGGGGSGGGGSGGGGSGGGGSGGGGS*DIQMTQSPSSLSASVGD*
*RVTITCSASSSVSYMNWYQQTPGKAPKRWIYDTSKLASGVPSRFSGSGSGTDYTFTISSLQPEDIATYYCQ*
*QWSSNPFTFGCGTKLQITR*

(G3A H1L4 huOT3 H2L2 F405L) heavy chain full amino acid sequence (N to C terminal) [*G3A* VH1-CH1-CH2-CH3] (Second polypeptide chain, SEQ ID NO: 75)
*EVQLVESGGGLVKPGGSLRLSCAASGFAFSTYDMSWVRQAPGKGLEWVSTISSGGSYTYYADSVKGRFT*
*ISRDNAKNSLYLQMNSLRAEDTAVYYCAPTTVVPFAYWGQGTLVTVSA*ASTKGPSVFPLAPSSKSTSGG
TAALGCLVKDYFPEPVTVSWNSGALTSGVHTFPAVLQSSGLYSLSSVVTVPSSSLGTQTYICNVN
HKPSNTKVDKRVEPKSCDKTHTCPPCPAPELLGGPSVFLFPPKPKDTLMISRTPEVTCVVVDVSH
EDPEVKFNWYVDGVEVHNAKTKPREEQYASTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTTPP
VLDSDGSFLLYSKLTVDKSRWQQGNVFSCSVMHEALHNHYTQKSLSLSPGK

(HER2 LH K409R) heavy chain full amino acid sequence (N to C terminal) [*HER2 VH*-CH1-CH2-CH3] (Third polypeptide chain, SEQ ID NO: 76)
*EVQLVESGGGLVQPGGSLRLSCAASGFNIKDTYIHWVRQAPGKGLEWVARIYPTNGYTRYADSVKGRF*
*TISADTSKNTAYLQMNSLRAEDTAVYYCSRWGGDGFYAMDYWGQGTLVTVSS*ASTKGPSVFPLAPSSK
STSGGTAALGCLVKDYFPEPVTVSWNSGALTSGVHTFPAVLQSSGLYSLSSVVTVPSSSLGTQTYI
CNVNHKPSNTKVDKRVEPKSCDKTHTCPPCPAPELLGGPSVFLFPPKPKDTLMISRTPEVTCVVV
DVSHEDPEVKFNWYVDGVEVHNAKTKPREEQYASTYRVVSVLTVLHQDWLNGKEYKCAVSN
KALPAPIEKTISKAKGQPREPQVYTLPPSRDELTKNQVSLTCLVKGFYPSDIAVEWESNGQPENN
YKTTPPVLDSDGSFFLYSRLTVDKSRWQQGNVFSCSVMHEALHNHYTQKSLSLSPGK

(G3A H1L4 huOT3 H2L5) light chain full amino acid sequence (N to C terminal) [*G3A L4*-CL-linker-huOT3 scFv] (First polypeptide chain, SEQ ID NO: 77)

*DIQMTQSPSSLSASVGDRVTITCKASQNVRTVVAWYQQKPGKAPKTLIYLASNRHTGVPSRFSGSGSGTE*
*FTLTISNLQPEDFATYYCLQHWSYPLTFGSGTKLEVK*RTVAAPSVFIFPPSDEQLKSGTASVVCLLNN
FYPREAKVQWKVDNALQSGNSQEkSVTEQDSKDSTYSLSSTLTLSKADYEKHKVYACEVTHQG
LSSPVTKSFNRGECTSGGGGSGGGGSGGGGS*QVQLQQSGAEVAKPGASVKVSCKASGYTFTRYTM*
*HWVRQAPGQGLEWMGYINPSRGYTNYNQKFKDRATLTRDKSISTAYMELSRLRSDDTAVYYCARYYDD*
*HYSLDYWGQGTTLTVSS*GGGGSGGGGSGGGGSGGGGSGGGGSGGGGS*DIQMTQSPSSLSASVG*
*DRVTITCSASSSVSYMNWYQQKPGKAPKRWIYDTSKLASGVPSRFSGSGSGTDFTLTISSLQPEDFATYY*
*CQQWSSNPFTFGSGTKLEINR*

(HER2 LH) light chain full amino acid sequence (N to C terminal) [*HER2 VL*-CL-linker-huOKT3 scFv] (Fourth polypeptide chain, SEQ ID NO: 78)

*DIQMTQSPSSLSASVGDRVTITCRASQDVNTAVAWYQQKPGKAPKLLIYSASFLYSGVPSRFSGSRSGTD*
*FTLTISSLQPEDFATYYCQQHYTTPPTFGQGTKVEIK*RTVAAPSVFIFPPSDEQLKSGTASVVCLLNNF
YPREAKVQWKVDNALQSGNSQESVTEQDSKDSTYSLSSTLTLSKADYEKHKVYACEVTHQGLS
SPVTKSFNRGECTSGGGGSGGGGSGGGGS*QVQLVQSGGGVVQPGRSLRLSCKASGYTFTRYTMH*
*WVRQAPGKCLEWIGYINPSRGYTNYNQKFKDRFTISRDNSKNTAFLQMDSLRPEDTGVYFCARYYDDH*
*YSLDYWGQGTPVTVSS*GGGGSGGGGSGGGGSGGGGSGGGGSGGGGS*DIQMTQSPSSLSASVGD*
*RVTITCSASSSVSYMNWYQQTPGKAPKRWIYDTSKLASGVPSRFSGSGSGTDYTFTISSLQPEDIATYYCQ*
*QWSSNPFTFGCGTKLQITR*

(G3A H1L4 huOT3 H2L5 F405L) heavy chain full amino acid sequence (N to C terminal) [*G3A* VH1-CH1-CH2-CH3] (Second polypeptide chain, SEQ ID NO: 79)

*EVQLVESGGGLVKPGGSLRLSCAASGFAFSTYDMSWVRQAPGKGLEWVSTISSGGSYTYYADSVKGRFT*
*ISRDNAKNSLYLQMNSLRAEDTAVYYCAPTTVVPFAYWGQGTLVTVSA*ASTKGPSVFPLAPSSKSTSGG
TAALGCLVKDYFPEPVTVSWNSGALTSGVHTFPAVLQSSGLYSLSSVVTVPSSSLGTQTYICNVN
HKPSNTKVDKRVEPKSCDKTHTCPPCPAPELLGGPSVFLFPPKPKDTLMISRTPEVTCVVVDVSH
EDPEVKFNWYVDGVEVHNAKTKPREEQYASTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTTPP
VLDSDGSFLLYSKLTVDKSRWQQGNVFSCSVMHEALHNHYTQKSLSLSPGK

(HER2 LH K409R) heavy chain full amino acid sequence (N to C terminal) [*HER2 VH*-CH1-CH2-CH3] (Third polypeptide chain, SEQ ID NO: 80)

*EVQLVESGGGLVQPGGSLRLSCAASGFNIKDTYIHWVRQAPGKGLEWVARIYPTNGYTRYADSVKGRF*
*TISADTSKNTAYLQMNSLRAEDTAVYYCSRWGGDGFYAMDYWGQGTLVTVSS*ASTKGPSVFPLAPSSK
STSGGTAALGCLVKDYFPEPVTVSWNSGALTSGVHTFPAVLQSSGLYSLSSVVTVPSSSLGTQTYI
CNVNHKPSNTKVDKRVEPKSCDKTHTCPPCPAPELLGGPSVFLFPPKPKDTLMISRTPEVTCVVV
DVSHEDPEVKFNWYVDGVEVHNAKTKPREEQYASTYRVVSVLTVLHQDWLNGKEYKCAVSN
KALPAPIEKTISKAKGQPREPQVYTLPPSRDELTKNQVSLTCLVKGFYPSDIAVEWESNGQPENN
YKTTPPVLDSDGSFFLYSRLTVDKSRWQQGNVFSCSVMHEALHNHYTQKSLSLSPGK

FIG. 33

BC105 light chain acid sequence (N to C terminal) [*VL*-CL-linker-C825 scFv]
(SEQ ID NO: 98)

*DIQMTQSPSSLSVSVGDRVTITCKASQNVRTVVAWYQQKPGLAPKTLIYLASNRHTGVPSRFSGSGSGTD FTFTISSLQPEDIATYFCQQHWSYPLTFGQGTKVEVKR*TVAAPSVFIFPPSDEQLKSGTASVVCLLNN FYPREAKVQWKVDNALQSGNSQESVTEQDSKDSTYSLSSTLTLSKADYEKHKVYACEVTHQGL SSPVTKSFNRGECGGGGSGGGGSAS*HVKLQESGPGLVQPSQSLSLTCTVSGFSLTDYGVHWVRQSP GKGLEWLGVIWSGGGTAYNTALISRLNIYRDNSKNQVFLEMNSLQAEDTAMYYCARRGSYPYNYFDAW GCGTTVTVSS*GGGGSGGGGSGGGGS*QAVVIQESALTTPPGETVTLTCGSSTGAVTASNYANWVQEKP DHCFTGLIGGHNNRPPGVPARFSGSLIGDKAALTIAGTQTEDEAIYFCALWYSDHWVIGGGTRLTVLG*

BC105 heavy chain full amino acid sequence (N to C terminal) [*VH*-CH1-CH2-CH3]
(SEQ ID NO: 99)

*EVQLLESGGGLVQPGGSLRLSCAASGFAFSTYDMSWVRQAPGKGLEWVATISSGGSYTYYLDSVKGRF TISRDSSKNTLYLQMNSLQAEDSAIYYCAPTTVVPFAYWGQGTLVTVSS*ASTKGPSVFPLAPSSKSTSGG TAALGCLVKDYFPEPVTVSWNSGALTSGVHTFPAVLQSSGLYSLSSVVTVPSSSLGTQTYICNVN HKPSNTKVDKRVEPKSCDKTHTCPPCPAPELLGGPSVFLFPPKPKDTLMISRTPEVTCVVVDVSH EDPEVKFNWYVDGVEVHNAKTKPREEQYASTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSPGK

FIG. 34

BC155 light chain acid sequence (N to C terminal) [*VL*-CL-linker-huC825 scFv]
(SEQ ID NO: 102)

*DIQMTQSQSSLSTSVGDRVTITCKASQNVRTVVAWYQQKPGKSPKTLIYLASNRHTGVPSRFSGSGSGTE FTLTISNVQPEDFADYFCLQHWSYPLTFGSGTKLEIKR*TVAAPSVFIFPPSDEQLKSGTASVVCLLNN FYPREAKVQWKVDNALQSGNSQESVTEQDSKDSTYSLSSTLTLSKADYEKHKVYACEVTHQGL SSPVTKSFNRGECTSGGGGSGGGGSGGGGS*HVQLVESGGGLVQPGGSLRLSCAASGFSLTDYGVH WVRQAPGKGLEWLGVIWSGGGTAYNTALISRFTISRDNSKNTLYLQMNSLRAEDTAVYYCARRGSYPYN YFDAWGCGTLVTVSS*GGGGSGGGGSGGGGSGGGGSGGGGSGGGGS*QAVVTQEPSLTVSPGGTV TLTCGSSTGAVTASNYANWVQQKPGQCPRGLIGGHNNRPPGVPARFSGSLLGGKAALTLLGAQPEDE AEYYCALWYSDHWVIGGGTKLTVLG*

BC155 heavy chain full amino acid sequence (N to C terminal) [*VH*-CH1-CH2-CH3]
(SEQ ID NO: 103)

*EVQLVESGGGLVKPGGSLRLSCAASGFAFSTYDMSWVRQAPGKRLEWVATISSGGSYTYYLDSVKGRFT ISRDNAKNSLYLQMNSLRAEDTAVYYCAPTTVVPFAYWGQGTLVTVSS*ASTKGPSVFPLAPSSKSTSGG TAALGCLVKDYFPEPVTVSWNSGALTSGVHTFPAVLQSSGLYSLSSVVTVPSSSLGTQTYICNVN HKPSNTKVDKRVEPKSCDKTHTCPPCPAPELLGGPSVFLFPPKPKDTLMISRTPEVTCVVVDVSH EDPEVKFNWYVDGVEVHNAKTKPREEQYASTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSPGK

FIG. 35

TC159 full amino acid sequence (N to C terminal) [*VH*-linker-*VL*-linker-huC825-spacer-P53] (SEQ ID NO: 104)

*EVQLVESGGGLVKPGGSLRLSCAASGFAFSTYDMSWVRQAPGKRLEWVATISSGGSYTYYLDSVKGRFTISRDNAKNSLYLQMNSLRAEDTAVYYCAPTTVVPFAYWGQGTLVTVSS*GGGGSGGGGSGGGGSGGGGSGGGGSGGGGS*DIQMTQSQSSLSTSVGDRVTITCKASQNVRTVVAWYQQKPGKSPKTLIYLASNRHTGVPSRFSGSGSGTEFTLTISNVQPEDFADYFCLQHWSYPLTFGSGTKLEIKR*GGGGSGGGGSGGGGSGGGGS*HVQLVESGGGLVQPGGSLRLSCAASGFSLTDYGVHWVRQAPGKGLEWLGVIWSGGGTAYNTALISRFTISRDNSKNTLYLQMNSLRAEDTAVYYCARRGSYPYNYFDAWGCGTLVTVSS*GGGGSGGGGSGGGGSGGGGSGGGGSGGGGS*QAVVTQEPSLTVSPGGTVTLTCGSSTGAVTASNYANWVQQKPGQCPRGLIGGHNNRPPGVPARFSGSLLGGKAALTLLGAQPEDEAEYYCALWYSDHWVIGGGTKLTVLG*
TPLGDTTHTSGKPLDGEYFTLQIRGRERFEMFRELNEALELKDAQAGKEPGGSGGAPHHHHHH

FIG. 36

TC160 full amino acid sequence (N to C terminal) [*VL*-linker-*VH*-linker-huC825-spacer-P53] (SEQ ID NO: 105)

*DIQMTQSQSSLSTSVGDRVTITCKASQNVRTVVAWYQQKPGKSPKTLIYLASNRHTGVPSRFSGSGSGTEFTLTISNVQPEDFADYFCLQHWSYPLTFGSGTKLEIKR*GGGGSGGGGSGGGGSGGGGSGGGGSGGGGS*EVQLVESGGGLVKPGGSLRLSCAASGFAFSTYDMSWVRQAPGKRLEWVATISSGGSYTYYLDSVKGRFTISRDNAKNSLYLQMNSLRAEDTAVYYCAPTTVVPFAYWGQGTLVTVSS*GGGGSGGGGSGGGGSGGGGS*HVQLVESGGGLVQPGGSLRLSCAASGFSLTDYGVHWVRQAPGKGLEWLGVIWSGGGTAYNTALISRFTISRDNSKNTLYLQMNSLRAEDTAVYYCARRGSYPYNYFDAWGCGTLVTVSS*GGGGSGGGGSGGGGSGGGGSGGGGSGGGGS*QAVVTQEPSLTVSPGGTVTLTCGSSTGAVTASNYANWVQQKPGQCPRGLIGGHNNRPPGVPARFSGSLLGGKAALTLLGAQPEDEAEYYCALWYSDHWVIGGGTKLTVLG*TPLGDTTHTSGKPLDGEYFTLQIRGRERFEMFRELNEALELKDAQAGKEPGGSGGAPHHHHHH

FIG. 37

| | | Purity of protein (% of total protein at expected size) | | | | | | | | | |
|---|---|---|---|---|---|---|---|---|---|---|---|
| Protein | Yield (mg/L) | Original | after 5x FT | week 1 at 37c | week 2 at 37c | week 3 at 37c | week 4 at 37c | week 5 at 37c | week 1 at 40c | week 2 at 40c | week 3 at 40c |
| TC159 | 1.92 | 95.38% | unstable | unstable | unstable | unstable | unstable | unstable | unstable | unstable | unstable |
| TC160 | 1.78 | 94.23% | unstable | unstable | unstable | unstable | unstable | unstable | unstable | unstable | unstable |
| TC170 | 47.35 | 91.31% | 89.93% | 88.32% | 91.66% | 85.84% | 84.75% | 83.25% | 83.53% | 82.62% | 82.55% |
| TC171 | 17.96 | 92.51% | 86.21% | 91.60% | 88.29% | 90.48% | 89.85% | 88.79% | 86.75 | 86.46% | 84.69% |

FIG. 38A

| Sample | ka1 (1/Ms) | kd1 (1/s) | ka2 (1/s) | kd2 (1/s) | KD (M) | Fold change (relative to BC015, lower is better) |
|---|---|---|---|---|---|---|
| BC105 | 4.43E+06 | 2.36E-02 | 2.38E-03 | 6.97E-04 | 1.21E-09 | 10.20 |
| BC155 | 4.13E+06 | 2.12E-03 | 3.28E-03 | 1.64E-03 | 1.71E-10 | 1.45 |
| **BC015** | **4.36E+06** | **1.41E-03** | **3.07E-03** | **1.77E-03** | **1.18E-10** | **1.00** |
| BC016 | 5.50E+06 | 5.11E-04 | 5.41E-02 | 5.04E-03 | 7.92E-12 | 0.07 |

FIG. 38B

| Sample | ka1 (1/Ms) | kd1 (1/s) | ka2 (1/s) | kd2 (1/s) | KD (M) | Fold change (relative to TC170, lower is better) |
|---|---|---|---|---|---|---|
| TC159 | 4.09E+06 | 1.81E-03 | 6.13E-03 | 3.15E-04 | 2.16E-11 | 1.4 |
| TC160 | 3.43E+06 | 2.02E-03 | 6.78E-03 | 6.54E-04 | 5.18E-11 | 3.4 |
| **TC170** | **3.54E+06** | **7.28E-04** | **6.46E-03** | **5.38E-04** | **1.58E-11** | **1.0** |
| TC171 | 3.34E+06 | 8.86E-04 | 6.63E-03 | 6.28E-04 | 2.30E-11 | 1.5 |
| TC213 | 3.44E+06 | 8.57E-04 | 6.36E-03 | 6.11E-04 | 2.18E-11 | 1.4 |
| TC234 | 4.65E+06 | 9.66E-04 | 5.66E-03 | 3.53E-04 | 1.22E-11 | 0.8 |
| TC235 | 3.38E+06 | 9.81E-04 | 5.61E-03 | 5.10E-04 | 2.42E-11 | 1.5 |

FIG. 39

| | Colo205 | | LS174T | | SW1222 | |
|---|---|---|---|---|---|---|
| | binding EC50 (nM, lower is better) | fold change (relative to TC170, lower is better) | binding EC50 (nM, lower is better) | fold change (relative to TC170, lower is better) | binding EC50 (nM, lower is better) | fold change (relative to TC170, lower is better) |
| TC159 | 2.47 | 3.34 | 1.22 | 3.94 | 0.4 | 0.24 |
| TC160 | 1.2 | 1.62 | 0.56 | 1.81 | 0.36 | 0.22 |
| **TC170** | **0.74** | **1.00** | **0.31** | **1.00** | **1.65** | **1.00** |
| TC171 | 1.04 | 1.41 | 0.56 | 1.81 | 1.77 | 1.07 |
| TC213 | 0.55 | 0.74 | 0.23 | 0.74 | 1.05 | 0.64 |
| TC234 | 0.71 | 0.96 | 0.21 | 0.68 | 2.05 | 1.24 |
| TC235 | 0.53 | 0.72 | 0.22 | 0.71 | 1.03 | 0.62 |

FIG. 40A
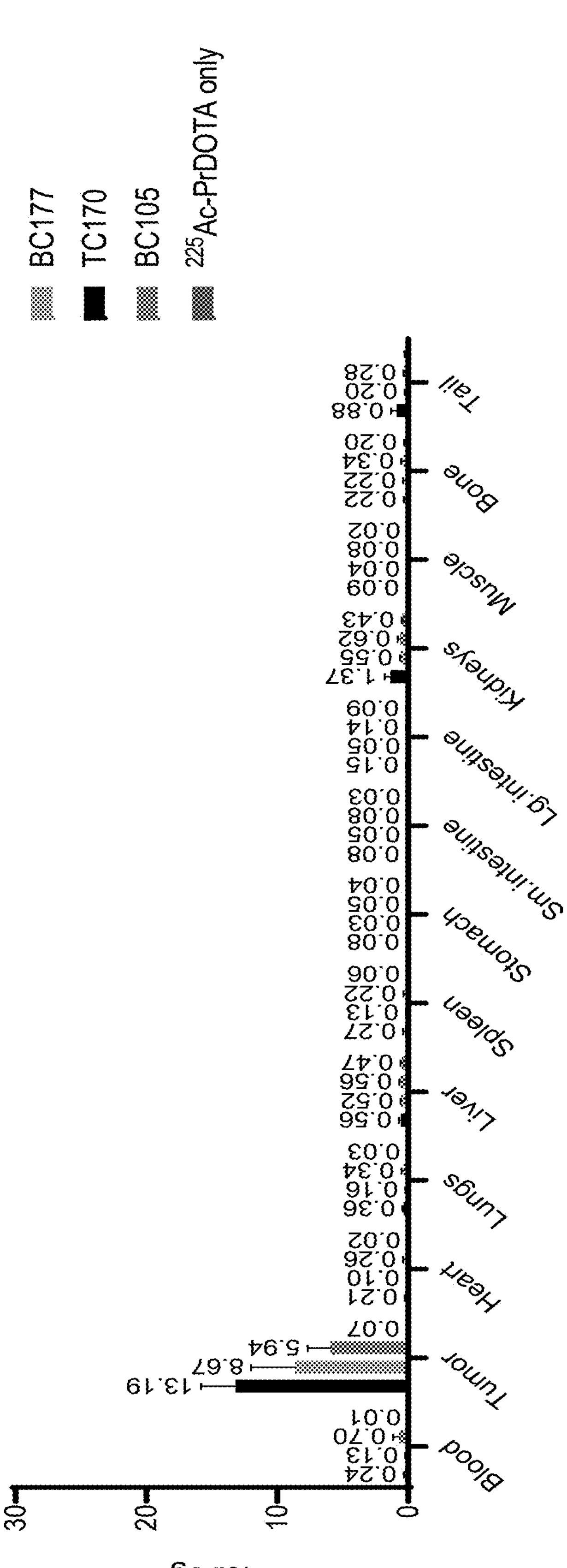

| Organ | 100ug TC170 | 250ug TC170 | 500ug TC170 | 3-step BC105 + CA | 3-step BC177 + CA | DOTA only |
|---|---|---|---|---|---|---|
| Blood | 0.58 | 2.00 | 7.55 | 0.85 | 4.51 | 0.01 |
| Tumor | 87.79 | 179.77 | 152.37 | 31.60 | 175.75 | 0.28 |
| Heart | 0.68 | 1.94 | 7.45 | 0.05 | 2.54 | 0.04 |
| lungs | 0.69 | 2.43 | 6.17 | 0.43 | 2.96 | 0.05 |
| liver | 0.83 | 2.02 | 5.87 | 0.28 | 4.47 | 0.22 |
| spleen | 0.80 | 2.22 | 7.31 | -0.04 | 3.09 | 0.07 |
| stomach | 0.21 | 0.61 | 0.87 | 0.05 | 0.40 | 0.06 |
| sm.intestine | 0.28 | 0.79 | 2.19 | 0.10 | 1.03 | 0.07 |
| lg.intestine | 0.66 | 0.77 | 1.55 | 0.47 | 0.96 | 0.49 |
| kidneys | 4.32 | 15.45 | 33.99 | 0.94 | 3.09 | 0.99 |
| muscle | 0.14 | 0.46 | 0.90 | -0.06 | 0.70 | 0.01 |
| bone | 0.38 | 0.67 | 1.71 | 1.25 | 0.82 | 0.08 |
| Tail | 2.09 | 5.20 | 7.87 | 0.42 | 1.52 | 0.98 |

| Organ | 100ug TC170 | 250ug TC170 | 500ug TC170 | 3-step BC105 + CA | 3-step BC177 + CA | DOTA only |
|---|---|---|---|---|---|---|
| Blood | 0.024 | 0.052 | 0.168 | 0.054 | 0.045 | 0 |
| Tumor | 7.738 | 15.944 | 28.822 | 11.79 | 8.3475 | 0.066 |
| Heart | 0.044 | 0.094 | 0.306 | 0.034 | 0.05 | 0.01 |
| lungs | 0.05 | 0.104 | 0.344 | 0.068 | 0.07 | 0.018 |
| liver | 0.06 | 0.116 | 0.31 | 0.062 | 0.1 | 0.036 |
| spleen | 0.066 | 0.108 | 0.314 | 0.04 | 0.075 | 0.024 |
| stomach | 0.104 | 0.07 | 0.134 | 0.14 | 0.0875 | 0.148 |
| sm.intestine | 0.066 | 0.06 | 0.176 | 0.066 | 0.0525 | 0.026 |
| lg.intestine | 0.522 | 2.456 | 0.674 | 0.882 | 0.505 | 0.708 |
| kidneys | 0.95 | 1.074 | 3.268 | 0.45 | 0.57 | 0.508 |
| muscle | 0.014 | 0.022 | 0.06 | 0.014 | 0.0175 | 0.008 |
| bone | 0.026 | 0.042 | 0.152 | 0.03 | 0.0325 | 0.014 |
| tail | 0.212 | 0.364 | 1.4 | 0.17 | 0.24 | 0.245 |

| Organ | DOTA only | 3-step BC177 + CA | TC170 | TC234 | TC235 | TC213 |
|---|---|---|---|---|---|---|
| Blood | 0.006 | 0.026 | 0.048 | 0.114 | 0.58 | 0.422 |
| Heart | 0.006 | 0.036 | 0.068 | 0.118 | 0.338 | 0.29 |
| lungs | 0.006 | 0.04 | 0.066 | 0.104 | 0.362 | 0.374 |
| liver | 0.032 | 0.056 | 0.092 | 0.18 | 0.736 | 0.49 |
| spleen | 0.014 | 0.034 | 0.068 | 0.102 | 0.418 | 0.364 |
| stomach | 0.026 | 0.032 | 0.05 | 0.032 | 0.084 | 0.08 |
| sm.intestine | 0.034 | 0.036 | 0.05 | 0.06 | 0.166 | 0.134 |
| lg.intestine | 0.118 | 0.094 | 0.176 | 0.13 | 0.244 | 0.254 |
| kidneys | 0.166 | 0.364 | 0.576 | 1.006 | 5.122 | 1.9425 |
| muscle | 0.002 | 0.01 | 0.014 | 0.022 | 0.08 | 0.052 |
| bone | 0.01 | 0.02 | 0.048 | 0.076 | 0.194 | 0.156 |
| tail | 0.558 | 0.504 | 0.58 | 0.32 | 0.956 | 0.47 |

ANTI-GPA33 MULTI-SPECIFIC ANTIBODIES AND USES THEREOF

CROSS-REFERENCE TO RELATED APPLICATIONS

This application is a U.S. National Stage Application under 35 U.S.C. § 371 of International Patent Application No. PCT/US2021/059634, filed Nov. 17, 2021, which claims the benefit of and priority to U.S. Provisional Patent Application No. 63/115,326 filed Nov. 18, 2020, the entire contents of which are incorporated herein by reference.

STATEMENT OF GOVERNMENT SUPPORT

This invention was made with government support under grant number CA008748 awarded by the National Institutes of Health (NIH). The government has certain rights in the invention.

TECHNICAL FIELD

The present technology relates generally to the preparation of immunoglobulin-related compositions (e.g., multi-specific antibodies or antigen binding fragments thereof) that specifically bind GPA33 protein and uses of the same. In particular, the present technology relates to the preparation of GPA33 binding multi-specific antibodies and their use in detecting and treating cancer.

Sequence Listing

The instant application contains a Sequence Listing which has been submitted electronically in ASCII format and is hereby incorporated by reference in its entirety. Said ASCII copy, created on Feb. 11, 2022, is named 115872-2363_SL.txt and is 430,494 bytes in size.

BACKGROUND

The following description of the background of the present technology is provided simply as an aid in understanding the present technology and is not admitted to describe or constitute prior art to the present technology.

GPA33 is a transmembrane glycoprotein abundantly expressed in over 95% of colorectal cancer (CRC), with low levels of normal-tissue expression (colon and bowel epithelium). Two humanized IgG1 antibodies, huA33 (Ludwig Cancer Institute) (U.S. Pat. No. 6,342,587) and KRN330 (Kyowa Hakko Kirin Pharma, Inc., Japan), and one GPA33×CD3 bispecific Dual-Affinity Re-Targeting (DART) antibody, MGD007 (Macrogenics Inc, Rockville, MD) (U.S. Pat. No. 9,932,400), have been tested in humans (Bendell, J. C., et al., *Invest New Drugs* 32(4): 682-690 (2014); Infante, J. R., et al., *Eur. J Cancer.* 49(6): 1169-1175 (2013)). Toxicities of IgG1 were minimal, but tumor response was observed mainly in stable diseases, most likely because of the modest ADCC and CMC activity. HuA33 has also been extensively studied as a directly radiolabeled antibody (Herbertson, R. A., et al., *J Nucl Med* 55(4): 534-539 (2014)) and in multistep targeting (MST) (Cheal, S. M., et al., *Eur J Nucl Med Mot Imaging* 43(5): 925-937 (2016))[14]. MST using $^{177}$Lu showed the most promise, achieving permanent cures of CRC in preclinical models without causing clinical or histological toxicities. However, huA33 is immunogenic (Ritter, G., et al., *Cancer Res* 61(18): 6851-9 (2001)).

Accordingly, there is an urgent need for novel immunoglobulin-related compositions that are effective in treating GPA33-associated malignancies.

SUMMARY OF THE PRESENT TECHNOLOGY

In one aspect, the present disclosure provide an antibody or antigen binding fragment thereof comprising a heavy chain immunoglobulin variable domain ($V_H$) and a light chain immunoglobulin variable domain ($V_L$), wherein: (a) the $V_H$ comprises an amino acid sequence of any one of SEQ ID NOs: 1-3; and/or (b) the $V_L$ comprises an amino acid sequence of any one of SEQ ID NOs: 4-10. The antibody may further comprise an Fc domain of an isotype selected from the group consisting of IgG1, IgG2, IgG3, IgG4, IgA1, IgA2, IgM, IgD, and IgE. In some embodiments, the antibody comprises an IgG1 constant region comprising one or more amino acid substitutions selected from the group consisting of N297A and K322A. Additionally or alternatively, in some embodiments, the antibody comprises an IgG4 constant region comprising a S228P mutation. In certain embodiments, the antigen binding fragment is selected from the group consisting of Fab, F(ab')$_2$, Fab', scF$_v$, and F$_v$. In some embodiments, the antibody or antigen binding fragment is a monoclonal antibody, chimeric antibody, humanized antibody, a multi-specific antibody, or a bispecific antibody. In certain embodiments, the antibody or antigen binding fragment binds to a GPA33 polypeptide comprising the amino acid sequence of SEQ ID NO: 101. In some embodiments, the epitope is a conformational epitope.

In any and all embodiments of the bispecific antibody disclosed herein, the bispecific antibody comprises an immunoglobulin, said immunoglobulin comprising two identical heavy chains and two identical light chains, said light chains being a first light chain and a second light chain, wherein the first light chain is fused to a first single chain variable fragment (scFv), via a peptide linker, to create a first light chain fusion polypeptide, and wherein the second light chain is fused to a second scFv, via a peptide linker, to create a second light chain fusion polypeptide, wherein the first scFv is fused to the carboxyl end of the first light chain, and wherein the second scFv is fused to the carboxyl end of the second light chain. In some embodiments, the first and second scFv are identical, and wherein the first and second light chain fusion polypeptides are identical. Additionally or alternatively, in some embodiments of the bispecific antibody of the present technology, the immunoglobulin binds to GPA33, and the first and second scFvs bind to CD3.

In another aspect, the present disclosure provides an antibody comprising a heavy chain (HC) amino acid sequence comprising an antibody comprising a heavy chain (HC) amino acid sequence comprising SEQ ID NO: 23, SEQ ID NO: 27, SEQ ID NO: 60, SEQ ID NO: 62, SEQ ID NO: 64, SEQ ID NO: 67, SEQ ID NO: 71, SEQ ID NO: 75, SEQ ID NO: 79, or a variant thereof having one or more conservative amino acid substitutions, and/or a light chain (LC) amino acid sequence comprising SEQ ID NO: 21, SEQ ID NO: 25, SEQ ID NO: 59, SEQ ID NO: 61, SEQ ID NO: 63, SEQ ID NO: 65, SEQ ID NO: 69, SEQ ID NO: 73, SEQ ID NO: 77, or a variant thereof having one or more conservative amino acid substitutions. In certain embodiments, the antibody comprises a HC amino acid sequence and a LC amino acid sequence selected from the group consisting of: SEQ ID NO: 23 and SEQ ID NO: 21 (BC015 (G3A H1L4)); SEQ ID NO: 27 and SEQ ID NO: 25 (BC016 (G3A H3L3)); SEQ ID NO: 60 and SEQ ID NO: 59 (BC369 (G3A H1L4 huOKT3)); SEQ ID NO: 62 and SEQ ID NO: 61 (BC373

(G3A H1L4 huOT3 H2L2)); and SEQ ID NO: 64 and SEQ ID NO: 63 (BC377 (G3A H1L4 huOT3 H2L4)), respectively.

In another aspect, the present disclosure provides an antibody comprising a first HC amino acid sequence, a second HC amino acid sequence, a first LC amino acid sequence and a second LC amino acid sequence selected from the group consisting of SEQ ID NO: 67, SEQ ID NO: 68, SEQ ID NO: 65 and SEQ ID NO: 66 (HD152); SEQ ID NO: 71, SEQ ID NO: 72, SEQ ID NO: 69 and SEQ ID NO: 70 (HD156); SEQ ID NO: 75, SEQ ID NO: 76, SEQ ID NO: 73 and SEQ ID NO: 74 (HD160); and SEQ ID NO: 79, SEQ ID NO: 80, SEQ ID NO: 77 and SEQ ID NO: 78 (HD164), respectively.

In one aspect, the present disclosure provides an antibody or antigen binding fragment thereof comprising a $V_L$ sequence that is at least 95%, or at least 99% identical to any one of SEQ ID NOs: 4-10; and/or (b) a $V_H$ sequence that is at least 95%, or at least 99% identical to any one of SEQ ID NOs: 1-3.

In another aspect, the present disclosure provides an antibody comprising a light chain sequence that is at least 95%, or at least 99% identical to the light chain sequence present in SEQ ID NO: 21, SEQ ID NO: 25, SEQ ID NO: 59, SEQ ID NO: 61, SEQ ID NO: 63, SEQ ID NO: 65, SEQ ID NO: 69, SEQ ID NO: 73, or SEQ ID NO: 77; and/or (b) a heavy chain sequence that is at least 95%, or at least 99% identical to the heavy chain sequence present in SEQ ID NO: 23, SEQ ID NO: 27, SEQ ID NO: 60, SEQ ID NO: 62, SEQ ID NO: 64, SEQ ID NO: 67, SEQ ID NO: 71, SEQ ID NO: 75, or SEQ ID NO: 79.

In any of the above embodiments, the antibody or antigen binding fragment is a chimeric antibody, a humanized antibody, a multi-specific antibody, or a bispecific antibody. In any and all embodiments of the bispecific antibody disclosed herein, the bispecific antibody comprises an immunoglobulin, said immunoglobulin comprising two identical heavy chains and two identical light chains, said light chains being a first light chain and a second light chain, wherein the first light chain is fused to a first single chain variable fragment (scFv), via a peptide linker, to create a first light chain fusion polypeptide, and wherein the second light chain is fused to a second scFv, via a peptide linker, to create a second light chain fusion polypeptide, wherein the first scFv is fused to the carboxyl end of the first light chain, and wherein the second scFv is fused to the carboxyl end of the second light chain. In some embodiments, the first and second scFv are identical, and wherein the first and second light chain fusion polypeptides are identical. Additionally or alternatively, in some embodiments of the bispecific antibody of the present technology, the immunoglobulin binds to GPA33, and the first and second scFvs bind to CD3.

Additionally or alternatively, in some embodiments, the antibody comprises an IgG1 constant region comprising one or more amino acid substitutions selected from the group consisting of N297A and K322A. In certain embodiments, the antibody of the present technology comprises an IgG4 constant region comprising a S228P mutation. In any of the above embodiments, the antibody binds to a GPA33 polypeptide comprising the amino acid sequence of SEQ ID NO: 101. In some embodiments, the epitope is a conformational epitope.

In one aspect, the present disclosure provides a multi-specific antibody or antigen binding fragment comprising an amino acid sequence that is at least 95% identical to an amino acid sequence selected from any one of SEQ ID NOs: 11, 13, 15, 17, 19, or 29-58. In certain embodiments, the multi-specific antibody or antigen binding fragment comprises an amino acid sequence selected from any one of SEQ ID NOs: 11, 13, 15, 17, 19, or 29-58.

In one aspect, the present disclosure provides a multi-specific antigen binding fragment comprising a first polypeptide chain, wherein: the first polypeptide chain comprises in the N-terminal to C-terminal direction: (i) a heavy chain variable domain of a first immunoglobulin that is capable of specifically binding to a first epitope; (ii) a flexible peptide linker comprising the amino acid sequence $(GGGGS)_6$ (SEQ ID NO: 108); (iii) a light chain variable domain of the first immunoglobulin; (iv) a flexible peptide linker comprising the amino acid sequence $(GGGGS)_4$ (SEQ ID NO: 109); (v) a heavy chain variable domain of a second immunoglobulin that is capable of specifically binding to a second epitope; (vi) a flexible peptide linker comprising the amino acid sequence $(GGGGS)_6$ (SEQ ID NO: 108); (vii) a light chain variable domain of the second immunoglobulin; (viii) a flexible peptide linker sequence comprising the amino acid sequence TPLGDTTHT (SEQ ID NO: 110); and (ix) a self-assembly disassembly (SADA) polypeptide, wherein the heavy chain variable domain of the first immunoglobulin or the heavy chain variable domain of the second immunoglobulin is selected from any one of SEQ ID NOs: 1-3, and/or the light chain variable domain of the first immunoglobulin or the light chain variable domain of the second immunoglobulin is selected from any one of SEQ ID NOs: 4-10.

In another aspect, the present disclosure provides a multi-specific antigen binding fragment comprising a first polypeptide chain, wherein: the first polypeptide chain comprises in the N-terminal to C-terminal direction: (i) a light chain variable domain of a first immunoglobulin that is capable of specifically binding to a first epitope; (ii) a flexible peptide linker comprising the amino acid sequence $(GGGGS)_6$ (SEQ ID NO: 108); (iii) a heavy chain variable domain of the first immunoglobulin; (iv) a flexible peptide linker comprising the amino acid sequence $(GGGGS)_4$ (SEQ ID NO: 109); (v) a heavy chain variable domain of a second immunoglobulin that is capable of specifically binding to a second epitope; (vi) a flexible peptide linker comprising the amino acid sequence $(GGGGS)_6$ (SEQ ID NO: 108); (vii) a light chain variable domain of the second immunoglobulin; (viii) a flexible peptide linker sequence comprising the amino acid sequence TPLGDTTHT (SEQ ID NO: 110); and (ix) a self-assembly disassembly (SADA) polypeptide; wherein the heavy chain variable domain of the first immunoglobulin or the heavy chain variable domain of the second immunoglobulin is selected from any one of SEQ ID NOs: 1-3, and/or the light chain variable domain of the first immunoglobulin or the light chain variable domain of the second immunoglobulin is selected from any one of SEQ ID NOs: 4-10.

In certain embodiments of the multi-specific antigen binding fragments disclosed herein, the SADA polypeptide comprises a tetramerization, pentamerization, or hexamerization domain. In some embodiments, the SADA polypeptide comprises a tetramerization domain of any one of p53, p63, p73, hnRNPC, SNA-23, Stefin B, KCNQ4, and CBFA2T1. Additionally or alternatively, in some embodiments, the multi-specific antigen binding fragment comprises an amino acid sequence selected from SEQ ID NOs: 11, 13, 15, 17, 19, or 29-58.

In one aspect, the present disclosure provides a multi-specific antibody comprising a first polypeptide chain, a second polypeptide chain, a third polypeptide chain and a fourth polypeptide chain, wherein the first and second polypeptide chains are covalently bonded to one another, the second and third polypeptide chains are covalently bonded to one another, and the third and fourth polypeptide chain are covalently bonded to one another, and wherein: (a) each of the first polypeptide chain and the fourth polypeptide chain comprises in the N-terminal to C-terminal direction: (i) a light chain variable domain of a first immunoglobulin that is capable of specifically binding to a first epitope; (ii) a light chain constant domain of the first immunoglobulin; (iii) a flexible peptide linker comprising the amino acid sequence $(GGGGS)_3$ (SEQ ID NO: 111); and (iv) a light chain variable domain of a second immunoglobulin that is linked to a complementary heavy chain variable domain of the second immunoglobulin, or a heavy chain variable domain of a second immunoglobulin that is linked to a complementary light chain variable domain of the second immunoglobulin, wherein the light chain and heavy chain variable domains of the second immunoglobulin are capable of specifically binding to a second epitope, and are linked together via a flexible peptide linker comprising the amino acid sequence $(GGGGS)_6$ (SEQ ID NO: 108) to form a single-chain variable fragment; and (b) each of the second polypeptide chain and the third polypeptide chain comprises in the N-terminal to C-terminal direction: (i) a heavy chain variable domain of the first immunoglobulin that is capable of specifically binding to the first epitope; and (ii) a heavy chain constant domain of the first immunoglobulin; and wherein the heavy chain variable domain of the first immunoglobulin is selected from the group consisting of: SEQ ID NOs: 1-3, and/or the light chain variable domain of the first immunoglobulin is selected from the group consisting of: SEQ ID NOs: 4-10.

In some embodiments of the multi-specific antibody or multi-specific antigen binding fragment described herein, the antibody or antigen binding fragment comprises a catalytic antibody, an immune checkpoint inhibitor, or an immune checkpoint activator. In any and all embodiments of the multi-specific antibody or multi-specific antigen binding fragment described herein, the antibody or antigen binding fragment binds to CD3, CD4, CD8, CD20, CD19, CD21, CD23, CD46, CD80, HLA-DR, CD74, CD22, CD14, CD15, CD16, CD123, CD32, CD64, TCR gamma/delta, NKp46, KIR, PD-1, PD-L1, LAG3, CD28, B7H3, STEAP1, HER2, EGFR, CEA, CECAM5, Transferrin receptor, FAP, NKG2D-ligands, TRAIL, FasL, cathepsin G, granzyme, carboxypeptidase, beta-lactamase, DOTA(metal) complex, benzyl-DOTA(metal) complex, proteus-DOTA(metal) complex, NOGADA-proteus-DOTA(metal) complex, Star-DFO (metal) complex, DFO(metal) complex, or a small molecule DOTA hapten. Examples of small molecule DOTA haptens include (i) DOTA-Phe-Lys(HSG)-D-Tyr-Lys(HSG)-$NH_2$; (ii) Ac-Lys(HSG)D-Tyr-Lys(HSG)-Lys(Tscg-Cys)-$NH_2$; (iii) DOTA-D-Asp-D-Lys(HSG)-D-Asp-D-Lys(HSG)-$NH_2$; (iv) DOTA-D-Glu-D-Lys(HSG)-D-Glu-D-Lys(HSG)-$NH_2$; (v) DOTA-D-Tyr-D-Lys(HSG)-D-Glu-D-Lys(HSG)-$NH_2$; (vi) DOTA-D-Ala-D-Lys(HSG)-D-Glu-D-Lys(HSG)-$NH_2$; (vii) DOTA-D-Phe-D-Lys(HSG)-D-Tyr-D-Lys(HSG)-$NH_2$; (viii) Ac-D-Phe-D-Lys(DOTA)-D-Tyr-D-Lys(DOTA)-$NH_2$; (ix) Ac-D-Phe-D-Lys(DTPA)-D-Tyr-D-Lys(DTPA)-$NH_2$; (x) Ac-D-Phe-D-Lys(Bz-DTPA)-D-Tyr-D-Lys(Bz-DTPA)-$NH_2$; (xi) Ac-D-Lys(HSG)-D-Tyr-D-Lys(HSG)-D-Lys(Tscg-Cys)-$NH_2$; (xii) DOTA-D-Phe-D-Lys(HSG)-D-Tyr-D-Lys(HSG)-D-Lys(Tscg-Cys)-$NH_2$; (xiii) (Tscg-Cys)-D-Phe-D-Lys(HSG)-D-Tyr-D-Lys(HSG)-D-Lys(DOTA)-$NH_2$; (xiv) Tscg-D-Cys-D-Glu-D-Lys(HSG)-D-Glu-D-Lys(HSG)-$NH_2$; (xv) (Tscg-Cys)-D-Glu-D-Lys(HSG)-D-Glu-D-Lys(HSG)-$NH_2$; (xvi) Ac-D-Cys-D-Lys(DOTA)-D-Tyr-D-Ala-D-Lys(DOTA)-D-Cys-$NH_2$; (xvii) Ac-D-Cys-D-Lys(DTPA)-D-Tyr-D-Lys(DTPA)-$NH_2$; (xviii) Ac-D-Lys(DTPA)-D-Tyr-D-Lys(DTPA)-D-Lys(Tscg-Cys)-$NH_2$; and (xix) Ac-D-Lys(DOTA)-D-Tyr-D-Lys(DOTA)-D-Lys(Tscg-Cys)-$NH_2$, (xx) BnDOTA, (xxi) DOTA, (xxii) BnDOTA-biotin, and (xxiii) DOTA-biotin. Additionally or alternatively, in some embodiments, the multi-specific antibody or multi-specific antigen binding fragment binds to T cells, B-cells, myeloid cells, plasma cells, or mast-cells.

In one aspect, the present disclosure provides a heterodimeric multi-specific antibody comprising a first polypeptide chain, a second polypeptide chain, a third polypeptide chain and a fourth polypeptide chain, wherein the first and second polypeptide chains are covalently bonded to one another, the second and third polypeptide chains are covalently bonded to one another, and the third and fourth polypeptide chain, and wherein: (a) the first polypeptide chain comprises in the N-terminal to C-terminal direction: (i) a light chain variable domain of a first immunoglobulin (VL-1) that is capable of specifically binding to a first epitope; (ii) a light chain constant domain of the first immunoglobulin (CL-1); (iii) a flexible peptide linker comprising the amino acid sequence $(GGGGS)_3$ (SEQ ID NO: 111); and (iv) a light chain variable domain of a second immunoglobulin (VL-2) that is linked to a complementary heavy chain variable domain of the second immunoglobulin (VH-2), or a heavy chain variable domain of a second immunoglobulin (VH-2) that is linked to a complementary light chain variable domain of the second immunoglobulin (VL-2), wherein VL-2 and VH-2 are capable of specifically binding to a second epitope, and are linked together via a flexible peptide linker comprising the amino acid sequence $(GGGGS)_6$ (SEQ ID NO: 108) to form a single-chain variable fragment; (b) the second polypeptide comprises in the N-terminal to C-terminal direction: (i) a heavy chain variable domain of the first immunoglobulin (VH-1) that is capable of specifically binding to the first epitope; (ii) a first CH1 domain of the first immunoglobulin (CH1-1); and (iii) a first heterodimerization domain of the first immunoglobulin, wherein the first heterodimerization domain is incapable of forming a stable homodimer with another first heterodimerization domain; (c) the third polypeptide comprises in the N-terminal to C-terminal direction: (i) a heavy chain variable domain of a third immunoglobulin (VH-3) that is capable of specifically binding to a third epitope; (ii) a second CH1 domain of the third immunoglobulin (CH1-3); and (iii) a second heterodimerization domain of the third immunoglobulin, wherein the second heterodimerization domain comprises an amino acid sequence or a nucleic acid sequence that is distinct from the first heterodimerization domain of the first immunoglobulin, wherein the second heterodimerization domain is incapable of forming a stable homodimer with another second heterodimerization domain, and wherein the second heterodimerization domain of the third immunoglobulin is configured to form a heterodimer with the first heterodimerization domain of the first immunoglobulin; (d) the fourth polypeptide comprises in the N-terminal to C-terminal direction: (i) a light chain variable domain of the third immunoglobulin (VL-3) that is capable of specifically binding to the third epitope; (ii) a light chain constant domain of the third immunoglobulin (CL-3); (iii) a flexible peptide linker comprising the amino acid sequence $(GGGGS)_3$ (SEQ ID NO: 111); and (iv) a light chain variable domain of a fourth immunoglobulin (VL-4) that is linked to a complementary heavy chain variable domain of the fourth immunoglobulin ($V_H$-4), or a heavy chain variable domain of a fourth immunoglobulin (VH-4) that is linked to a complementary light chain variable domain of the fourth immunoglobulin (VL-4), wherein VL-4 and VH-4 are capable of specifically binding to the fourth epitope, and are linked together via a flexible peptide linker comprising the amino acid sequence $(GGGGS)_6$ (SEQ ID NO: 108) to form a single-chain variable fragment; wherein VL-1 and/or VL-3 comprises a $V_L$ amino acid sequence selected from any one of SEQ ID NOs: 4-10, and wherein VH-1 and/or VH-3 comprises a $V_H$ amino acid sequence selected from any one of SEQ ID NOs: 1-3. In some embodiments, the multi-specific antibody binds to GPA33 and at least one of CD3, CD4, CD8, CD20, CD19, CD21, CD23, CD46, CD80, HLA-DR, CD74, CD22, CD14, CD15, CD16, CD123, CD32, CD64, TCR gamma/delta, NKp46, KIR, PD-1, PD-L1, LAG3, CD28, B7H3, STEAP1, HER2, EGFR, CEA, CECAM5, Transferrin receptor, FAP, NKG2D-ligands, TRAIL, FasL, cathepsin G, granzyme, carboxypeptidase, beta-lactamase, DOTA(metal) complex, benzyl-DOTA(metal) complex, proteus-DOTA(metal) complex, NOGADA-proteus-DOTA(metal) complex, Star-DFO (metal) complex, DFO(metal) complex, or a small molecule DOTA hapten. Examples of small molecule DOTA haptens include (i) DOTA-Phe-Lys(HSG)-D-Tyr-Lys(HSG)-$NH_2$; (ii) Ac-Lys(HSG)D-Tyr-Lys(HSG)-Lys(Tscg-Cys)-$NH_2$; (iii) DOTA-D-Asp-D-Lys(HSG)-D-Asp-D-Lys(HSG)-$NH_2$; (iv) DOTA-D-Glu-D-Lys(HSG)-D-Glu-D-Lys(HSG)-$NH_2$; (v) DOTA-D-Tyr-D-Lys(HSG)-D-Glu-D-Lys(HSG)-$NH_2$; (vi) DOTA-D-Ala-D-Lys(HSG)-D-Glu-D-Lys(HSG)-$NH_2$; (vii) DOTA-D-Phe-D-Lys(HSG)-D-Tyr-D-Lys(HSG)-$NH_2$; (viii) Ac-D-Phe-D-Lys(DOTA)-D-Tyr-D-Lys(DOTA)-$NH_2$; (ix) Ac-D-Phe-D-Lys(DTPA)-D-Tyr-D-Lys(DTPA)-$NH_2$; (x) Ac-D-Phe-D-Lys(Bz-DTPA)-D-Tyr-D-Lys(Bz-DTPA)-$NH_2$; (xi) Ac-D-Lys(HSG)-D-Tyr-D-Lys(HSG)-D-Lys (Tscg-Cys)-$NH_2$; (xii) DOTA-D-Phe-D-Lys(HSG)-D-Tyr-D-Lys(HSG)-D-Lys(Tscg-Cys)-$NH_2$; (xiii) (Tscg-Cys)-D-Phe-D-Lys(HSG)-D-Tyr-D-Lys(HSG)-D-Lys(DOTA)-$NH_2$; (xiv) Tscg-D-Cys-D-Glu-D-Lys(HSG)-D-Glu-D-Lys (HSG)-$NH_2$; (xv) (Tscg-Cys)-D-Glu-D-Lys(HSG)-D-Glu-D-Lys(HSG)-$NH_2$; (xvi) Ac-D-Cys-D-Lys(DOTA)-D-Tyr-D-Ala-D-Lys(DOTA)-D-Cys-$NH_2$; (xvii) Ac-D-Cys-D-Lys (DTPA)-D-Tyr-D-Lys(DTPA)-$NH_2$; (xviii) Ac-D-Lys (DTPA)-D-Tyr-D-Lys(DTPA)-D-Lys(Tscg-Cys)-$NH_2$; and (xix) Ac-D-Lys(DOTA)-D-Tyr-D-Lys(DOTA)-D-Lys(Tscg-Cys)-$NH_2$, (xx) BnDOTA, (xxi) DOTA, (xxii) BnDOTA-biotin, and (xxiii) DOTA-biotin. Additionally or alternatively, in some embodiments, the multi-specific antibody binds to T cells, B-cells, myeloid cells, plasma cells, or mast-cells. In some embodiments of the multi-specific antibody or multi-specific antigen binding fragment described herein, the antibody or antigen binding fragment comprises a catalytic antibody, an immune checkpoint inhibitor, or an immune checkpoint activator.

In any of the above embodiments, the antibody of the present technology lacks $\alpha$-1,6-fucose modifications.

In any of the SADA-polypeptide containing multi-specific antibodies or antigen binding fragments disclosed herein, the antibody or antigen binding fragment does not cross into gut epithelium or gut lumen when the antibody or antigen binding fragment is intravenously or intraperitoneally administered to a subject.

In one aspect, the present disclosure provides a recombinant nucleic acid sequence encoding any of the antibodies or antigen binding fragments described herein. In some embodiments, the recombinant nucleic acid sequence is selected from the group consisting of: SEQ ID NOs: 12, 14, 16, 18, 20, 22, 24, 26 and 28.

In another aspect, the present disclosure provides a host cell or vector comprising any of the recombinant nucleic acid sequences disclosed herein.

In one aspect, the present disclosure provides a composition comprising an antibody or antigen binding fragment of the present technology and a pharmaceutically-acceptable carrier, wherein the antibody or antigen binding fragment is optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

In another aspect, the present disclosure provides a method for treating a GPA33-associated cancer in a subject in need thereof, comprising administering to the subject an effective amount of any and all embodiments of the antibodies or antigen binding fragments of the present technology. In some embodiments, the GPA33-associated cancer is colorectal cancer, T cell leukemia, *Pseudomyxoma peritonei*, appendiceal cancer, pancreatic cancer, or gastric cancer. The GPA33-associated cancer may be colorectal cancer with a MSI genotype or a MSS genotype. Additionally or alternatively, in some embodiments, the colorectal cancer is associated with a KRAS G12D mutation or a p53 mutation.

Additionally or alternatively, in some embodiments of the method, the antibody or antigen binding fragment is administered to the subject separately, sequentially or simultaneously with an additional therapeutic agent. Examples of additional therapeutic agents include one or more of alkylating agents, platinum agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents, T cells, or an immuno-modulating/stimulating antibody.

In another aspect, the present disclosure provides a method for detecting a tumor in a subject in vivo comprising (a) administering to the subject an effective amount of the antibody or antigen binding fragment of the present technology, wherein the antibody or antigen binding fragment is configured to localize to a tumor expressing GPA33 and is labeled with a radioisotope; and (b) detecting the presence of a tumor in the subject by detecting radioactive levels emitted by the antibody or antigen binding fragment that are higher than a reference value. In some embodiments, the subject is diagnosed with or is suspected of having cancer. Radioactive levels emitted by the antibody or antigen binding fragment may be detected using positron emission tomography or single photon emission computed tomography.

Additionally or alternatively, in some embodiments, the method further comprises administering to the subject an effective amount of an immunoconjugate comprising an antibody or antigen binding fragment of the present technology conjugated to a radionuclide. In some embodiments, the radionuclide is an alpha particle-emitting isotope, a beta particle-emitting isotope, an Auger-emitter, or any combination thereof. Examples of beta particle-emitting isotopes include $^{86}Y$, $^{90}Y$, $^{89}Sr$, $^{165}Dy$, $^{186}Re$, $^{188}Re$, $^{177}Lu$, and $^{67}Cu$. In some embodiments of the method, nonspecific FcR-dependent binding in normal tissues is eliminated or reduced (e.g., via N297A mutation in Fc region, which results in aglycosylation).

Also disclosed herein are kits for the detection and/or treatment of GPA33-associated cancers, comprising at least one immunoglobulin-related composition of the present technology (e.g., any antibody or antigen binding fragment described herein), or a functional variant (e.g., substitutional variant) thereof and instructions for use. In certain embodiments, the immunoglobulin-related composition is coupled to one or more detectable labels. In one embodiment, the one or more detectable labels comprise a radioactive label, a fluorescent label, or a chromogenic label.

Additionally or alternatively, in some embodiments, the kit further comprises a secondary antibody that specifically binds to an anti-GPA33 immunoglobulin-related composition described herein. In some embodiments, the secondary antibody is coupled to at least one detectable label selected from the group consisting of a radioactive label, a fluorescent label, or a chromogenic label.

In another aspect, the present disclosure provides a method for selecting a subject for pretargeted radioimmunotherapy comprising (a) administering to the subject an effective amount of a complex comprising a radiolabeled DOTA hapten and a multi-specific antibody or antigen binding fragment of the present technology that binds to the radiolabeled DOTA hapten and a GPA33 antigen, wherein the complex is configured to localize to a tumor expressing the GPA33 antigen recognized by the multi-specific antibody or antigen binding fragment of the complex; (b) detecting radioactive levels emitted by the complex; and (c) selecting the subject for pretargeted radioimmunotherapy when the radioactive levels emitted by the complex are higher than a reference value.

In one aspect, the present disclosure provides a method for increasing tumor sensitivity to radiation therapy in a subject diagnosed with a GPA33-associated cancer comprising administering to the subject an effective amount of a complex comprising a radiolabeled-DOTA hapten and a multi-specific antibody or antigen binding fragment of the present technology that recognizes and binds to the radiolabeled-DOTA hapten and a GPA33 target antigen, wherein the complex is configured to localize to a tumor expressing the GPA33 target antigen recognized by the multi-specific antibody or antigen binding fragment of the complex.

In another aspect, the present disclosure provides a method for treating cancer in a subject in need thereof comprising administering to the subject an effective amount of a complex comprising a radiolabeled-DOTA hapten and a multi-specific antibody or antigen binding fragment of the present technology that recognizes and binds to the radiolabeled-DOTA hapten and a GPA33 target antigen, wherein the complex is configured to localize to a tumor expressing the GPA33 target antigen recognized by the multi-specific antibody or antigen binding fragment of the complex.

In any of the above embodiments of the methods disclosed herein, the complex is administered intravenously, intramuscularly, intraarterially, intrathecally, intracapsularly, intraorbitally, intradermally, intraperitoneally, transtracheally, subcutaneously, intracerebroventricularly, orally, intratumorally, or intranasally. In some embodiments of the methods disclosed herein, the subject is human. Additionally or alternatively, in any of the above embodiments of the methods disclosed herein, the radiolabeled-DOTA hapten comprises $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, $^{255}$Fm, $^{86}$Y, $^{90}$Y, $^{89}$Sr, $^{165}$Dy, $^{186}$Re, $^{188}$Re, $^{177}$Lu, $^{67}$Cu, $^{111}$In, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, $^{203}$Pb, $^{68}$Ga, $^{227}$Th, or $^{64}$Cu, and optionally comprises an alpha particle-emitting isotope, a beta particle-emitting isotope, or an Auger-emitter.

In one aspect, the present disclosure provides a method for increasing tumor sensitivity to radiation therapy in a subject diagnosed with a GPA33-associated cancer comprising (a) administering an effective amount of an anti-DOTA multi-specific antibody or antigen binding fragment of the present technology to the subject, wherein the anti-DOTA multi-specific antibody or antigen binding fragment is configured to localize to a tumor expressing a GPA33 target antigen; and (b) administering an effective amount of a radiolabeled-DOTA hapten to the subject, wherein the radiolabeled-DOTA hapten is configured to bind to the anti-DOTA multi-specific antibody or antigen binding fragment. In another aspect, the present disclosure provides a method for treating cancer in a subject in need thereof comprising (a) administering an effective amount of an anti-DOTA multi-specific antibody or antigen binding fragment of the present technology to the subject, wherein the anti-DOTA multi-specific antibody or antigen binding fragment is configured to localize to a tumor expressing a GPA33 target antigen; and (b) administering an effective amount of a radiolabeled-DOTA hapten to the subject, wherein the radiolabeled-DOTA hapten is configured to bind to the anti-DOTA multi-specific antibody or antigen binding fragment. In some embodiments, the methods of the present technology further comprise administering an effective amount of a clearing agent to the subject prior to administration of the radiolabeled-DOTA hapten.

Additionally or alternatively, in any of the above embodiments of the methods disclosed herein, the radiolabeled-DOTA hapten comprises $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, $^{255}$Fm, $^{86}$Y, $^{90}$Y, $^{89}$Sr, $^{165}$Dy, $^{186}$Re, $^{188}$Re, $^{177}$Lu, $^{67}$Cu, $^{111}$In, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, $^{203}$Pb, $^{68}$Ga, $^{227}$Th, or $^{64}$Cu, and optionally comprises an alpha particle-emitting isotope, a beta particle-emitting isotope, or an Auger-emitter. In any of the above embodiments of the methods disclosed herein, the subject is human.

In one aspect, the present disclosure provides an ex vivo armed T cell that is coated or complexed with an effective amount of an anti-GPA33 multi-specific antibody of the present technology, wherein the anti-GPA33 multi-specific antibody includes a CD3 binding domain. In some embodiments, the anti-GPA33 multi-specific antibody is an immunoglobulin comprising two heavy chains and two light chains, wherein each of the light chains is fused to a single chain variable fragment (scFv), and wherein at least one scFv of the anti-GPA33 multi-specific antibody comprises the CD3 binding domain. Also disclosed herein are methods for treating a GPA33-associated cancer in a subject in need thereof comprising administering to the subject an effective amount of the ex vivo armed T cell disclosed herein.

BRIEF DESCRIPTION OF THE DRAWINGS

FIG. 1 shows the design of two bispecific antibodies that comprise the anti-GPA33 sequences described herein.

FIGS. 2A-2B represent the SEC-HPLC purity of clones TC170 and TC213 after repeated freeze and thaw cycles, indicated by the relative fraction of total protein in the correct size (FIG. 2A) and the concentration of the antibody (FIG. 2B). FIGS. 2C-2D represent the stability of clones TC170, TC171, BC015 and BC016 at 37° C. (FIG. 2C) or 40° C. (FIG. 2D), indicated by the relative fraction of total protein in the correct size.

FIG. 3A shows the binding kinetics of BC155, BC015 and BC016 analyzed by surface plasmon resonance (SPR) at 25° C. FIG. 3B shows the binding kinetics of TC159, TC160, TC170, and TC171 analyzed by surface plasmon resonance (SPR) at 25° C.

FIGS. 6A-6C show the images of mice or non-human primate (NHP) treated with TC170. FIG. 6A shows SPECT images of xenograft tumor (SW1222) bearing mice administered intravenously with (1) [$^{177}$Lu]DOTA alone (at T=0), (2) BC015 (at T=−48 h), a clearing agent (T=−4 h) and [$^{177}$Lu]DOTA (T=0), or (3) BC015 (T=−48) and [$^{177}$Lu] DOTA (T=0). Images were taken 24 hours after the injection of [$^{177}$Lu]DOTA (T=24 h). FIG. 6B shows SPECT images of mice bearing intraperitoneal tumors and treated with TC170 (T=0) and [$^{177}$Lu]BnDOTA (T=48 hr). Measurements reflect mean signal intensity by SPECT imaging. FIG. 6C shows the PET/CT images of an NHP injected with either: [$^{86}$Y]DOTA alone (A), TC170 and [$^{86}$Y]DOTA (B, 24 hours apart) or a separate GPA33 IgG-[L]-scFv and [$^{86}$Y]DOTA (C, 24 hours apart). All reagents were administered intravenously. Images were acquired 24 hours after the administration of [$^{86}$Y]DOTA. Images are normalized to the same scaling (SUV=3). Uptake values (% ID) were calculated computationally from these images.

FIG. 9 shows the yield, and stability after initial purification, after repeated free-thaw cycles, and after 32 days at 40° C. of the various $V_H$ and $V_L$ pairings of the anti-GPA33 antibody clones of the present technology.

FIG. 10 shows binding affinity of the various $V_H$ and $V_L$ pairings of the anti-GPA33 antibody clones of the present technology to GPA33 protein as determined by SPR analysis.

FIG. 11 shows binding affinity of the various $V_H$ and $V_L$ pairings of the anti-GPA33 antibody clones of the present technology to GPA33+ cell lines as determined by SPR analysis.

FIG. 12 shows the amino acid sequences of three rehumanized variable heavy immunoglobulin domains ($V_H$) (SEQ ID NOs: 1-3). Amino acid sequences of $V_H$-CDR1-3 are underlined.

FIG. 13 shows the amino acid sequences of seven rehumanized variable light immunoglobulin domains ($V_L$) (SEQ ID NOs: 4-10). Amino acid sequences of $V_L$-CDR1-3 are underlined.

FIG. 14 shows the amino acid and nucleic acid sequences of TC170, a GPA33×DOTA SADA clone (SEQ ID NO: 11 and SEQ ID NO: 12, respectively). $V_H$ and $V_L$ amino acid sequences are italicized, and $V_H$-CDR1-3 and $V_L$-CDR1-3 amino acid sequences of the GPA33 antigen binding fragment are underlined with solid lines. Amino acid sequences of linkers and spacers are bolded. P53 SADA polypeptide amino acid sequence is underlined with a dashed line.

FIG. 15 shows the amino acid and nucleic acid sequences of TC171, a GPA33×DOTA SADA clone (SEQ ID NO: 13 and SEQ ID NO: 14, respectively). $V_H$ and $V_L$ amino acid sequences are italicized, and $V_H$-CDR1-3 and $V_L$-CDR1-3 amino acid sequences of the GPA33 antigen binding fragment are underlined with solid lines. Amino acid sequences of linkers and spacer are bolded. P53 SADA polypeptide amino acid sequence is underlined with a dashed line.

FIG. 16 shows the amino acid and nucleic acid sequences of TC213, a GPA33×DOTA SADA clone (SEQ ID NO: 15 and SEQ ID NO: 16, respectively). $V_H$ and $V_L$ amino acid sequences are italicized, and $V_H$-CDR1-3 and $V_L$-CDR1-3 amino acid sequences of the GPA33 antigen binding fragment are underlined with solid lines. Amino acid sequences of linkers and spacer are bolded. P53 SADA polypeptide amino acid sequence is underlined with a dashed line.

FIG. 17 shows the amino acid and nucleic acid sequences of TC234, a GPA33×DOTA SADA clone (SEQ ID NO: 17 and SEQ ID NO: 18, respectively). $V_H$ and $V_L$ amino acid sequences are italicized, and $V_H$-CDR1-3 and $V_L$-CDR1-3 amino acid sequences of the GPA33 antigen binding fragment are underlined with solid lines. Amino acid sequences of linkers and spacer are bolded. P53 SADA polypeptide amino acid sequence is underlined with a dashed line.

FIG. 18 shows the amino acid and nucleic acid sequences of TC235, a GPA33×DOTA SADA clone (SEQ ID NO: 19 and SEQ ID NO: 20, respectively). $V_H$ and $V_L$ amino acid sequences are italicized, and $V_H$-CDR1-3 and $V_L$-CDR1-3 amino acid sequences of the GPA33 antigen binding fragment are underlined with solid lines. Amino acid sequences of linkers and spacer are bolded. P53 SADA polypeptide amino acid sequence is underlined with a dashed line.

FIG. 19 shows the light chain (LC) amino acid and nucleic acid sequences of BC015, a GPA33×DOTA IgG-[L]-scFv clone (SEQ ID NO: 21 and SEQ ID NO: 22, respectively). The $V_L$ amino acid sequences are italicized, and $V_L$-CDR1-3 amino acid sequences of the GPA33 antigen binding fragment are further underlined. Amino acid sequences of linkers are bolded. BC015 may interchangeably referred to herein as BC177.

FIG. 20 shows the heavy chain (HC) amino acid and nucleic acid sequences of BC015, a GPA33×DOTA IgG-[L]-scFv clone (SEQ ID NO: 23 and SEQ ID NO: 24, respectively). The $V_H$ amino acid sequence is italicized, and $V_H$-CDR1-3 amino acid sequences are further underlined. Amino acid sequences of linkers are bolded. BC015 may interchangeably referred to herein as BC177.

FIG. 21 shows the light chain (LC) amino acid and nucleic acid sequences of BC016, a GPA33×DOTA IgG-[L]-scFv clone (SEQ ID NO: 25 and SEQ ID NO: 26, respectively). The $V_L$ amino acid sequences are italicized, and $V_L$-CDR1-3 amino acid sequences of the GPA33 antigen binding fragment are further underlined. Amino acid sequences of linkers are bolded.

FIG. 22 shows the heavy chain (HC) amino acid and nucleic acid sequences of BC016, a GPA33×DOTA IgG-[L]-scFv clone (SEQ ID NO: 27 and SEQ ID NO: 28, respectively). The $V_H$ amino acid sequence is italicized, and $V_H$-CDR1-3 amino acid sequences are further underlined. Amino acid sequences of linkers are bolded.

FIG. 23 shows the amino acid sequences of TC252-TC263, GPA33×CD3 SADA clones (SEQ ID NOs: 29-40). $V_H$ and $V_L$ amino acid sequences are italicized, and $V_H$-CDR1-3 and $V_L$-CDR1-3 amino acid sequences of the GPA33 antigen binding fragment are further underlined with solid lines. Amino acid sequences of linkers and spacer are bolded. P53 SADA polypeptide amino acid sequence is underlined with a dashed line.

FIG. 24 shows the amino acid sequences of TC264-TC267, GPA33×HER2×DOTA SADA clones (SEQ ID NOs: 41-44). $V_H$ and $V_L$ amino acid sequences are italicized. Amino acid sequences of linkers and spacer are bolded. P53 SADA polypeptide amino acid sequence is underlined with a dashed line.

FIG. 25 shows the amino acid sequences of TC268-TC279, GPA33×HER2×CD3 SADA clones (SEQ ID NOs: 45-56). $V_H$ and $V_L$ amino acid sequences are italicized. Amino acid sequences of linkers and spacer are bolded. P53 SADA polypeptide amino acid sequence is underlined with a dashed line.

FIG. 26 shows the amino acid sequence of TC280, a GPA33×CD276×DOTA SADA clone (SEQ ID NO: 57).). $V_H$ and $V_L$ amino acid sequences are italicized. Amino acid sequences of linkers and spacer are bolded. P53 SADA polypeptide amino acid sequence is underlined with a dashed line.

FIG. 27 shows the amino acid sequence of TC281, a GPA33×CD276×CD3 SADA clone (SEQ ID NO: 58). $V_H$ and $V_L$ amino acid sequences are italicized. Amino acid sequences of linkers and spacer are bolded. P53 SADA polypeptide amino acid sequence is underlined with a dashed line.

FIG. 28 shows the LC and HC amino acid sequences of GPA33×CD3 IgG-[L]-scFv clones BC369 (SEQ ID NOs: 59-60, respectively), BC373 (SEQ ID NOs: 61-62, respectively) and BC377 (SEQ ID NOs: 63-64, respectively). The $V_H$ and $V_L$ amino acid sequences are italicized. Amino acid sequences of linkers are bolded.

FIG. 29 shows amino acid sequences of the first LC, second LC, first HC and second HC of HD152, a GPA33×HER2×DOTA IgG-L-scFv antibody (SEQ ID NO: 65, SEQ ID NO: 66, SEQ ID NO: 67, and SEQ ID NO: 68, respectively).

FIG. 30 shows amino acid sequences of the first LC, second LC, first HC and second HC of HD156, a GPA33×HER2×CD3 IgG-L-scFv antibody (SEQ ID NO: 69, SEQ ID NO: 70, SEQ ID NO: 71, and SEQ ID NO: 72 respectively).

FIG. 31 shows amino acid sequences of the first LC, second LC, first HC and second HC of HD160, a GPA33×HER2×CD3 IgG-L-scFv antibody (SEQ ID NO: 73, SEQ ID NO: 74, SEQ ID NO: 75, and SEQ ID NO: 76, respectively).

FIG. 32 shows amino acid sequences of the first LC, second LC, first HC and second HC of HD164, a GPA33×HER2×CD3 IgG-L-scFv antibody (SEQ ID NO: 77, SEQ ID NO: 78, SEQ ID NO: 79, and SEQ ID NO: 80, respectively).

FIG. 33 shows the LC and HC amino acid sequences of BC105 (SEQ ID NO: 98, SEQ ID NO: 99), a previously described clone based on GPA33×DOTA IgG-[L]-scFv platform. The $V_H$ and $V_L$ amino acid sequences are italicized. Amino acid sequences of linkers are bolded.

FIG. 34 shows the LC and HC amino acid sequences of BC155 (SEQ ID NO: 102, SEQ ID NO: 103), a previously described clone based on GPA33×DOTA IgG-[L]-scFv platform. The $V_H$ and $V_L$ amino acid sequences are italicized. Amino acid sequences of linkers are bolded.

FIG. 35 shows the amino acid sequence of TC159 (SEQ ID NO: 104), a previously described clone based on GPA33×DOTA SADA platform. $V_H$ and $V_L$ amino acid sequences are italicized, and $V_H$-CDR1-3 and $V_L$-CDR1-3 amino acid sequences are further underlined with solid lines. Amino acid sequences of linkers and spacer are bolded. P53 SADA polypeptide amino acid sequence is underlined with a dashed line.

FIG. 36 shows the amino acid sequence of TC160 (SEQ ID NO: 105), a previously described clone based on GPA33×DOTA SADA platform. $V_H$ and $V_L$ amino acid sequences are italicized, and $V_H$-CDR1-3 and $V_L$-CDR1-3 amino acid sequences are further underlined with solid lines. Amino acid sequences of linkers and spacer are bolded. P53 SADA polypeptide amino acid sequence is underlined with a dashed line.

FIG. 37 shows antibody characteristics of clones TC159, TC160, TC170 and TC171 during expression and purification.

FIG. 38A shows the binding affinity of IgG-L-scFv bispecific antibody clones BC105, BC155, BC015 and BC016 to GPA33 by SPR.

FIG. 38B shows the binding affinity of SADA bispecific antibody clones TC159, TC160, TC170, TC171, TC213, TC234, and TC235 to GPA33 by SPR.

FIG. 39 shows binding affinity of SADA bispecific antibody clones TC159, TC160, TC170, TC171, TC213, TC234, and TC235 to GPA33+ cell lines.

FIGS. 40AC-40E show the effects of $^{225}$Ac-*Proteus* DOTA PRIT with BC177, TC170, and BC105 on white blood cell (WBC) counts, platelet counts, and red blood cell (RBC) counts, respectively. BC015 may interchangeably referred to herein as BC177.

DETAILED DESCRIPTION

Figure 1A:
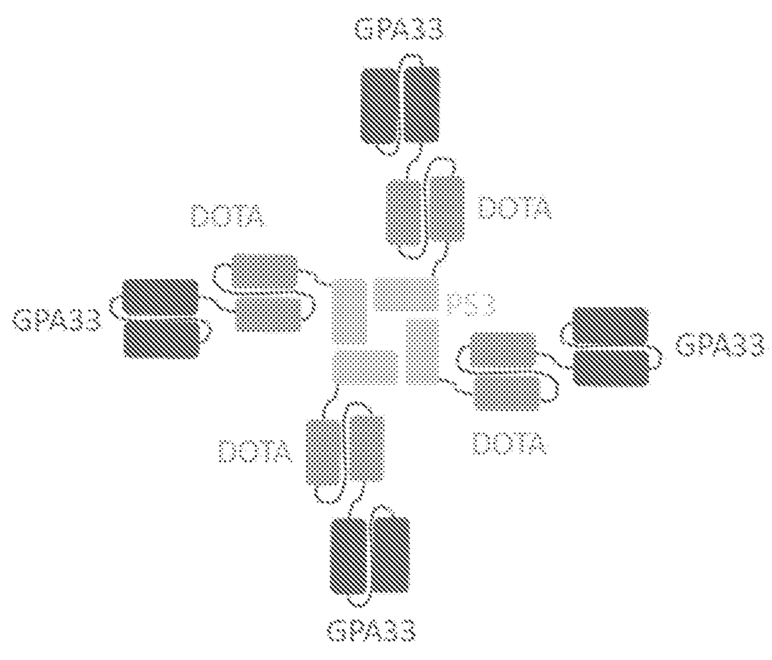
FIG. 1A shows the design of a Self-Assembling-Self-Disassembling bispecific antibody (GPA33×DOTA SADA).

It is to be appreciated that certain aspects, modes, embodiments, variations and features of the present methods are described below in various levels of detail in order to provide a substantial understanding of the present technology. It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

The present disclosure generally provides immunoglobulin-related compositions (e.g., antibodies or antigen binding fragments thereof), which can specifically bind to GPA33 polypeptides. The immunoglobulin-related compositions of the present technology are useful in methods for detecting or treating GPA33-associated cancers in a subject in need thereof. Accordingly, the various aspects of the present methods relate to the preparation, characterization, and manipulation of anti-GPA33 antibodies. The immunoglobulin-related compositions of the present technology are useful alone or in combination with additional therapeutic agents for treating cancer. In some embodiments, the immunoglobulin-related composition is a monoclonal antibody, a humanized antibody, a chimeric antibody, a bispecific antibody, or a multi-specific antibody.

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization; Anderson* (1999) *Nucleic Acid Hybridization*; Hames and Higgins eds. (1984) *Transcription and Translation; Immobilized Cells and Enzymes* (IRL Press (1986)); Perbal (1984)*A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*. Methods to detect and measure levels of polypeptide gene expression products (i.e., gene translation level) are well-known in the art and include the use of polypeptide detection methods such as antibody detection and quantification techniques. (See also, Strachan & Read, *Human Molecular Genetics*, Second Edition. (John Wiley and Sons, Inc., NY, 1999)).

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including but not limited to, orally, intranasally, parenterally (intravenously, intramuscularly, intraperitoneally, or subcutaneously), rectally, intrathecally, intratumorally or topically. Administration includes self-administration and the administration by another.

An "adjuvant" refers to one or more substances that cause stimulation of the immune system. In this context, an adjuvant is used to enhance an immune response to one or more vaccine antigens or antibodies. An adjuvant may be administered to a subject before, in combination with, or after administration of the vaccine. Examples of chemical compounds used as adjuvants include aluminum compounds, oils, block polymers, immune stimulating complexes, vitamins and minerals (e.g., vitamin E, vitamin A, selenium, and vitamin B12), Quil A (saponins), bacterial and fungal cell wall components (e.g., lipopolysaccarides, lipoproteins, and glycoproteins), hormones, cytokines, and co-stimulatory factors.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. As used herein, "antibodies" (includes intact immunoglobulins) and "antigen binding fragments" specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4$ $M^{-1}$ greater or at least $10^5$ $M^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., *Immunology,* 3rd Ed., W. H. Freeman & Co., New York, 1997.

More particularly, antibody refers to a polypeptide ligand comprising at least a light chain immunoglobulin variable region or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Typically, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds GPA33 protein will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). "Immunoglobulin-related compositions" as used herein, refers to antibodies (including monoclonal antibodies, polyclonal antibodies, humanized antibodies, chimeric antibodies, recombinant antibodies, multi-specific antibodies, bispecific antibodies, etc.,) as well as antibody fragments. An antibody or antigen binding fragment thereof specifically binds to an antigen.

As used herein, the term "antibody-related polypeptide" means antigen-binding antibody fragments, including single-chain antibodies, that can comprise the variable region(s) alone, or in combination, with all or part of the following polypeptide elements: hinge region, $CH_1$, $CH_2$, and $CH_3$ domains of an antibody molecule. Also included in the technology are any combinations of variable region(s) and hinge region, $CH_1$, $CH_2$, and $CH_3$ domains. Antibody-related molecules useful in the present methods, e.g., but are not limited to, Fab, Fab' and $F(ab')_2$, Fd, single-chain Fvs (scFv), single-chain antibodies, disulfide-linked Fvs (sdFv) and fragments comprising either a $V_L$ or $V_H$ domain. Examples include: (i) a Fab fragment, a monovalent fragment consisting of the $V_L$, $V_H$, CL and $CH_1$ domains; (ii) a $F(ab')_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., *Nature* 341: 544-546, 1989), which consists of a \Tx domain; and (vi) an isolated complementarity determining region (CDR). As such "antibody fragments" or "antigen binding fragments" can comprise a portion of a full length antibody, generally the antigen binding or variable region thereof. Examples of antibody fragments or antigen binding fragments include Fab, Fab', $F(ab')_2$, and Fv fragments; diabodies; linear antibodies; single-chain antibody molecules; and multi-specific antibodies formed from antibody fragments.

"Bispecific antibody" or "BsAb", as used herein, refers to an antibody that can bind simultaneously to two targets that have a distinct structure, e.g., two different target antigens, two different epitopes on the same target antigen, or a hapten and a target antigen or epitope on a target antigen. A variety of different bispecific antibody structures are known in the art. In some embodiments, each antigen binding moiety in a bispecific antibody includes $V_H$ and/or $V_L$ regions; in some such embodiments, the $V_H$ and/or $V_L$ regions are those found in a particular monoclonal antibody. In some embodiments, the bispecific antibody contains two antigen binding moieties, each including $V_H$ and/or $V_L$ regions from different monoclonal antibodies. In some embodiments, the bispecific antibody contains two antigen binding moieties, wherein one of the two antigen binding moieties includes an immunoglobulin molecule having $V_H$ and/or $V_L$ regions that contain CDRs from a first monoclonal antibody, and the other antigen binding moiety includes an antibody fragment (e.g., Fab, F(ab'), $F(ab')_2$, Fd, Fv, dAB, scFv, etc.) having $V_H$ and/or $V_L$ regions that contain CDRs from a second monoclonal antibody.

As used herein, the term "antibody-dependent cell-mediated cytotoxicity" or "ADCC", refers to a mechanism of cell-mediated immune defense whereby an effector cell of the immune system actively lyses a target cell, such as a tumor cell, whose membrane-surface antigens have been bound by antibodies, such as anti-GPA33 antibodies.

As used herein, an "antigen" refers to a molecule to which an antibody (or antigen binding fragment thereof) can selectively bind. The target antigen may be a protein, carbohydrate, nucleic acid, lipid, hapten, or other naturally occurring or synthetic compound. In some embodiments, the target antigen may be a polypeptide (e.g., a GPA33 polypeptide). An antigen may also be administered to an animal to generate an immune response in the animal.

The term "antigen binding fragment" refers to a fragment of the whole immunoglobulin structure which possesses a part of a polypeptide responsible for binding to antigen. Examples of the antigen binding fragment useful in the present technology include scFv, $(scFv)_2$, scFvFc, Fab, Fab' and $F(ab')_2$, but are not limited thereto. Any of the above-noted antibody fragments are obtained using conventional techniques known to those of skill in the art, and the fragments are screened for binding specificity and neutralization activity in the same manner as are intact antibodies.

As used herein, "binding affinity" means the strength of the total noncovalent interactions between a single binding site of a molecule (e.g., an antibody) and its binding partner (e.g., an antigen or antigenic peptide). The affinity of a molecule X for its partner Y can generally be represented by the dissociation constant ($K_D$). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

As used herein, the term "biological sample" means sample material derived from living cells. Biological samples may include tissues, cells, protein or membrane extracts of cells, and biological fluids (e.g., ascites fluid or cerebrospinal fluid (CSF)) isolated from a subject, as well as tissues, cells and fluids present within a subject. Biological samples of the present technology include, but are not limited to, samples taken from breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, thymus, blood, hair, buccal, skin, serum, plasma, CSF, semen, prostate fluid, seminal fluid, urine, feces, sweat, saliva, sputum, mucus, bone marrow, lymph, and tears. Biological samples can also be obtained from biopsies of internal organs or from cancers. Biological samples can be obtained from subjects for diagnosis or research or can be obtained from non-diseased individuals, as controls or for basic research. Samples may be obtained by standard methods including, e.g., venous puncture and surgical biopsy. In certain embodiments, the biological sample is a tissue sample obtained by needle biopsy.

As used herein, the term "CDR grafting" means replacing at least one CDR of an "acceptor" antibody by a CDR "graft" from a "donor" antibody possessing a desirable antigen specificity. As used herein, the term "CDR-grafted antibody" means an antibody in which at least one CDR of an "acceptor" antibody is replaced by a CDR "graft" from a "donor" antibody possessing a desirable antigen specificity.

As used herein, the term "chimeric antibody" means an antibody in which the Fc constant region of a monoclonal antibody from one species (e.g., a mouse Fc constant region) is replaced, using recombinant DNA techniques, with an Fc constant region from an antibody of another species (e.g., a human Fc constant region). See generally, Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 0125,023; Better et al., *Science* 240: 1041-1043, 1988; Liu et al., *Proc. Natl. Acad. Sci. USA* 84: 3439-3443, 1987; Liu et al., *J. Immunol* 139: 3521-3526, 1987; Sun et al., *Proc. Natl. Acad. Sci. USA* 84: 214-218, 1987; Nishimura et al., *Cancer Res* 47: 999-1005, 1987; Wood et al., *Nature* 314: 446-449, 1885; and Shaw et al., *J. Natl. Cancer Inst.* 80: 1553-1559, 1988.

As used herein, a "clearing agent" is an agent that binds to excess bispecific antibody that is present in the blood compartment of a subject to facilitate rapid clearance via kidneys. The use of the clearing agent prior to hapten administration (e.g., DOTA) facilitates better tumor-to-background ratios in pretargeted radioimmunotherapy (PRIT) systems. Examples of clearing agents include 500 kD-dextran-DOTA-Bn(Y) (Orcutt et al., *Mol Cancer Ther.* 11(6): 1365-1372 (2012)), 500 kD aminodextran-DOTA conjugate, antibodies against the pretargeting antibody, etc.

As used herein, the term "complement-dependent cytotoxicity" or "CDC" generally refers to an effector function of IgG and IgM antibodies, which trigger classical complement pathway when bound to a surface antigen, inducing formation of a membrane attack complex and target cell lysis. The antibody of the present invention, by binding to GPA33, induces CDC against cancer cells.

As used herein, the term "conjugated" refers to the association of two molecules by any method known to those in the art. Suitable types of associations include chemical bonds and physical bonds. Chemical bonds include, for example, covalent bonds and coordinate bonds. Physical bonds include, for instance, hydrogen bonds, dipolar interactions, van der Waal forces, electrostatic interactions, hydrophobic interactions and aromatic stacking.

As used herein, the term "consensus FR" means a framework (FR) antibody region in a consensus immunoglobulin sequence. The FR regions of an antibody do not contact the antigen.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, the term "diabodies" refers to small antibody fragments with two antigen-binding sites, which fragments comprise a heavy-chain variable domain ($V_H$) connected to a light-chain variable domain ($V_L$) in the same polypeptide chain ($V_H V_L$). By using a linker that is too short to allow pairing between the two domains on the same chain, the domains are forced to pair with the complementary domains of another chain and create two antigen binding sites. Diabodies are described more fully in, e.g., EP 404,097; WO 93/11161; and Hollinger et al., *Proc Natl Acad Sci USA,* 90: 6444-6448 (1993).

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition described herein. As used herein, a "therapeutically effective amount" of a composition refers to composition levels in which the physiological effects of a disease or condition are ameliorated or eliminated. A therapeutically effective amount can be given in one or more administrations.

As used herein, the term "effector cell" means an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fc receptors and carry out specific immune functions. An effector cell can induce antibody-dependent cell-mediated cytotoxicity (ADCC), e.g., a neutrophil capable of inducing ADCC. For example, monocytes, macrophages, neutrophils, eosinophils, and lymphocytes which express FcαR are involved in specific killing of target cells and presenting antigens to other components of the immune system, or binding to cells that present antigens.

As used herein, the term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. In some embodiments, an "epitope" of the GPA33 protein is a region of the protein to which the anti-GPA33 antibodies of the present technology specifically bind. In some embodiments, the epitope is a conformational epitope or a non-conformational epitope. To screen for anti-GPA33 antibodies which bind to an epitope, a routine cross-blocking assay such as that described in Antibodies, *A Laboratory Manual*, Cold Spring Harbor Laboratory, Ed Harlow and David Lane (1988), can be performed. This assay can be used to determine if an anti-GPA33 antibody binds the same site or epitope as an anti-GPA33 antibody of the present technology. Alternatively, or additionally, epitope mapping can be performed by methods known in the art. For example, the antibody sequence can be mutagenized such as by alanine scanning, to identify contact residues. In a different method, peptides corresponding to different regions of GPA33 protein can be used in competition assays with the test antibodies or with a test antibody and an antibody with a characterized or known epitope.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gene" means a segment of DNA that contains all the information for the regulated biosynthesis of an RNA product, including promoters, exons, introns, and other untranslated regions that control expression.

As used herein, "homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, "humanized" forms of non-human (e.g., murine) antibodies are chimeric antibodies which contain minimal sequence derived from non-human immunoglobulin. For the most part, humanized antibodies are human immunoglobulins in which hypervariable region residues of the recipient are replaced by hypervariable region residues from a non-human species (donor antibody) such as mouse, rat, rabbit or nonhuman primate having the desired specificity, affinity, and capacity. In some embodiments, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains (e.g., Fab, Fab', $F(ab')_2$, or Fv), in which all or substantially all of the hypervariable loops correspond to those of a non-human immunoglobulin and all or substantially all of the FR regions are those of a human immunoglobulin consensus FR sequence although the FR regions may include one or more amino acid substitutions that improve binding affinity. The number of these amino acid substitutions in the FR are typically no more than 6 in the H chain, and in the L chain, no more than 3. The humanized antibody optionally may also comprise at least a portion of an immunoglobulin constant region (Fc), typically that of a human immunoglobulin. For further details, see Jones et al., *Nature* 321:

522-525 (1986); Reichmann et al., *Nature* 332:323-329 (1988); and Presta, *Curr. Op. Struct. Biol.* 2:593-596 (1992). See e.g., Ahmed & Cheung, *FEBS Letters* 588(2):288-297 (2014). By way of example, a humanized version of a murine antibody to a given antigen has on both of its heavy and light chains (1) constant regions of a human antibody; (2) framework regions from the variable domains of a human antibody; and (3) CDRs from the murine antibody. When necessary, one or more residues in the human framework regions can be changed to residues at the corresponding positions in the murine antibody so as to preserve the binding affinity of the humanized antibody to the antigen. This change is sometimes called "back mutation." Similarly, forward mutations may be made to revert back to murine sequence for a desired reason, e.g., stability or affinity to antigen.

As used herein, the term "hypervariable region" refers to the amino acid residues of an antibody which are responsible for antigen-binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest,* 5th Ed. Public Health Service, National Institutes of Health, Bethesda, MD. (1991)) and/or those residues from a "hypervariable loop" (e.g., residues 26-32 (L1), 50-52 (L2) and 91-96 (L3) in the $V_L$, and 26-32 (H1), 52A-55 (H2) and 96-101 (H3) in the $V_H$ (Chothia and Lesk *J Mol. Biol.* 196:901-917 (1987)).

As used herein, the terms "identical" or percent "identity", when used in the context of two or more nucleic acids or polypeptide sequences, refer to two or more sequences or subsequences that are the same or have a specified percentage of amino acid residues or nucleotides that are the same (i.e., about 60%, 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein)), when compared and aligned for maximum correspondence over a comparison window or designated region as measured using a BLAST or BLAST 2.0 sequence comparison algorithms with default parameters described below, or by manual alignment and visual inspection (e.g., NCBI web site). Such sequences are then said to be "substantially identical." This term also refers to, or can be applied to, the complement of a test sequence. The term also includes sequences that have deletions and/or additions, as well as those that have substitutions. In some embodiments, identity exists over a region that is at least about 25 amino acids or nucleotides in length, or 50-100 amino acids or nucleotides in length.

As used herein, an "immunogen" refers to any antigen that is capable of inducing humoral and/or cell-mediated immune response rather than immunological tolerance.

As used herein, the term "intact antibody" or "intact immunoglobulin" means an antibody that has at least two heavy (H) chain polypeptides and two light (L) chain polypeptides interconnected by disulfide bonds. Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: $FR_1$, $CDR_1$, $FR_2$, $CDR_2$, $FR_3$, $CDR_3$, $FR_4$. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

As used herein, the term "linker" refers to a functional group (e.g., chemical or polypeptide) that covalently attaches two or more polypeptides or nucleic acids so that they are connected to one another. As used herein, a "peptide linker" refers to one or more amino acids used to couple two proteins together (e.g., to couple $V_H$ and $V_L$ domains). In certain embodiments, the linker comprises amino acids having the sequence $(GGGGS)_n$ (SEQ ID NO: 112), wherein n is at least 1, 2, 3, 4, 5, 6, 7, 8, 9, 10, 11, 12, 12, 14, or 15.

The term "monoclonal antibody" as used herein refers to an antibody obtained from a population of substantially homogeneous antibodies, i.e., the individual antibodies comprising the population are identical except for possible naturally occurring mutations that may be present in minor amounts. For example, a monoclonal antibody can be an antibody that is derived from a single clone, including any eukaryotic, prokaryotic, or phage clone, and not the method by which it is produced. A monoclonal antibody composition displays a single binding specificity and affinity for a particular epitope. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. Monoclonal antibodies can be prepared using a wide variety of techniques known in the art including, e.g., but not limited to, hybridoma, recombinant, and phage display technologies. For example, the monoclonal antibodies to be used in accordance with the present methods may be made by the hybridoma method first described by Kohler et al., *Nature* 256:495 (1975), or may be made by recombinant DNA methods (See, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

As used herein, the term "nucleic acid" or "polynucleotide" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the term “pharmaceutically acceptable carrier” is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington’s Pharmaceutical Sciences ($20^{th}$ edition, ed. A. Gennaro, 2000, Lippincott, Williams & Wilkins, Philadelphia, Pa.).

As used herein, the term “polyclonal antibody” means a preparation of antibodies derived from at least two (2) different antibody-producing cell lines. The use of this term includes preparations of at least two (2) antibodies that contain antibodies that specifically bind to different epitopes or regions of an antigen.

As used herein, the terms “polypeptide,” “peptide” and “protein” are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature.

As used herein, “PRIT” or “pretargeted radioimmunotherapy” refers to a multistep process that resolves the slow blood clearance of tumor targeting antibodies, which contributes to undesirable toxicity to normal tissues such as bone marrow. In pre-targeting, a radionuclide or other diagnostic or therapeutic agent is attached to a small hapten. A pre-targeting bispecific antibody, which has binding sites for the hapten as well as a target antigen, is administered first. Unbound antibody is then allowed to clear from circulation and the hapten is subsequently administered.

As used herein, the term “recombinant” when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, the term “separate” therapeutic use refers to an administration of at least two active ingredients at the same time or at substantially the same time by different routes.

As used herein, the term “sequential” therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term “simultaneous” therapeutic use refers to the administration of at least two active ingredients by the same route and at the same time or at substantially the same time.

As used herein, the terms “single-chain antibodies” or “single-chain Fv (scFv)” refer to an antibody fusion molecule of the two domains of the Fv fragment, $V_L$ and $V_H$. Single-chain antibody molecules may comprise a polymer with a number of individual molecules, for example, dimer, trimer or other polymers. Furthermore, although the two domains of the $F_v$ fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single-chain F, (scFv)). Bird et al. (1988) *Science* 242:423-426 and Huston et al. (1988) *Proc Natl Acad Sci* 85:5879-5883. Such single-chain antibodies can be prepared by recombinant techniques or enzymatic or chemical cleavage of intact antibodies.

As used herein, “specifically binds” refers to a molecule (e.g., an antibody or antigen binding fragment thereof) which recognizes and binds another molecule (e.g., an antigen), but that does not substantially recognize and bind other molecules. The terms “specific binding,” “specifically binds to,” or is “specific for” a particular molecule (e.g., a polypeptide, or an epitope on a polypeptide), as used herein, can be exhibited, for example, by a molecule having a $K_D$ for the molecule to which it binds to of about $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M. The term “specifically binds” may also refer to binding where a molecule (e.g., an antibody or antigen binding fragment thereof) binds to a particular polypeptide (e.g., a GPA33 polypeptide), or an epitope on a particular polypeptide, without substantially binding to any other polypeptide, or polypeptide epitope.

As used herein, “sequence liabilities” refer to any feature in nucleic acid or amino acid sequences that can affect the heterogeneity of the immunoglobulin-related compositions of the present disclosure. Such sequence liabilities include but not limited to, any sequence motifs that are prone to deamidation, isomerization, cleavage, oxidation, and glycosylation.

As used herein, the terms “subject”, “patient”, or “individual” can be an individual organism, a vertebrate, a mammal, or a human. In some embodiments, the subject, patient or individual is a human.

As used herein, the term “therapeutic agent” is intended to mean a compound that, when present in an effective amount, produces a desired therapeutic effect on a subject in need thereof.

“Treating” or “treatment” as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment of disorders as described herein are intended to mean “substantial,” which includes total but also less than total treatment, and wherein some biologically or medically relevant result is achieved. The treatment may be a continuous prolonged treatment for a chronic disease or a single, or few time administrations for the treatment of an acute condition.

Amino acid sequence modification(s) of the anti-GPA33 antibodies described herein are contemplated. Such modifications can be introduced to improve the binding affinity and/or other biological properties of the antibody, for example, to render the encoded amino acid aglycosylated, or to destroy the antibody's ability to bind to C1q, Fc receptor, or to activate the complement system. Amino acid sequence variants of an anti-GPA33 antibody are prepared by introducing appropriate nucleotide changes into the antibody nucleic acid, by peptide synthesis, or by chemical modifications. Such modifications include, for example, deletions from, and/or insertions into and/or substitutions of, residues within the amino acid sequences of the antibody. Any combination of deletion, insertion, and substitution is made to obtain the antibody of interest, as long as the obtained antibody possesses the desired properties. The modification also includes the change of the pattern of glycosylation of the protein. The sites of greatest interest for substitutional mutagenesis include the hypervariable regions, but FR alterations are also contemplated.

Conservative amino acid substitutions are amino acid substitutions that change a given amino acid to a different amino acid with similar biochemical properties (e.g., charge, hydrophobicity and size). "Conservative substitutions" are shown in the Table below.

TABLE 1

| Amino Acid Substitutions | | |
|---|---|---|
| Original Residue | Exemplary Substitutions | Conservative Substitutions |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

One type of substitutional variant involves substituting one or more hypervariable region residues of a parent antibody. A convenient way for generating such substitutional variants involves affinity maturation using phage display. Specifically, several hypervariable region sites (e.g., 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen. Such contact residues and neighboring residues are candidates for substitution according to the techniques elaborated herein. Once such variants are generated, the panel of variants is subjected to screening as described herein and antibodies with similar or superior properties in one or more relevant assays may be selected for further development.

CRC and GPA33

Colorectal cancers (CRCs) constitute the 3rd leading cause of cancer death in the United States (Siegel, R. L., et al., *CA Cancer J Clin* 67(3): 177-193 (2017)) and account for 10% of all cancers in men and 9.2% in women worldwide (Ferlay, J., et al., *Int J Cancer* 136(5): E359-386 (2015)). Although there has been steady yearly 3% decline in the incidence from 2004 to 2013, 135,000 new cases are expected in 2017 in the United States alone. Although localized and regional diseases can be curable, the prognosis of metastatic CRCs (mCRCs) is poor, with a 5-year survival rate of only 14% (Siegel, R. L., et al., *CA Cancer J Clin* 67(3): 177-193 (2017)). CRC is a heterogeneous disease and can be subdivided into 4 consensus molecular subtypes (CMS) based on gene expression analysis, i.e., CMS1-4. MSI tumors mainly belong to CMS1 (14% of all CRC patients) and are characterized by genome hypermutation and microsatellite instability, due to deficiencies in DNA repair pathways. Presumably, hypermutation creates a plethora of neoantigens that are presented on the cell surface and attract T cells into tumors. Indeed, CMS1 has a strong molecular signature of immune system activation and evasion. ICIs function by reinvigorating repressed tumor infiltrating lymphocytes (TILs) to regain tumoricidal capabilities and therefore, MSI tumors are the most responsive CRC tumors to ICIs. However, MSI tumors account for <5% of mCRC; for the majority of mCRC, the efficacy of ICIs so far has been disappointing. Peritoneal carcinomatosis is typically the terminal phase of incurable CRC. Unlike metastasis to liver and lung, it is usually unresectable, unresponsive to chemotherapy and radiation, causing significant morbidity. Current treatment is mostly palliative, consisting of cytoreduction surgery (CRS) and hyperthemic chemotherapy (HIPEC), which are effective in only a small percentage of patients with small volume disease.

One potentially useful target for colon cancer is the 43 kD transmembrane glycoprotein A33 (GPA33). Human Glycoprotein A33 (GPA33 or A33) is a single-pass type I membrane protein that belongs to the CTX family of cell adhesion molecular within the immunoglobulin family. GPA33 comprises one Ig-like C2-type domain and one Ig-like V-type domain. The predicted mature protein includes a single transmembrane domain, an extracellular region and an intracellular tail. GPA33 plays a role in intracellular traffic, cell-cell recognition/signaling and recycling to the cell surface. The amino acid sequence of human GPA33 is provided below:

(SEQ ID NO: 100)

MVGKMWPVLWTLCAVRVTVDAISVETPQDVLRASQGKSVTLPCTYHTST

SSREGLIQWDKLLLTHTERVVIWPFSNKNYIHGELYKNRVSISNNAEQS

DASITIDQLTMADNGTYECSVSLMSDLEGNTKSRVRLLVLVPPSKPECG

-continued

IEGETIIGNNIQLTCQSKEGSPTPQYSWKRYNILNQEQPLAQPASGQPV

SLKNISTDTSGYYICTSSNEEGTQFCNITVAVRSPSMNVALYVGIAVGV

VAALIIIGIIIYCCCCRGKDDNTEDKEDARPNREAYEEPPEQLRELSRE

REEEDDYRQEEQRSTGRESPDHLDQ

The amino acid sequence of the ectodomain of GPA33 (Ile22-Val235) is provided below:

(SEQ ID NO: 101)

ISVETPQDVLRASQGKSVTLPCTYHTSTSSREGLIQWDKLLLTHTERVV

IWPFSNKNYIHGELYKNRVSISNNAEQSDASITIDQLTMADNGTYECSV

SLMSDLEGNTKSRVRLLVLVPPSKPECGIEGETIIGNNIQLTCQSKEGS

PTPQYSWKRYNILNQEQPLAQPASGQPVSLKNISTDTSGYYICTSSNEE

GTQFCNITVAVRSPSMNV.

GPA33 is abundantly expressed in over 95% of colorectal cancer (CRC), with low levels of normal-tissue expression (colon and bowel epithelium). It exhibits long-term residence (>100 hours) in cell membrane in tumors, relative to intestine, with minimal internalization and minimal vascular shedding. Monoclonal antibodies such as huA33 taken up by CRC can persist for up to 6 weeks, in contrast to gut retention with half-time of 32 hours (Ackerman, M. E., et al., *Cancer Immunol Immunother* 57(7): 1017-1027 (2008)). The natural shedding of normal gut cells is functionally equivalent to a clearance. As a membrane junctional complex component, GPA33 exhibits negligible internalization and much slower turnover than most membrane components.

Immunoglobulin-Related Compositions of the Present Technology

The present technology describes methods and compositions for the generation and use of anti-GPA33 immunoglobulin-related compositions (e.g., anti-GPA33 antibodies or antigen binding fragments thereof). The immunoglobulin-related compositions of the present technology may be useful in the diagnosis, or treatment of GPA33-associated cancers. Anti-GPA33 immunoglobulin-related compositions within the scope of the present technology include, e.g., but are not limited to, monoclonal, chimeric, humanized, multispecific antibodies and diabodies that specifically bind the target polypeptide, a homolog, derivative or a fragment thereof. The present disclosure also provides antigen binding fragments of any of the anti-GPA33 antibodies disclosed herein, wherein the antigen binding fragment is selected from the group consisting of Fab, $F(ab)'_2$, Fab', $scF_v$, and $F_v$. Representative amino acid sequences of the anti-GPA33 immunoglobulin-related compositions of the present technology are described in FIGS. 14-32.

In one aspect, the present disclosure provides an antibody or antigen binding fragment thereof comprising a heavy chain immunoglobulin variable domain ($V_H$) and a light chain immunoglobulin variable domain ($V_L$), wherein: (a) the $V_H$ comprises an amino acid sequence selected from any one of SEQ ID NOs: 1-3; and/or (b) the $V_L$ comprises an amino acid sequence selected from any one of SEQ ID NOs: 4-10.

In some embodiments, the antibody further comprises a Fc domain of any isotype, e.g., but are not limited to, IgG (including IgG1, IgG2, IgG3, and IgG4), IgA (including $IgA_1$ and $IgA_2$), IgD, IgE, or IgM, and IgY. Non-limiting examples of constant region sequences include:

Human IgD constant region, Uniprot: P01880

(SEQ ID NO: 81)

APTKAPDVFPIISGCRHPKDNSPVVLACLITGYHPTSVTVTWYMGTQSQPQRTFPEIQRR

DSYYMTSSQLSTPLQQWRQGEYKCVVQHTASKSKKEIFRWPESPKAQASSVPTAQPQA

EGSLAKATTAPATTRNTGRGGEEKKKEKEKEEQEERETKTPECPSHTQPLGVYLLTPAV

QDLWLRDKATFTCFVVGSDLKDAHLTWEVAGKVPTGGVEEGLLERHSNGSQSQHSRLT

LPRSLWNAGTSVTCTLNHPSLPPQRLMALREPAAQAPVKLSLNLLASSDPPEAASWLLC

EVSGFSPPNILLMWLEDQREVNTSGFAPARPPPQPGSTTFWAWSVLRVPAPPSPQPATYT

CVVSHEDSRTLLNASRSLEVSYVTDHGPMK

Human IgG1 constant region, Uniprot: P01857

(SEQ ID NO: 82)

ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFFLYSKLTVDK

SRWQQGNVFSCSVMHEALHNHYTQKSLSLSPGK

Human IgG2 constant region, Uniprot: P01859

(SEQ ID NO: 83)

ASTKGPSVFPLAPCSRSTSESTAALGCLVKDYFPEPVTVSWNSGALTSGVHTFPAVLQSS

GLYSLSSVVTVPSSNFGTQTYTCNVDHKPSNTKVDKTVERKCCVECPPCPAPPVAGPSV

FLFPPKPKDTLMISRTPEVTCVVVDVSHEDPEVQFNWYVDGVEVHNAKTKPREEQFNST

-continued

FRVVSVLTVVHQDWLNGKEYKCKVSNKGLPAPIEKTISKTKGQPREPQVYTLPPSREEM

TKNQVSLTCLVKGFYPSDISVEWESNGQPENNYKTTPPMLDSDGSFFLYSKLTVDKSRW

QQGNVFSCSVMHEALHNHYTQKSLSLSPGK

Human IgG3 constant region, Uniprot: P01860

(SEQ ID NO: 84)

ASTKGPSVFPLAPCSRSTSGGTAALGCLVKDYFPEPVTVSWNSGALTSGVHTFPAVLQSS

GLYSLSSVVTVPSSSLGTQTYTCNVNHKPSNTKVDKRVELKTPLGDTTHTCPRCPEPKSC

DTPPPCPRCPEPKSCDTPPPCPRCPEPKSCDTPPPCPRCPAPELLGGPSVFLFPPKPKDTLMI

SRTPEVTCVVVDVSHEDPEVQFKWYVDGVEVHNAKTKPREEQYNSTFRVVSVLTVLHQ

DWLNGKEYKCKVSNKALPAPIEKTISKTKGQPREPQVYTLPPSREEMTKNQVSLTCLVK

GFYPSDIAVEWESSGQPENNYNTTPPMLDSDGSFFLYSKLTVDKSRWQQGNIFSCSVMH

EALHNRFTQKSLSLSPGK

Human IgM constant region, Uniprot: P01871

(SEQ ID NO: 85)

GSASAPTLFPLVSCENSPSDTSSVAVGCLAQDFLPDSITLSWKYKNNSDISSTRGFPSVLR

GGKYAATSQVLLPSKDVMQGTDEHVVCKVQHPNGNKEKNVPLPVIAELPPKVSVFVPP

RDGFFGNPRKSKLICQATGFSPRQIQVSWLREGKQVGSGVTTDQVQAEAKESGPTTYKV

TSTLTIKESDWLGQSMFTCRVDHRGLTFQQNASSMCVPDQDTAIRVFAIPPSFASIFLTKS

TKLTCLVTDLTTYDSVTISWTRQNGEAVKTHTNISESHPNATFSAVGEASICEDDWNSGE

RFTCTVTHTDLPSPLKQTISRPKGVALHRPDVYLLPPAREQLNLRESATITCLVTGFSPAD

VFVQWMQRGQPLSPEKYVTSAPMPEPQAPGRYFAHSILTVSEEEWNTGETYTCVAHEA

LPNRVTERTVDKSTGKPTLYNVSLVMSDTAGTCY

Human IgG4 constant region, Uniprot: P01861

(SEQ ID NO: 86)

ASTKGPSVFPLAPCSRSTSESTAALGCLVKDYFPEPVTVSWNSGALTSGVHTFPAVLQSS

GLYSLSSVVTVPSSSLGTKTYTCNVDHKPSNTKVDKRVESKYGPPCPSCPAPEFLGGPSV

FLFPPKPKDTLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVYTLPPSQEEM

TKNQVSLTCLVKGFYPSDIAVEWESNGQPENNYKTTPPVLDSDGSFFLYSRLTVDKSRW

QEGNVFSCSVMHEALHNHYTQKSLSLSLGK

Human IgA1 constant region, Uniprot: P01876

(SEQ ID NO: 87)

ASPTSPKVFPLSLCSTQPDGNVVIACLVQGFFPQEPLSVTWSESGQGVTARNFPPSQDAS

GDLYTTSSQLTLPATQCLAGKSVTCHVKHYTNPSQDVTVPCPVPSTPPTPSPSTPPTPSPS

CCHPRLSLHRPALEDLLLGSEANLTCTLTGLRDASGVTFTWTPSSGKSAVQGPPERDLC

GCYSVSSVLPGCAEPWNHGKTFTCTAAYPESKTPLTATLSKSGNTFRPEVHLLPPPSEEL

ALNELVTLTCLARGFSPKDVLVRWLQGSQELPREKYLTWASRQEPSQGTTTFAVTSILR

VAAEDWKKGDTFSCMVGHEALPLAFTQKTIDRLAGKPTHVNVSVVMAEVDGTCY

Human IgA2 constant region, Uniprot: P01877

(SEQ ID NO: 88)

ASPTSPKVFPLSLDSTPQDGNVVVACLVQGFFPQEPLSVTWSESGQNVTARNFPPSQDAS

GDLYTTSSQLTLPATQCPDGKSVTCHVKHYTNPSQDVTVPCPVPPPPPCCHPRLSLHRPA

LEDLLLGSEANLTCTLTGLRDASGATFTWTPSSGKSAVQGPPERDLCGCYSVSSVLPGC

AQPWNHGETFTCTAAHPELKTPLTANITKSGNTFRPEVHLLPPPSEELALNELVTLTCLA

RGFSPKDVLVRWLQGSQELPREKYLTWASRQEPSQGTTTFAVTSILRVAAEDWKKGDT

-continued

```
FSCMVGHEALPLAFTQKTIDRMAGKPTHVNVSVVMAEVDGTCY

Human Ig kappa constant region, Uniprot: P01834
                                                    (SEQ ID NO: 89)
TVAAPSVFIFPPSDEQLKSGTASVVCLLNNFYPREAKVQWKVDNALQSGNSQESVTEQD

SKDSTYSLSSTLTLSKADYEKHKVYACEVTHQGLSSPVTKSFNRGEC
```

In some embodiments, the immunoglobulin-related compositions of the present technology comprise a heavy chain constant region that is at least 80%, at least 85%, at least 90%, at least 95%, at least 99%, or is 100% identical to SEQ ID NOs: 81-88. Additionally or alternatively, in some embodiments, the immunoglobulin-related compositions of the present technology comprise a light chain constant region that is at least 80%, at least 85%, at least 90%, at least 95%, at least 99%, or is 100% identical to SEQ ID NO: 89.

In some embodiments, the immunoglobulin-related compositions of the present technology bind to the extracellular domain of a GPA33 polypeptide. In some embodiments, the immunoglobulin-related compositions of the present technology bind to an epitope of a GPA33 polypeptide comprising at least five to eight consecutive amino acid residues of SEQ ID NO: 101. In some embodiments, the epitope is a conformational epitope or non-conformational epitope.

In another aspect, the present disclosure provides an isolated immunoglobulin-related composition (e.g., an antibody or antigen binding fragment thereof) comprising a heavy chain (HC) amino acid sequence comprising SEQ ID NO: 23, SEQ ID NO: 27, SEQ ID NO: 60, SEQ ID NO: 62, SEQ ID NO: 64, SEQ ID NO: 67, SEQ ID NO: 71, SEQ ID NO: 75, SEQ ID NO: 79, or a variant thereof having one or more conservative amino acid substitutions. Additionally or alternatively, in some embodiments, the immunoglobulin-related compositions of the present technology comprise a light chain (LC) amino acid sequence comprising SEQ ID NO: 21, SEQ ID NO: 25, SEQ ID NO: 59, SEQ ID NO: 61, SEQ ID NO: 63, SEQ ID NO: 65, SEQ ID NO: 69, SEQ ID NO: 73, SEQ ID NO: 77, or a variant thereof having one or more conservative amino acid substitutions.

In some embodiments, the immunoglobulin-related compositions of the present technology comprise a HC amino acid sequence and a LC amino acid sequence selected from the group consisting of: SEQ ID NO: 23 and SEQ ID NO: 21 (BC015 (G3A H1L4)); SEQ ID NO: 27 and SEQ ID NO: 25 (BC016 (G3A H3L3)); SEQ ID NO: 60 and SEQ ID NO: 59 (BC369 (G3A H1L4 huOKT3)); SEQ ID NO: 62 and SEQ ID NO: 61 (BC373 (G3A H1L4 huOT3 H2L2)); and SEQ ID NO: 64 and SEQ ID NO: 63 (BC377 (G3A H1L4 huOT3 H2L4)), respectively.

In some embodiments, the immunoglobulin-related compositions of the present technology comprise a first HC amino acid sequence, a second HC amino acid sequence, a first LC amino acid sequence and a second LC amino acid sequence selected from the group consisting of SEQ ID NO: 67, SEQ ID NO: 68, SEQ ID NO: 65 and SEQ ID NO: 66 (HD152); SEQ ID NO: 71, SEQ ID NO: 72, SEQ ID NO: 69 and SEQ ID NO: 70 (HD156); SEQ ID NO: SEQ ID NO: 76, SEQ ID NO: 73 and SEQ ID NO: 74 (HD160); and SEQ ID NO: 79, SEQ ID NO: 80, SEQ ID NO: 77 and SEQ ID NO: 78 (HD164), respectively.

In any of the above embodiments of the immunoglobulin-related compositions, the HC and LC immunoglobulin variable domain sequences form an antigen binding site that binds to an epitope of a GPA33 polypeptide comprising at least five to eight consecutive amino acid residues of the ectodomain of GPA33 (SEQ ID NO: 101). In some embodiments, the epitope is a conformational epitope or a non-conformational epitope.

In some embodiments, the HC and LC immunoglobulin variable domain sequences are components of the same polypeptide chain. In other embodiments, the HC and LC immunoglobulin variable domain sequences are components of different polypeptide chains. In certain embodiments, the antibody is a full-length antibody.

In some embodiments, the immunoglobulin-related compositions of the present technology bind specifically to at least one GPA33 polypeptide. In some embodiments, the immunoglobulin-related compositions of the present technology bind at least one GPA33 polypeptide with a dissociation constant ($K_D$) of about $10^{-3}$ M, $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M. In certain embodiments, the immunoglobulin-related compositions are monoclonal antibodies, chimeric antibodies, humanized antibodies, bispecific antibodies, or multi-specific antibodies. In some embodiments, the antibodies comprise a human antibody framework region.

In certain embodiments, the immunoglobulin-related composition includes one or more of the following characteristics: (a) the light chain immunoglobulin variable domain sequence is at least 80%, at least 85%, at least 90%, at least 95%, or at least 99% identical to the light chain immunoglobulin variable domain sequence present in any one of SEQ ID NOs: 4, 5, 6, 7, 8, 9, or 10; and/or (b) a heavy chain immunoglobulin variable domain sequence that is at least 80%, at least 85%, at least 90%, at least 95%, or at least 99% identical to the heavy chain immunoglobulin variable domain sequence present in any one of SEQ ID NOs: 1, 2, or 3. In another aspect, one or more amino acid residues in the immunoglobulin-related compositions provided herein are substituted with another amino acid. The substitution may be a “conservative substitution” as defined herein.

In one aspect, the present disclosure provides an immunoglobulin-related composition comprising an amino acid sequence that is at least 80%, at least 85%, at least 90%, at least 95%, or at least 99% identical to an amino acid sequence selected from SEQ ID NOs: 11, 13, 15, 17, 19, or 29-58. In certain embodiments, the immunoglobulin-related composition comprises an amino acid sequence selected from any one of SEQ ID NOs: 11, 13, 15, 17, 19, or 29-58.

In some embodiments, the immunoglobulin-related composition comprises (a) a LC sequence that is at least 80%, at least 85%, at least 90%, at least 95%, or at least 99% identical to the LC sequence present in any one of SEQ ID NO: 21, SEQ ID NO: 25, SEQ ID NO: 59, SEQ ID NO: 61, SEQ ID NO: 63, SEQ ID NO: 65, SEQ ID NO: 69, SEQ ID NO: 73, or SEQ ID NO: 77; and/or (b) a HC sequence that is at least 80%, at least 85%, at least 90%, at least 95%, or at least 99% identical to the HC sequence present in any one of SEQ ID NO: 23, SEQ ID NO: 27, SEQ ID NO: 60, SEQ ID NO: 62, SEQ ID NO: 64, SEQ ID NO: 67, SEQ ID NO: 71, SEQ ID NO: 75, or SEQ ID NO: 79.

In one aspect, the present disclosure provides a multi-specific antigen binding fragment comprising a first polypeptide chain, wherein: the first polypeptide chain comprises in the N-terminal to C-terminal direction: (i) a heavy chain variable domain of a first immunoglobulin that is capable of specifically binding to a first epitope; (ii) a flexible peptide linker comprising the amino acid sequence $(GGGGS)_6$ (SEQ ID NO: 108); (iii) a light chain variable domain of the first immunoglobulin; (iv) a flexible peptide linker comprising the amino acid sequence $(GGGGS)_4$ (SEQ ID NO: 109); (v) a heavy chain variable domain of a second immunoglobulin that is capable of specifically binding to a second epitope; (vi) a flexible peptide linker comprising the amino acid sequence $(GGGGS)_6$ (SEQ ID NO: 108); (vii) a light chain variable domain of the second immunoglobulin; (viii) a flexible peptide linker sequence comprising the amino acid sequence TPLGDTTHT (SEQ ID NO: 110); and (ix) a self-assembly disassembly (SADA) polypeptide, wherein the heavy chain variable domain of the first immunoglobulin or the heavy chain variable domain of the second immunoglobulin is selected from any one of SEQ ID NOs: 1-3, and/or the light chain variable domain of the first immunoglobulin or the light chain variable domain of the second immunoglobulin is selected from any one of SEQ ID NOs: 4-10.

In another aspect, the present disclosure provides a multispecific antigen binding fragment comprising a first polypeptide chain, wherein: the first polypeptide chain comprises in the N-terminal to C-terminal direction: (i) a light chain variable domain of a first immunoglobulin that is capable of specifically binding to a first epitope; (ii) a flexible peptide linker comprising the amino acid sequence $(GGGGS)_6$ (SEQ ID NO: 108); (iii) a heavy chain variable domain of the first immunoglobulin; (iv) a flexible peptide linker comprising the amino acid sequence $(GGGGS)_4$ (SEQ ID NO: 109); (v) a heavy chain variable domain of a second immunoglobulin that is capable of specifically binding to a second epitope; (vi) a flexible peptide linker comprising the amino acid sequence $(GGGGS)_6$ (SEQ ID NO: 108); (vii) a light chain variable domain of the second immunoglobulin; (viii) a flexible peptide linker sequence comprising the amino acid sequence TPLGDTTHT (SEQ ID NO: 110); and (ix) a self-assembly disassembly (SADA) polypeptide, wherein the heavy chain variable domain of the first immunoglobulin or the heavy chain variable domain of the second immunoglobulin is selected from any one of SEQ ID NOs: 1-3, and/or the light chain variable domain of the first immunoglobulin or the light chain variable domain of the second immunoglobulin is selected from any one of SEQ ID NOs: 4-10.

In one aspect, the present disclosure provides a multispecific antigen binding fragment comprising a first polypeptide chain, wherein: the first polypeptide chain comprises in the N-terminal to C-terminal direction: (i) a heavy chain variable domain of a first immunoglobulin that is capable of specifically binding to a first epitope; (ii) a flexible peptide linker comprising the amino acid sequence $(GGGGS)_6$ (SEQ ID NO: 108); (iii) a light chain variable domain of the first immunoglobulin; (iv) a flexible peptide linker comprising the amino acid sequence $(GGGGS)_4$ (SEQ ID NO: 109); (v) a light chain variable domain of a second immunoglobulin that is capable of specifically binding to a second epitope; (vi) a flexible peptide linker comprising the amino acid sequence $(GGGGS)_6$ (SEQ ID NO: 108); (vii) a heavy chain variable domain of the second immunoglobulin; (viii) a flexible peptide linker comprising the amino acid sequence $(GGGGS)_4$ (SEQ ID NO: 109); (ix) a heavy chain variable domain of a third immunoglobulin that is capable of specifically binding to a third epitope; (x) a flexible peptide linker comprising the amino acid sequence $(GGGGS)_6$ (SEQ ID NO: 108); (xi) a light chain variable domain of the third immunoglobulin; (xii) a flexible peptide linker sequence comprising the amino acid sequence TPLGDTTHT (SEQ ID NO: 110); and (xiii) a self-assembly disassembly (SADA) polypeptide, wherein the heavy chain variable domain of the first immunoglobulin or the heavy chain variable domain of the second immunoglobulin or the heavy chain variable domain of the third immunoglobulin is selected from any one of SEQ ID NOs: 1-3, and/or the light chain variable domain of the first immunoglobulin or the light chain variable domain of the second immunoglobulin or the light chain variable domain of the third immunoglobulin is selected from any one of SEQ ID NOs: 4-10.

In another aspect, the present disclosure provides a multispecific antigen binding fragment comprising a first polypeptide chain, wherein: the first polypeptide chain comprises in the N-terminal to C-terminal direction: (i) a light chain variable domain of a first immunoglobulin that is capable of specifically binding to a first epitope; (ii) a flexible peptide linker comprising the amino acid sequence $(GGGGS)_6$ (SEQ ID NO: 108); (iii) a heavy chain variable domain of the first immunoglobulin; (iv) a flexible peptide linker comprising the amino acid sequence $(GGGGS)_4$ (SEQ ID NO: 109); (v) a light chain variable domain of a second immunoglobulin that is capable of specifically binding to a second epitope; (vi) a flexible peptide linker comprising the amino acid sequence $(GGGGS)_6$ (SEQ ID NO: 108); (vii) a heavy chain variable domain of the second immunoglobulin; (viii) a flexible peptide linker comprising the amino acid sequence $(GGGGS)_4$ (SEQ ID NO: 109); (ix) a heavy chain variable domain of a third immunoglobulin that is capable of specifically binding to a third epitope; (x) a flexible peptide linker comprising the amino acid sequence $(GGGGS)_6$ (SEQ ID NO: 108); (xi) a light chain variable domain of the third immunoglobulin; (xii) a flexible peptide linker sequence comprising the amino acid sequence TPLGDTTHT (SEQ ID NO: 110); and (xiii) a self-assembly disassembly (SADA) polypeptide, wherein the heavy chain variable domain of the first immunoglobulin or the heavy chain variable domain of the second immunoglobulin or the heavy chain variable domain of the third immunoglobulin is selected from any one of SEQ ID NOs: 1-3, and/or the light chain variable domain of the first immunoglobulin or the light chain variable domain of the second immunoglobulin or the light chain variable domain of the third immunoglobulin is selected from any one of SEQ ID NOs: 4-10.

In certain embodiments of the multispecific antigen binding fragments disclosed herein, the SADA polypeptide comprises a tetramerization, pentamerization, or hexamerization domain. In some embodiments, the SADA polypeptide comprises a tetramerization domain of any one of p53, p63, p73, hnRNPC, SNA-23, Stefin B, KCNQ4, and CBFA2T1. Additionally or alternatively, in some embodiments, the multispecific antigen binding fragment comprises an amino acid sequence selected from the group consisting of SEQ ID NOs: 11, 13, 15, 17, 19, or 29-58.

In any of the SADA-polypeptide containing multi-specific antibodies or antigen binding fragments disclosed herein, the antibody or antigen binding fragment does not cross into gut epithelium or gut lumen when the antibody or antigen binding fragment is intravenously or intraperitoneally administered to a subject.

In one aspect, the present disclosure provides a multispecific antibody comprising a first polypeptide chain, a second polypeptide chain, a third polypeptide chain and a fourth polypeptide chain, wherein the first and second polypeptide chains are covalently bonded to one another, the second and third polypeptide chains are covalently bonded to one another, and the third and fourth polypeptide chain are covalently bonded to one another, and wherein: (a) each of the first polypeptide chain and the fourth polypeptide chain comprises in the N-terminal to C-terminal direction: (i) a light chain variable domain of a first immunoglobulin that is capable of specifically binding to a first epitope; (ii) a light chain constant domain of the first immunoglobulin; (iii) a flexible peptide linker comprising the amino acid sequence $(GGGGS)_3$ (SEQ ID NO: 111); and (iv) a light chain variable domain of a second immunoglobulin that is linked to a complementary heavy chain variable domain of the second immunoglobulin, or a heavy chain variable domain of a second immunoglobulin that is linked to a complementary light chain variable domain of the second immunoglobulin, wherein the light chain and heavy chain variable domains of the second immunoglobulin are capable of specifically binding to a second epitope, and are linked together via a flexible peptide linker comprising the amino acid sequence $(GGGGS)_6$ (SEQ ID NO: 108) to form a single-chain variable fragment; and (b) each of the second polypeptide chain and the third polypeptide chain comprises in the N-terminal to C-terminal direction: (i) a heavy chain variable domain of the first immunoglobulin that is capable of specifically binding to the first epitope; and (ii) a heavy chain constant domain of the first immunoglobulin; and wherein the heavy chain variable domain of the first immunoglobulin or the heavy chain variable domain of the second immunoglobulin is selected from any one of SEQ ID NOs: 1-3, and/or the light chain variable domain of the first immunoglobulin or the light chain variable domain of the second immunoglobulin is selected from any one of SEQ ID NOs: 4-10.

In another aspect, the present disclosure provides a heterodimeric multispecific antibody comprising a first polypeptide chain, a second polypeptide chain, a third polypeptide chain and a fourth polypeptide chain, wherein the first and second polypeptide chains are covalently bonded to one another, the second and third polypeptide chains are covalently bonded to one another, and the third and fourth polypeptide chain, and wherein: (a) the first polypeptide chain comprises in the N-terminal to C-terminal direction: (i) a light chain variable domain of a first immunoglobulin (VL-1) that is capable of specifically binding to a first epitope; (ii) a light chain constant domain of the first immunoglobulin (CL-1); (iii) a flexible peptide linker comprising the amino acid sequence $(GGGGS)_3$ (SEQ ID NO: 111); and (iv) a light chain variable domain of a second immunoglobulin (VL-2) that is linked to a complementary heavy chain variable domain of the second immunoglobulin (VH-2), or a heavy chain variable domain of a second immunoglobulin (VH-2) that is linked to a complementary light chain variable domain of the second immunoglobulin (VL-2), wherein VL-2 and VH-2 are capable of specifically binding to a second epitope, and are linked together via a flexible peptide linker comprising the amino acid sequence $(GGGGS)_6$ (SEQ ID NO: 108) to form a single-chain variable fragment; (b) the second polypeptide comprises in the N-terminal to C-terminal direction: (i) a heavy chain variable domain of the first immunoglobulin (VH-1) that is capable of specifically binding to the first epitope; (ii) a first CH1 domain of the first immunoglobulin (CH1-1); and (iii) a first heterodimerization domain of the first immunoglobulin, wherein the first heterodimerization domain is incapable of forming a stable homodimer with another first heterodimerization domain; (c) the third polypeptide comprises in the N-terminal to C-terminal direction: (i) a heavy chain variable domain of a third immunoglobulin (VH-3) that is capable of specifically binding to a third epitope; (ii) a second CH1 domain of the third immunoglobulin (CH1-3); and (iii) a second heterodimerization domain of the third immunoglobulin, wherein the second heterodimerization domain comprises an amino acid sequence or a nucleic acid sequence that is distinct from the first heterodimerization domain of the first immunoglobulin, wherein the second heterodimerization domain is incapable of forming a stable homodimer with another second heterodimerization domain, and wherein the second heterodimerization domain of the third immunoglobulin is configured to form a heterodimer with the first heterodimerization domain of the first immunoglobulin; (d) the fourth polypeptide comprises in the N-terminal to C-terminal direction: (i) a light chain variable domain of the third immunoglobulin (VL-3) that is capable of specifically binding to the third epitope; (ii) a light chain constant domain of the third immunoglobulin (CL-3); (iii) a flexible peptide linker comprising the amino acid sequence $(GGGGS)_3$ (SEQ ID NO: 111); and (iv) a light chain variable domain of a fourth immunoglobulin (VL-4) that is linked to a complementary heavy chain variable domain of the fourth immunoglobulin (VH-4), or a heavy chain variable domain of a fourth immunoglobulin (VH-4) that is linked to a complementary light chain variable domain of the fourth immunoglobulin (VL-4), wherein VL-4 and VH-4 are capable of specifically binding to the fourth epitope, and are linked together via a flexible peptide linker comprising the amino acid sequence $(GGGGS)_6$ (SEQ ID NO: 108) to form a single-chain variable fragment; wherein VL-1 and/or VL-3 comprises a VL amino acid sequence selected from any one of SEQ ID NOs: 4-10, and wherein VH-1 and/or VH-3 comprises a $V_H$ amino acid sequence selected from any one of SEQ ID NOs: 1-3. In some embodiments, the second epitope and the fourth epitope are identical or distinct.

In any and all embodiments of the multispecific antibodies disclosed herein, the multi-specific antibodies bind to one or more of CD3, CD4, CD8, CD20, CD19, CD21, CD23, CD46, CD80, HLA-DR, CD74, CD22, CD14, CD15, CD16, CD123, CD32, CD64, TCR gamma/delta, NKp46, KIR, PD-1, PD-L1, LAG3, CD28, B7H3, STEAP1, HER2, EGFR, CEA, CECAM5, Transferrin receptor, FAP, NKG2D-ligands, TRAIL, FasL, cathepsin G, granzyme, carboxypeptidase, beta-lactamase, DOTA(metal) complex, benzyl-DOTA(metal) complex, *proteus*-DOTA(metal) complex, NOGADA-*proteus*-DOTA(metal) complex, Star-DFO (metal) complex, DFO(metal) complex, or a small molecule DOTA hapten. In some embodiments of the multispecific antibody or multispecific antigen binding fragment described herein, the antibody or antigen binding fragment comprises a catalytic antibody, an immune checkpoint inhibitor, or an immune checkpoint activator.

In certain embodiments, the immunoglobulin-related compositions contain an IgG1 constant region comprising one or more amino acid substitutions selected from the group consisting of N297A, K322A, L234A and L235A. Additionally or alternatively, in some embodiments, the immunoglobulin-related compositions contain an IgG4 constant region comprising a S228P mutation.

In some aspects, the anti-GPA33 immunoglobulin-related compositions described herein contain structural modifications to facilitate rapid binding and cell uptake and/or slow release. In some aspects, the anti-GPA33 immunoglobulin-related composition of the present technology (e.g., an antibody) may contain a deletion in the CH2 constant heavy chain region to facilitate rapid binding and cell uptake and/or slow release. In some aspects, a Fab fragment is used to facilitate rapid binding and cell uptake and/or slow release. In some aspects, a $F(ab)'_2$ fragment is used to facilitate rapid binding and cell uptake and/or slow release.

In one aspect, the present technology provides a nucleic acid sequence encoding a heavy chain or a light chain of an immunoglobulin-related composition described herein. Also disclosed herein are recombinant nucleic acid sequences encoding any of the antibodies described herein. In some embodiments, the nucleic acid sequence is selected from the group consisting of SEQ ID NOs: 12, 14, 16, 18, 20, 22, 24, 26 and 28. In another aspect, the present technology provides a host cell expressing any nucleic acid sequence encoding a heavy chain or a light chain of an immunoglobulin-related composition described herein.

In another aspect, the present technology provides a cell (e.g., an immune cell, such as a T cell) that is coated with any and all embodiments of the multispecific antibody disclosed herein.

The immunoglobulin-related compositions of the present technology (e.g., an anti-GPA33 antibody) can be monospecific, bispecific, trispecific or of greater multi-specificity. Multi-specific antibodies can be specific for different epitopes of one or more GPA33 polypeptides or can be specific for both the GPA33 polypeptide(s) as well as for heterologous compositions, such as a heterologous polypeptide or solid support material. See, e.g., WO 93/17715; WO 92/08802; WO 91/00360; WO 92/05793; Tutt et al., *J. Immunol.* 147: 60-69 (1991); U.S. Pat. Nos. 5,573,920, 4,474,893, 5,601,819, 4,714,681, 4,925,648; 6,106,835; Kostelny et al., *J. Immunol.* 148: 1547-1553 (1992). In some embodiments, the immunoglobulin-related compositions are chimeric. In certain embodiments, the immunoglobulin-related compositions are humanized.

The immunoglobulin-related compositions of the present technology can further be recombinantly fused to a heterologous polypeptide at the N- or C-terminus or chemically conjugated (including covalently and non-covalently conjugations) to polypeptides or other compositions. For example, the immunoglobulin-related compositions of the present technology can be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

In any of the above embodiments of the immunoglobulin-related compositions of the present technology, the antibody or antigen binding fragment may be optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof. For a chemical bond or physical bond, a functional group on the immunoglobulin-related composition typically associates with a functional group on the agent. Alternatively, a functional group on the agent associates with a functional group on the immunoglobulin-related composition.

The functional groups on the agent and immunoglobulin-related composition can associate directly. For example, a functional group (e.g., a sulfhydryl group) on an agent can associate with a functional group (e.g., sulfhydryl group) on an immunoglobulin-related composition to form a disulfide. Alternatively, the functional groups can associate through a cross-linking agent (i.e., linker). Some examples of cross-linking agents are described below. The cross-linker can be attached to either the agent or the immunoglobulin-related composition. The number of agents or immunoglobulin-related compositions in a conjugate is also limited by the number of functional groups present on the other. For example, the maximum number of agents associated with a conjugate depends on the number of functional groups present on the immunoglobulin-related composition. Alternatively, the maximum number of immunoglobulin-related compositions associated with an agent depends on the number of functional groups present on the agent.

In yet another embodiment, the conjugate comprises one immunoglobulin-related composition associated to one agent. In one embodiment, a conjugate comprises at least one agent chemically bonded (e.g., conjugated) to at least one immunoglobulin-related composition. The agent can be chemically bonded to an immunoglobulin-related composition by any method known to those in the art. For example, a functional group on the agent may be directly attached to a functional group on the immunoglobulin-related composition. Some examples of suitable functional groups include, for example, amino, carboxyl, sulfhydryl, maleimide, isocyanate, isothiocyanate and hydroxyl.

The agent may also be chemically bonded to the immunoglobulin-related composition by means of cross-linking agents, such as dialdehydes, carbodiimides, dimaleimides, and the like. Cross-linking agents can, for example, be obtained from Pierce Biotechnology, Inc., Rockford, Ill. The Pierce Biotechnology, Inc. web-site can provide assistance. Additional cross-linking agents include the platinum cross-linking agents described in U.S. Pat. Nos. 5,580,990; and 6,133,038 of Kreatech Biotechnology, B.V., Amsterdam, The Netherlands.

Alternatively, the functional group on the agent and immunoglobulin-related composition can be the same. Homobifunctional cross-linkers are typically used to cross-link identical functional groups. Examples of homobifunctional cross-linkers include EGS (i.e., ethylene glycol bis [succinimidylsuccinate]), DSS (i.e., disuccinimidyl suberate), DMA (i.e., dimethyl adipimidate.2HCl), DTSSP (i.e., 3,3'-dithiobis[sulfosuccinimidylpropionate])), DPDPB (i.e., 1,4-di-[3'-(2'-pyridyldithio)-propionamido]butane), and BMH (i.e., bis-maleimidohexane). Such homobifunctional cross-linkers are also available from Pierce Biotechnology, Inc.

In other instances, it may be beneficial to cleave the agent from the immunoglobulin-related composition. The web-site of Pierce Biotechnology, Inc. described above can also provide assistance to one skilled in the art in choosing suitable cross-linkers which can be cleaved by, for example, enzymes in the cell. Thus the agent can be separated from the immunoglobulin-related composition. Examples of cleavable linkers include SMPT (i.e., 4-succinimidyloxycarbonyl-methyl-a-[2-pyridyldithio]toluene), Sulfo-LC-SPDP (i.e., sulfosuccinimidyl 6-(3-[2-pyridyldithio]-propionamido)hexanoate), LC-SPDP (i.e., succinimidyl 6-(3-[2-pyridyldithio]-propionamido)hexanoate), Sulfo-LC-SPDP (i.e., sulfosuccinimidyl 6-(3-[2-pyridyldithio]-propionamido)hexanoate), SPDP (i.e., N-succinimidyl 3-[2-pyridyldithio]-propionamidohexanoate), and AEDP (i.e., 3-[(2-aminoethyl)dithio]propionic acid HCl).

In another embodiment, a conjugate comprises at least one agent physically bonded with at least one immunoglobulin-related composition. Any method known to those in the art can be employed to physically bond the agents with the immunoglobulin-related compositions. For example, the immunoglobulin-related compositions and agents can be mixed together by any method known to those in the art. The order of mixing is not important. For instance, agents can be physically mixed with immunoglobulin-related compositions by any method known to those in the art. For example, the immunoglobulin-related compositions and agents can be placed in a container and agitated, by for example, shaking the container, to mix the immunoglobulin-related compositions and agents.

The immunoglobulin-related compositions can be modified by any method known to those in the art. For instance, the immunoglobulin-related composition may be modified by means of cross-linking agents or functional groups, as described above.

A. Methods of Preparing Anti-GPA33 Antibodies of the Present Technology

Overview. Initially, a target polypeptide is chosen to which an antibody of the present technology can be raised. For example, an antibody may be raised against the full-length GPA33 protein, or to a portion of the extracellular domain of the GPA33 protein. Techniques for generating antibodies directed to such target polypeptides are well known to those skilled in the art. Examples of such techniques include, for example, but are not limited to, those involving display libraries, xeno or human mice, hybridomas, and the like. Target polypeptides within the scope of the present technology include any polypeptide derived from GPA33 protein containing the extracellular domain which is capable of eliciting an immune response. In certain embodiments, the extracellular domain comprises the amino acid sequence of SEQ ID NO: 101.

It should be understood that recombinantly engineered antibodies and antibody fragments, e.g., antibody-related polypeptides, which are directed to GPA33 protein and fragments thereof are suitable for use in accordance with the present disclosure.

Anti-GPA33 antibodies that can be subjected to the techniques set forth herein include monoclonal and polyclonal antibodies, and antibody fragments such as Fab, Fab', F(ab')$_2$, Fd, scFv, diabodies, antibody light chains, antibody heavy chains and/or antibody fragments. Methods useful for the high yield production of antibody Fv-containing polypeptides, e.g., Fab' and F(ab')$_2$ antibody fragments have been described. See U.S. Pat. No. 5,648,237.

Generally, an antibody is obtained from an originating species. More particularly, the nucleic acid or amino acid sequence of the variable portion of the light chain, heavy chain or both, of an originating species antibody having specificity for a target polypeptide antigen is obtained. An originating species is any species which was useful to generate the antibody of the present technology or library of antibodies, e.g., rat, mouse, rabbit, chicken, monkey, human, and the like.

Phage or phagemid display technologies are useful techniques to derive the antibodies of the present technology. Techniques for generating and cloning monoclonal antibodies are well known to those skilled in the art. Expression of sequences encoding antibodies of the present technology, can be carried out in *E. coli.*

Due to the degeneracy of nucleic acid coding sequences, other sequences which encode substantially the same amino acid sequences as those of the naturally occurring proteins may be used in the practice of the present technology These include, but are not limited to, nucleic acid sequences including all or portions of the nucleic acid sequences encoding the above polypeptides, which are altered by the substitution of different codons that encode a functionally equivalent amino acid residue within the sequence, thus producing a silent change. It is appreciated that the nucleotide sequence of an immunoglobulin according to the present technology tolerates sequence homology variations of up to 25% as calculated by standard methods ("Current Methods in Sequence Comparison and Analysis," *Macromolecule Sequencing and Synthesis, Selected Methods and Applications*, pp. 127-149, 1998, Alan R. Liss, Inc.) so long as such a variant forms an operative antibody which recognizes GPA33 proteins. For example, one or more amino acid residues within a polypeptide sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the present technology are proteins or fragments or derivatives thereof which are differentially modified during or after translation, e.g., by glycosylation, proteolytic cleavage, linkage to an antibody molecule or other cellular ligands, etc. Additionally, an immunoglobulin encoding nucleic acid sequence can be mutated in vitro or in vivo to create and/or destroy translation, initiation, and/or termination sequences or to create variations in coding regions and/or form new restriction endonuclease sites or destroy pre-existing ones, to facilitate further in vitro modification. Any technique for mutagenesis known in the art can be used, including but not limited to in vitro site directed mutagenesis, *J. Biol. Chem.* 253:6551, use of Tab linkers (Pharmacia), and the like.

Preparation of Polyclonal Antisera and Immunogens. Methods of generating antibodies or antibody fragments of the present technology typically include immunizing a subject (generally a non-human subject such as a mouse or rabbit) with a purified GPA33 protein or fragment thereof, or with a cell expressing the GPA33 protein or fragment thereof. An appropriate immunogenic preparation can contain, e.g., a recombinantly-expressed GPA33 protein or a chemically-synthesized GPA33 peptide. The extracellular domain of the GPA33 protein, or a portion or fragment thereof, can be used as an immunogen to generate an anti-GPA33 antibody that binds to the GPA33 protein, or a portion or fragment thereof using standard techniques for polyclonal and monoclonal antibody preparation. In certain embodiments, the extracellular domain comprises the amino acid sequence of SEQ ID NO: 101. In some embodiments, the antigenic GPA33 peptide comprises at least 10, at least 20, at least 30, at least at least 50, at least 60, at least 70, at least 80, at least 90, or at least 100 amino acid residues. Longer antigenic peptides are sometimes desirable over shorter antigenic peptides, depending on use and according to methods well known to those skilled in the art. Multimers of a given epitope are sometimes more effective than a monomer.

An appropriate immunogenic preparation can contain, e.g., a recombinantly-expressed GPA33 protein or a chemically-synthesized GPA33 peptide comprising amino acid sequence of SEQ ID NO: 101. The extracellular domain of the GPA33 protein, or a portion or fragment thereof, can be used as an immunogen to generate an anti-GPA33 antibody that binds to the extracellular domain of the GPA33 protein.

If needed, the immunogenicity of the GPA33 protein (or fragment thereof) can be increased by fusion or conjugation to a carrier protein such as keyhole limpet hemocyanin (KLH) or ovalbumin (OVA). Many such carrier proteins are known in the art. Synthetic dendromeric trees can be added to reactive amino acid side chains, e.g., lysine, to enhance the immunogenic properties of GPA33 protein. Also, CpG-dinucleotide motifs can be added to enhance the immunogenic properties of the GPA33 protein. One can also combine the GPA33 protein with a conventional adjuvant such as Freund's complete or incomplete adjuvant to increase the subject's immune reaction to the polypeptide. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory compounds. These techniques are standard in the art.

Alternatively, nanoparticles, for example, virus-like particles (VLPs), can be used to present antigens, e.g., GPA33 protein, to a host animal. Virus-like particles are multiprotein structures that mimic the organization and conformation of authentic native viruses without being infectious, since they do not carry any viral genetic material (Urakami A, et al, Clin Vaccine Immunol 24: e00090-17 (2017)). When introduced to a host immune system, VLPs can evoke effective immune responses, making them attractive carriers of foreign antigens. An important advantage of a VLP-based antigen presenting platform is that it can display antigens in a dense, repetitive manner. Thus, antigen-bearing VLPs are able to induce strong B-cell responses by effectively enabling the cross-linking of B cell receptors (BCRs). VLPs may be genetically manipulated to fine their properties, e.g., immunogenicity. These techniques are standard in the art.

The isolation of sufficient purified protein or polypeptide to which an antibody is to be raised may be time consuming and sometimes technically challenging. Additional challenges associated with conventional protein-based immunization include concerns over safety, stability, scalability and consistency of the protein antigen. Nucleic acid (DNA and RNA) based immunizations have emerged as promising alternatives. DNA vaccines are usually based on bacterial plasmids that encode the polypeptide sequence of candidate antigen, e.g., GPA33. With a robust eukaryotic promoter, the encoded antigen can be expressed to yield enough levels of transgene expression once the host is inoculated with the plasmids (Galvin T. A., et al., *Vaccine* 2000, 18:2566-2583). Modern DNA vaccine generation relies on DNA synthesis, possibly one-step cloning into the plasmid vector and subsequent isolation of the plasmid, which takes significantly less time and cost to manufacture. The resulting plasmid DNA is also highly stable at room temperature, avoiding cold transportation and leading to substantially extended shelf-life. These techniques are standard in the art.

Alternatively, nucleic acid sequences encoding the antigen of interest, e.g., GPA33, can be synthetically introduced into a mRNA molecule. The mRNA is then delivered into a host animal, whose cells would recognize and translate the mRNA sequence to the polypeptide sequence of the candidate antigen, e.g., GPA33, thus triggering the immune response to the foreign antigen. An attractive feature of mRNA antigen or mRNA vaccine is that mRNA is a non-infectious, non-integrating platform. There is no potential risk of infection or insertional mutagenesis associated with DNA vaccines. In addition, mRNA is degraded by normal cellular processes and has a controllable in vivo half-life through modification of design and delivery methods (Kariko, K., et al., *Mol Ther* 16: 1833-1840 (2008); Kauffman, K. J., et al., *J. Control Release* 240, 227-234 (2016); Guan, S. & Rosenecker, J., *Gene Ther* 24, 133-143 (2017); Thess, A., et al. *Mol Ther* 23, 1456-1464 (2015)). These techniques are standard in the art.

In describing the present technology, immune responses may be described as either "primary" or "secondary" immune responses. A primary immune response, which is also described as a "protective" immune response, refers to an immune response produced in an individual as a result of some initial exposure (e.g., the initial "immunization" or "priming") to a particular antigen, e.g., GPA33 protein. In some embodiments, the immunization can occur as a result of vaccinating the individual with a vaccine containing the antigen. For example, the vaccine can be a GPA33 vaccine comprising one or more GPA33 protein-derived antigens. A primary immune response can become weakened or attenuated over time and can even disappear or at least become so attenuated that it cannot be detected. Accordingly, the present technology also relates to a "secondary" immune response, which is also described here as a "memory immune response." The term secondary immune response refers to an immune response elicited in an individual after a primary immune response has already been produced.

Thus, a secondary immune response can be elicited, e.g., to enhance an existing immune response that has become weakened or attenuated, or to recreate a previous immune response that has either disappeared or can no longer be detected (e.g., "boosting"). The secondary or memory immune response can be either a humoral (antibody) response or a cellular response. A secondary or memory humoral response occurs upon stimulation of memory B cells that were generated at the first presentation of the antigen. Delayed type hypersensitivity (DTH) reactions are a type of cellular secondary or memory immune response that are mediated by $CD4^+$ T cells. A first exposure to an antigen primes the immune system and additional exposure (s) results in a DTH.

Following appropriate immunization, the anti-GPA33 antibody can be prepared from the subject's serum. If desired, the antibody molecules directed against the GPA33 protein can be isolated from the mammal (e.g., from the blood) and further purified by well-known techniques, such as polypeptide A chromatography to obtain the IgG fraction.

Monoclonal Antibody. In one embodiment of the present technology, the antibody is an anti-GPA33 monoclonal antibody. For example, in some embodiments, the anti-GPA33 monoclonal antibody may be a human or a mouse anti-GPA33 monoclonal antibody. For preparation of monoclonal antibodies directed towards the GPA33 protein, or derivatives (e.g., the anti-GPA33 antibodies of the present technology), fragments, analogs or homologs thereof, any technique that provides for the production of antibody molecules by continuous cell line culture can be utilized. Such techniques include, but are not limited to, the hybridoma technique (See, e.g., Kohler & Milstein, 1975. *Nature* 256: 495-497); the trioma technique; the human B-cell hybridoma technique (See, e.g., Kozbor, et al., 1983. *Immunol. Today* 4: 72) and the EBV hybridoma technique to produce human monoclonal antibodies (See, e.g., Cole, et al., 1985. In: MONOCLONAL ANTIBODIES AND CANCER THERAPY, Alan R. Liss, Inc., pp. 77-96). Human monoclonal antibodies can be utilized in the practice of the present technology and can be produced by using human hybridomas (See, e.g., Cote, et al., 1983. *Proc Natl Acad Sci*

*USA* 80: 2026-2030) or by transforming human B-cells with Epstein Barr Virus in vitro (See, e.g., Cole, et al., 1985. In: MONOCLONAL ANTIBODIES AND CANCER THERAPY, Alan R. Liss, Inc., pp. 77-96). For example, a population of nucleic acids that encode regions of antibodies can be isolated. PCR utilizing primers derived from sequences encoding conserved regions of antibodies is used to amplify sequences encoding portions of antibodies from the population and then DNAs encoding antibodies or fragments thereof, such as variable domains, are reconstructed from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for an antigen or epitope present on the GPA33 protein. Alternatively, hybridomas expressing anti-GPA33 monoclonal antibodies of the present technology can be prepared by immunizing a subject and then isolating hybridomas from the subject's spleen using routine methods. See, e.g., Milstein et al., (Galfre and Milstein, *Methods Enzymol* (1981) 73: 3-46). Screening the hybridomas using standard methods will produce monoclonal antibodies of varying specificity (i.e., for different epitopes) and affinity. A selected monoclonal antibody with the desired properties, e.g., GPA33 binding, can be used as expressed by the hybridoma; it can be bound to a molecule such as polyethylene glycol (PEG) to alter its properties, or a cDNA encoding it can be isolated, sequenced and manipulated in various ways. Other manipulations include substituting or deleting particular amino acyl residues that contribute to instability of the antibody during storage or after administration to a subject, and affinity maturation techniques to improve affinity of the antibody of the GPA33 protein.

Hybridoma Technique. In some embodiments, the antibody of the present technology is an anti-GPA33 monoclonal antibody produced by a hybridoma which includes a B cell obtained from a transgenic non-human animal, e.g., a transgenic mouse, having a genome comprising a human heavy chain transgene and a light chain transgene fused to an immortalized cell. Hybridoma techniques include those known in the art and taught in Harlow et al., *Antibodies: A Laboratory Manual* Cold Spring Harbor Laboratory, Cold Spring Harbor, NY, 349 (1988); Hammerling et al., *Monoclonal Antibodies And T-Cell Hybridomas,* 563-681 (1981). Other methods for producing hybridomas and monoclonal antibodies are well known to those of skill in the art.

Phage Display Technique. As noted above, the antibodies of the present technology can be produced through the application of recombinant DNA and phage display technology. For example, anti-GPA33 antibodies, can be prepared using various phage display methods known in the art. In phage display methods, functional antibody domains are displayed on the surface of a phage particle which carries polynucleotide sequences encoding them. Phages with a desired binding property are selected from a repertoire or combinatorial antibody library (e.g., human or murine) by selecting directly with an antigen, typically an antigen bound or captured to a solid surface or bead. Phages used in these methods are typically filamentous phage including fd and M13 with Fab, Fv or disulfide stabilized Fv antibody domains that are recombinantly fused to either the phage gene III or gene VIII protein. In addition, methods can be adapted for the construction of Fab expression libraries (See, e.g., Huse, et al., *Science* 246: 1275-1281, 1989) to allow rapid and effective identification of monoclonal Fab fragments with the desired specificity for a GPA33 polypeptide, e.g., a polypeptide or derivatives, fragments, analogs or homologs thereof. Other examples of phage display methods that can be used to make the antibodies of the present technology include those disclosed in Huston et al., *Proc. Natl. Acad. Sci U.S.A.,* 85: 5879-5883, 1988; Chaudhary et al., *Proc. Natl. Acad. Sci U.S.A.,* 87: 1066-1070, 1990; Brinkman et al., *J Immunol. Methods* 182: 41-50, 1995; Ames et al., *J Immunol. Methods* 184: 177-186, 1995; Kettleborough et al., *Eur. J. Immunol.* 24: 952-958, 1994; Persic et al., *Gene* 187: 9-18, 1997; Burton et al., *Advances in Immunology* 57: 191-280, 1994; PCT/GB91/01134; WO 90/02809; WO 91/10737; WO 92/01047; WO 92/18619; WO 93/11236; WO 95/15982; WO 95/20401; WO 96/06213; WO 92/01047 (Medical Research Council et al.); WO 97/08320 (Morphosys); WO 92/01047 (CAT/MRC); WO 91/17271 (Affymax); and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743. Methods useful for displaying polypeptides on the surface of bacteriophage particles by attaching the polypeptides via disulfide bonds have been described by Lohning, U.S. Pat. No. 6,753,136. As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and $F(ab')_2$ fragments can also be employed using methods known in the art such as those disclosed in WO 92/22324; Mullinax et al., *BioTechniques* 12: 864-869, 1992; and Sawai et al., *AJRI* 34: 26-34, 1995; and Better et al., *Science* 240: 1041-1043, 1988.

Generally, hybrid antibodies or hybrid antibody fragments that are cloned into a display vector can be selected against the appropriate antigen in order to identify variants that maintain good binding activity, because the antibody or antibody fragment will be present on the surface of the phage or phagemid particle. See, e.g., Barbas III et al., *Phage Display, A Laboratory Manual* (Cold Spring Harbor Laboratory Press, Cold Spring Harbor, N.Y., 2001). However, other vector formats could be used for this process, such as cloning the antibody fragment library into a lytic phage vector (modified T7 or Lambda Zap systems) for selection and/or screening.

Expression of Recombinant Anti-GPA33 Antibodies. As noted above, the antibodies of the present technology can be produced through the application of recombinant DNA technology. Recombinant polynucleotide constructs encoding an anti-GPA33 antibody of the present technology typically include an expression control sequence operably-linked to the coding sequences of the antibody chains, including naturally-associated or heterologous promoter regions. As such, another aspect of the technology includes vectors containing one or more nucleic acid sequences encoding an anti-GPA33 antibody of the present technology. For recombinant expression of one or more of the polypeptides of the present technology, the nucleic acid containing all or a portion of the nucleotide sequence encoding the anti-GPA33 antibody of the present technology is inserted into an appropriate cloning vector, or an expression vector (i.e., a vector that contains the necessary elements for the transcription and translation of the inserted polypeptide coding sequence) by recombinant DNA techniques well known in the art and as detailed below. Methods for producing diverse populations of vectors have been described by Lerner et al., U.S. Pat. Nos. 6,291,160 and 6,680,192.

In general, expression vectors useful in recombinant DNA techniques are often in the form of plasmids. In the present disclosure, "plasmid" and "vector" can be used interchangeably as the plasmid is the most commonly used form of vector. However, the present technology is intended to include such other forms of expression vectors that are not technically plasmids, such as viral vectors (e.g., replication defective retroviruses, adenoviruses and adeno-associated viruses), which serve equivalent functions. Such viral vectors permit infection of a subject and expression of a construct in that subject. In some embodiments, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences encoding the anti-GPA33 antibody of the present technology, and the collection and purification of the anti-GPA33 antibodies of the present technology. See generally, U.S. 2002/0199213. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. Vectors can also encode signal peptide, e.g., pectate lyase, useful to direct the secretion of extracellular antibody fragments. See U.S. Pat. No. 5,576,195.

The recombinant expression vectors of the present technology comprise a nucleic acid encoding a protein with GPA33 binding properties in a form suitable for expression of the nucleic acid in a host cell, which means that the recombinant expression vectors include one or more regulatory sequences, selected on the basis of the host cells to be used for expression that is operably-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, e.g., in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc. Typical regulatory sequences useful as promoters of recombinant polypeptide expression (e.g., anti-GPA33 antibody), include but are not limited to, promoters of 3-phosphoglycerate kinase and other glycolytic enzymes. Inducible yeast promoters include, among others, promoters from alcohol dehydrogenase, isocytochrome C, and enzymes responsible for maltose and galactose utilization. In one embodiment, a polynucleotide encoding an anti-GPA33 antibody of the present technology is operably-linked to an ara B promoter and expressible in a host cell. See U.S. Pat. No. 5,028,530. The expression vectors of the present technology can be introduced into host cells to thereby produce polypeptides or peptides, including fusion polypeptides, encoded by nucleic acids as described herein (e.g., anti-GPA33 antibody, etc.).

Another aspect of the present technology pertains to anti-GPA33 antibody-expressing host cells, which contain a nucleic acid encoding one or more anti-GPA33 antibodies. The recombinant expression vectors of the present technology can be designed for expression of an anti-GPA33 antibody in prokaryotic or eukaryotic cells. For example, an anti-GPA33 antibody can be expressed in bacterial cells such as *Escherichia coli*, insect cells (using baculovirus expression vectors), fungal cells, e.g., yeast, yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, e.g., using T7 promoter regulatory sequences and T7 polymerase. Methods useful for the preparation and screening of polypeptides having a predetermined property, e.g., anti-GPA33 antibody, via expression of stochastically generated polynucleotide sequences has been previously described. See U.S. Pat. Nos. 5,763,192; 5,723,323; 5,814,476; 5,817,483; 5,824,514; 5,976,862; 6,492,107; 6,569,641.

Expression of polypeptides in prokaryotes is most often carried out in *E. coli* with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (i) to increase expression of recombinant polypeptide; (ii) to increase the solubility of the recombinant polypeptide; and (iii) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31-40), pMAL (New England Biolabs, Beverly, Mass.) and pRITS (Pharmacia, Piscataway, N.J.) that fuse glutathione S-transferase (GST), maltose E binding polypeptide, or polypeptide A, respectively, to the target recombinant polypeptide.

Examples of suitable inducible non-fusion *E. coli* expression vectors include pTrc (Amrann et al., (1988) *Gene* 69: 301-315) and pET 11d (Studier et al., GENE EXPRESSION TECHNOLOGY: METHODS IN ENZYMOLOGY 185, Academic Press, San Diego, Calif. (1990) 60-89). Methods for targeted assembly of distinct active peptide or protein domains to yield multifunctional polypeptides via polypeptide fusion has been described by Pack et al., U.S. Pat. Nos. 6,294,353; 6,692,935. One strategy to maximize recombinant polypeptide expression, e.g., an anti-GPA33 antibody, in *E. coli* is to express the polypeptide in host bacteria with an impaired capacity to proteolytically cleave the recombinant polypeptide. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in the expression host, e.g., *E. coli* (See, e.g., Wada, et al., 1992. *Nucl Acids Res* 20: 2111-2118). Such alteration of nucleic acid sequences of the present technology can be carried out by standard DNA synthesis techniques.

In another embodiment, the anti-GPA33 antibody expression vector is a yeast expression vector. Examples of vectors for expression in yeast *Saccharomyces cerevisiae* include pYepSec1 (Baldari, et al., 1987. *EMBO J.* 6: 229-234), pMFa (Kurjan and Herskowitz, *Cell* 30: 933-943, 1982), pJRY88 (Schultz et al., *Gene* 54: 113-123, 1987), pYES2 (Invitrogen Corporation, San Diego, Calif), and picZ (Invitrogen Corp, San Diego, Calif). Alternatively, an anti-GPA33 antibody can be expressed in insect cells using baculovirus expression vectors. Baculovirus vectors available for expression of polypeptides, e.g., an anti-GPA33 antibody, in cultured insect cells (e.g., SF9 cells) include the pAc series (Smith, et al., *Mol Cell Biol* 3: 2156-2165, 1983) and the pVL series (Lucklow and Summers, 1989. *Virology* 170: 31-39).

In yet another embodiment, a nucleic acid encoding an anti-GPA33 antibody of the present technology is expressed in mammalian cells using a mammalian expression vector. Examples of mammalian expression vectors include, e.g., but are not limited to, pCDM8 (Seed, *Nature* 329: 840, 1987) and pMT2PC (Kaufman, et al., *EMBO J.* 6: 187-195, 1987). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells that are useful for expression of the anti-GPA33 antibody of the present technology, see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid in a particular cell type (e.g., tissue-specific regulatory elements). Tissue-specific regulatory elements are known in the art. Non-limiting examples of suitable tissue-specific promoters include the albumin promoter (liver-specific; Pinkert, et al., *Genes Dev.* 1: 268-277, 1987), lymphoid-specific promoters (Calame and Eaton, *Adv. Immunol.* 43: 235-275, 1988), promoters of T cell receptors (Winoto and Baltimore, *EMBO J.* 8: 729-733, 1989) and immunoglobulins (Banerji, et al., 1983. *Cell* 33: 729-740; Queen and Baltimore, *Cell* 33: 741-748, 1983.), neuron-specific promoters (e.g., the neurofilament promoter; Byrne and Ruddle, *Proc Natl Acad Sci USA* 86: 5473-5477, 1989), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, *Science* 249: 374-379, 1990) and the α-fetoprotein promoter (Campes and Tilghman, *Genes Dev.* 3: 537-546, 1989).

Another aspect of the present methods pertains to host cells into which a recombinant expression vector of the present technology has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an anti-GPA33 antibody can be expressed in bacterial cells such as *E. coli*, insect cells, yeast or mammalian cells. Mammalian cells are a suitable host for expressing nucleotide segments encoding immunoglobulins or fragments thereof. See Winnacker, *From Genes To Clones*, (VCH Publishers, NY, 1987). A number of suitable host cell lines capable of secreting intact heterologous proteins have been developed in the art, and include Chinese hamster ovary (CHO) cell lines, various COS cell lines, HeLa cells, L cells and myeloma cell lines. In some embodiments, the cells are non-human. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Queen et al., *Immunol. Rev.* 89: 49, 1986. Illustrative expression control sequences are promoters derived from endogenous genes, cytomegalovirus, SV40, adenovirus, bovine papillomavirus, and the like. Co et al., *J Immunol.* 148: 1149, 1992. Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, electroporation, biolistics or viral-based transfection. Other methods used to transform mammalian cells include the use of polybrene, protoplast fusion, liposomes, electroporation, and microinjection (See generally, Sambrook et al., *Molecular Cloning*). Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals. The vectors containing the DNA segments of interest can be transferred into the host cell by well-known methods, depending on the type of cellular host.

Non-limiting examples of suitable vectors include those designed for propagation and expansion, or for expression or both. For example, a cloning vector can be selected from the group consisting of the pUC series, the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as lamda-GT10, lamda-GT11, lamda-ZapII (Stratagene), lamda-EMBL4, and lamda-NM1149, can also be used. Non-limiting examples of plant expression vectors include pBI110, pBI101.2, pBI101.3, pBI121 and pBIN19 (Clontech). Non-limiting examples of animal expression vectors include pEUK-C1, pMAM and pMAMneo (Clontech). The TOPO cloning system (Invitrogen, Calsbad, CA, Carlsbad, CA) can also be used in accordance with the manufacturer's recommendations.

In certain embodiments, the vector is a mammalian vector. In certain embodiments, the mammalian vector contains at least one promoter element, which mediates the initiation of transcription of mRNA, the antibody-coding sequence, and signals required for the termination of transcription and polyadenylation of the transcript. In certain embodiments, the mammalian vector contains additional elements, such as, for example, enhancers, Kozak sequences and intervening sequences flanked by donor and acceptor sites for RNA splicing. In certain embodiments, highly efficient transcription can be achieved with, for example, the early and late promoters from SV40, the long terminal repeats (LTRS) from retroviruses, for example, RSV, HTLVI, HIVI and the early promoter of the cytomegalovirus (CMV). Cellular elements can also be used (e.g., the human actin promoter). Non-limiting examples of mammalian expression vectors include, vectors such as pIRESlneo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen, Calsbad, CA), PSVL and PMSG (Pharmacia, Uppsala, Sweden), pRSVcat (ATCC 37152), pSV2dhfr (ATCC 37146) and pBC12MI (ATCC 67109). Non-limiting examples of mammalian host cells that can be used in combination with such mammalian vectors include human Hela 293, HEK 293, H9 and Jurkat cells, mouse 3T3, NIH3T3 and C127 cells, Cos 1, Cos 7 and CV 1, quail QC1-3 cells, mouse L cells and Chinese hamster ovary (CHO) cells.

In certain embodiments, the vector is a viral vector, for example, retroviral vectors, parvovirus-based vectors, e.g., adeno-associated virus (AAV)-based vectors, AAV-adenoviral chimeric vectors, and adenovirus-based vectors, and lentiviral vectors, such as Herpes simplex (HSV)-based vectors. In certain embodiments, the viral vector is manipulated to render the virus replication deficient. In certain embodiments, the viral vector is manipulated to eliminate toxicity to the host. These viral vectors can be prepared using standard recombinant DNA techniques described in, for example, Sambrook et al., Molecular Cloning, a Laboratory Manual, 2d edition, Cold Spring Harbor Press, Cold Spring Harbor, N.Y. (1989); and Ausubel et al., Current Protocols in Molecular Biology, Greene Publishing Associates and John Wiley & Sons, New York, N.Y. (1994).

In certain embodiments, a vector or polynucleotide described herein can be transferred to a cell (e.g., an ex vivo cell) by conventional techniques and the resulting cell can be cultured by conventional techniques to produce an anti-GPA33 antibody or antigen binding fragment described herein. Accordingly, provided herein are cells comprising a polynucleotide encoding an anti-GPA33 antibody or antigen binding fragment thereof operably linked to a regulatory expression element (e.g., promoter) for expression of such sequences in the host cell. In certain embodiments, a vector encoding the heavy chain operably linked to a promoter and a vector encoding the light chain operably linked to a promoter can be co-expressed in the cell for expression of the entire anti-GPA33 antibody or antigen binding fragment. In certain embodiments, a cell comprises a vector comprising a polynucleotide encoding both the heavy chain and the light chain of an anti-GPA33 antibody or antigen binding fragment described herein that are operably linked to a promoter. In certain embodiments, a cell comprises two different vectors, a first vector comprising a polynucleotide encoding a heavy chain operably linked to a promoter, and a second vector comprising a polynucleotide encoding a light chain operably linked to a promoter. In certain embodiments, a first cell comprises a first vector comprising a polynucleotide encoding a heavy chain of an anti-GPA33 antibody or antigen binding fragment described herein, and a second cell comprises a second vector comprising a polynucleotide encoding a light chain of an anti-GPA33 antibody or antigen binding fragment described herein. In certain embodiments, provided herein is a mixture of cells comprising said first cell and said second cell. Examples of cells include, but are not limited to, a human cell, a human cell line, *E. coli* (e.g., *E. coli* TB-1, TG-2, DH5a, XL-Blue MRF' (Stratagene), SA2821 and Y1090), *B. subtilis, P. aerugenosa, S. cerevisiae, N. crassa*, insect cells (e.g., Sf9, Ea4) and the like.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the anti-GPA33 antibody or can be introduced on a separate vector. Cells stably transfected with the introduced nucleic acid can be identified by drug selection (e.g., cells that have incorporated the selectable marker gene will survive, while the other cells die).

A host cell that includes an anti-GPA33 antibody of the present technology, such as a prokaryotic or eukaryotic host cell in culture, can be used to produce (i.e., express) recombinant anti-GPA33 antibody. In one embodiment, the method comprises culturing the host cell (into which a recombinant expression vector encoding the anti-GPA33 antibody has been introduced) in a suitable medium such that the anti-GPA33 antibody is produced. In another embodiment, the method further comprises the step of isolating the anti-GPA33 antibody from the medium or the host cell. Once expressed, collections of the anti-GPA33 antibody, e.g., the anti-GPA33 antibodies or the anti-GPA33 antibody-related polypeptides are purified from culture media and host cells. The anti-GPA33 antibody can be purified according to standard procedures of the art, including HPLC purification, column chromatography, gel electrophoresis and the like. In one embodiment, the anti-GPA33 antibody is produced in a host organism by the method of Boss et al., U.S. Pat. No. 4,816,397. Usually, anti-GPA33 antibody chains are expressed with signal sequences and are thus released to the culture media. However, if the anti-GPA33 antibody chains are not naturally secreted by host cells, the anti-GPA33 antibody chains can be released by treatment with mild detergent. Purification of recombinant polypeptides is well known in the art and includes ammonium sulfate precipitation, affinity chromatography purification technique, column chromatography, ion exchange purification technique, gel electrophoresis and the like (See generally Scopes, Protein Purification (Springer-Verlag, N.Y., 1982).

Polynucleotides encoding anti-GPA33 antibodies, e.g., the anti-GPA33 antibody coding sequences, can be incorporated in transgenes for introduction into the genome of a transgenic animal and subsequent expression in the milk of the transgenic animal. See, e.g., U.S. Pat. Nos. 5,741,957, 5,304,489, and 5,849,992. Suitable transgenes include coding sequences for light and/or heavy chains in operable linkage with a promoter and enhancer from a mammary gland specific gene, such as casein or β-lactoglobulin. For production of transgenic animals, transgenes can be microinjected into fertilized oocytes, or can be incorporated into the genome of embryonic stem cells, and the nuclei of such cells transferred into enucleated oocytes.

Single-Chain Antibodies. In one embodiment, the anti-GPA33 antibody of the present technology is a single-chain anti-GPA33 antibody. According to the present technology, techniques can be adapted for the production of single-chain antibodies specific to a GPA33 protein (See, e.g., U.S. Pat. No. 4,946,778). Examples of techniques which can be used to produce single-chain Fvs and antibodies of the present technology include those described in U.S. Pat. Nos. 4,946,778 and 5,258,498; Huston et al., *Methods in Enzymology,* 203: 46-88, 1991; Shu, L. et al., *Proc Natl Acad Sci USA,* 90: 7995-7999, 1993; and Skerra et al., *Science* 240: 1038-1040, 1988.

Chimeric and Humanized Antibodies. In one embodiment, the anti-GPA33 antibody of the present technology is a chimeric anti-GPA33 antibody. In one embodiment, the anti-GPA33 antibody of the present technology is a humanized anti-GPA33 antibody. In one embodiment of the present technology, the donor and acceptor antibodies are monoclonal antibodies from different species. For example, the acceptor antibody is a human antibody (to minimize its antigenicity in a human), in which case the resulting CDR-grafted antibody is termed a "humanized" antibody.

Recombinant anti-GPA33 antibodies, such as chimeric and humanized monoclonal antibodies, comprising both human and non-human portions, can be made using standard recombinant DNA techniques, and are within the scope of the present technology. For some uses, including in vivo use of the anti-GPA33 antibody of the present technology in humans as well as use of these agents in in vitro detection assays, it is possible to use chimeric, humanized, or bispecific antibodies. Such chimeric and humanized monoclonal antibodies can be produced by recombinant DNA techniques known in the art. Such useful methods include, e.g., but are not limited to, methods described in International Application No. PCT/US86/02269; U.S. Pat. No. 5,225,539; European Patent No. 184187; European Patent No. 171496; European Patent No. 173494; PCT International Publication No. WO 86/01533; U.S. Pat. Nos. 4,816,567; 5,225,539; European Patent No. 125023; Better, et al., 1988. *Science* 240: 1041-1043; Liu, et al., 1987. *Proc Natl Acad Sci USA* 84: 3439-3443; Liu, et al., 1987. *J. Immunol.* 139: 3521-3526; Sun, et al., 1987. *Proc Natl Acad Sci USA* 84: 214-218; Nishimura, et al., 1987. *Cancer Res.* 47: 999-1005; Wood, et al., 1985. *Nature* 314: 446-449; Shaw, et al., 1988. *J. Natl. Cancer Inst.* 80: 1553-1559; Morrison (1985) *Science* 229: 1202-1207; Oi, et al. (1986) *BioTechniques* 4: 214; Jones, et al., 1986. *Nature* 321: 552-525; Verhoeyan, et al., 1988. *Science* 239: 1534; Morrison, *Science* 229: 1202, 1985; Oi et al., *BioTechniques* 4: 214, 1986; Gillies et al., *J. Immunol. Methods,* 125: 191-202, 1989; U.S. Pat. No. 5,807,715; and Beidler, et al., 1988. *J. Immunol.* 141: 4053-4060. For example, antibodies can be humanized using a variety of techniques including CDR-grafting (EP 0 239 400; WO 91/09967; U.S. Pat. Nos. 5,530,101; 5,585,089; 6,248,516; EP460167), veneering or resurfacing (EP 0 592 106; EP 0 519 596; Padlan E. A., *Molecular Immunology,* 28: 489-498, 1991; Studnicka et al., *Protein Engineering* 7: 805-814, 1994; Roguska et al., *PNAS* 91: 969-973, 1994), and chain shuffling (U.S. Pat. No. 5,565,332). In one embodiment, a cDNA encoding a murine anti-GPA33 antibody is digested with a restriction enzyme selected specifically to remove the sequence encoding the Fc constant region, and the equivalent portion of a cDNA encoding a human Fc constant region is substituted (See Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 125,023; Better et al. (1988) *Science* 240: 1041-1043; Liu et al. (1987) *Proc Natl Acad Sci USA* 84: 3439-3443; Liu et al. (1987) *J Immunol* 139: 3521-3526; Sun et al. (1987) *Proc Natl Acad Sci USA* 84: 214-218; Nishimura et al. (1987) *Cancer Res* 47: 999-1005; Wood et al. (1985) *Nature* 314: 446-449; and Shaw et al. (1988) *J. Natl. Cancer Inst.* 80: 1553-1559; U.S. Pat. Nos. 6,180,370; 6,300,064; 6,696,248; 6,706,484; 6,828,422.

In one embodiment, the present technology provides the construction of humanized anti-GPA33 antibodies that are unlikely to induce a human anti-mouse antibody (hereinafter referred to as "HAMA") response, while still having an effective antibody effector function. As used herein, the terms "human" and "humanized", in relation to antibodies, relate to any antibody which is expected to elicit a therapeutically tolerable weak immunogenic response in a human subject. In one embodiment, the present technology provides for humanized anti-GPA33 antibodies, heavy and light chain immunoglobulins.

CDR-Grafted Antibodies. In some embodiments, the anti-GPA33 antibody of the present technology is an anti-GPA33 CDR-grafted antibody. Generally the donor and acceptor antibodies used to generate the anti-GPA33 CDR-grafted antibody are monoclonal antibodies from different species; typically the acceptor antibody is a human antibody (to minimize its antigenicity in a human), in which case the resulting CDR-grafted antibody is termed a "humanized" antibody. The graft may be of a single CDR (or even a portion of a single CDR) within a single $V_H$ or $V_L$ of the acceptor antibody, or can be of multiple CDRs (or portions thereof) within one or both of the $V_H$ and $V_L$. Frequently, all three CDRs in all variable domains of the acceptor antibody will be replaced with the corresponding donor CDRs, though one needs to replace only as many as necessary to permit adequate binding of the resulting CDR-grafted antibody to GPA33 protein. Methods for generating CDR-grafted and humanized antibodies are taught by Queen et al. U.S. Pat. Nos. 5,585,089; 5,693,761; 5,693,762; and Winter U.S. Pat. No. 5,225,539; and EP 0682040. Methods useful to prepare $V_H$ and $V_L$ polypeptides are taught by Winter et al., U.S. Pat. Nos. 4,816,397; 6,291,158; 6,291,159; 6,291,161; 6,545,142; EP 0368684; EP0451216; and EP0120694.

After selecting suitable framework region candidates from the same family and/or the same family member, either or both the heavy and light chain variable regions are produced by grafting the CDRs from the originating species into the hybrid framework regions. Assembly of hybrid antibodies or hybrid antibody fragments having hybrid variable chain regions with regard to either of the above aspects can be accomplished using conventional methods known to those skilled in the art. For example, DNA sequences encoding the hybrid variable domains described herein (i.e., frameworks based on the target species and CDRs from the originating species) can be produced by oligonucleotide synthesis and/or PCR. The nucleic acid encoding CDR regions can also be isolated from the originating species antibodies using suitable restriction enzymes and ligated into the target species framework by ligating with suitable ligation enzymes. Alternatively, the framework regions of the variable chains of the originating species antibody can be changed by site-directed mutagenesis.

Since the hybrids are constructed from choices among multiple candidates corresponding to each framework region, there exist many combinations of sequences which are amenable to construction in accordance with the principles described herein. Accordingly, libraries of hybrids can be assembled having members with different combinations of individual framework regions. Such libraries can be electronic database collections of sequences or physical collections of hybrids.

This process typically does not alter the acceptor antibody's FRs flanking the grafted CDRs. However, one skilled in the art can sometimes improve antigen binding affinity of the resulting anti-GPA33 CDR-grafted antibody by replacing certain residues of a given FR to make the FR more similar to the corresponding FR of the donor antibody. Suitable locations of the substitutions include amino acid residues adjacent to the CDR, or which are capable of interacting with a CDR (See, e.g., U.S. Pat. No. 5,585,089, especially columns 12-16). Or one skilled in the art can start with the donor FR and modify it to be more similar to the acceptor FR or a human consensus FR. Techniques for making these modifications are known in the art. Particularly if the resulting FR fits a human consensus FR for that position, or is at least 90% or more identical to such a consensus FR, doing so may not increase the antigenicity of the resulting modified anti-GPA33 CDR-grafted antibody significantly compared to the same antibody with a fully human FR.

Multi-specific fusion proteins. Multi-specific fusion proteins, such as bispecific antibodies (BsAbs) and bispecific antibody fragments (BsFab), have at least one arm that specifically binds to, for example, GPA33 and at least one other arm that specifically binds to a second target antigen.

A bispecific antibody is an antibody that can bind simultaneously to two targets that have a distinct structure, e.g., two different target antigens, two different epitopes on the same target antigen, or a hapten and a target antigen or epitope on a target antigen. A bispecific antibody can be made, for example, by combining heavy chains and/or light chains that recognize different epitopes of the same or different antigen. In some embodiments, by molecular function, a bispecific binding agent binds one antigen (or epitope) on one of its two binding arms (one VH/VL pair), and binds a different antigen (or epitope) on its second arm (a different VH/VL pair). By this definition, a bispecific binding agent has two distinct antigen binding arms (in both specificity and CDR sequences), and is monovalent for each antigen to which it binds.

Bispecific antibodies (BsAb) and bispecific antibody fragments (BsFab) of the present technology have at least one arm that specifically binds to, for example, GPA33 and at least one other arm that specifically binds to a second target antigen. In some embodiments, the second target antigen is an antigen or epitope of a B-cell, a T-cell, a myeloid cell, a plasma cell, or a mast-cell. Additionally or alternatively, in certain embodiments, the second target antigen is selected from the group consisting of CD3, CD4, CD8, CD20, CD19, CD21, CD23, CD46, CD80, HLA-DR, CD74, CD22, CD14, CD15, CD16, CD123, CD32, CD64, TCR gamma/delta, NKp46, KIR, PD-1, PD-L1, LAG3, CD28, B7H3, STEAP1, HER2, EGFR, CEA, CECAM5, Transferrin receptor, FAP, NKG2D-ligands, TRAIL, FasL, cathepsin G, granzyme, carboxypeptidase, and beta-lactamase. In certain embodiments, the BsAbs are capable of binding to tumor cells that express GPA33 antigen on the cell surface. In some embodiments, the BsAbs have been engineered to facilitate killing of tumor cells by directing (or recruiting) cytotoxic T cells to a tumor site. Other exemplary BsAbs include those with a first antigen binding site specific for GPA33 and a second antigen binding site specific for a small molecule hapten (e.g., DTP A, IMP288, DOTA, DOTA-Bn, DOTA-desferrioxamine, DOTA(metal) complex, benzyl-DOTA(metal) complex, *proteus*-DOTA(metal) complex, NOGADA-*proteus*-DOTA(metal) complex, Star-DFO(metal) complex, DFO(metal) complex, other DOTA-chelates described herein, Biotin, fluorescein, or those disclosed in Goodwin, D A. et al, 1994, *Cancer Res.* 54(22):5937-5946). In some embodiments, the bispecific antibody or bispecific antigen binding fragment comprises a catalytic antibody, an immune checkpoint inhibitor, or an immune checkpoint activator.

A variety of multi-specific fusion proteins can be produced using molecular engineering. For example, BsAbs have been constructed that either utilize the full immunoglobulin framework (e.g., IgG), single chain variable fragment (scFv), or combinations thereof. In some embodiments, the bispecific fusion protein is divalent, comprising, for example, a scFv with a single binding site for one antigen and a Fab fragment with a single binding site for a second antigen. In some embodiments, the bispecific fusion protein is divalent, comprising, for example, a scFv with a single binding site for one antigen and another scFv fragment with a single binding site for a second antigen. In other embodiments, the bispecific fusion protein is tetravalent, comprising, for example, an immunoglobulin (e.g., IgG) with two binding sites for one antigen and two identical scFvs for a second antigen. BsAbs composed of two scFv units in tandem have been shown to be a clinically successful bispecific antibody format. In some embodiments, BsAbs comprise two single chain variable fragments (scFvs) in tandem have been designed such that a scFv that binds a tumor antigen (e.g., GPA33) is linked with a scFv that engages T cells (e.g., by binding CD3). In this way, T cells are recruited to a tumor site such that they can mediate cytotoxic killing of the tumor cells. See e.g., Dreier et al., *J. Immunol.* 170: 4397-4402 (2003); Bargou et al., *Science* 321: 974-977 (2008). In some embodiments, BsAbs comprise two single chain variable fragments (scFvs) in tandem have been designed such that a scFv that binds a tumor antigen (e.g., GPA33) is linked with a scFv that engages a small molecule DOTA hapten.

Recent methods for producing multi-specific fusion proteins include engineered recombinant monoclonal antibodies which have additional cysteine residues so that they crosslink more strongly than the more common immunoglobulin isotypes. See, e.g., FitzGerald et al., *Protein Eng.* 10(10):1221-1225 (1997). Another approach is to engineer recombinant fusion proteins linking two or more different single-chain antibody or antibody fragment segments with the needed dual specificities. See, e.g., Coloma et al., *Nature Biotech.* 15:159-163 (1997). A variety of bispecific fusion proteins can be produced using molecular engineering.

Multi-specific fusion proteins linking two or more different single-chain antibodies or antibody fragments are produced in a similar manner. Recombinant methods can be used to produce a variety of fusion proteins. In some certain embodiments, a BsAb according to the present technology comprises an immunoglobulin, which immunoglobulin comprises a heavy chain and a light chain, and an scFv. In some certain embodiments, the scFv is linked to the C-terminal end of the heavy chain of any GPA33 immunoglobulin disclosed herein (e.g., IgG(H)-scFv). In some certain embodiments, scFvs are linked to the C-terminal end of the light chain of any GPA33 immunoglobulin disclosed herein (e.g., IgG(L)-scFv). In some embodiments, administration of the IgG(L)-scFv bispecific antibody inhibits cancer progression and/or proliferation in the subject to a greater degree compared to an anti-GPA33×CD3 monomeric BITE, an anti-GPA33×CD3 dimeric BITE, an anti-GPA33×CD3 BITE-Fc, an anti-GPA33×CD3 IgG heterodimer, or an anti-GPA33×CD3 IgG(H)-scFv.

In various embodiments, scFvs are linked to heavy or light chains via a linker sequence. Appropriate linker sequences necessary for the in-frame connection of the heavy chain Fd to the scFv are introduced into the $V_L$ and $V_{kappa}$ domains through PCR reactions. The DNA fragment encoding the scFv is then ligated into a staging vector containing a DNA sequence encoding the CH1 domain. The resulting scFv-CH1 construct is excised and ligated into a vector containing a DNA sequence encoding the Vu region of a GPA33 antibody. The resulting vector can be used to transfect an appropriate host cell, such as a mammalian cell for the expression of the multi-specific fusion protein.

In some embodiments, a linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide (e.g., first and/or second antigen binding sites). In some embodiments, a linker is employed in a multi-specific fusion protein described herein based on specific properties imparted to the multi-specific fusion protein such as, for example, an increase in stability. In some embodiments, a multi-specific fusion protein of the present technology comprises a G4S linker (SEQ ID NO: 113). In some certain embodiments, a multi-specific fusion protein of the present technology comprises a $(G4S)_n$ linker, wherein n is 1, 2, 3, 4, 5, 6, 7, 8, 9, 10, 11, 12, 13, 14, 15 or more (SEQ ID NO: 115).

Self assembly disassembly (SADA) Conjugates. In some embodiments, the anti-GPA33 antibodies of the present technology comprise one or more SADA domains. SADA domains can be designed and/or tailored to achieve environmentally-dependent multimerization with beneficial kinetic, thermodynamic, and/or pharmacologic properties. For example, it is recognized that SADA domains may be part of a conjugate that permit effective delivery of a payload to a target site of interest while minimizing the risk off-target interactions. The anti-GPA33 antibodies of the present technology may comprise a SADA domain linked to one or more binding domains. In some embodiments, such conjugates are characterized in that they multimerize to form a complex of a desired size under relevant conditions (e.g., in a solution in which the conjugate is present above a threshold concentration or pH and/or when present at a target site characterized by a relevant level or density of receptors for the payload), and disassemble to a smaller form under other conditions (e.g., absent the relevant environmental multimerization trigger).

A SADA conjugate may have improved characteristics compared to a conjugate without a SADA domain. In some embodiments, improved characteristics of a multimeric conjugate include: increased avidity/binding to a target, increased specificity for target cells or tissues, and/or extended initial serum half-life. In some embodiments, improved characteristics include that through dissociation to smaller states (e.g., dimeric or monomeric), a SADA conjugate exhibits reduced non-specific binding, decreased toxicity, and/or improved renal clearance. In some embodiments, a SADA conjugate comprises a SADA polypeptide having an amino acid sequence that shows at least 75% identity with that of a human homo-multimerizing polypeptide and is characterized by one or more multimerization dissociation constants ($K_D$).

In some embodiments, a SADA conjugate is constructed and arranged so that it adopts a first multimerization state and one or more higher-order multimerization states. In some embodiments, a first multimerization state is less than about −70 kDa in size. In some embodiments, a first multimerization state is an unmultimerized state (e.g., a monomer or a dimer). In some embodiments, a first multimerization state is a monomer. In some embodiments, a first multimerization state is a dimer. In some embodiments, a first multimerization state is a multimerized state (e.g., a trimer or a tetramer). In some embodiments, a higher-order multimerization states is a homo-tetramer or higher-order homo-multimer greater than 150 kDa in size. In some embodiments, a higher-order homo-multimerized conjugate is stable in aqueous solution when the conjugate is present at a concentration above the SADA polypeptide $K_D$. In some embodiments, a SADA conjugate transitions from a higher-order multimerization state(s) to a first multimerization state under physiological conditions when the concentration of the conjugate is below the SADA polypeptide $K_D$.

In some embodiments, a SADA polypeptide is covalently linked to a binding domain via a linker. Any suitable linker known in the art can be used. In some embodiments, a SADA polypeptide is linked to a binding domain via a polypeptide linker. In some embodiments, a polypeptide linker is a Gly-Ser linker. In some embodiments, a polypeptide linker is or comprises a sequence of (GGGGS)n, where n represents the number of repeating GGGGS units and is 1, 2, 3, 4, 5, 6, 7, 8, 9, 10, 11, 12, 13, 14, 15, 16, 17, 18, 19, 20, 25, 30 or more (SEQ ID NO: 116). In some embodiments, a binding domain is directly fused to a SADA polypeptide.

In some embodiments, a SADA domain is a human polypeptide or a fragment and/or derivative thereof. In some embodiments, a SADA domain is substantially non-immunogenic in a human. In some embodiments, a SADA polypeptide is stable as a multimer. In some embodiments, a SADA polypeptide lacks unpaired cysteine residues. In some embodiments, a SADA polypeptide does not have large exposed hydrophobic surfaces. In some embodiments, a SADA domain has or is predicted to have a structure comprising helical bundles that can associate in a parallel or anti-parallel orientation. In some embodiments, a SADA polypeptide is capable of reversible multimerization. In some embodiments, a SADA domain is a tetramerization domain, a heptamerization domain, a hexamerization domain or an octamerization domain. In certain embodiments, a SADA domain is a tetramerization domain. In some embodiments, a SADA domain is composed of a multimerization domains which are each composed of helical bundles that associate in a parallel or anti-parallel orientation. In some embodiments, a SADA domain is selected from the group of one of the following human proteins: p53, p63, p73, heterogeneous nuclear Ribonucleoprotein C (hnRNPC), N-terminal domain of Synaptosomal-associated protein 23 (SNAP-23), Stefin B (Cystatin B), Potassium voltage-gated channel subfamily KQT member 4 (KCNQ4), or Cyclin-D-related protein (CBFA2T1). Examples of suitable SADA domains are described in PCT/US2018/031235, which is hereby incorporated by reference in its entirely. Provided below are polypeptide sequences for exemplary SADA domains.

```
Human p53 tetramerization domain amino acid sequence (321-359)
                                                  (SEQ ID NO: 90)
KPLDGEYFTLQIRGRERFEMFRELNEALELKDAQAGKEP

Human p63 tetramerization domain amino acid sequence (396-450)
                                                  (SEQ ID NO: 91)
RSPDDELLYLPVRGRETYEMLLKIKESLELMQYLPQHTIETYRQQQQQQHQHLLQKQ

Human p73 tetramerization domain amino acid sequence (348-399)
                                                  (SEQ ID NO: 92)
RHGDEDTYYLQVRGRENFEILMKLKESLELMELVPQPLVDSYRQQQQLLQRP.

Human HNRNPC tetramerization domain amino acid sequence (194-220)
                                                  (SEQ ID NO: 93)
QAIKKELTQIKQKVDSLLENLEKIEKE

Human SNAP-23 tetramerization domain amino acid sequence (23-76)
                                                  (SEQ ID NO: 94)
STRRILGLAIESQDAGIKTITMLDEQKEQLNRIEEGLDQINKDMRETEKTLTEL

Human Stefin B tetramerizaiton domain amino acid sequence (2-98)
                                                  (SEQ ID NO: 95)
MCGAPSATQPATAETQHIADQVRSQLEEKENKKFPVFKAVSFKSQVVAGTNYFIKVHV
GDEDFVHLRVFQSLPHENKPLTLSNYQTNKAKHDELTYF

KCNQ4 tetramerizaiton domain amino acid sequence (611-640)
                                                  (SEQ ID NO: 96)
DEISMMGRVVKVEKQVQSIEHKLDLLLGFY

CBFA2T1 tetramerizaiton domain amino acid sequence (462-521)
                                                  (SEQ ID NO: 97)
TVAEAKRQAAEDALAVINQQEDSSESCWNCGRKASETCSGCNTARYCGSFCQHKDWE
KHH
```

In some embodiments, a SADA polypeptide is or comprises a tetramerization domain of p53, p63, p73, heterogeneous nuclear Ribonucleoprotein C (hnRNPC), N-terminal domain of Synaptosomal-associated protein 23 (SNAP-23), Stefin B (Cystatin B), Potassium voltage-gated channel subfamily KQT member 4 (KCNQ4), or Cyclin-D-related protein (CBFA2T1). In some embodiments, a SADA polypeptide is or comprises a sequence that is at least 75%, 80%, 85%, 90%, 91%, 92%, 93%, 94%, 95%, 96%, 97%, 98%, 99% or 100% identical to a sequence as set forth in any one of SEQ ID NOs: 90-97.

Fc Modifications. In some embodiments, the anti-GPA33 antibodies of the present technology comprise a variant Fc region, wherein said variant Fc region comprises at least one amino acid modification relative to a wild-type Fc region (or the parental Fc region), such that said molecule has an altered affinity for an Fc receptor (e.g., an FcγR), provided that said variant Fc region does not have a substitution at positions that make a direct contact with Fc receptor based on crystallographic and structural analysis of Fc-Fc receptor interactions such as those disclosed by Sondermann et al., *Nature,* 406:267-273 (2000). Examples of positions within the Fc region that make a direct contact with an Fc receptor such as an FcγR, include amino acids 234-239 (hinge region), amino acids 265-269 (B/C loop), amino acids 297-299 (C7E loop), and amino acids 327-332 (F/G) loop.

In some embodiments, an anti-GPA33 antibody of the present technology has an altered affinity for activating and/or inhibitory receptors, having a variant Fc region with one or more amino acid modifications, wherein said one or more amino acid modification is a N297 substitution with alanine, or a K322 substitution with alanine. Additionally or alternatively, in some embodiments, the Fc regions of the GPA33 antibodies disclosed herein comprise two amino acid substitutions, Leu234Ala and Leu235Ala (so called LALA mutations) to eliminate FcγRIIa binding. The LALA mutations are commonly used to alleviate the cytokine induction from T cells, thus reducing toxicity of the antibodies (Wines B D, et al., *J Immunol* 164:5313-5318 (2000)).

Glycosylation Modifications. In some embodiments, anti-GPA33 antibodies of the present technology have an Fc region with variant glycosylation as compared to a parent Fc region. In some embodiments, variant glycosylation includes the absence of fucose; in some embodiments, variant glycosylation results from expression in GnT1-deficient CHO cells.

In some embodiments, the antibodies of the present technology, may have a modified glycosylation site relative to an appropriate reference antibody that binds to an antigen of interest (e.g., GPA33), without altering the functionality of the antibody, e.g., binding activity to the antigen. As used herein, "glycosylation sites" include any specific amino acid sequence in an antibody to which an oligosaccharide (i.e., carbohydrates containing two or more simple sugars linked together) will specifically and covalently attach.

Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. For example, an Fc-glycoform (hGPA33-IgGln) that lacks certain oligosaccharides including fucose and terminal N-acetylglucosamine may be produced in special CHO cells and exhibit enhanced ADCC effector function.

In some embodiments, the carbohydrate content of an immunoglobulin-related composition disclosed herein is modified by adding or deleting a glycosylation site. Methods for modifying the carbohydrate content of antibodies are well known in the art and are included within the present technology, see, e.g., U.S. Pat. No. 6,218,149; EP 0359096B1; U.S. Patent Publication No. US 2002/0028486; International Patent Application Publication WO 03/035835; U.S. Patent Publication No. 2003/0115614; U.S. Pat. Nos. 6,218,149; 6,472,511; all of which are incorporated herein by reference in their entirety. In some embodiments, the carbohydrate content of an antibody (or relevant portion or component thereof) is modified by deleting one or more endogenous carbohydrate moieties of the antibody. In some certain embodiments, the present technology includes deleting the glycosylation site of the Fc region of an antibody, by modifying position 297 from asparagine to alanine.

Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example N-acetylglucosaminyltransferase III (GnTIII), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al., 1999, *Nat. Biotechnol.* 17: 176-180; Davies et al., 2001, *Biotechnol. Bioeng.* 74:288-294; Shields et al., 2002, *J. Biol. Chem.* 277:26733-26740; Shinkawa et al., 2003, *J. Biol. Chem.* 278:3466-3473; U.S. Pat. No. 6,602,684; U.S. patent application Ser. No. 10/277,370; U.S. patent application Ser. No. 10/113,929; International Patent Application Publications WO 00/61739A1; WO 01/292246A1; WO 02/311140A1; WO 02/30954A1; POTILLEGENT™ technology (Biowa, Inc. Princeton, N.J.); GLYCOMAB™ glycosylation engineering technology (GLYCART biotechnology AG, Zurich, Switzerland); each of which is incorporated herein by reference in its entirety. See, e.g., International Patent Application Publication WO 00/061739; U.S. Patent Application Publication No. 2003/0115614; Okazaki et al., 2004, *JMB,* 336: 1239-49.

Fusion Proteins. In one embodiment, the anti-GPA33 antibody of the present technology is a fusion protein. The anti-GPA33 antibodies of the present technology, when fused to a second protein, can be used as an antigenic tag. Examples of domains that can be fused to polypeptides include not only heterologous signal sequences, but also other heterologous functional regions. The fusion does not necessarily need to be direct, but can occur through linker sequences. Moreover, fusion proteins of the present technology can also be engineered to improve characteristics of the anti-GPA33 antibodies. For instance, a region of additional amino acids, particularly charged amino acids, can be added to the N-terminus of the anti-GPA33 antibody to improve stability and persistence during purification from the host cell or subsequent handling and storage. Also, peptide moieties can be added to an anti-GPA33 antibody to facilitate purification. Such regions can be removed prior to final preparation of the anti-GPA33 antibody. The addition of peptide moieties to facilitate handling of polypeptides are familiar and routine techniques in the art. The anti-GPA33 antibody of the present technology can be fused to marker sequences, such as a peptide which facilitates purification of the fused polypeptide. In select embodiments, the marker amino acid sequence is a hexa-histidine peptide (SEQ ID NO: 114), such as the tag provided in a pQE vector (QIAGEN, Inc., Chatsworth, Calif), among others, many of which are commercially available. As described in Gentz et al., *Proc. Natl. Acad. Sci. USA* 86: 821-824, 1989, for instance, hexa-histidine (SEQ ID NO: 114) provides for convenient purification of the fusion protein. Another peptide tag useful for purification, the "HA" tag, corresponds to an epitope derived from the influenza hemagglutinin protein. Wilson et al., *Cell* 37: 767, 1984.

Thus, any of these above fusion proteins can be engineered using the polynucleotides or the polypeptides of the present technology. Also, in some embodiments, the fusion proteins described herein show an increased half-life in vivo.

Fusion proteins having disulfide-linked dimeric structures (due to the IgG) can be more efficient in binding and neutralizing other molecules compared to the monomeric secreted protein or protein fragment alone. Fountoulakis et al., *J. Biochem.* 270: 3958-3964, 1995.

Similarly, EP-A-O 464 533 (Canadian counterpart 2045869) discloses fusion proteins comprising various portions of constant region of immunoglobulin molecules together with another human protein or a fragment thereof. In many cases, the Fc part in a fusion protein is beneficial in therapy and diagnosis, and thus can result in, e.g., improved pharmacokinetic properties. See EP-A 0232 262. Alternatively, deleting or modifying the Fc part after the fusion protein has been expressed, detected, and purified, may be desired. For example, the Fc portion can hinder therapy and diagnosis if the fusion protein is used as an antigen for immunizations. In drug discovery, e.g., human proteins, such as hIL-5, have been fused with Fc portions for the purpose of high-throughput screening assays to identify antagonists of hIL-5. Bennett et al., *J. Molecular Recognition* 8: 52-58, 1995; Johanson et al., *J. Biol. Chem.,* 270: 9459-9471, 1995.

Labeled Anti-GPA33 antibodies. In one embodiment, the anti-GPA33 antibody of the present technology is coupled with a label moiety, i.e., detectable group. The particular label or detectable group conjugated to the anti-GPA33 antibody is not a critical aspect of the technology, so long as it does not significantly interfere with the specific binding of the anti-GPA33 antibody of the present technology to the GPA33 protein. The detectable group can be any material having a detectable physical or chemical property. Such detectable labels have been well-developed in the field of immunoassays and imaging. In general, almost any label useful in such methods can be applied to the present technology. Thus, a label is any composition detectable by spectroscopic, photochemical, biochemical, immunochemical, electrical, optical or chemical means. Labels useful in the practice of the present technology include magnetic beads (e.g., Dynabeads™), fluorescent dyes (e.g., fluorescein isothiocyanate, Texas red, rhodamine, and the like), radiolabels (e.g., $^{3}$H, $^{14}$C, $^{35}$S, $^{125}$I, $^{121}$I, $^{131}$I, $^{112}$In, $^{99m}$Tc), other imaging agents such as microbubbles (for ultrasound imaging), $^{18}$F, $^{11}$C, $^{15}$O, $^{89}$Zr (for Positron emission tomography), $^{99m}$TC, $^{111}$In (for Single photon emission tomography), enzymes (e.g., horse radish peroxidase, alkaline phosphatase and others commonly used in an ELISA), and calorimetric labels such as colloidal gold or colored glass or plastic (e.g., polystyrene, polypropylene, latex, and the like) beads. Patents that describe the use of such labels include U.S. Pat. Nos. 3,817,837; 3,850,752; 3,939,350; 3,996,345; 4,277,437; 4,275,149; and 4,366,241, each incorporated herein by reference in their entirety and for all purposes. See also Handbook of Fluorescent Probes and Research Chemicals (6$^{th}$ Ed., Molecular Probes, Inc., Eugene OR.).

The label can be coupled directly or indirectly to the desired component of an assay according to methods well known in the art. As indicated above, a wide variety of labels can be used, with the choice of label depending on factors such as required sensitivity, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, e.g., biotin, thyroxine, and cortisol, it can be used in conjunction with the labeled, naturally-occurring anti-ligands. Alternatively, any haptenic or antigenic compound can be used in combination with an antibody, e.g., an anti-GPA33 antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds useful as labeling moieties, include, but are not limited to, e.g., fluorescein and its derivatives, rhodamine and its derivatives, dansyl, umbelliferone, and the like. Chemiluminescent compounds useful as labeling moieties, include, but are not limited to, e.g., luciferin, and 2,3-dihydrophthalazinediones, e.g., luminol. For a review of various labeling or signal-producing systems which can be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Finally, simple colorimetric labels can be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies, e.g., the anti-GPA33 antibodies. In this case, antigen-coated particles are agglutinated by samples comprising the target antibodies. In this format, none of the components need be labeled and the presence of the target antibody is detected by simple visual inspection.

B. Identifying and Characterizing the Anti-GPA33 Antibodies of the Present Technology Methods for identifying and/or screening the anti-GPA33 antibodies of the present technology. Methods useful to identify and screen antibodies against GPA33 polypeptides for those that possess the desired specificity to GPA33 protein (e.g., those that bind to the extracellular domain of GPA33 protein (e.g., comprising the amino acid sequence of SEQ ID NO: 101)) include any immunologically-mediated techniques known within the art. Components of an immune response can be detected in vitro by various methods that are well known to those of ordinary skill in the art. For example, (1) surface plasmon resonance (SPR) for detection and measurement of antibody-antigen affinity and kinetics; (2) cytotoxic T lymphocytes can be incubated with radioactively labeled target cells and the lysis of these target cells detected by the release of radioactivity; (3) helper T lymphocytes can be incubated with antigens and antigen presenting cells and the synthesis and secretion of cytokines measured by standard methods (Windhagen A et al., *Immunity,* 2: 373-80, 1995); (4) antigen presenting cells can be incubated with whole protein antigen and the presentation of that antigen on MHC detected by either T lymphocyte activation assays or biophysical methods (Harding et al., *Proc. Natl. Acad. Sci.,* 86: 4230-4, 1989); (5) mast cells can be incubated with reagents that cross-link their Fc-epsilon receptors and histamine release measured by enzyme immunoassay (Siraganian et al., *TIPS,* 4: 432-437, 1983); and (6) enzyme-linked immunosorbent assay (ELISA).

Similarly, products of an immune response in either a model organism (e.g., mouse) or a human subject can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., *Blood,* 72: 1310-5, 1988); (3) the proliferation of peripheral blood mononuclear cells (PBMCs) in response to mitogens or mixed lymphocyte reaction can be measured using $^{3}$H-thymidine; (4) the phagocytic capacity of granulocytes, macrophages, and other phagocytes in PBMCs can be measured by placing PBMCs in wells together with labeled particles (Peters et al., *Blood,* 72: 1310-5, 1988); and (5) the differentiation of immune system cells can be measured by labeling PBMCs with antibodies to CD molecules such as CD4 and CD8 and measuring the fraction of the PBMCs expressing these markers.

In one embodiment, anti-GPA33 antibodies of the present technology are selected using display of GPA33 peptides on the surface of replicable genetic packages. See, e.g., U.S. Pat. Nos. 5,514,548; 5,837,500; 5,871,907; 5,885,793; 5,969,108; 6,225,447; 6,291,650; 6,492,160; EP 585 287; EP 605522; EP 616640; EP 1024191; EP 589 877; EP 774 511; EP 844 306. Methods useful for producing/selecting a filamentous bacteriophage particle containing a phagemid genome encoding for a binding molecule with a desired specificity has been described. See, e.g., EP 774 511; U.S. Pat. Nos. 5,871,907; 5,969,108; 6,225,447; 6,291,650; 6,492,160.

In some embodiments, anti-GPA33 antibodies of the present technology are selected using display of GPA33 peptides on the surface of a yeast host cell. Methods useful for the isolation of scFv polypeptides by yeast surface display have been described by Kieke et al., *Protein Eng.* 1997 November; 10(11): 1303-10.

In some embodiments, anti-GPA33 antibodies of the present technology are selected using ribosome display. Methods useful for identifying ligands in peptide libraries using ribosome display have been described by Mattheakis et al., *Proc. Natl. Acad. Sci. USA* 91: 9022-26, 1994; and Hanes et al., *Proc. Natl. Acad. Sci. USA* 94: 4937-42, 1997.

In certain embodiments, anti-GPA33 antibodies of the present technology are selected using tRNA display of GPA33 peptides. Methods useful for in vitro selection of ligands using tRNA display have been described by Merryman et al., *Chem. Biol.,* 9: 741-46, 2002.

In one embodiment, anti-GPA33 antibodies of the present technology are selected using RNA display. Methods useful for selecting peptides and proteins using RNA display libraries have been described by Roberts et al. *Proc. Natl.*

*Acad. Sci. USA,* 94: 12297-302, 1997; and Nemoto et al., *FEBS Lett.,* 414: 405-8, 1997. Methods useful for selecting peptides and proteins using unnatural RNA display libraries have been described by Frankel et al., *Curr. Opin. Struct. Biol.,* 13: 506-12, 2003.

In some embodiments, anti-GPA33 antibodies of the present technology are expressed in the periplasm of gram negative bacteria and mixed with labeled GPA33 protein. See WO 02/34886. In clones expressing recombinant polypeptides with affinity for GPA33 protein, the concentration of the labeled GPA33 protein bound to the anti-GPA33 antibodies is increased and allows the cells to be isolated from the rest of the library as described in Harvey et al., *Proc. Natl. Acad. Sci.* 22: 9193-98 2004 and U.S. Pat. Publication No. 2004/0058403.

After selection of the desired anti-GPA33 antibodies, it is contemplated that said antibodies can be produced in large volume by any technique known to those skilled in the art, e.g., prokaryotic or eukaryotic cell expression and the like. The anti-GPA33 antibodies which are, e.g., but not limited to, anti-GPA33 hybrid antibodies or fragments can be produced by using conventional techniques to construct an expression vector that encodes an antibody heavy chain in which the CDRs and, if necessary, a minimal portion of the variable region framework, that are required to retain original species antibody binding specificity (as engineered according to the techniques described herein) are derived from the originating species antibody and the remainder of the antibody is derived from a target species immunoglobulin which can be manipulated as described herein, thereby producing a vector for the expression of a hybrid antibody heavy chain.

Measurement of GPA33 Binding. In some embodiments, a GPA33 binding assay refers to an assay format wherein GPA33 protein and an anti-GPA33 antibody are mixed under conditions suitable for binding between the GPA33 protein and the anti-GPA33 antibody and assessing the amount of binding between the GPA33 protein and the anti-GPA33 antibody. The amount of binding is compared with a suitable control, which can be the amount of binding in the absence of the GPA33 protein, the amount of the binding in the presence of a non-specific immunoglobulin composition, or both. The amount of binding can be assessed by any suitable method. Binding assay methods include, e.g., SPR, ELISA, radioimmunoassays, scintillation proximity assays, fluorescence energy transfer assays, liquid chromatography, membrane filtration assays, and the like. Biophysical assays for the direct measurement of GPA33 protein binding to anti-GPA33 antibody are, e.g., nuclear magnetic resonance, fluorescence, fluorescence polarization, surface plasmon resonance (BIACORE chips) and the like. Specific binding is determined by standard assays known in the art, e.g., radioligand binding assays, ELISA, FRET, immunoprecipitation, SPR, NMR (2D-NMR), mass spectroscopy and the like. If the specific binding of a candidate anti-GPA33 antibody is at least 1 percent greater than the binding observed in the absence of the candidate anti-GPA33 antibody, the candidate anti-GPA33 antibody is useful as an anti-GPA33 antibody of the present technology.

Uses of the Anti-GPA33 Antibodies of the Present Technology

General. The anti-GPA33 antibodies of the present technology are useful in methods known in the art relating to the localization and/or quantitation of GPA33 protein (e.g., for use in measuring levels of the GPA33 protein within appropriate physiological samples, for use in diagnostic methods, for use in imaging the polypeptide, and the like). Antibodies of the present technology are useful to isolate a GPA33 protein by standard techniques, such as affinity chromatography or immunoprecipitation. An anti-GPA33 antibody of the present technology can facilitate the purification of natural immunoreactive GPA33 proteins from biological samples, e.g., mammalian sera or cells as well as recombinantly-produced immunoreactive GPA33 proteins expressed in a host system. Moreover, anti-GPA33 antibodies of the present technology can be used to detect an immunoreactive GPA33 protein (e.g., in plasma, a cellular lysate or cell supernatant) in order to evaluate the abundance and pattern of expression of the immunoreactive polypeptide. The anti-GPA33 antibodies of the present technology can be used diagnostically to monitor immunoreactive GPA33 protein levels in tissue as part of a clinical testing procedure, e.g., to determine the efficacy of a given treatment regimen. As noted above, the detection can be facilitated by coupling (i.e., physically linking) the anti-GPA33 antibodies of the present technology to a detectable substance.

Detection of GPA33 protein. An exemplary method for detecting the presence or absence of an immunoreactive GPA33 protein in a biological sample involves obtaining a biological sample from a test subject and contacting the biological sample with an anti-GPA33 antibody of the present technology capable of detecting an immunoreactive GPA33 protein such that the presence of an immunoreactive GPA33 protein is detected in the biological sample. Detection may be accomplished by means of a detectable label attached to the antibody.

The term "labeled" with regard to the anti-GPA33 antibody is intended to encompass direct labeling of the antibody by coupling (i.e., physically linking) a detectable substance to the antibody, as well as indirect labeling of the antibody by reactivity with another compound that is directly labeled, such as a secondary antibody. Examples of indirect labeling include detection of a primary antibody using a fluorescently-labeled secondary antibody and end-labeling of a DNA probe with biotin such that it can be detected with fluorescently-labeled streptavidin.

In some embodiments, the anti-GPA33 antibodies disclosed herein are conjugated to one or more detectable labels. For such uses, anti-GPA33 antibodies may be detectably labeled by covalent or non-covalent attachment of a chromogenic, enzymatic, radioisotopic, isotopic, fluorescent, toxic, chemiluminescent, nuclear magnetic resonance contrast agent or other label. Examples of suitable chromogenic labels include diaminobenzidine and 4-hydroxyazo-benzene-2-carboxylic acid. Examples of suitable enzyme labels include malate dehydrogenase, staphylococcal nuclease, Δ-5-steroid isomerase, yeast-alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotopic labels include $^{3}H$, $^{111}In$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, $^{109}Pd$, etc. $^{111}In$ is an exemplary isotope where in vivo imaging is used since it avoids the problem of dehalogenation of the $^{125}I$ or $^{131}I$-labeled GPA33-binding antibodies by the liver. In addition, this isotope has a more favorable gamma emission energy for imaging (Perkins et al, *Eur. J. Nucl. Med.* 70:296-301 (1985); Carasquillo et al., *J. Nucl. Med.* 25:281-287 (1987)). For example, $^{111}In$ coupled to monoclonal antibodies with 1-(P-isothiocyanatobenzyl)-DPTA exhibits little uptake in non-tumorous tissues, particularly the liver, and enhances specificity of tumor localization (Esteban et al., *J. Nucl. Med.* 28:861-870 (1987)). Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label. Examples of suitable toxin labels include diphtheria toxin, ricin, and cholera toxin.

Examples of chemiluminescent labels include a luminol label, an isoluminol label, an aromatic acridinium ester label, an imidazole label, an acridinium salt label, an oxalate ester label, a luciferin label, a luciferase label, and an aequorin label. Examples of nuclear magnetic resonance contrasting agents include heavy metal nuclei such as Gd, Mn, and iron.

The detection method of the present technology can be used to detect an immunoreactive GPA33 protein in a biological sample in vitro as well as in vivo. In vitro techniques for detection of an immunoreactive GPA33 protein include enzyme linked immunosorbent assays (ELISAs), Western blots, immunoprecipitations, radioimmunoassay, and immunofluorescence. Furthermore, in vivo techniques for detection of an immunoreactive GPA33 protein include introducing into a subject a labeled anti-GPA33 antibody of the present technology. For example, the anti-GPA33 antibody can be labeled with a radioactive marker whose presence and location in a subject can be detected by standard imaging techniques. In one embodiment, the biological sample contains GPA33 protein molecules from the test subject.

Immunoassay and Imaging. An anti-GPA33 antibody of the present technology can be used to assay immunoreactive GPA33 protein levels in a biological sample (e.g., human plasma) using antibody-based techniques. For example, protein expression in tissues can be studied with classical immunohistological methods. Jalkanen, M. et al., *J Cell Biol* 101: 976-985, 1985; Jalkanen, M. et al., *J Cell Biol* 105: 3087-3096, 1987. Other antibody-based methods useful for detecting protein gene expression include immunoassays, such as the enzyme linked immunosorbent assay (ELISA) and the radioimmunoassay (MA). Suitable antibody assay labels are known in the art and include enzyme labels, such as, glucose oxidase, and radioisotopes or other radioactive agent, such as iodine ($^{125}$I, $^{121}$I, $^{131}$I) carbon ($^{14}$C), sulfur ($^{35}$S), tritium ($^{3}$H), indium ($^{112}$In), and technetium ($^{99m}$Tc), and fluorescent labels, such as fluorescein, rhodamine, and green fluorescent protein (GFP), as well as biotin.

In addition to assaying immunoreactive GPA33 protein levels in a biological sample, anti-GPA33 antibodies of the present technology may be used for in vivo imaging of GPA33. Antibodies useful for this method include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the anti-GPA33 antibodies by labeling of nutrients for the relevant scFv clone.

An anti-GPA33 antibody of the present technology which has been labeled with an appropriate detectable imaging moiety, such as a radioisotope (e.g., $^{131}$I, $^{112}$In, $^{99m}$Tc), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled anti-GPA33 antibody will then accumulate at the location of cells which contain the specific target polypeptide. For example, labeled anti-GPA33 antibodies of the present technology will accumulate within the subject in cells and tissues in which the GPA33 protein has localized.

Thus, the present technology provides a diagnostic method of a medical condition, which involves: (a) assaying the expression of immunoreactive GPA33 protein by measuring binding of an anti-GPA33 antibody of the present technology in cells or body fluid of an individual; (b) comparing the amount of immunoreactive GPA33 protein present in the sample with a standard reference, wherein an increase or decrease in immunoreactive GPA33 protein levels compared to the standard is indicative of a medical condition.

Affinity Purification. The anti-GPA33 antibodies of the present technology may be used to purify immunoreactive GPA33 protein from a sample. In some embodiments, the antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "*Handbook of Experimental Immunology*" 4th Ed., Blackwell Scientific Publications, Oxford, England, Chapter 10 (1986); Jacoby et al., *Meth. Enzym.* 34 Academic Press, N.Y. (1974)).

The simplest method to bind the antigen to the antibody-support matrix is to collect the beads in a column and pass the antigen solution down the column. The efficiency of this method depends on the contact time between the immobilized antibody and the antigen, which can be extended by using low flow rates. The immobilized antibody captures the antigen as it flows past. Alternatively, an antigen can be contacted with the antibody-support matrix by mixing the antigen solution with the support (e.g., beads) and rotating or rocking the slurry, allowing maximum contact between the antigen and the immobilized antibody. After the binding reaction has been completed, the slurry is passed into a column for collection of the beads. The beads are washed using a suitable washing buffer and then the pure or substantially pure antigen is eluted.

An antibody or polypeptide of interest can be conjugated to a solid support, such as a bead. In addition, a first solid support such as a bead can also be conjugated, if desired, to a second solid support, which can be a second bead or other support, by any suitable means, including those disclosed herein for conjugation of a polypeptide to a support. Accordingly, any of the conjugation methods and means disclosed herein with reference to conjugation of a polypeptide to a solid support can also be applied for conjugation of a first support to a second support, where the first and second solid support can be the same or different.

Appropriate linkers, which can be cross-linking agents, for use for conjugating a polypeptide to a solid support include a variety of agents that can react with a functional group present on a surface of the support, or with the polypeptide, or both. Reagents useful as cross-linking agents include homo-bi-functional and, in particular, hetero-bi-functional reagents. Useful bi-functional cross-linking agents include, but are not limited to, N-STAB, dimaleimide, DTNB, N-SATA, N-SPDP, SMCC and 6-HYNIC. A cross-linking agent can be selected to provide a selectively cleavable bond between a polypeptide and the solid support. For example, a photolabile cross-linker, such as 3-amino-(2-nitrophenyl)propionic acid can be employed as a means for cleaving a polypeptide from a solid support. (Brown et al., *Mol. Divers*, pp, 4-12 (1995); Rothschild et al., *Nucl Acids Res,* 24:351-66 (1996); and U.S. Pat. No. 5,643,722). Other cross-linking reagents are well-known in the art. (See, e.g., Wong (1991), supra; and Hermanson (1996), supra).

An antibody or polypeptide can be immobilized on a solid support, such as a bead, through a covalent amide bond formed between a carboxyl group functionalized bead and the amino terminus of the polypeptide or, conversely, through a covalent amide bond formed between an amino group functionalized bead and the carboxyl terminus of the polypeptide. In addition, a bi-functional trityl linker can be attached to the support, e.g., to the 4-nitrophenyl active ester on a resin, such as a Wang resin, through an amino group or a carboxyl group on the resin via an amino resin. Using a bi-functional trityl approach, the solid support can require treatment with a volatile acid, such as formic acid or trifluoroacetic acid to ensure that the polypeptide is cleaved and can be removed. In such a case, the polypeptide can be deposited as a beadless patch at the bottom of a well of a solid support or on the flat surface of a solid support. After addition of a matrix solution, the polypeptide can be desorbed into a MS.

Hydrophobic trityl linkers can also be exploited as acid-labile linkers by using a volatile acid or an appropriate matrix solution, e.g., a matrix solution containing 3-HPA, to cleave an amino linked trityl group from the polypeptide. Acid lability can also be changed. For example, trityl, monomethoxytrityl, dimethoxytrityl or trimethoxytrityl can be changed to the appropriate p-substituted, or more acid-labile tritylamine derivatives, of the polypeptide, i.e., trityl ether and tritylamine bonds can be made to the polypeptide. Accordingly, a polypeptide can be removed from a hydrophobic linker, e.g., by disrupting the hydrophobic attraction or by cleaving tritylether or tritylamine bonds under acidic conditions, including, if desired, under typical MS conditions, where a matrix, such as 3-HPA acts as an acid.

Orthogonally cleavable linkers can also be useful for binding a first solid support, e.g., a bead to a second solid support, or for binding a polypeptide of interest to a solid support. Using such linkers, a first solid support, e.g., a bead, can be selectively cleaved from a second solid support, without cleaving the polypeptide from the support; the polypeptide then can be cleaved from the bead at a later time. For example, a disulfide linker, which can be cleaved using a reducing agent, such as DTT, can be employed to bind a bead to a second solid support, and an acid cleavable bi-functional trityl group could be used to immobilize a polypeptide to the support. As desired, the linkage of the polypeptide to the solid support can be cleaved first, e.g., leaving the linkage between the first and second support intact. Trityl linkers can provide a covalent or hydrophobic conjugation and, regardless of the nature of the conjugation, the trityl group is readily cleaved in acidic conditions.

For example, a bead can be bound to a second support through a linking group which can be selected to have a length and a chemical nature such that high density binding of the beads to the solid support, or high density binding of the polypeptides to the beads, is promoted. Such a linking group can have, e.g., "tree-like" structure, thereby providing a multiplicity of functional groups per attachment site on a solid support. Examples of such linking group; include polylysine, polyglutamic acid, penta-erythrole and tris-hydroxy-aminomethane.

Noncovalent Binding Association. An antibody or polypeptide can be conjugated to a solid support, or a first solid support can also be conjugated to a second solid support, through a noncovalent interaction. For example, a magnetic bead made of a ferromagnetic material, which is capable of being magnetized, can be attracted to a magnetic solid support, and can be released from the support by removal of the magnetic field. Alternatively, the solid support can be provided with an ionic or hydrophobic moiety, which can allow the interaction of an ionic or hydrophobic moiety, respectively, with a polypeptide, e.g., a polypeptide containing an attached trityl group or with a second solid support having hydrophobic character.

A solid support can also be provided with a member of a specific binding pair and, therefore, can be conjugated to a polypeptide or a second solid support containing a complementary binding moiety. For example, a bead coated with avidin or with streptavidin can be bound to a polypeptide having a biotin moiety incorporated therein, or to a second solid support coated with biotin or derivative of biotin, such as iminobiotin.

It should be recognized that any of the binding members disclosed herein or otherwise known in the art can be reversed. Thus, biotin, e.g., can be incorporated into either a polypeptide or a solid support and, conversely, avidin or other biotin binding moiety would be incorporated into the support or the polypeptide, respectively. Other specific binding pairs contemplated for use herein include, but are not limited to, hormones and their receptors, enzyme, and their substrates, a nucleotide sequence and its complementary sequence, an antibody and the antigen to which it interacts specifically, and other such pairs knows to those skilled in the art.

A. Diagnostic Uses of Anti-GPA33 Antibodies of the Present Technology

General. The anti-GPA33 antibodies of the present technology are useful in diagnostic methods. As such, the present technology provides methods using the antibodies in the diagnosis of GPA33 activity in a subject. Anti-GPA33 antibodies of the present technology may be selected such that they have any level of epitope binding specificity and very high binding affinity to a GPA33 protein. In general, the higher the binding affinity of an antibody the more stringent wash conditions can be performed in an immunoassay to remove nonspecifically bound material without removing target polypeptide. Accordingly, anti-GPA33 antibodies of the present technology useful in diagnostic assays usually have binding affinities of about $10^8$ $M^{-1}$, $10^9$ $M^{-1}$, $10^{10}$ $M^{-1}$, $10^{11}$ $M^{-1}$ or $10^{12}$ $M^{-1}$ to GPA33. Further, it is desirable that anti-GPA33 antibodies used as diagnostic reagents have a sufficient kinetic on-rate to reach equilibrium under standard conditions in at least 12 h, at least five (5) h, or at least one (1) hour.

Anti-GPA33 antibodies can be used to detect an immunoreactive GPA33 protein in a variety of standard assay formats. Such formats include immunoprecipitation, Western blotting, ELISA, radioimmunoassay, and immunometric assays. See Harlow & Lane, *Antibodies, A Laboratory Manual* (Cold Spring Harbor Publications, New York, 1988); U.S. Pat. Nos. 3,791,932; 3,839,153; 3,850,752; 3,879,262; 4,034,074, 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Biological samples can be obtained from any tissue or body fluid of a subject. In certain embodiments, the subject is at an early stage of cancer. In one embodiment, the early stage of cancer is determined by the level or expression pattern of GPA33 protein in a sample obtained from the subject. In certain embodiments, the sample is selected from the group consisting of urine, blood, serum, plasma, saliva, amniotic fluid, cerebrospinal fluid (CSF), and biopsied body tissue.

Immunometric or sandwich assays are one format for the diagnostic methods of the present technology. See U.S. Pat. Nos. 4,376,110, 4,486,530, 5,914,241, and 5,965,375. Such assays use one antibody, e.g., an anti-GPA33 antibody or a population of anti-GPA33 antibodies, e.g., the anti-GPA33 antibodies of the present technology, immobilized to a solid phase, and another anti-GPA33 antibody or a population of anti-GPA33 antibodies in solution. Typically, the solution anti-GPA33 antibody or population of anti-GPA33 antibodies is labeled. If an antibody population is used, the population can contain antibodies binding to different epitope specificities within the target polypeptide. Accordingly, the same population can be used for both solid phase and solution antibody. If anti-GPA33 monoclonal antibodies are used, first and second GPA33 monoclonal antibodies having different binding specificities are used for the solid and solution phase. Solid phase (also referred to as "capture") and solution (also referred to as "detection") antibodies can be contacted with target antigen in either order or simultaneously. If the solid phase antibody is contacted first, the assay is referred to as being a forward assay. Conversely, if the solution antibody is contacted first, the assay is referred to as being a reverse assay. If the target is contacted with both antibodies simultaneously, the assay is referred to as a simultaneous assay. After contacting the GPA33 protein with the anti-GPA33 antibody, a sample is incubated for a period that usually varies from about 10 min to about 24 hr and is usually about 1 hr. A wash step is then performed to remove components of the sample not specifically bound to the anti-GPA33 antibody being used as a diagnostic reagent. When solid phase and solution antibodies are bound in separate steps, a wash can be performed after either or both binding steps. After washing, binding is quantified, typically by detecting a label linked to the solid phase through binding of labeled solution antibody. Usually for a given pair of antibodies or populations of antibodies and given reaction conditions, a calibration curve is prepared from samples containing known concentrations of target antigen. Concentrations of the immunoreactive GPA33 protein in samples being tested are then read by interpolation from the calibration curve (i.e., standard curve). Analyte can be measured either from the amount of labeled solution antibody bound at equilibrium or by kinetic measurements of bound labeled solution antibody at a series of time points before equilibrium is reached. The slope of such a curve is a measure of the concentration of the GPA33 protein in a sample.

Suitable supports for use in the above methods include, e.g., nitrocellulose membranes, nylon membranes, and derivatized nylon membranes, and also particles, such as agarose, a dextran-based gel, dipsticks, particulates, microspheres, magnetic particles, test tubes, microtiter wells, SEPHADEX™ (Amersham Pharmacia Biotech, Piscataway N.J.), and the like. Immobilization can be by absorption or by covalent attachment. Optionally, anti-GPA33 antibodies can be joined to a linker molecule, such as biotin for attachment to a surface bound linker, such as avidin.

In some embodiments, the present disclosure provides an anti-GPA33 antibody of the present technology conjugated to a diagnostic agent. The diagnostic agent may comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope. A diagnostic agent is a molecule which is administered conjugated to an antibody moiety, i.e., antibody or antibody fragment, or subfragment, and is useful in diagnosing or detecting a disease by locating the cells containing the antigen.

Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MM). U.S. Pat. No. 6,331,175 describes MRI technique and the preparation of antibodies conjugated to a MM enhancing agent and is incorporated in its entirety by reference. In some embodiments, the diagnostic agents are selected from the group consisting of radioisotopes, enhancing agents for use in magnetic resonance imaging, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates may be coupled to the antibodies of the present technology using standard chemistries. The chelate is normally linked to the antibody by a group which enables formation of a bond to the molecule with minimal loss of immunoreactivity and minimal aggregation and/or internal cross-linking. Other methods and reagents for conjugating chelates to antibodies are disclosed in U.S. Pat. No. 4,824,659. Particularly useful metal-chelate combinations include 2-benzyl-DTPA and its monomethyl and cyclohexyl analogs, used with diagnostic isotopes for radio-imaging. The same chelates, when complexed with non-radioactive metals, such as manganese, iron and gadolinium are useful for MRI, when used along with the GPA33 antibodies of the present technology.

Macrocyclic chelates such as NOTA (1,4,7-triaza-cyclononane-N,N',N"-triacetic acid), DOTA, and TETA (p-bromoacetamido-benzyl-tetraethylaminetetraacetic acid) are of use with a variety of metals and radiometals, such as radionuclides of gallium, yttrium and copper, respectively. Such metal-chelate complexes can be stabilized by tailoring the ring size to the metal of interest. Examples of other DOTA chelates include (i) DOTA-Phe-Lys(HSG)-D-Tyr-Lys(HSG)-$NH_2$; (ii) Ac-Lys(HSG)D-Tyr-Lys(HSG)-Lys(Tscg-Cys)-$NH_2$; (iii) DOTA-D-Asp-D-Lys(HSG)-D-Asp-D-Lys(HSG)-$NH_2$; (iv) DOTA-D-Glu-D-Lys(HSG)-D-Glu-D-Lys(HSG)-$NH_2$; (v) DOTA-D-Tyr-D-Lys(HSG)-D-Glu-D-Lys(HSG)-$NH_2$; (vi) DOTA-D-Ala-D-Lys(HSG)-D-Glu-D-Lys(HSG)-$NH_2$; (vii) DOTA-D-Phe-D-Lys(HSG)-D-Tyr-D-Lys(HSG)-$NH_2$; (viii) Ac-D-Phe-D-Lys(DOTA)-D-Tyr-D-Lys(DOTA)-$NH_2$; (ix) Ac-D-Phe-D-Lys(DTPA)-D-Tyr-D-Lys(DTPA)-$NH_2$; (x) Ac-D-Phe-D-Lys(Bz-DTPA)-D-Tyr-D-Lys(Bz-DTPA)-$NH_2$; (xi) Ac-D-Lys(HSG)-D-Tyr-D-Lys(HSG)-D-Lys(Tscg-Cys)-$NH_2$; (xii) DOTA-D-Phe-D-Lys(HSG)-D-Tyr-D-Lys(HSG)-D-Lys(Tscg-Cys)-$NH_2$; (xiii) (Tscg-Cys)-D-Phe-D-Lys(HSG)-D-Tyr-D-Lys(HSG)-D-Lys(DOTA)-$NH_2$; (xiv) Tscg-D-Cys-D-Glu-D-Lys(HSG)-D-Glu-D-Lys(HSG)-$NH_2$; (xv) (Tscg-Cys)-D-Glu- D-Lys(HSG)-D-Glu-D-Lys(HSG)-$NH_2$; (xvi) Ac-D-Cys-D-Lys(DOTA)-D-Tyr-D-Ala-D-Lys(DOTA)-D-Cys-$NH_2$; (xvii) Ac-D-Cys-D-Lys(DTPA)-D-Tyr-D-Lys(DTPA)-$NH_2$; (xviii) Ac-D-Lys(DTPA)-D-Tyr-D-Lys(DTPA)-D-Lys(Tscg-Cys)-$NH_2$; and (xix) Ac-D-Lys(DOTA)-D-Tyr-D-Lys(DOTA)-D-Lys(Tscg-Cys)-$NH_2$, (xx) BnDOTA, (xxi) DOTA, (xxii) BnDOTA-biotin, and (xxiii) DOTA-biotin.

Other ring-type chelates such as macrocyclic polyethers, which are of interest for stably binding nuclides, such as $^{223}Ra$ for RAIT are also contemplated.

B. Therapeutic Use of Anti-GPA33 Antibodies of the Present Technology

In one aspect, the immunoglobulin-related compositions (e.g., antibodies or antigen binding fragments thereof) of the present technology are useful for the treatment of GPA33-associated pathologies, such colorectal cancer, T cell leukemia, *Pseudomyxoma peritonei*, appendiceal cancer, pancreatic cancer, and gastric cancer. In some embodiments, the GPA33-associated cancer is a solid tumor. Such treatment can be used in patients identified as having pathologically high levels of the GPA33 (e.g., those diagnosed by the methods described herein) or in patients diagnosed with a disease known to be associated with such pathological levels.

In one aspect, the present disclosure provides a method for treating a GPA33-associated pathology in a subject in need thereof, comprising administering to the subject an effective amount of an antibody (or antigen binding fragment thereof) of the present technology. Examples of GPA33-associated pathologies that can be treated by the antibodies of the present technology include, but are not limited to: colorectal cancer, T cell leukemia, *Pseudomyxoma peritonei*, appendiceal cancer, pancreatic cancer, and gastric cancer. The GPA33 associated cancer may be colorectal cancer with a MSI genotype or a MSS genotype. Additionally or alternatively, in some embodiments, the colorectal cancer is associated with a KRAS G12D mutation or a p53 mutation.

The compositions of the present technology may be employed in conjunction with other therapeutic agents useful in the treatment of GPA33-associated cancers. For example, the antibodies or antigen binding fragments of the present technology may be separately, sequentially or simultaneously administered with at least one additional therapeutic agent selected from the group consisting of alkylating agents, platinum agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents and targeted biological therapy agents (e.g., therapeutic peptides described in U.S. Pat. No. 6,306,832, WO 2012007137, WO 2005000889, WO 2010096603 etc.). In some embodiments, the at least one additional therapeutic agent is a chemotherapeutic agent. Specific chemotherapeutic agents include, but are not limited to, cyclophosphamide, fluorouracil (or 5-fluorouracil or 5-FU), methotrexate, edatrexate (10-ethyl-10-deaza-aminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb, anthracyclines (e.g., daunorubicin and doxorubicin), bevacizumab, oxaliplatin, melphalan, etoposide, mechlorethamine, bleomycin, microtubule poisons, annonaceous acetogenins, or combinations thereof.

Additionally or alternatively, in some embodiments, the antibodies or antigen binding fragments of the present technology may be separately, sequentially or simultaneously administered with at least one additional immunomodulating/stimulating antibody including but not limited to anti-PD-1 antibody, anti-PD-L1 antibody, anti-PD-L2 antibody, anti-CTLA-4 antibody, anti-TIM3 antibody, anti-4-1BB antibody, anti-CD73 antibody, anti-GITR antibody, and anti-LAG-3 antibody.

The compositions of the present technology may optionally be administered as a single bolus to a subject in need thereof. Alternatively, the dosing regimen may comprise multiple administrations performed at various times after the appearance of tumors.

Administration can be carried out by any suitable route, including orally, intranasally, parenterally (intravenously, intramuscularly, intraperitoneally, or subcutaneously), rectally, intracranially, intratumorally, intrathecally, or topically. Administration includes self-administration and the administration by another. It is also to be appreciated that the various modes of treatment of medical conditions as described are intended to mean "substantial", which includes total but also less than total treatment, and wherein some biologically or medically relevant result is achieved.

In some embodiments, the antibodies of the present technology comprise pharmaceutical formulations which may be administered to subjects in need thereof in one or more doses. Dosage regimens can be adjusted to provide the desired response (e.g., a therapeutic response).

Typically, an effective amount of the antibody compositions of the present technology, sufficient for achieving a therapeutic effect, range from about 0.000001 mg per kilogram body weight per day to about 10,000 mg per kilogram body weight per day. Typically, the dosage ranges are from about 0.0001 mg per kilogram body weight per day to about 100 mg per kilogram body weight per day. For administration of anti-GPA33 antibodies, the dosage ranges from about 0.0001 to 100 mg/kg, and more usually 0.01 to 5 mg/kg every week, every two weeks or every three weeks, of the subject body weight. For example, dosages can be 1 mg/kg body weight or 10 mg/kg body weight every week, every two weeks or every three weeks or within the range of 1-10 mg/kg every week, every two weeks or every three weeks. In one embodiment, a single dosage of antibody ranges from 0.1-10,000 micrograms per kg body weight. In one embodiment, antibody concentrations in a carrier range from 0.2 to 2000 micrograms per delivered milliliter. An exemplary treatment regime entails administration once per every two weeks or once a month or once every 3 to 6 months. Anti-GPA33 antibodies may be administered on multiple occasions. Intervals between single dosages can be hourly, daily, weekly, monthly or yearly. Intervals can also be irregular as indicated by measuring blood levels of the antibody in the subject. In some methods, dosage is adjusted to achieve a serum antibody concentration in the subject of from about 75 μg/mL to about 125 μg/mL, 100 μg/mL to about 150 μg/mL, from about 125 μg/mL to about 175 μg/mL, or from about 150 μg/mL to about 200 μg/mL. Alternatively, anti-GPA33 antibodies can be administered as a sustained release formulation, in which case less frequent administration is required. Dosage and frequency vary depending on the half-life of the antibody in the subject. The dosage and frequency of administration can vary depending on whether the treatment is prophylactic or therapeutic. In prophylactic applications, a relatively low dosage is administered at relatively infrequent intervals over a long period of time. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In another aspect, the present disclosure provides a method for detecting cancer in a subject in vivo comprising (a) administering to the subject an effective amount of an antibody (or antigen binding fragment thereof) of the present technology, wherein the antibody is configured to localize to a cancer cell expressing GPA33 and is labeled with a radioisotope; and (b) detecting the presence of a tumor in the subject by detecting radioactive levels emitted by the antibody that are higher than a reference value. In some embodiments, the reference value is expressed as injected dose per gram (% ID/g). The reference value may be calculated by measuring the radioactive levels present in non-tumor (normal) tissues, and computing the average radioactive levels present in non-tumor (normal) tissues±standard deviation. In some embodiments, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 75:1, 80:1, 85:1, 90:1, 95:1 or 100:1.

In some embodiments, the subject is diagnosed with or is suspected of having cancer. Radioactive levels emitted by the antibody may be detected using positron emission tomography or single photon emission computed tomography.

Additionally or alternatively, in some embodiments, the method further comprises administering to the subject an effective amount of an immunoconjugate comprising an antibody of the present technology conjugated to a radionuclide. In some embodiments, the radionuclide is an alpha particle-emitting isotope, a beta particle-emitting isotope, an Auger-emitter, or any combination thereof. Examples of beta particle-emitting isotopes include $^{86}$Y, $^{90}$Y, $^{89}$Sr, $^{165}$Dy, $^{186}$Re, $^{188}$Re, $^{177}$Lu, and $^{67}$Cu. Examples of alpha particle-emitting isotopes include $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, and $^{255}$Fm. Examples of Auger-emitters include $^{111}$In, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$ Os, $^{192}$Ir, $^{201}$Tl, and $^{203}$Pb. In some embodiments of the method, nonspecific FcR-dependent binding in normal tissues is eliminated or reduced (e.g., via N297A mutation in Fc region, which results in aglycosylation). The therapeutic effectiveness of such an immunoconjugate may be determined by computing the area under the curve (AUC) tumor: AUC normal tissue ratio. In some embodiments, the immunoconjugate has a AUC tumor: AUC normal tissue ratio of about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 70:1, 75:1, 80:1, 85:1, 90:1, 95:1 or 100:1.

PRIT. In one aspect, the present disclosure provides a method for detecting tumors in a subject in need thereof comprising (a) administering to the subject an effective amount of a complex comprising a radiolabeled DOTA hapten and a multispecific antibody of the present technology that binds to the radiolabeled DOTA hapten and a GPA33 antigen, wherein the complex is configured to localize to a tumor expressing the GPA33 antigen recognized by the multispecific antibody of the complex; and (b) detecting the presence of solid tumors in the subject by detecting radioactive levels emitted by the complex that are higher than a reference value. In some embodiments, the subject is human.

In another aspect, the present disclosure provides a method for selecting a subject for pretargeted radioimmunotherapy comprising (a) administering to the subject an effective amount of a complex comprising a radiolabeled DOTA hapten and a multispecific antibody of the present technology that binds to the radiolabeled DOTA hapten and a GPA33 antigen, wherein the complex is configured to localize to a tumor expressing the GPA33 antigen recognized by the multispecific antibody of the complex; (b) detecting radioactive levels emitted by the complex; and (c) selecting the subject for pretargeted radioimmunotherapy when the radioactive levels emitted by the complex are higher than a reference value. In some embodiments, the subject is human.

Examples of DOTA haptens include (i) DOTA-Phe-Lys(HSG)-D-Tyr-Lys(HSG)-$NH_2$; (ii) Ac-Lys(HSG)D-Tyr-Lys(HSG)-Lys(Tscg-Cys)-$NH_2$; (iii) DOTA-D-Asp-D-Lys(HSG)-D-Asp-D-Lys(HSG)-$NH_2$; (iv) DOTA-D-Glu-D-Lys(HSG)-D-Glu-D-Lys(HSG)-$NH_2$; (v) DOTA-D-Tyr-D-Lys(HSG)-D-Glu-D-Lys(HSG)-$NH_2$; (vi) DOTA-D-Ala-D-Lys(HSG)-D-Glu-D-Lys(HSG)-$NH_2$; (vii) DOTA-D-Phe-D-Lys(HSG)-D-Tyr-D-Lys(HSG)-$NH_2$; (viii) Ac-D-Phe-D-Lys(DOTA)-D-Tyr-D-Lys(DOTA)-$NH_2$; (ix) Ac-D-Phe-D-Lys(DTPA)-D-Tyr-D-Lys(DTPA)-$NH_2$; (x) Ac-D-Phe-D-Lys(Bz-DTPA)-D-Tyr-D-Lys(Bz-DTPA)-$NH_2$; (xi) Ac-D-Lys(HSG)-D-Tyr-D-Lys(HSG)-D-Lys(Tscg-Cys)-$NH_2$; (xii) DOTA-D-Phe-D-Lys(HSG)-D-Tyr-D-Lys(HSG)-D-Lys(Tscg-Cys)-$NH_2$; (xiii) (Tscg-Cys)-D-Phe-D-Lys(HSG)-D-Tyr-D-Lys(HSG)-D-Lys(DOTA)-$NH_2$; (xiv) Tscg-D-Cys-D-Glu-D-Lys(HSG)-D-Glu-D-Lys(HSG)-$NH_2$; (xv) (Tscg-Cys)-D-Glu-D-Lys(HSG)-D-Glu-D-Lys(HSG)-$NH_2$; (xvi) Ac-D-Cys-D-Lys(DOTA)-D-Tyr-D-Ala-D-Lys(DOTA)-D-Cys-$NH_2$; (xvii) Ac-D-Cys-D-Lys(DTPA)-D-Tyr-D-Lys(DTPA)-$NH_2$; (xviii) Ac-D-Lys(DTPA)-D-Tyr-D-Lys(DTPA)-D-Lys(Tscg-Cys)-$NH_2$; (xix) Ac-D-Lys(DOTA)-D-Tyr-D-Lys(DOTA)-D-Lys(Tscg-Cys)-$NH_2$, (xx) BnDOTA, (xxi) DOTA, (xxii) BnDOTA-biotin, and (xxiii) DOTA-biotin. The radiolabel may be an alpha particle-emitting isotope, a beta particle-emitting isotope, or an Auger-emitter. Examples of radiolabels include $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, $^{255}$Fm, $^{86}$Y, $^{90}$Y, $^{89}$Sr, $^{165}$Dy, $^{186}$Re, $^{188}$Re, $^{177}$Lu, $^{67}$Cu, $^{111}$In, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, $^{203}$Pb, $^{68}$Ga, $^{227}$Th, or $^{64}$Cu.

In some embodiments of the methods disclosed herein, the radioactive levels emitted by the complex are detected using positron emission tomography or single photon emission computed tomography. Additionally or alternatively, in some embodiments of the methods disclosed herein, the subject is diagnosed with, or is suspected of having a GPA33-associated cancer such as colorectal cancer, T cell leukemia, *Pseudomyxoma peritonei*, appendiceal cancer, pancreatic cancer, and gastric cancer.

Additionally or alternatively, in some embodiments of the methods disclosed herein, the complex is administered intravenously, intramuscularly, intraarterially, intrathecally, intracapsularly, intraorbitally, intradermally, intraperitoneally, transtracheally, subcutaneously, intracerebroventricularly, orally, intratumorally, or intranasally. In certain embodiments, the complex is administered into the cerebral spinal fluid or blood of the subject.

In some embodiments of the methods disclosed herein, the radioactive levels emitted by the complex are detected between 2 to 120 hours after the complex is administered. In certain embodiments of the methods disclosed herein, the radioactive levels emitted by the complex are expressed as the percentage injected dose per gram tissue (% ID/g). The reference value may be calculated by measuring the radioactive levels present in non-tumor (normal) tissues, and computing the average radioactive levels present in non-tumor (normal) tissues±standard deviation. In some embodiments, the reference value is the standard uptake value (SUV). See Thie J A, *J Nucl Med.* 45(9):1431-4 (2004). In some embodiments, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

In another aspect, the present disclosure provides a method for increasing tumor sensitivity to radiation therapy in a subject diagnosed with a GPA33-associated cancer comprising (a) administering an effective amount of an anti-DOTA multispecific antibody of the present technology to the subject, wherein the anti-DOTA multispecific antibody is configured to localize to a tumor expressing a GPA33 antigen target; and (b) administering an effective amount of a radiolabeled-DOTA hapten to the subject, wherein the radiolabeled-DOTA hapten is configured to bind to the anti-DOTA multispecific antibody. In some embodiments, the subject is human.

The anti-DOTA multispecific antibody is administered under conditions and for a period of time (e.g., according to a dosing regimen) sufficient for it to saturate tumor cells. In some embodiments, unbound anti-DOTA multispecific antibody is removed from the blood stream after administration of the anti-DOTA multispecific antibody. In some embodiments, the radiolabeled-DOTA hapten is administered after a time period that may be sufficient to permit clearance of unbound anti-DOTA multispecific antibody.

The radiolabeled-DOTA hapten may be administered at any time between 1 minute to 4 or more days following administration of the anti-DOTA multispecific antibody. For example, in some embodiments, the radiolabeled-DOTA hapten is administered 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 1.25 hours, 1.5 hours, 1.75 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 48 hours, 72 hours, 96 hours, or any range therein, following administration of the anti-DOTA multispecific antibody. Alternatively, the radiolabeled-DOTA hapten may be administered at any time after 4 or more days following administration of the anti-DOTA multispecific antibody.

Additionally or alternatively, in some embodiments, the method further comprises administering an effective amount of a clearing agent to the subject prior to administration of the radiolabeled-DOTA hapten. A clearing agent can be any molecule (dextran or dendrimer or polymer) that can be conjugated with C825-hapten. In some embodiments, the clearing agent is no more than 2000 kD, 1500 kD, 1000 kD, 900 kD, 800 kD, 700 kD, 600 kD, 500 kD, 400 kD, 300 kD, 200 kD, 100 kD, 90 kD, 80 kD, 70 kD, 60 kD, 50 kD, 40 kD, 30 kD, 20 kD, 10 kD, or In some embodiments, the clearing agent is a 500 kD aminodextran-DOTA conjugate (e.g., 500 kD dextran-DOTA-Bn (Y), 500 kD dextran-DOTA-Bn (Lu), or 500 kD dextran-DOTA-Bn (In) etc.).

In some embodiments, the clearing agent and the radiolabeled-DOTA hapten are administered without further administration of the anti-DOTA multispecific antibody of the present technology. For example, in some embodiments, an anti-DOTA multispecific antibody of the present technology is administered according to a regimen that includes at least one cycle of: (i) administration of the anti-DOTA multispecific antibody of the present technology (optionally so that relevant tumor cells are saturated); (ii) administration of a radiolabeled-DOTA hapten and, optionally a clearing agent; (iii) optional additional administration of the radiolabeled-DOTA hapten and/or the clearing agent, without additional administration of the anti-DOTA multispecific antibody. In some embodiments, the method may comprise multiple such cycles (e.g., 1, 2, 3, 4, 5, 6, 7, 8, 9, 10 or more cycles).

Additionally or alternatively, in some embodiments of the method, the anti-DOTA multispecific antibody and/or the radiolabeled-DOTA hapten is administered intravenously, intramuscularly, intraarterially, intrathecally, intracapsularly, intraorbitally, intradermally, intraperitoneally, transtracheally, subcutaneously, intracerebroventricularly, intratumorally, orally or intranasally.

In one aspect, the present disclosure provides a method for increasing tumor sensitivity to radiation therapy in a subject diagnosed with a GPA33-associated cancer comprising administering to the subject an effective amount of a complex comprising a radiolabeled-DOTA hapten and a multispecific antibody of the present technology that recognizes and binds to the radiolabeled-DOTA hapten and a GPA33 antigen target, wherein the complex is configured to localize to a tumor expressing the GPA33 antigen target recognized by the multispecific antibody of the complex. The complex may be administered intravenously, intramuscularly, intraarterially, intrathecally, intracapsularly, intraorbitally, intradermally, intraperitoneally, transtracheally, subcutaneously, intracerebroventricularly, orally, intratumorally, or intranasally. In some embodiments, the subject is human.

In another aspect, the present disclosure provides a method for treating cancer in a subject in need thereof comprising (a) administering an effective amount of an anti-DOTA multispecific antibody of the present technology to the subject, wherein the anti-DOTA multispecific antibody is configured to localize to a tumor expressing a GPA33 antigen target; and (b) administering an effective amount of a radiolabeled-DOTA hapten to the subject, wherein the radiolabeled-DOTA hapten is configured to bind to the anti-DOTA multispecific antibody. The anti-DOTA multispecific antibody is administered under conditions and for a period of time (e.g., according to a dosing regimen) sufficient for it to saturate tumor cells. In some embodiments, unbound anti-DOTA multispecific antibody is removed from the blood stream after administration of the anti-DOTA multispecific antibody. In some embodiments, the radiolabeled-DOTA hapten is administered after a time period that may be sufficient to permit clearance of unbound anti-DOTA multispecific antibody. In some embodiments, the subject is human.

Accordingly, in some embodiments, the method further comprises administering an effective amount of a clearing agent to the subject prior to administration of the radiolabeled-DOTA hapten. The radiolabeled-DOTA hapten may be administered at any time between 1 minute to 4 or more days following administration of the anti-DOTA multispecific antibody. For example, in some embodiments, the radiolabeled-DOTA hapten is administered 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 1.25 hours, 1.5 hours, 1.75 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 48 hours, 72 hours, 96 hours, or any range therein, following administration of the anti-DOTA multispecific antibody. Alternatively, the radiolabeled-DOTA hapten may be administered at any time after 4 or more days following administration of the anti-DOTA multispecific antibody.

The clearing agent may be a 500 kD aminodextran-DOTA conjugate (e.g., 500 kD dextran-DOTA-Bn (Y), 500 kD dextran-DOTA-Bn (Lu), or 500 kD dextran-DOTA-Bn (In) etc.). In some embodiments, the clearing agent and the radiolabeled-DOTA hapten are administered without further administration of the anti-DOTA multispecific antibody. For example, in some embodiments, an anti-DOTA multispecific antibody is administered according to a regimen that includes at least one cycle of: (i) administration of the an anti-DOTA multispecific antibody of the present technology (optionally so that relevant tumor cells are saturated); (ii) administration of a radiolabeled-DOTA hapten and, optionally a clearing agent; (iii) optional additional administration of the radiolabeled-DOTA hapten and/or the clearing agent, without additional administration of the anti-DOTA multispecific antibody. In some embodiments, the method may comprise multiple such cycles (e.g., 1, 2, 3, 4, 5, 6, 7, 8, 9, 10 or more cycles).

Also provided herein are methods for treating cancer in a subject in need thereof comprising administering to the subject an effective amount of a complex comprising a radiolabeled-DOTA hapten and a multispecific antibody of the present technology that recognizes and binds to the radiolabeled-DOTA hapten and a GPA33 antigen target, wherein the complex is configured to localize to a tumor expressing the GPA33 antigen target recognized by the multispecific antibody of the complex. The therapeutic effectiveness of such a complex may be determined by computing the area under the curve (AUC) tumor: AUC normal tissue ratio. In some embodiments, the complex has a AUC tumor: AUC normal tissue ratio of about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

Ex vivo armed T cells. In one aspect, the present disclosure provides an ex vivo armed T cell that is coated or complexed with an effective amount of an anti-GPA33 multi-specific antibody of the present technology, wherein the anti-GPA33 multi-specific antibody includes a CD3 binding domain, wherein the anti-GPA33 multi-specific antibody is an immunoglobulin comprising two heavy chains and two light chains, wherein each of the light chains is fused to a single chain variable fragment (scFv). In some embodiments, at least one scFv of the anti-GPA33 multi-specific antibody comprises the CD3 binding domain. Additionally or alternatively, in some embodiments, at least one scFv of the anti-GPA33 multi-specific antibody comprises a DOTA binding domain.

Also disclosed herein are methods for treating a GPA33-associated cancer in a subject in need thereof comprising administering to the subject an effective amount of the ex vivo armed T cell disclosed herein.

Toxicity. Optimally, an effective amount (e.g., dose) of an anti-GPA33 antibody described herein will provide therapeutic benefit without causing substantial toxicity to the subject. Toxicity of the anti-GPA33 antibody described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the anti-GPA33 antibody described herein lies within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: *The Pharmacological Basis of Therapeutics, Ch.* 1 (1975).

Formulations of Pharmaceutical Compositions. According to the methods of the present technology, the anti-GPA33 antibody can be incorporated into pharmaceutical compositions suitable for administration. The pharmaceutical compositions generally comprise recombinant or substantially purified antibody and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions for administering the antibody compositions (See, e.g., *Remington's Pharmaceutical Sciences*, Mack Publishing Co., Easton, PA 18$^{th}$ ed., 1990). The pharmaceutical compositions are generally formulated as sterile, substantially isotonic and in full compliance with all Good Manufacturing Practice (GMP) regulations of the U.S. Food and Drug Administration. The pharmaceutical composition may further comprise an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. "Pharmaceutically-acceptable salts and esters" means salts and esters that are pharmaceutically-acceptable and have the desired pharmacological properties. Such salts include salts that can be formed where acidic protons present in the composition are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically-acceptable esters include esters formed from carboxy, sulfonyloxy, and phosphonoxy groups present in the anti-GPA33 antibody, e.g., $C_{1-6}$ alkyl esters. When there are two acidic groups present, a pharmaceutically-acceptable salt or ester can be a mono-acid-mono-salt or ester or a di-salt or ester; and similarly where there are more than two acidic groups present, some or all of such groups can be salified or esterified. An anti-GPA33 antibody named in this technology can be present in unsalified or unesterified form, or in salified and/or esterified form, and the naming of such anti-GPA33 antibody is intended to include both the original (unsalified and unesterified) compound and its pharmaceutically-acceptable salts and esters. Also, certain embodiments of the present technology can be present in more than one stereoisomeric form, and the naming of such anti-GPA33 antibody is intended to include all single stereoisomers and all mixtures (whether racemic or otherwise) of such stereoisomers. A person of ordinary skill in the art, would have no difficulty determining the appropriate timing, sequence and dosages of administration for particular drugs and compositions of the present technology.

Examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the anti-GPA33 antibody, use thereof in the compositions is contemplated. Supplementary active compounds can also be incorporated into the compositions.

A pharmaceutical composition of the present technology is formulated to be compatible with its intended route of administration. The anti-GPA33 antibody compositions of the present technology can be administered by parenteral, topical, intravenous, oral, subcutaneous, intraarterial, intradermal, transdermal, rectal, intracranial, intrathecal, intraperitoneal, intranasal; or intramuscular routes, or as inhalants. The anti-GPA33 antibody can optionally be administered in combination with other agents that are at least partly effective in treating various GPA33-associated cancers.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be desirable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating an anti-GPA33 antibody of the present technology in the required amount in an appropriate solvent with one or a combination of ingredients enumerated above, as required, followed by filtered sterilization. Generally, dispersions are prepared by incorporating the anti-GPA33 antibody into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The antibodies of the present technology can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the anti-GPA33 antibody can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the anti-GPA33 antibody is delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the anti-GPA33 antibody is formulated into ointments, salves, gels, or creams as generally known in the art.

The anti-GPA33 antibody can also be prepared as pharmaceutical compositions in the form of suppositories (e.g., with conventional suppository bases such as cocoa butter and other glycerides) or retention enemas for rectal delivery.

In one embodiment, the anti-GPA33 antibody is prepared with carriers that will protect the anti-GPA33 antibody against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

Kits

The present technology provides kits for the detection and/or treatment of GPA33-associated cancers, comprising at least one immunoglobulin-related composition of the present technology (e.g., any antibody or antigen binding fragment described herein), or a functional variant (e.g., substitutional variant) thereof. Optionally, the above described components of the kits of the present technology are packed in suitable containers and labeled for diagnosis and/or treatment of GPA33-associated cancers. The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic or diagnostic products, that contain information about, for example, the indications, usage, dosage, manufacture, administration, contraindications and/or warnings concerning the use of such therapeutic or diagnostic products.

The kits are useful for detecting the presence of an immunoreactive GPA33 protein in a biological sample, e.g., any body fluid including, but not limited to, e.g., serum, plasma, lymph, cystic fluid, urine, stool, cerebrospinal fluid, ascitic fluid or blood and including biopsy samples of body tissue. For example, the kit can comprise: one or more humanized, chimeric, bispecific, or multi-specific anti-GPA33 antibodies of the present technology (or antigen binding fragments thereof) capable of binding a GPA33 protein in a biological sample; means for determining the amount of the GPA33 protein in the sample; and means for comparing the amount of the immunoreactive GPA33 protein in the sample with a standard. One or more of the anti-GPA33 antibodies may be labeled. The kit components, (e.g., reagents) can be packaged in a suitable container. The kit can further comprise instructions for using the kit to detect the immunoreactive GPA33 protein.

For antibody-based kits, the kit can comprise, e.g., 1) a first antibody, e.g. a humanized, chimeric, bispecific, or multi-specific GPA33 antibody of the present technology (or an antigen binding fragment thereof), attached to a solid support, which binds to a GPA33 protein; and, optionally; 2) a second, different antibody which binds to either the GPA33 protein or to the first antibody, and is conjugated to a detectable label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit, e.g., for detection of a GPA33 protein in vitro or in vivo, or for treatment of GPA33-associated cancers in a subject in need thereof. In certain embodiments, the use of the reagents can be according to the methods of the present technology.

EXAMPLES

The present technology is further illustrated by the following Examples, which should not be construed as limiting in any way. The following Examples demonstrate the preparation, characterization, and use of illustrative anti-GPA33 antibodies of the present technology.

Example 1: Materials and Methods

Cell lines and human white cells. Cell lines LS174T, Colo205, and SW122 cells were purchased from ATCC or obtained from the Ludwig Institute (SW1222). All cells were authenticated by STR typing. Cells were maintained in RPMI medium supplemented with 10% FBS (Sigma, St. Louis, MO), 0.03% L-Glutamine (Gibco Laboratories, Gaithersburg, MD) and Pen/Strep (Gibco Laboratories, Gaithersburg, MD). Buffy coats from healthy donors were purchased from New York Blood Center (New York City, NY) and human PBMCs were isolated by Ficoll gradient of Buffy coats.

SEC-HPLC analysis. Size and purity of huA33-BsAb was analyzed using HPLC system (Shimadzu Scientific Instruments Inc., Columbia, MD). Monomeric species were identified using a molecular weight standard (Bio-Rad Laboratories, Hercules, CA) and percent monomer was calculated based on the relative area under curve (AUC) of different non-buffer peaks.

Antibodies and flow cytometry. Goat anti-human IgG-PE was purchased from Southern Biotech (Birmingham, AL). Biotinylated-[$Lu^{177}$]BnDOTA was synthesized by the Organic Synthesis Core at MSKCC. Streptavidin-PE was purchased from Biolegend (San Diego, CA). All FACS analysis was done using BD FACSCalibur, BD Fortessa (BD Biosciences, San Jose, CA) or the Attune NxT Flow] Cytometer (Invitrogen, Waltham, MA) and analyzed using FlowJo (FLOWJO, Ashland, OR).

FACS cell binding assays. Cells were incubated with 5 μg/mL of the primary anti-GPA33 antibodies for thirty minutes at 4° C. in PBS, and then a secondary phycoerythrin-labeled antibody specific for human Fc was added after washing off excessive primary antibody. Cells were fixed with 1% paraformaldehyde (PFA) prior to analysis on FACSCalibur cytometer (BD biosciences, Franklin Lakes, New Jersey, U.S.). Controls were cells with secondary antibody only, for which the mean fluorescent intensity (MFI) was set to 5.

Humanization of murine A33. Using CDR grafting, mouse A33 was humanized as $IgG_1$. 3 humanized $V_H$ sequences (SEQ ID NO: 1-3) and 8 humanized $V_L$ sequences (SEQ ID NO: 4-10) were combined to generate 24 different humanized A33 antibodies. The amino acid sequences of the 3 humanized $V_H$ and 8 humanized $V_L$ variants of A33 are shown in FIG. 12 and FIG. 13, respectively.

Binding kinetics was compared with that of chimeric antibody chA33 using Surface Plasmon resonance (SPR) analysis. The $V_H$ and $V_L$ sequences of chimeric antibody chA33 are provided below:

chA33 $V_H$ (SEQ ID NO: 106)

EVKLVESGGGLVKPGGSLKLSCAASGFAFSTYDMSWVRQTPEKRLEWVA
TISSGGSYTYYLDSVKGRFTISRDSARNTLYLQMSSLRSEDTALYYCAP
TTVVPFAYWGQGTLVTVSA chA33 $V_L$ (SEQ ID NO: 107)

DIVMTQSQKFMSTSVGDRVSITCKASQNVRTVVAWYQQKPGQSPKTLIY
LASNRHTGVPDRFTGSGSGTDFTLTISNVQSEDLADYFCLQHWSYPLTF
GSGTKLEVK

The yield, stability and binding affinity of the 24 different humanized A33 antibodies of the present technology are disclosed in FIGS. 9-11. As shown in FIG. 10, the combination of variable light chain VK4 (SEQ ID NO: 7) and variable heavy chain VH1 (SEQ ID NO: 1) exhibited the highest binding affinity to GPA33, with a KD of $1.68\times10^{-10}$ M. Thus, VK4 and VH1 were selected for constructing anti-GPA33 multi-specific antibodies.

SPR analysis. Human GPA33 (Novoprotein, Summit, NJ) was immobilized on CM5 chips. Five concentrations of 2-fold serially diluted huA33 IgG1 or huA33-BsAbs (starting at 20 nM) were flowed over the chip using a Biacore™ T100 system (GE Healthcare, Chicago, IL). Binding kinetics of huA33 were measured at 25° C. and binding kinetics of huA33-BsAbs were measured at both 25° C. and 37° C. The sensorgrams were fitted with two state binding model for both to derive kinetic parameters.

Engineering of anti-GPA33 bispecific antibodies based on IgG-[L]-scFv platform. The variable heavy and light chain gene sequences, i.e., VH1 and VK4, were codon optimized, synthesized, and inserted into a mammalian expression plasmid with the constant region gene of human IgG1 (contains N297A and K322A mutations). Anti-DOTA scFv or anti-CD3 scFv are attached to the C-terminus of the light chain of the anti-GPA33 antibodies. The HC and LC amino acid sequences and nucleic acid sequences of the anti-GPA33×DOTA bispecific antibodies BC015 and BC016 are shown in FIGS. 19-22. The HC and LC amino acid sequences of anti-GPA33×CD3 bispecific antibodies are shown in FIG. 28.

Engineering of heterodimeric anti-GPA33 trispecific antibodies based on IgG-[L]-scFv platform. The variable heavy and light chain gene sequences, i.e., VH1 and VK4, were codon optimized, synthesized, and inserted into a mammalian expression plasmid with the constant region gene of human IgG1 (contains N297A and K322A mutations). Anti-DOTA scFv or anti-CD3 scFv are attached to the C-terminus of anti-GPA33 VK4 LC.

Similarly, the variable heavy and light chain gene sequences of an anti-HER2 antibody were codon optimized, synthesized, and inserted into a mammalian expression plasmid with the constant region gene of human IgG1 (contains N297A and K322A mutations). The HER2 HC which harbors a K409R mutation forms a heterodimer with the anti-GPA33 VH1 HC, which harbors a F405L mutation. Anti-DOTA scFv or anti-CD3 scFv is attached to the C-terminus of the anti-HER2 LC. The HC and LC amino acid sequences of an anti-GPA33×HER2×DOTA trispecific antibody, and the 3 anti-GPA33×HER2×CD3 trispecific antibodies are shown in FIG. 29 and FIGS. 30-32, respectively.

Engineering of anti-GPA33 SADA multi-specific (e.g., bispecific or trispecific) antibodies. The variable heavy and light chain gene sequences, i.e., VH1 and VK4, were codon optimized, synthesized, and inserted into a mammalian expression plasmid to generate an anti-GPA33 scFv. One or more of the humanized C825 anti-DOTA scFv, OKT3 anti-CD3 scFv, or anti-CD276 scFv and a p53 SADA domain is attached to the C-terminus of the anti-GPA33 scFv.

Exemplary amino acid sequences of the anti-GPA33×anti-DOTA SADA multi-specific antibodies and anti-GPA33×anti-CD3 SADA multi-specific antibodies are shown in FIGS. 14-18, and 23. Exemplary amino acid sequences of the anti-GPA33×anti-HER2×anti-DOTA SADA multi-specific antibodies and anti-GPA33×anti-HER2×anti-CD3 SADA multi-specific antibodies are shown in FIGS. 24 and 25, respectively. Exemplary amino acid sequences of the anti-GPA33×anti-CD276×anti-DOTA SADA multi-specific antibodies and anti-GPA33×anti-CD276×anti-CD3 SADA multi-specific antibodies are shown in FIGS. 26 and 27, respectively.

Biodistribution assays. Female nude mice were implanted with SW1222 tumors on day 0 on their right flank. Established tumors were treated with BsAb on day 12 and DOTA[$^{177}Lu$] (1.85 to 18.5 MBq) on day 14. At 24 hours after administration of DOTA[177 Lu], tissues were excised for gamma scintillation counting (Perkin Elmer). SADA proteins containing the sequences for a humanized anti-GPA33 antibody and a humanized anti-DOTA antibody were expressed using the Expi293 Expression System (Invitrogen) and purified by affinity chromatography (GE, Ni-NTA Gravitrap, Cat #11003399) as described in Santich et al., Self-Assembling and DisAssembling (SADA) bispecific antibody (BsAb) platform for curative 2-step pre-targeted radioimmunotherapy, *Clin Cancer Res* (2020). Biochemical purity of >90% was confirmed via size-exclusion HPLC and antigen binding was assayed by Biacore and flow-cytometry. 8-week old female athymic nude mice were inoculated intraperitoneally (i.p.) with $5\times10^6$ cells of stably luciferase/GFP-transfected SW1222 in 200 μL media. Mice were included if the average radiance of the peritoneal cavity region of interest (ROI) on bioluminescence was $>1\times10^5$ p/s/cm$^2$/sr on day 24. BsAb was injected i.v. on day 26 or 27. Mice meeting inclusion criteria were injected intravenously (i.v.) with GPA33 SADA or non-specific GD2 SADA followed 48 h later with i.p. 1 mCi (37 MBq) (200 pmol) [$^{177}$Lu]Lu-DOTA-Bn. For comparison, additional mice were administered 250 μg (1.19 nmol) GPA33-BsAb (n=4) followed 24 hours later by i.v. 20 μg (2.21 nmol) CCA16-DOTAY clearing agent (CA) and after an additional 4 hours, i.p. 1 mCi (37 MBq) (200 pmol) [$^{177}$Lu]Lu-DOTA-Bn (3-step PRIT). A non-targeted control consisting of i.p. 1 mCi (37 MBq) (200 pmol) [$^{177}$Lu]Lu-DOTA-Bn was also included. Biodistribution was performed on all mice 24 hours after injection of i.p. $^{177}$Lu radiohapten. Statistical analysis for was conducted with Student's t-test on excel.

Binding to GPA33. Human GPA33 proteins were dissolved in 1×PBS to make 0.2 mg/ml stock solution and stored in −80° C. GPA33 proteins were immobilized onto the CMS sensor chip using Amine Coupling kit. GPA33 proteins were diluted in 10 μg/ml with 10 mM Sodium acetate, pH 4.5. Diluted GPA33 was immobilized at 500 RU onto active surface using Immobilization Wizard in the Biacore T200 Control Software. Reference surface was blank immobilized. Antibodies were diluted in HBS-EP buffer (10 mM HEPES, 150 mM NaCl, 3 mM EDTA, 0.05% Surfactant P20, pH 7.4) at varying concentrations (1.25-2.5-5-10-20 nM) prior to analysis. Samples (60 μl) were injected over the sensor surface at a flow rate of 30 μl/min over 1 min at 37° C. Following completion of the association phase, dissociation was monitored in HBS-EP buffer for 15 min at the same flow rate at 37° C. At the end of each cycle, the surface was regenerated using 20 mM NaOH at a flow rate of 50 μl/min over 2×15 sec.

The biosensor curves obtained following injection of the samples over the active surface were subtracted with the control curves obtained with the samples injected over the reference surface prior to kinetics analysis. All data were fitted with a 1:1 fitting model, KD=kd/ka, using the Biacore T200 Evaluation Software.

Binding to biotin-$^{175}$Lu-DOTABn. Biotin-$^{175}$Lu-DOTABn was dissolved in DMSO to make 10 mg/ml stock solution and stored in −80° C. Biotin-$^{175}$Lu-DOTABn was immobilized onto the SA sensor chip directly. Biotin-$^{175}$Lu-DOTABn was diluted to 200 ng/ml with HBS-P buffer (10 mM HEPES, 150 mM NaCl, 0.05% Surfactant P20, pH 7.4), and immobilized at 300 RU on active surface using SA Immobilization Wizard in the Biacore T200 Control Software. Reference surface was blank immobilized.

Samples were diluted in HBS-EP buffer at varying concentrations (1.25-2.5-5-10-20 nM) prior to analysis. Samples (30 μl) were injected over the sensor surface at a flow rate of 30 μl/min over 1 min. Following completion of the association phase, dissociation was monitored in HBS-EP buffer for 15 min at the same flow rate. At the end of each cycle, the surface was regenerated using 6M Guanidine-HCl, pH6.0 at a flow rate of 30 μl/min over 2×30 sec.

The biosensor curves obtained following injection of the samples over the active surface were used for kinetics analysis. All data were fitted with a 1:1 fitting model, KD=kd/ka, using the Biacore T200 Evaluation Software.

Figure 1B:
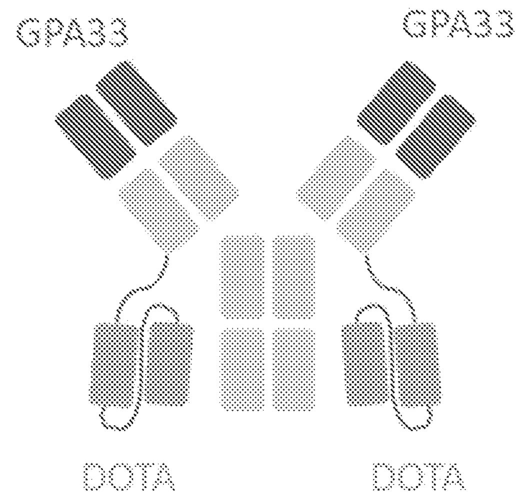
FIG. 1B shows the design of an IgG-[L]-scFv bispecific antibody (GPA33×DOTA IgG-[L]-scFv).
Figure 2A:
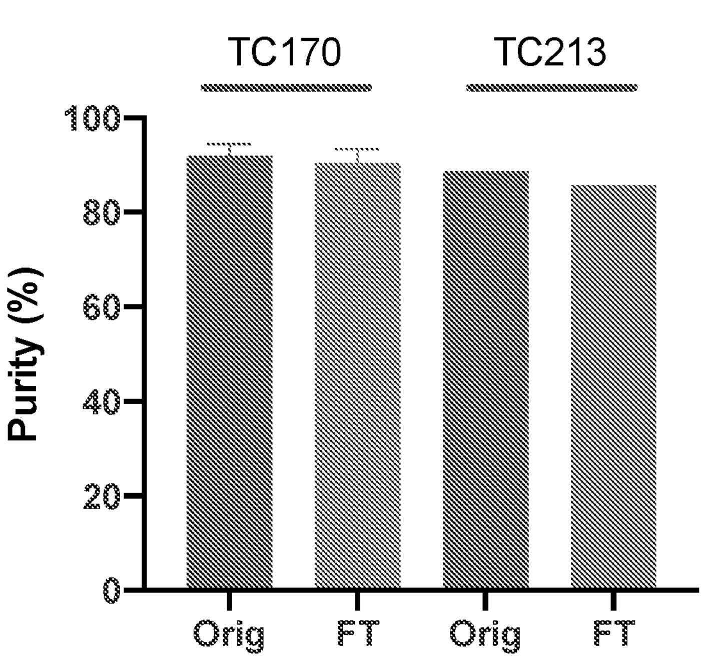
FIGS. 2A-2D show the stability of purified TC170, TC171, TC213, BC015, and BC016 bispecific antibodies.
Figure 2B:
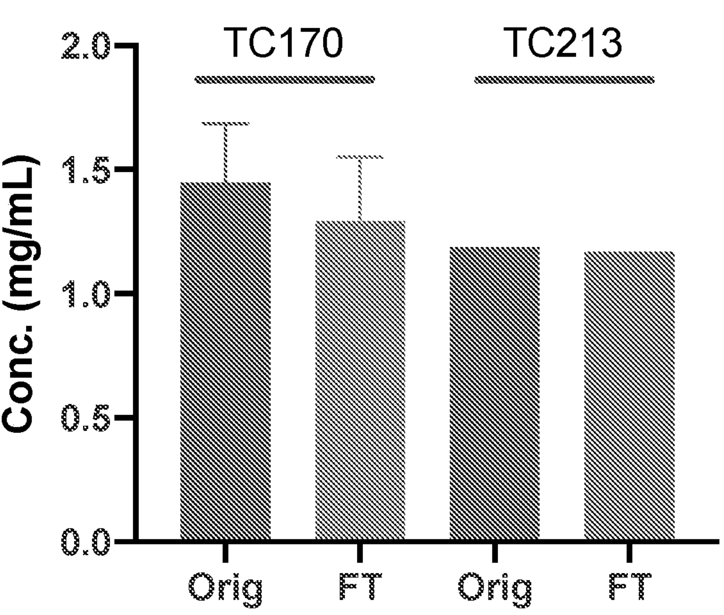
Figure 2C:
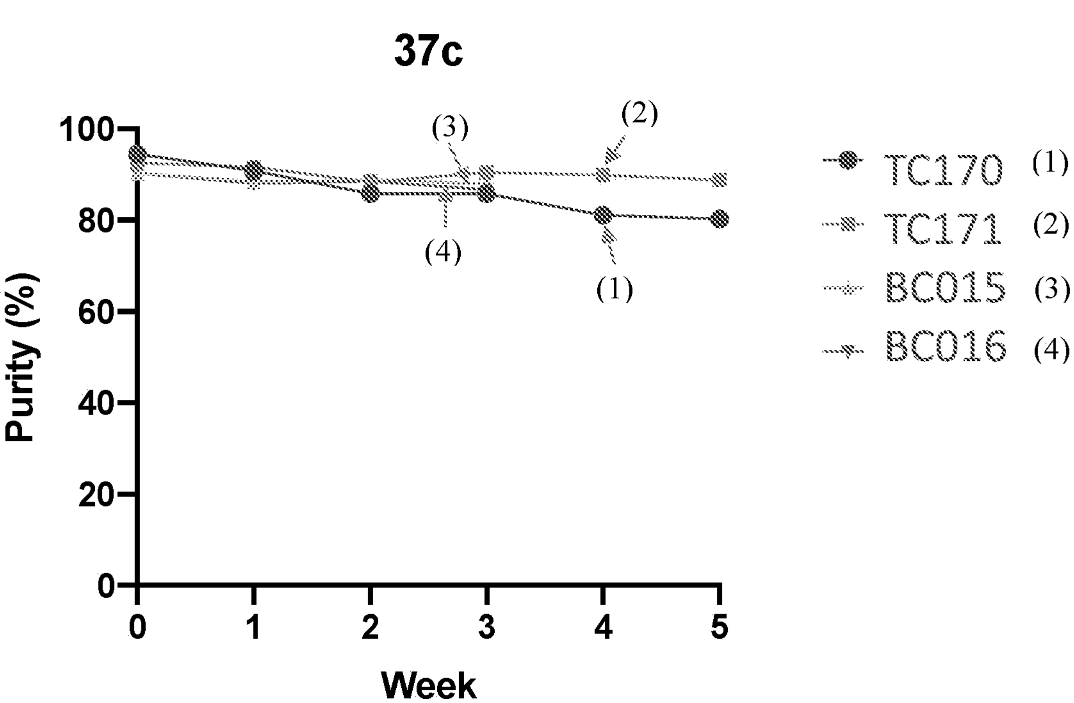
Figure 2D:
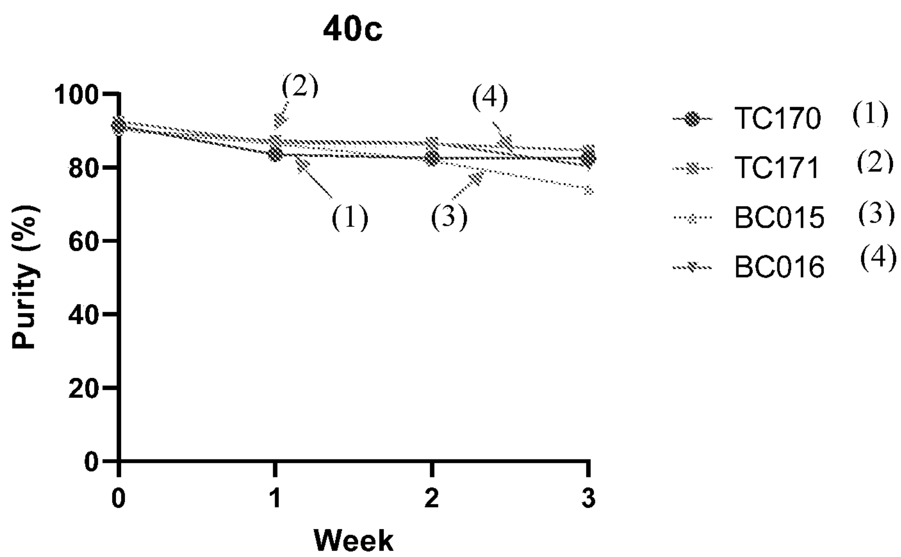

Example 2: GPA33 SADA and GPA33 IgG-[L]-scFvs Target Radiometal-Bn-DOTA Haptens to GPA33+ Colon Cancer Cells FIG. 9 describes the biochemical properties of the 24 anti-GPA33 LC and HC paired sequences in an IgG-format. Notably, the new humanizations express substantially better than the original murine sequence (G3A chimeric), indicative of the improved stability in these new sequences. FIG. 10 demonstrates the binding kinetics of these sequences against recombinant GPA33 using SPR. FIG. 11 demonstrates the cell binding activity of these clones against two GPA33+ colon cancer cell lines. FIGS. 1A-1B describe different antibody designs with specificity against both tumor antigen GPA33, and radiometal-Bn-DOTA. FIG. 1A depicts a self-assembling and disassembling (SADA) platform against GPA33 which has the second specificity to radiometal-Bn-DOTA. FIG. 1B illustrates an IgG-[L]-scFv platform that targets tumor antigen GPA33 and radiometal-Bn-DOTA. Radiometal-Bn-DOTA can be chelated to radioisotopes or used as an affinity handle for delivering other payloads.

FIGS. 2A-2D demonstrates the stability of both GPA33×DOTA SADA (TC170, TC171, TC213) and GPA33×DOTA IgG-[L]-scFv (BC015, BC016), which can be expressed and maintain purity >80% after repeated free and thaw cycles, and extended incubations at 37° C. or 40° C. FIG. 37 shows how these new GPA33 sequences were substantially more stable than alternative GPA33 sequences (see FIGS. 35-36) formatted as a SADA-BsAb.

FIGS. 3A-3B demonstrate the binding kinetics of GPA33×DOTA IgG-[L]-scFv BsAb (BC015, BC016, BC155, TC159, TC160, TC170, and TC171) against tumor antigen GPA33 (SPR), and FIGS. 38A-38B summarize the binding kinetics of these new IgG-L-scFv or SADA-BsAb formatted GPA33 sequences, which show remarkable improvements in binding affinity compared to older GPA33 clones BC105, BC155, TC159, and TC160 (see FIGS. 33-36). FIGS. 4A-4C and FIG. 39 summarize the cell binding activity (FACS) of TC170, TC171, BC015 and BC016.

Figure 4A:
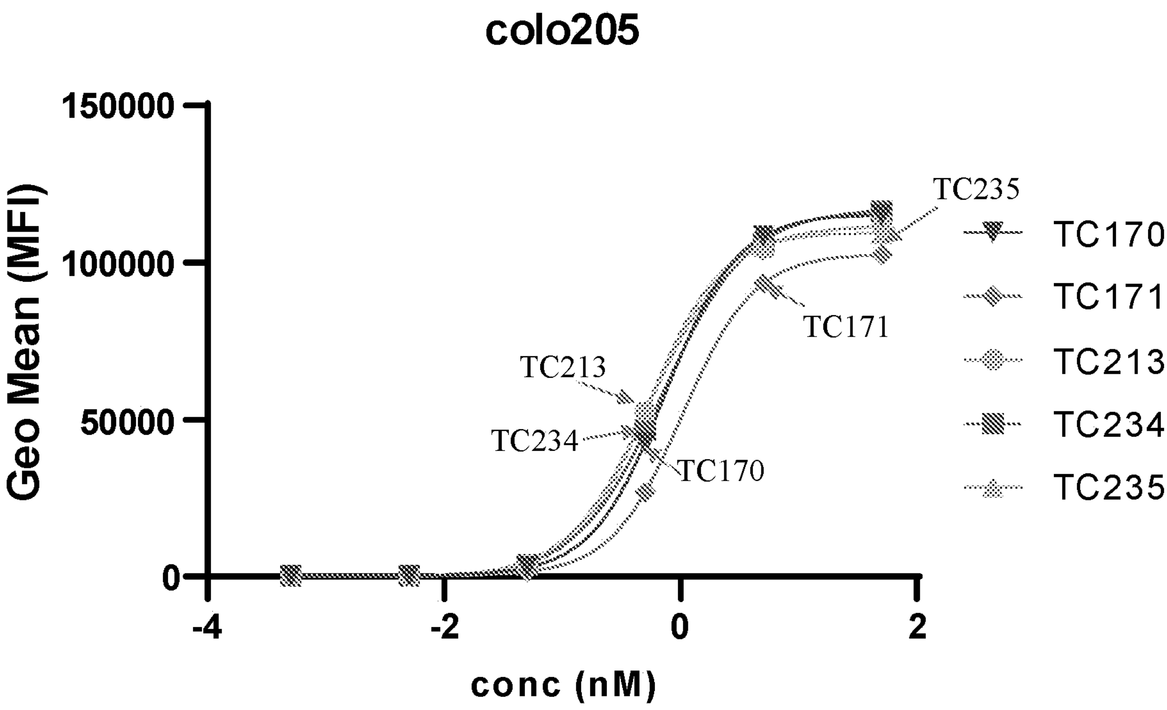
FIG. 4 shows the binding of TC170, TC171, TC213, TC234, TC235 (FIG. 4A); TC170, TC159, TC160 (FIG. 4B); and BC015, BC016 (FIG. 4C) to GPA33+ tumor cell lines by FACS at serial concentrations of the antibodies. Mean fluorescence intensity (MFI) is presented as geometric mean values.
Figure 4A:
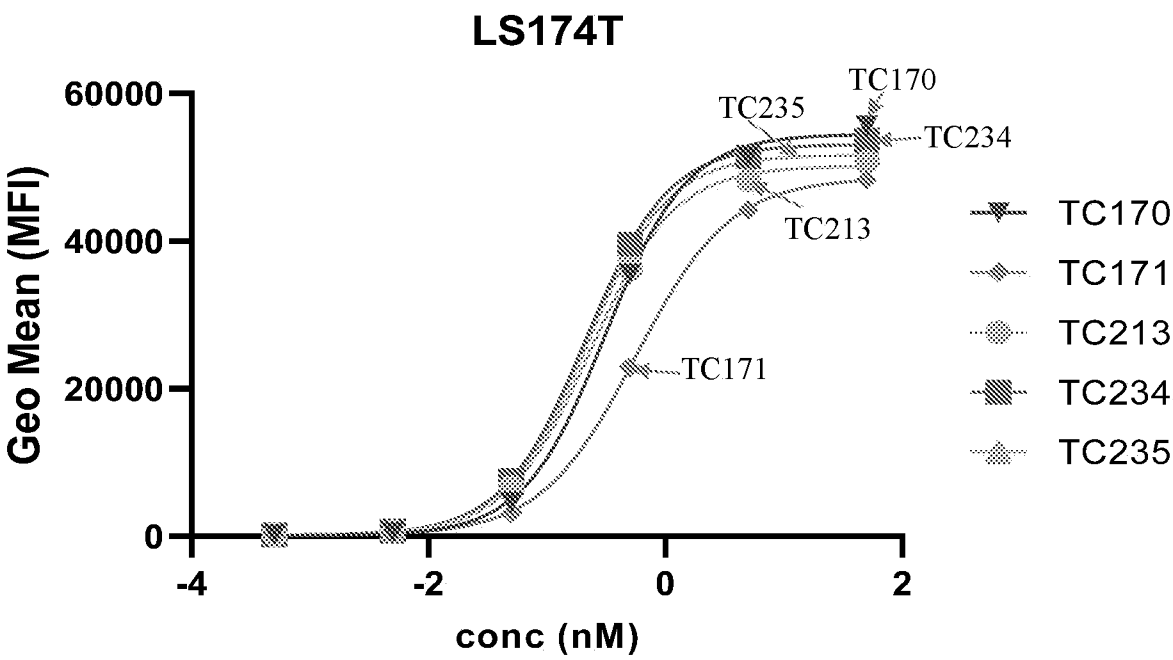
Figure 4A:
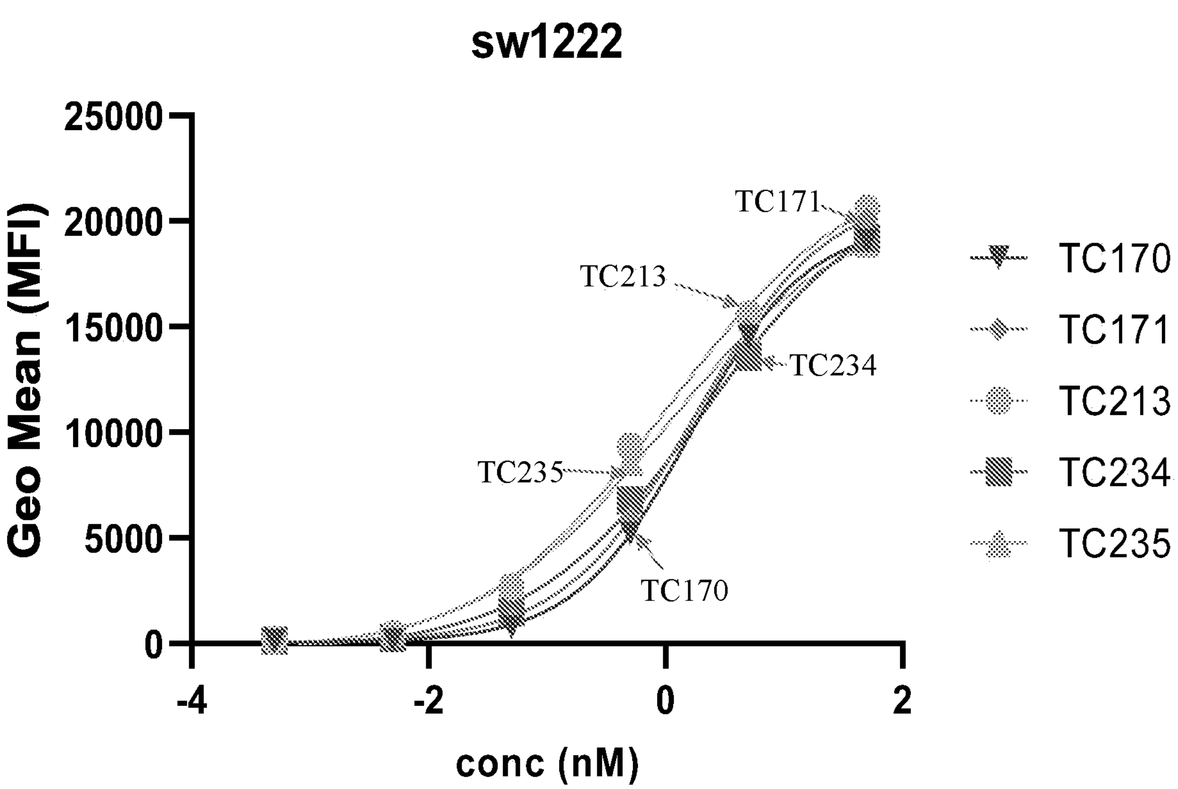
Figure 4B:
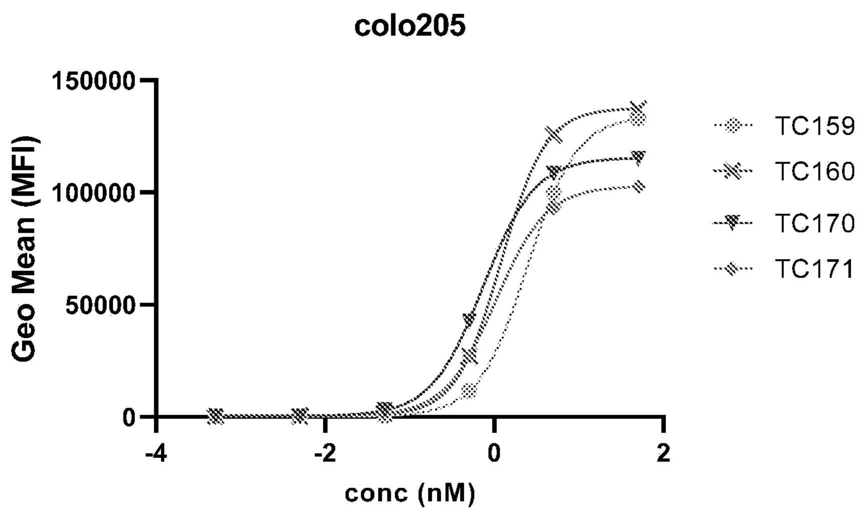
Figure 4C:
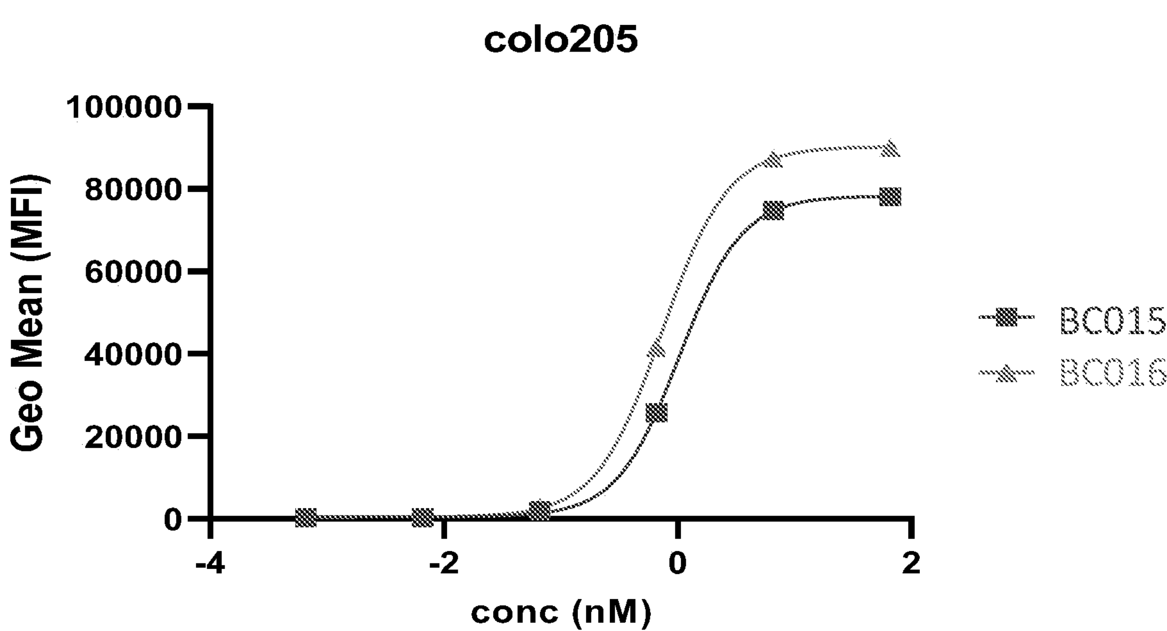
Figure 4C:
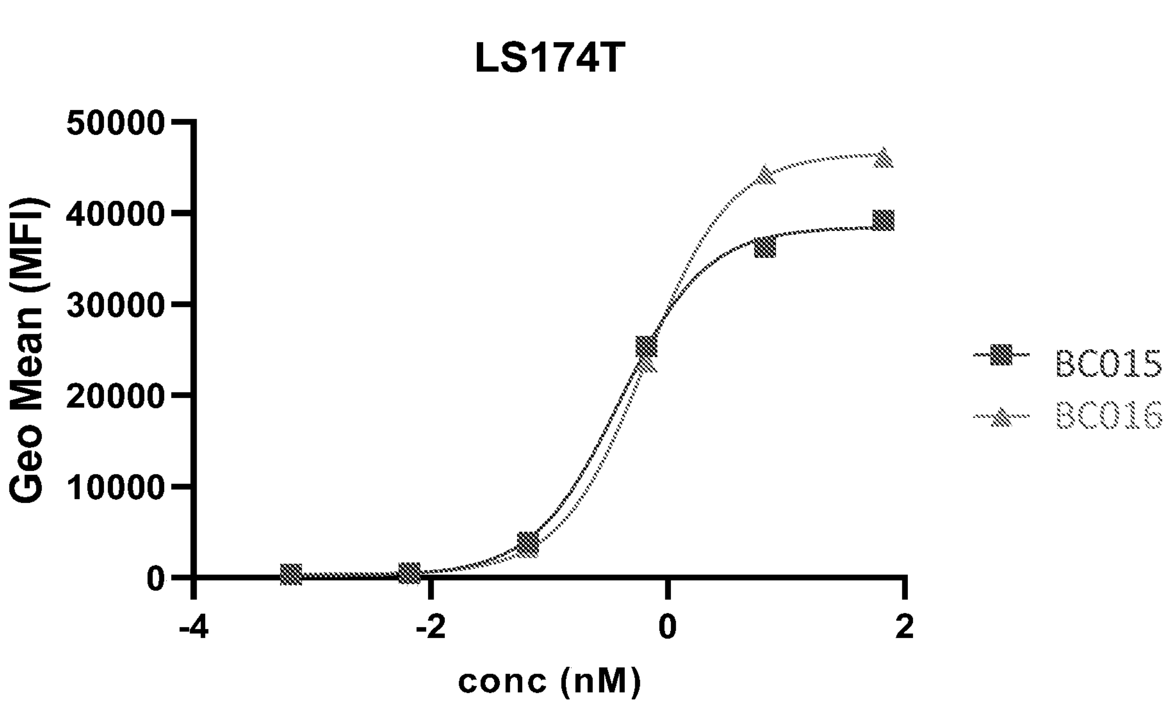
Figure 4C:
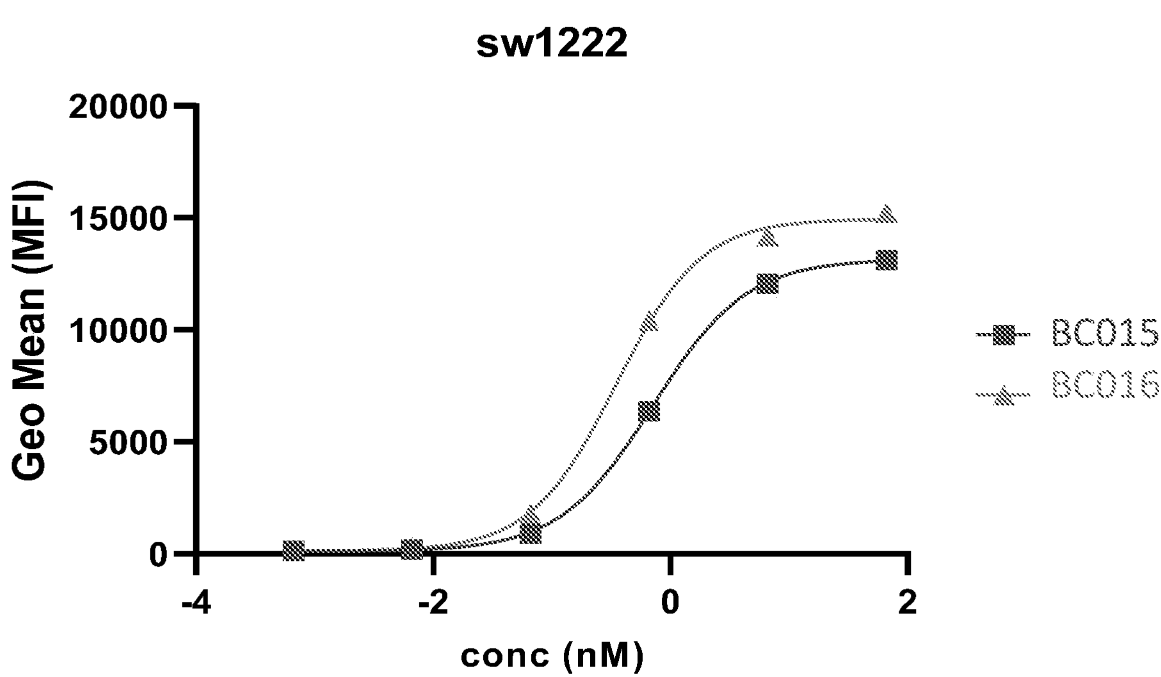

Binding to Colo 205 cell line. TC170/171 binds to Colo 205 with $IC_{50}$ at 0.74 and 1.04 nM respectively while TC159/160 binds to Colo 205 with $IC_{50}$ at 2.46 and 1.20 nM respectively. TC213/234/235 binds to Colo205 with $IC_{50}$ from 0.53 to 0.71 nM (FIGS. 4A-4B). Maximal binding intensity as measured by gMFI (highest SADA BsAb conc. at 50 nM used in this assay) range from 100,000 to 138,000 for all tested SADAs. While VH and VL anti-GPA33 scFv orientation minimally affects target binding as suggested by $IC_{50}$ of the TC170/171 and TC159/160 pairings, the 3 pI variants TC213/234/235 display similar $IC_{50}$ compared to parental TC170.

Binding to LS 174T cell line. TC170/171 binds to LS 174T with $IC_{50}$ at 0.31 and 0.56 nM respectively while TC159/160 binds to LS 174T with $IC_{50}$ at 1.22 and 0.56 nM respectively. TC213/234/235 share similar $IC_{50}$ (0.22-0.23 nM) (FIGS. 4A-4B). LS 174T expresses lower amount of surface human GPA33 with half the maximal binding intensity compared to Colo 205, all tested GPA33 SADAs display similar gMFI (SADA BsAb conc. at 50 nM). While VH and VL anti-GPA33 scFv orientation minimally affect target binding as suggested by $IC_{50}$ of the TC170/171 and TC159/

160 pairings, the 3 pI variants TC213/234/235 again display similar $IC_{50}$ compared to parental TC170.

Binding to SW 1222 cell line. TC170/171 binds to SW 1222 with $IC_{50}$ at 1.65 and 1.78 nM respectively while TC159/160 binds to SW 1222 with $IC_{50}$ at 0.40 and 0.36 nM respectively. TC213/234/235 share similar $IC_{50}$ (1.02-2.05 nM) (FIGS. 4A-4B). Maximal binding intensity as measured by gMFI (highest SADA BsAb conc. at 50 nM used in this assay) range from 17,000 to 22,000 for all tested SADAs. While VH and VL anti-GPA33 scfv orientation minimally affect target binding as suggested by $IC_{50}$ of the TC170/171 and TC159/160 pairings, the 3 pI variants TC213/234/235 again display similar $IC_{50}$ compared to parental TC170.

Taken together, all tested GPA33 SADAs show similar $IC_{50}$ and binding intensity to the colorectal cell lines. Anti-GPA33 scFv VH and VL orientation does not significantly modify the target binding. Importantly, as shown by SPR, mutations to TC170 (TC213, TC234, TC235) to change the isoelectric point (PI) do not impact binding. Additionally, TC159 and TC160 show diminished binding activity compared to TC170.

GPA33 BsAb binding kinetics to GPA33 antigen are summarized below:

| Sample | ka1 (1/Ms) | kd1 (1/s) | ka2 (1/s) | kd2 (1/s) | KD (M) | $Chi^2$ ($RU^2$) |
|---|---|---|---|---|---|---|
| BC105 | 4.43E+06 | 2.36E−02 | 2.38E−03 | 6.97E−04 | 1.21E−09 | 0.0735 |
| BC155 | 4.13E+06 | 2.12E−03 | 3.28E−03 | 1.64E−03 | 1.71E−10 | 0.855 |
| BC177 | 4.36E+06 | 1.41E−03 | 3.07E−03 | 1.77E−03 | 1.18E−10 | 0.656 |
| BC178 | 5.50E+06 | 5.11E−04 | 5.41E−02 | 5.04E−03 | 7.92E−12 | 1.21 |
| TC170 | 3.54E+06 | 7.28E−04 | 6.46E−03 | 5.38E−04 | 1.58E−11 | 0.479 |
| TC171 | 3.34E+06 | 8.86E−04 | 6.63E−03 | 6.28E−04 | 2.30E−11 | 0.294 |
| TC213 | 3.44E+06 | 8.57E−04 | 6.36E−03 | 6.11E−04 | 2.18E−11 | 0.327 |
| TC234 | 4.65E+06 | 9.66E−04 | 5.66E−03 | 3.53E−04 | 1.22E−11 | 0.468 |
| TC235 | 3.38E+06 | 9.81E−04 | 5.61E−03 | 5.10E−04 | 2.42E−11 | 0.234 |
| TC159 | 4.09E+06 | 1.81E−03 | 6.13E−03 | 3.15E−04 | 2.16E−11 | 0.103 |
| TC160 | 3.43E+06 | 2.02E−03 | 6.78E−03 | 6.54E−04 | 5.18E−11 | 0.146 |

GPA33 BsAb binding kinetics to biotin-$^{175}$Lu-DOTABn are summarized below:

| Sample | ka (1/Ms) | kd (1/s) | KD (M) | t ½ (s) |
|---|---|---|---|---|
| BC105 | 4.50E+05 | 4.75E−05 | 1.06E−10 | 14584.4 |
| BC155 | 8.59E+04 | 5.03E−05 | 5.86E−10 | 13778.7 |
| BC177 | 9.54E+05 | 1.78E−04 | 1.87E−10 | 3894.8 |
| BC178 | 5.22E+05 | 1.13E−04 | 2.16E−10 | 6141.9 |
| TC170 | 4.32E+05 | 1.39E−06 | 3.22E−12 | 497784.5 |
| TC171 | 2.98E+05 | 1.13E−06 | 3.80E−12 | 612139.6 |
| TC213 | 4.14E+05 | 4.53E−06 | 1.10E−11 | 152880.6 |
| TC234 | 4.16E+05 | 3.21E−06 | 7.70E−12 | 216242.4 |
| TC235 | 4.49E+05 | 1.17E−05 | 2.60E−11 | 59319.3 |
| TC159 | 3.73E+05 | 3.05E−05 | 8.17E−11 | 22753.6 |
| TC160 | 3.16E+05 | 3.69E−05 | 1.17E−10 | 18769.7 |

These results demonstrated that GPA33 SADA binds to GPA33 antigen with higher affinity than GPA33 BsAb-IgG. Orientation of variable heavy (VH) and light chain (VL) of GPA33 scFv does not affect the binding (TC170 vs TC171). However, GPA33 scFv derived from another clone appears to bind with preferred VH and VL orientation (TC159 3-fold higher affinity than TC160). Single to triple mutations within the GPA33 scFv do not significantly alter the binding affinity (TC170 vs TC213/234/235).

Similarly, GPA33 SADA binds to biotin-$^{175}$Lu-DOTABn with substantially higher affinity than GPA33 BsAb-IgG. Orientation of variable heavy (VH) and light chain (VL) of GPA33 scFv does not affect the binding (TC170 vs TC171 and TC159 vs TC160) to biotin-$^{175}$Lu-DOTABn because both SADAs share identical C825 scFv sequence. TC213 and TC235 which have double and triple mutations in the GPA33 scFv respectively appear to have weaker binding to biotin-$^{175}$Lu-DOTABn compared to parental TC170. The C825 sequences in TC213 and TC235 are the same as TC170.

FIGS. 5A-5D show the in vivo biodistribution of both SADA and IgG-L-scFv designs, demonstrating similar high uptake in the tumor and low uptake in other non-targeted organs. When combined with a N-acetylgalactosamino Dendron-clearing agent (described in Cheal, S. M., et al., *Bioconjug Chem* 31: 501-506 (2019)), BC015 (3-step) shows a high therapeutic index, consistent with previous versions of this format [Cheal, S. M., et al., *J Nucl Med,* 2017. 58(11): p. 1735-1742, Cheal, S. M., et al., *Eur Nucl Med Mol Imaging,* 2016. 43(5): p. 925-937]. TC170, however, displayed similar or better therapeutic indexes without the use of any clearing agents (2-step), simplifying the clinical translation.

Figure 5A:
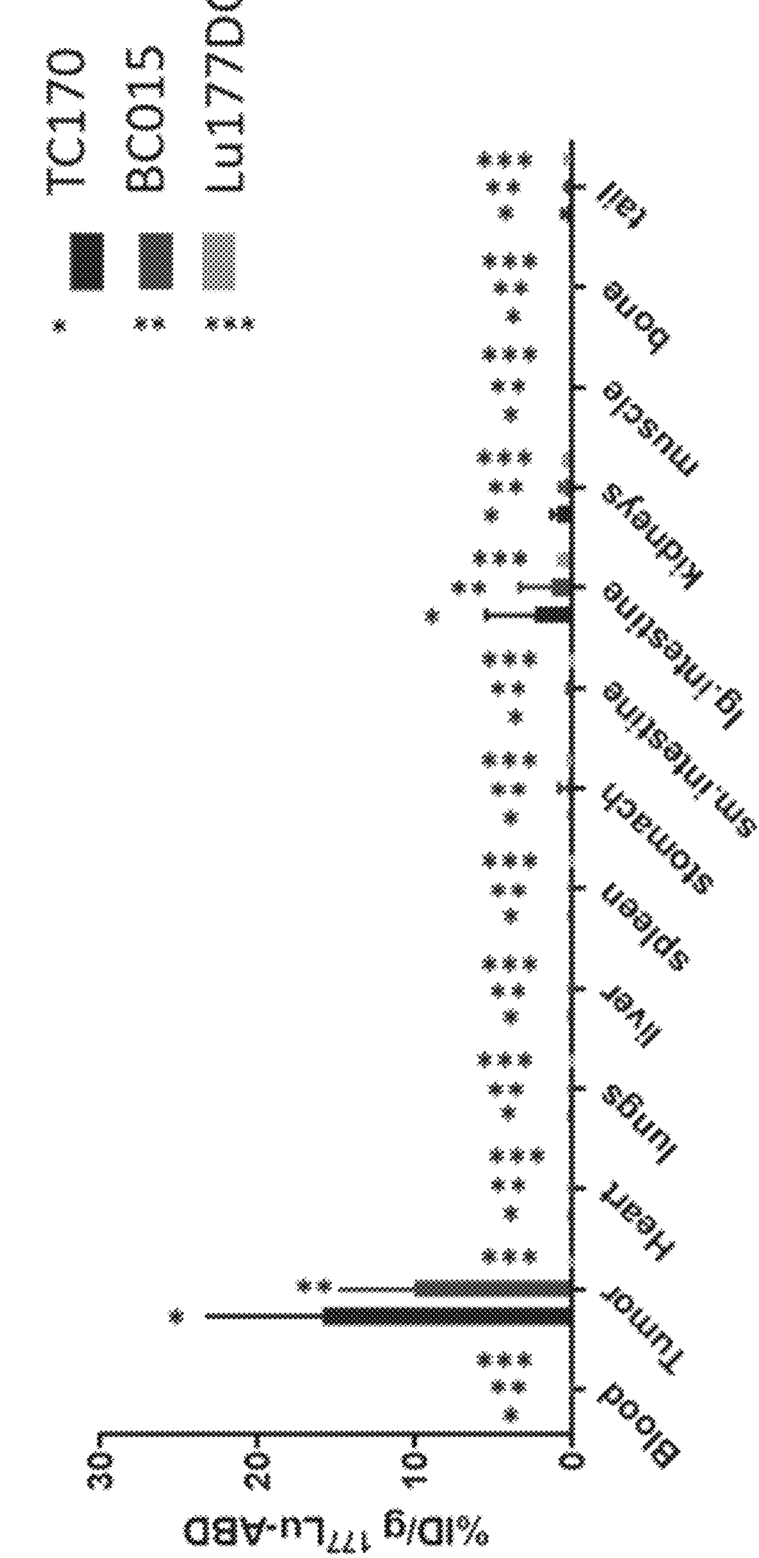
FIGS. 5A-5D show the biodistribution of TC170 and BC015 using in vivo mouse models. TC170 (48 hours prior, T=−48 h) and BC015 (24 hours prior, T=−24 h) were intravenously administered to xenograft tumor bearing (SW1222) nude mice. 20 hours after BC015 administration, BC015-treated mice were given a N-acetylgalactosamino Dendron-clearing agent (described in Cheal, S. M., et al., *Bioconjug Chem* 31: 501-506 (2019)) (4 hours prior, T=−4 h) intravenously. At T=0, 48 hours after the original doses of BC015 and TC170, [$^{177}$Lu]DOTA (FIG. 5A) or [$^{225}$Ac] *Proteus* (described in Cheal, S. M., et al., Alpha radioimmunotherapy using 225Ac-*proteus*-DOTA for solid tumors—safety at curative doses. Theranostics, 2020.) (FIG. 5B) payloads were given to the mice intravenously. After 24 hours (T=+24 h), mice were dissected and organs were isolated for measurement of uptake of each radiometal payload. Uptake values are presented as the normalized percent of injected dose, per gram of tissue. Similarly, administration routes of TC170 were compared in xenograft tumor bearing (SW1222) nude mice (FIG. 5C). TC170 was injected intraperitoneally or intravenously 48 hours (T=−48 h) prior to the doses of [$^{225}$Ac]*Proteus* payloads at T=0. After 24 hours (T=+24 h), mice were dissected, and organs were isolated for measurement of uptake of each radiometal payload. Uptake values are presented as the normalized percent of injected dose, per gram of tissue. Targeting of intraperitoneal disease were compared in FIG. 5D, where mice bearing intraperitoneal tumors (SW1222) were treated with 1 mCi of [$^{177}$Lu]BnDOTA 48 hours after treatment with either TC170 or BC105. BC105 treated mice also were treated with clearing agent 4 hours before administration of radiation. Bar graphs depict activity 24 hours after dose administration.
Figure 5B:
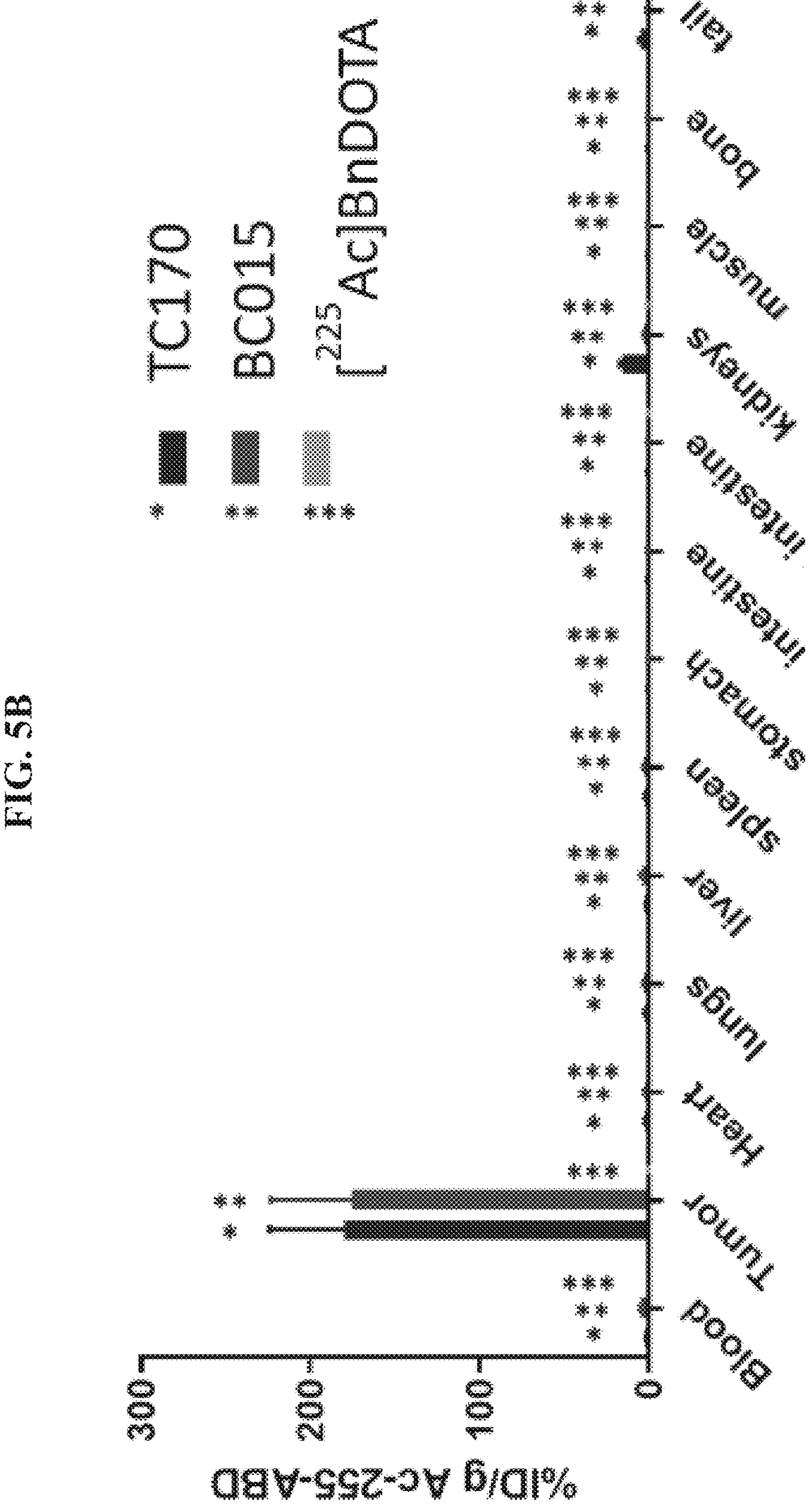
Figure 5C:
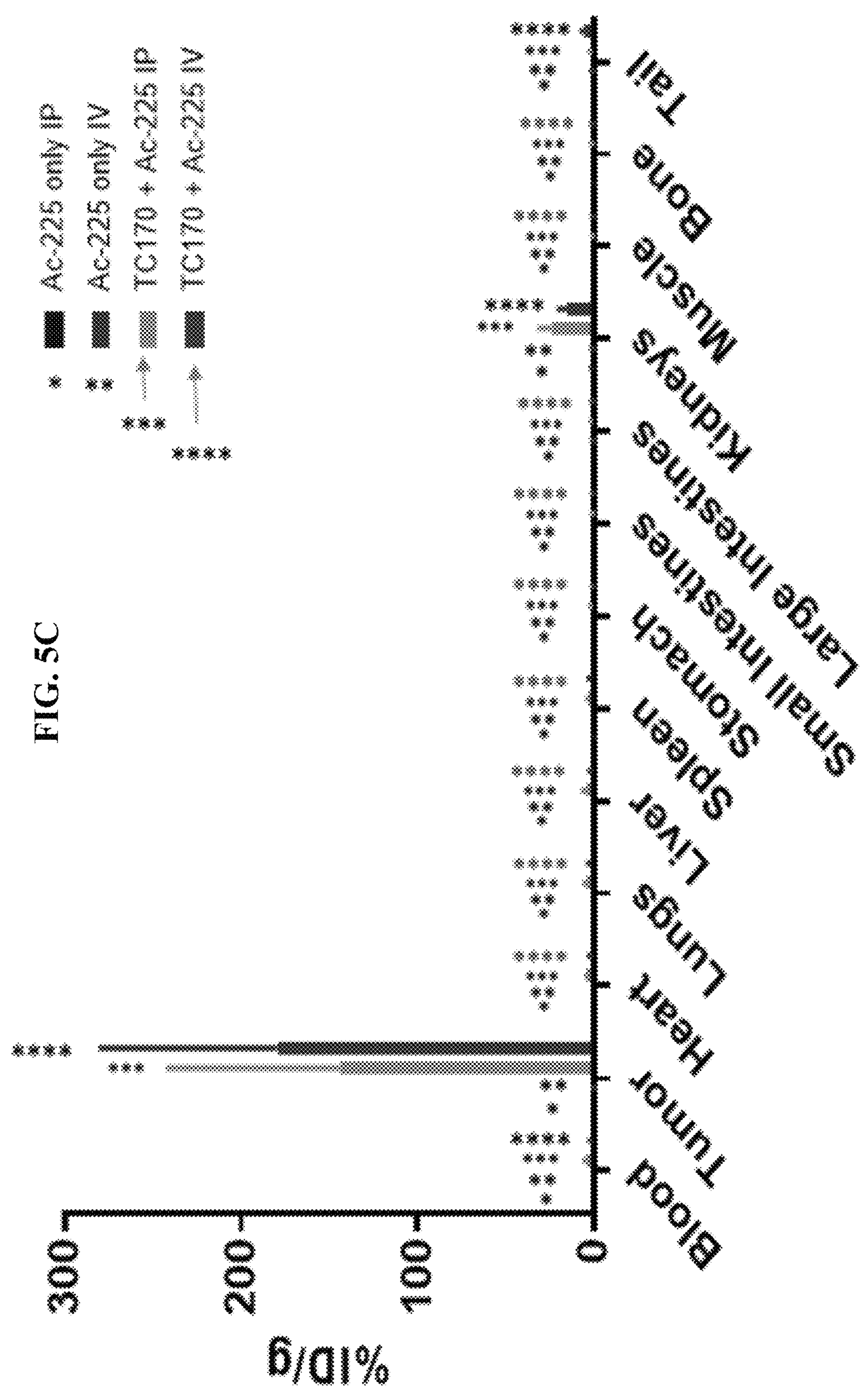
Figure 5D:
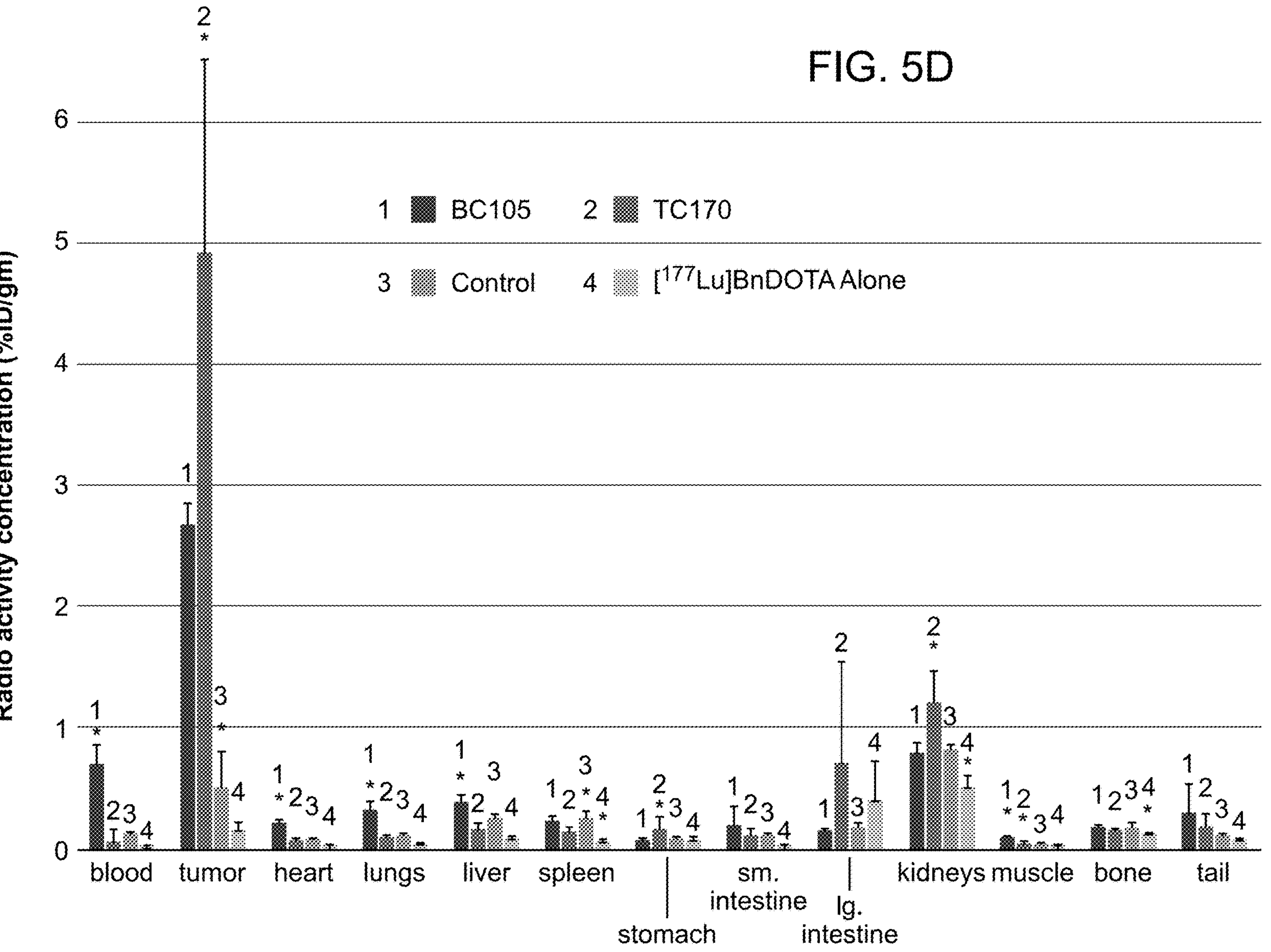

FIG. 5D demonstrates that the 2-step approach using TC170 is also superior than previous 3-step approaches using BC105, both in targeting intraperitoneal disease and reducing blood exposure. Tumor burden in mass (g) was 0.369±0.239 (mean±SD) grams obtained on biodistribution and was found to be distributed throughout the peritoneal cavity, adhering to the peritoneal lining and all intraperitoneal organ surfaces. At 24 hours after injection, the amount of radioactivity absorbed in harvested intraperitoneal SW1222 xenograft tumors treated with SADA-GPA33 (4.92±1.59 [mean±SD] percentage injected dose per gram [% ID/g]) was significantly greater than that of harvested tumors treated with the traditional 3 step PRIT to GPA33 (2.68±0.179% ID/g, p=0.043) or with negative control SADA-GD2 (0.513±0.293% ID/g, p<0.001). In mice treated with SADA-GPA33, the ratio of tumor-to-organ radioactivity uptake was 19.6±5.08 (average, propagated error) for all organs (p<0.001), 4.12±0.734 (p=0.002) for kidneys, 30.5±6.14 (p<0.001) for liver, and 122.8±22.6 (p<0.001) for blood.

Figure 6B:
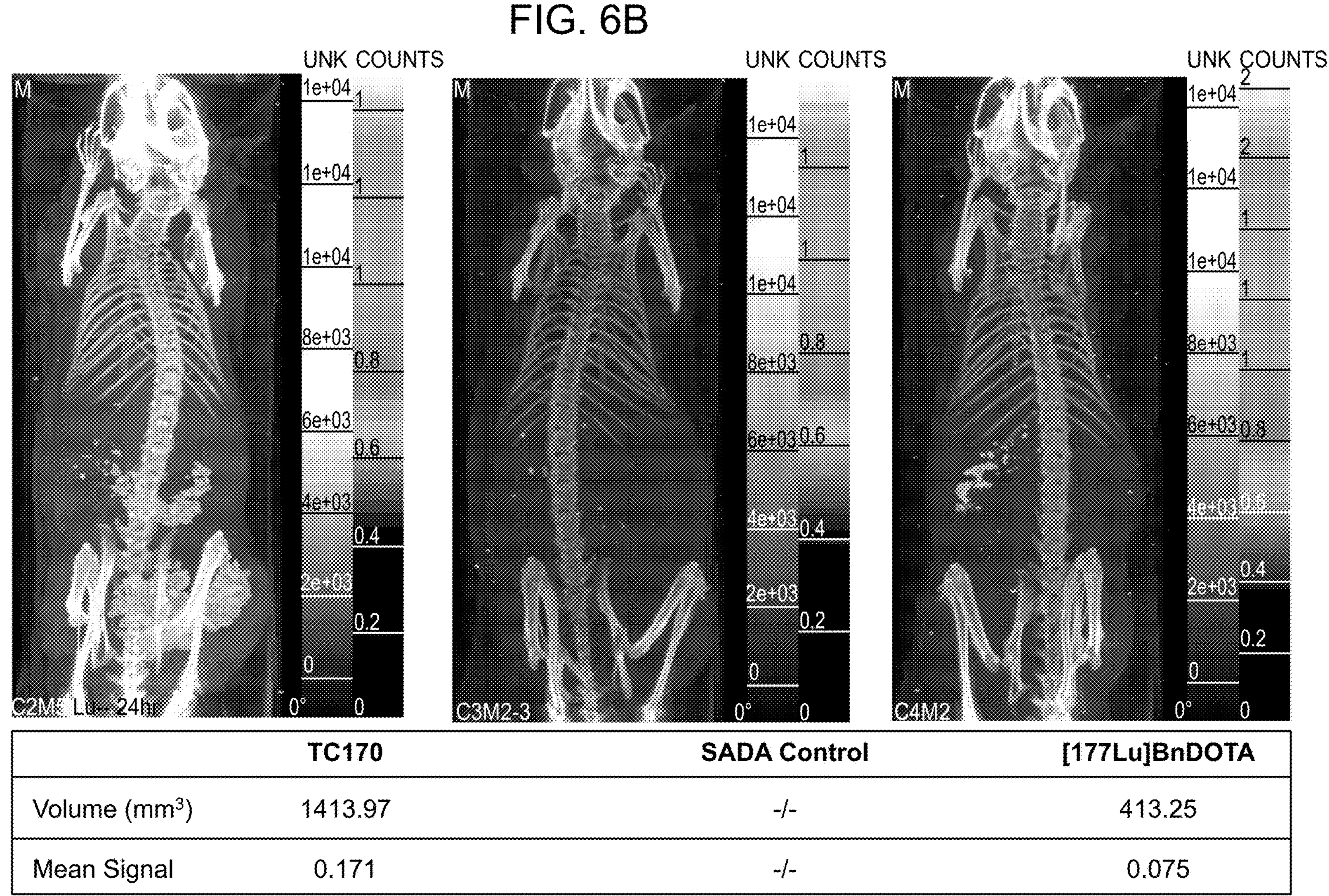
Figure 6C:
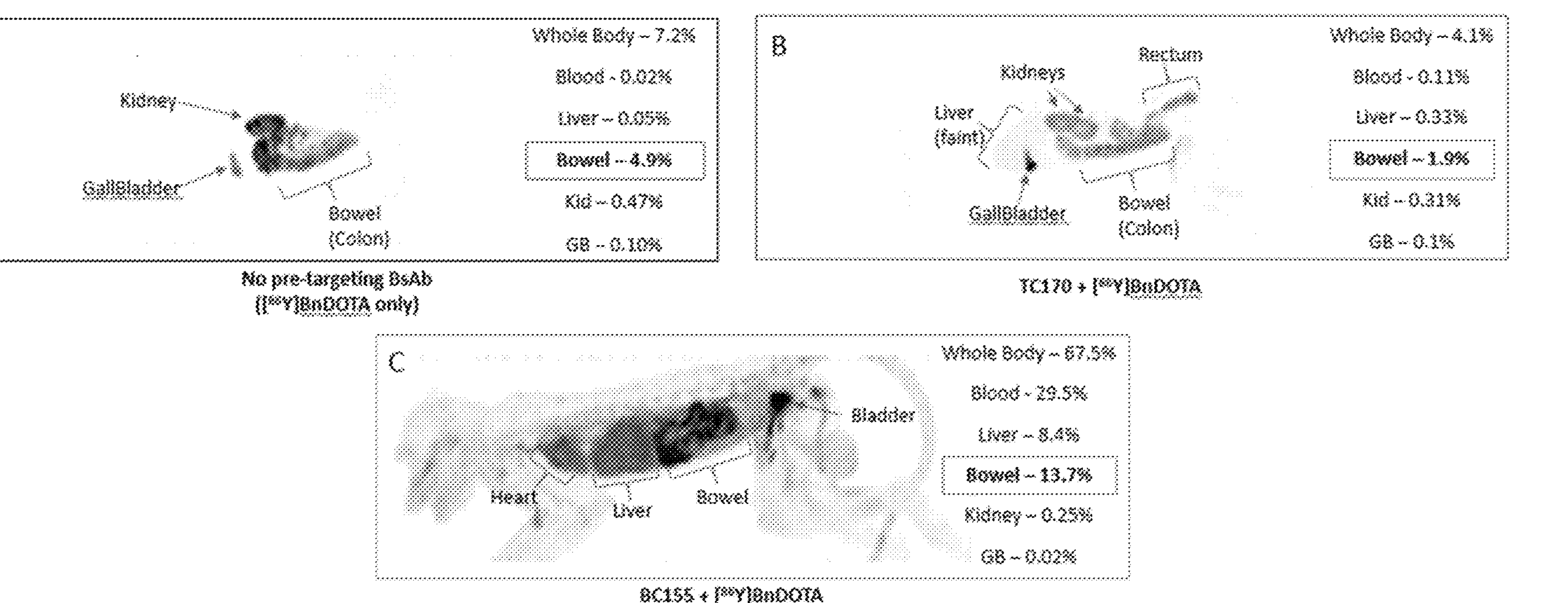
Figure 6D:
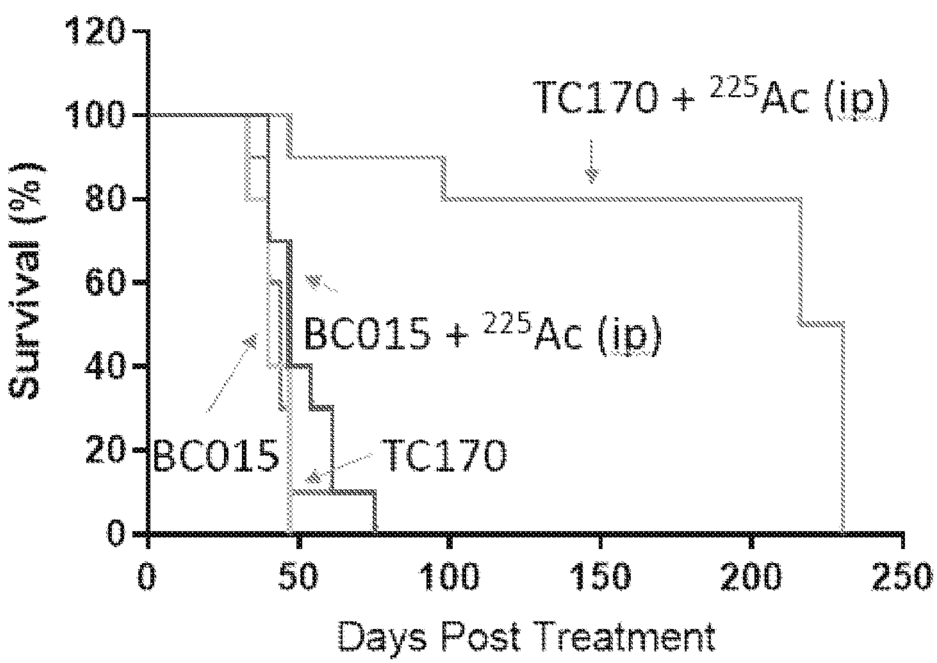
FIG. 6D shows the Kaplan-Meier Survival Curves of xenograft tumor (SW1222) bearing mice treated with 1) BC015 only (N=5), 2) TC170 only (N=10), 3) BC015, a clearing agent, and [$^{225}$Ac]*Proteus* payloads (N=10), or 4) TC170 and [$^{225}$Ac]*Proteus* payloads (N=10). BC015 was administered intraperitoneally 20 hours before the clearing agent and 24 hours before the [$^{225}$Ac]*Proteus* payloads whereas TC170 was given intraperitoneally 48 hours before the [$^{225}$Ac]*Proteus* payloads. Kaplan-Meier survival analysis was performed.

FIG. 6 shows imaging data from mice (FIGS. 6A and 6B) or NHP (FIG. 6C) treated with BsAb and either $^{177}$Lu (SPECT) or $^{86}$Y (PET). Importantly, in the study using non-human primate (NHP), gut uptake of TC170 was markedly lower than an IgG-[L]-scFv formatted GPA33 bispecific (BC155, FIG. 6C), which showed substantial uptake in the colon where GPA33 is natively expressed. Since this humanized sequence crosses react with NHP GPA33, it indicates that the SADA format can dramatically reduce the unwanted binding to normal tissues in human. This is achieved perhaps by limited transport into the lumen of the gut, due to faster renal clearance, and a lack of binding to FcRn. This suggests that GPA33×DOTA SADA would demonstrate substantially higher therapeutic indices in human patients compared to conventional approaches. Lastly, as shown in FIG. 6D, TC170 can be used to treat tumors in a mouse model of intraperitoneal CRC, with a substantially improved survival over a 3-step approach using an IgG-L-scFv formatted BsAb.

These results demonstrate that the anti-GPA33 immunoglobulin-related compositions of the present technology are useful in methods for detecting GPA33 polypeptides in a biological sample and treating GPA33(+) cancer in a subject in need thereof.

Example 3: T Cell Engaging GPA33 SADA and GPA33 IgG-[L]-scFvs

Figure 7A:
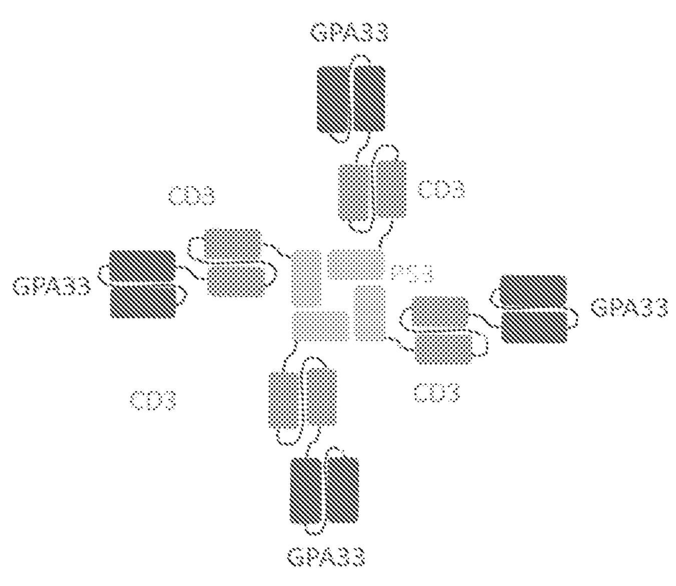
FIG. 7A shows a design of a GPA33×CD3 SADA bispecific antibody that targets tumor antigen GPA33 and CD3 on T cells.
Figure 7B:
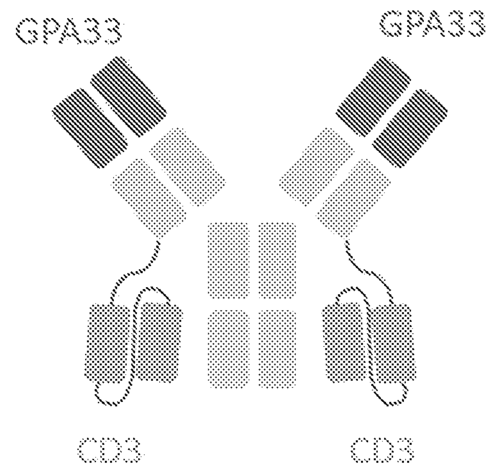
FIG. 7B shows a design of a GPA33×CD3 IgG-[L]-scFv bispecific antibody that targets tumor antigen GPA33 and CD3 on T cells.

FIGS. 7A-7B show designs of a SADA formatted and IgG-[L]-scFv formatted bispecific antibody that targets tumor antigen GPA33 on tumors and CD3 on T cells. In these designs, T cells can be recruited to the GPA33+ tumor sites and elicit cytotoxicity to tumor cells. In addition, in the IgG-[L]-scFv GPA33×CD3 bispecific antibody, N297A and K322A mutations in the heavy chain constant region minimize Fc function and improve in vivo biodistribution through reduced non-specific FcR mediated uptake and limit cytokine storm (TC252-TC263 (FIG. 23), and BC369, BC373, BC377 (FIG. 28)).

Cytotoxicity is evaluated using a $^{51}$Cr release assay. Briefly, target cells are incubated with sodium chromate (100 μCi per one million cells) for one hour and mixed with human T-cells (10:1 E:T) and serially titrated BsAb, in triplicate. After four hours, released $^{51}$Cr is measured using a gamma counter (Perkins-Elmer). Cell lysis is calculated using the formula [Sample Lysis−Spontaneous lysis]/[Total Lysis−Spontaneous Lysis], where spontaneous lysis measures released $^{51}$Cr from target cells without antibody or T-cells, and total lysis measures released $^{51}$Cr from target cells mixed with 10% SDS. Specific lysis is calculated by subtracting the measured release from a sample without BsAb (T-cells and target cells only) from the calculated cell lysis. To calculate the EC50, curves are fitted using a four-parameter logistic fitting with GraphPad Prism 8.

It is anticipated that the anti-GPA33 immunoglobulin-related compositions of the present technology will exhibit potent in vitro and/or in vivo cytotoxic activity against one or more GPA33-associated cancers. Accordingly, the immunoglobulin-related compositions of the present technology are useful to treat a GPA33-associated cancer in a subject in need thereof.

Figure 40B:
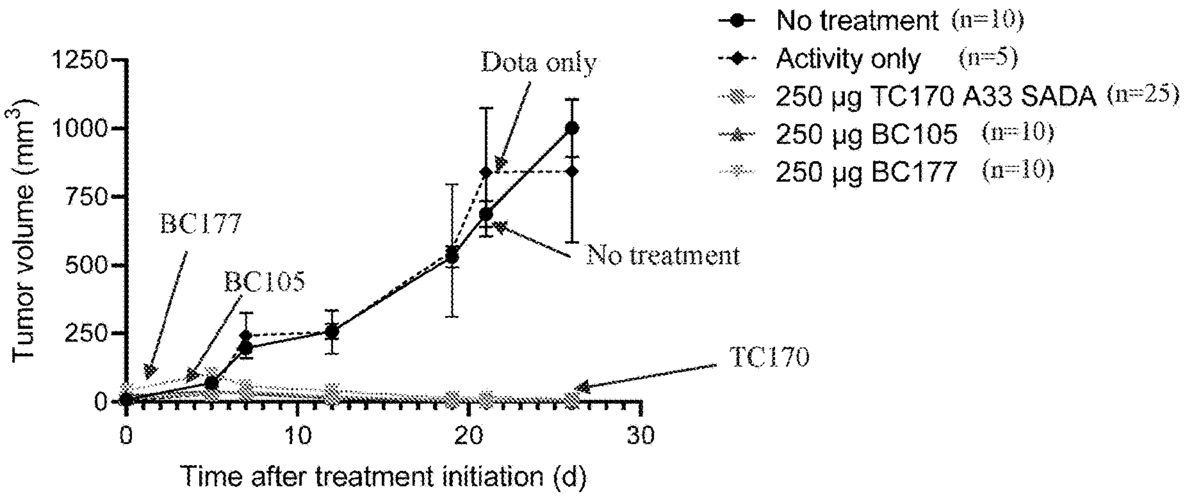
FIGS. 40A-40B show tissue uptake (FIG. 40A) and anti-tumor effects (FIG. 40B) of $^{225}$Ac-*Proteus* DOTA PRIT with BC177, TC170, and BC105 in SW1222 tumor-bearing female athymic nude mouse model.

Example 4: Multi-Specific Antibodies Targeting GPA33, and Radiometal-Bn-DOTA with $^{225}$Ac-PrDOTA PRIT Female athymic nude mice were implanted with SW1222 tumors on day 0 on their right flank. PRIT study was initiated ~1 week post-inoculation of 5 million cells/mouse. Animals were divided into the following treatment groups: No treatment (n=10); 250 μg TC170 (n=30); 250 μg BC177 (n=15); 250 μg BC105 (n=15) and $^{225}$Ac-PrDOTA only (n=5). All animals received single-cycle treatment of 2 μCi (0.7 nmol)~106 kBq/nmol of $^{225}$Ac-PrDOTA. TC170 SADA constructs showed exceptional in vivo targeting to A33 expressing SW1222 tumors (FIG. 40A) relative to the bispecific antibody BC177 (a.k.a. BC015). Animals treated with BC177, BC105, or TC170 exhibited robust treatment efficacy using Ac-225 proteus (FIG. 40B).

| Construct | 0 mm$^3$ | up to 5 mm$^3$ | 5-10 mm$^3$ | 10-20 mm$^3$ | >25 mm$^3$ |
|---|---|---|---|---|---|
| TC170 | 1/25 | 9/25 | 7/25 | 4/25 | 4/25 |
| BC105 | 3/10 | 6/10 | 1/10 | | |
| BC177 | 2/10 | 2/10 | 3/10 | 2/10 | 1/10 |

Figure 40C:
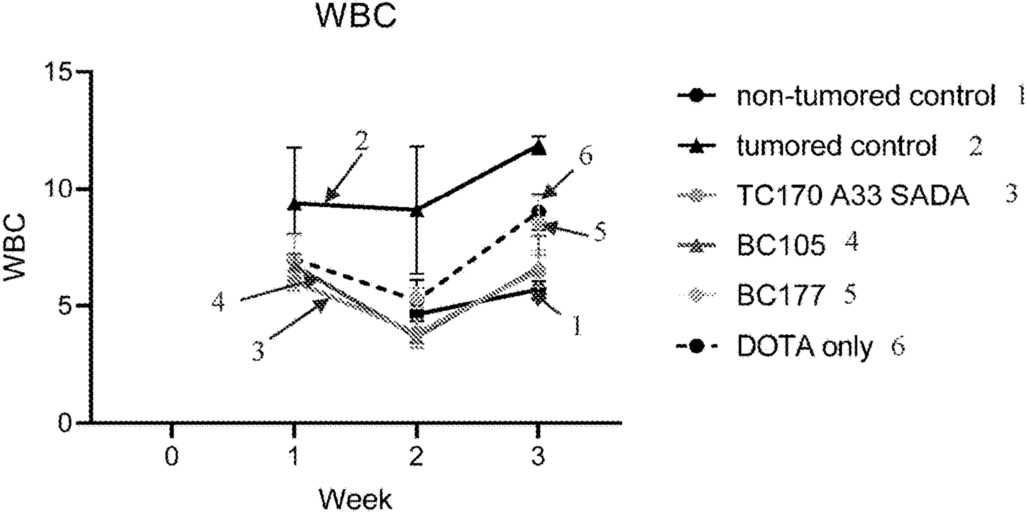
Figure 40D:
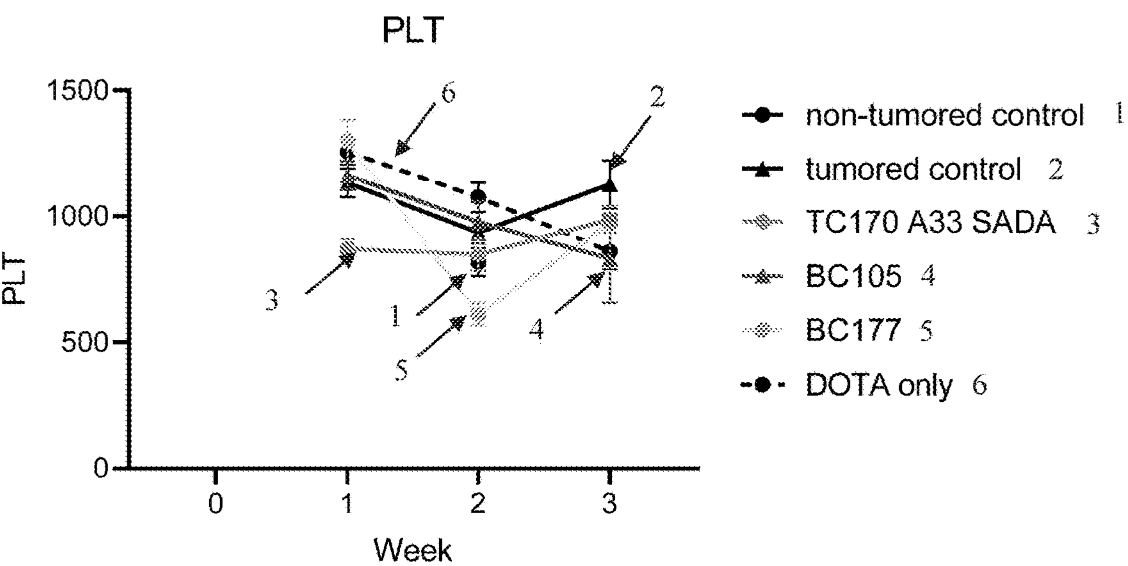
Figure 40E:
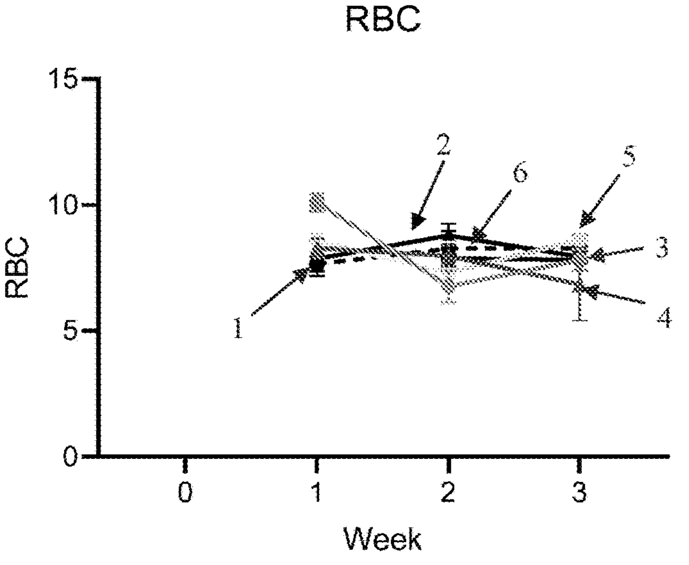

Moreover, none of the animals treated with BC177, BC105, or TC170 displayed a significant reduction in hematologic parameters, such as WBCs, RBCs, platelets, (FIGS. 40C-40E) etc.

These results demonstrate that the anti-GPA33 immunoglobulin-related compositions of the present technology exhibited potent in vivo cytotoxic activity against one or more GPA33-associated cancers. Accordingly, the immunoglobulin-related compositions of the present technology are useful to treat a GPA33-associated cancer in a subject in need thereof.

Example 5: Multi-Specific Antibodies Targeting GPA33, and Radiometal-Bn-DOTA with $^{177}$Lu-Bn-DOTA PRIT Methods. Female athymic nude mice (strain: Hsd:Athymic Nude-Foxn$^{1nu}$, Envigo, aged 6-8 weeks, average weight for six-week-old and eight-week-old animals: 18.6 and 21.0 g, respectively) were used for all experiments. The subcutaneous SW1222 tumor model (~100-500 mm$^3$ by caliper measurement, assuming ellipsoid geometry for calculation of tumor volume) was used in this study.

Female athymic nude mice were implanted subcutaneously with 5×10$^6$ million SW1222 cells 2-week (day −14) before treatment was started. Group 1 mice were given radiohapten $^{177}$Lu-Bn-DOTA on day 2. Group 2 mice were given antibody GPA33 BsAb-IgG (BC177) on day 0, followed by CA (dextran-CA 62.5 ug, 0.125 nmol dextran) 4 h prior to administration of radiohapten $^{177}$Lu-Bn-DOTA on day 2. Group 3 and 4 mice were given antibody GPA33 SADA (TC170) on day 0, followed by radiohapten $^{177}$Lu-Bn-DOTA on day 2.

All reagents were formulated for injection in 250 μL normal sterile isotonic saline solution (NSS). For all injections, mice were gently warmed with a heat lamp and placed on a restrainer. Their tails were sterilized with alcohol pads, and single-bolus injections were placed into the lateral tail vein.

Weights and tumor volumes were measured once per week, and overall mouse health was evaluated at least three times per week. Mice were sacrificed once tumor volumes reached 1,500-2,000 mm$^3$. Established tumors (50-500 mm$^3$) were observed in 10-14 days; tumor volumes (TVs) were estimated using the formula for the volume (V) of an ellipsoid: V=4/3π(length/2×width/2×height/2), with dimensions in millimeters. All reagents were administered intravenously via a lateral tail vein.

Figure 41A:
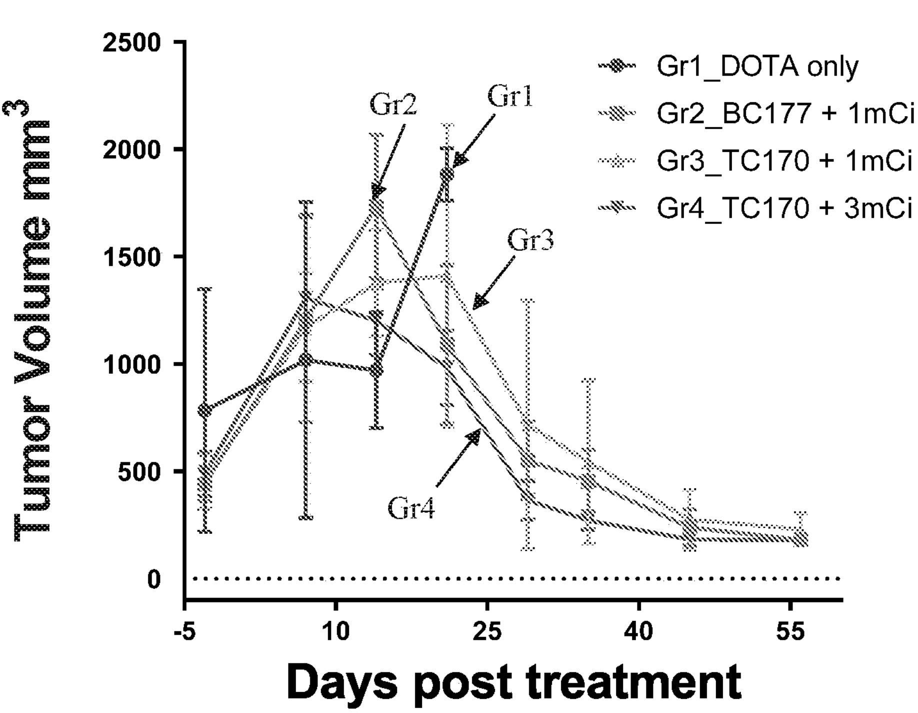
FIGS. 41A-41B show tumor regression and survival in SW1222 tumor-bearing female athymic nude mice treated with BC177+1 mCi $^{177}$Lu-Bn-DOTA, TC170+1 mCi $^{177}$Lu-Bn-DOTA, or TC170+3 mCi $^{177}$Lu-Bn-DOTA.
Figure 41B:
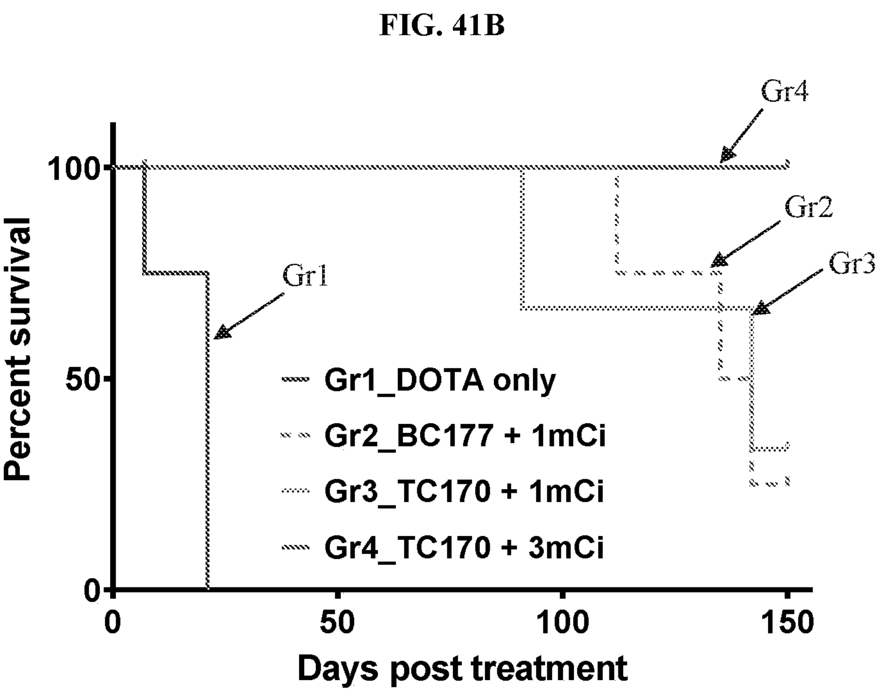

Results. SW1222 xenograft tumors regressed across all treatment groups using GPA33 BsAb and radiohapten $^{177}$Lu-Bn-DOTA (FIGS. 41A-41B). Mice treated with GPA33 SADA (TC170) showed more rapid tumor regression and higher survival than GPA33 IgG (BC177) group. More importantly there is no tumor regrowth up until day 184 in mice treated with TC170 for both low (1 mCi) and high (3 mCi) dose radiohapten. Tumor regrew in one mouse from BC177 group and was euthanized due to ulceration in the tumor (400 mm$^3$).

These results demonstrate that the anti-GPA33 immunoglobulin-related compositions of the present technology exhibited potent in vivo cytotoxic activity against one or more GPA33-associated cancers. Accordingly, the immunoglobulin-related compositions of the present technology are useful to treat a GPA33-associated cancer in a subject in need thereof.

Example 6: Ex Vivo Distribution of Multi-Specific Antibodies Targeting GPA33, and Radiometal-Bn-DOTA with $^{177}$Lu-ABD PRIT and $^{225}$Ac-ABD PRIT Methods. Female athymic nude mice (strain: Hsd:Athymic Nude-Foxn$^{1nu}$, Envigo, aged 6-8 weeks, average weight for six-week-old and eight-week-old animals: 18.6 and 21.0 g, respectively) were used for all experiments. The subcutaneous SW1222 tumor model (~100-500 mm$^3$ by caliper measurement, assuming ellipsoid geometry for calculation of tumor volume) was used in this study.

Distribution study 1 and 2. Female athymic nude mice were implanted subcutaneously with 5×10$^6$ million SW 1222 cells 2-week (day −14) before treatment was started. Group 1 mice were given radiohapten $^{225}$Ac-4-aminobenzyl-DOTA (ABD) or $^{177}$Lu-ABD on day 2. Group 2-4 mice were given antibody GPA33 SADA TC170 on day 0, followed by radiohapten $^{225}$Ac-ABD or $^{177}$Lu-ABD on day 2. Group 5 and 6 mice were given antibody GPA33 clone BC177 and GPA33 clone BC105 BsAb respectively on day 1, followed by CA (dextran-CA 62.5 ug, 0.125 nmol dextran) 4 h prior to administration of radiohapten $^{225}$Ac-ABD or $^{177}$Lu-ABD on day 2. All reagents were formulated for injection in 250 μL normal sterile isotonic saline solution (NSS). For all injections, mice were gently warmed with a heat lamp and placed on a restrainer. Their tails were sterilized with alcohol pads, and single-bolus injections were placed into the lateral tail vein.

Distribution study 3. Female athymic nude mice were not implanted with any xenograft. These tumor-free mice were used at the age of 7-9 weeks. Group 1 mice were given radiohapten $^{177}$Lu-ABD on day 2. Group 2 mice were given antibody GPA33 BsAb-IgG (BC177) on day 0, followed by CA (dextran-CA 62.5 ug, 0.125 nmol dextran) 4 h prior to administration of radiohapten $^{177}$Lu-ABD on day 2. Group 3 to 6 mice were given antibody GPA33 SADA (TC170, TC213, TC234 and TC235) on day 0, followed by radiohapten $^{177}$Lu-ABD on day 2. All reagents were formulated for injection in 250 μL normal sterile isotonic saline solution (NSS). For all injections, mice were gently warmed with a heat lamp and placed on a restrainer. Their tails were sterilized with alcohol pads, and single-bolus injections were placed into the lateral tail vein.

Biodistribution experiments. For biodistribution assay following radiohapten injection, mice were euthanized by $CO_2$ (g) asphyxiation and tumor and selected organs were harvested, rinsed with PBS and allowed to air dry, weighed, and radioassayed by gamma scintillation counting (Perkin Elmer Wallac Wizard 3"). Count rates were background- and decay-corrected, converted to activities using a system calibration factor specific for the isotope, normalized to the administered activity, and expressed as percent injected activity per gram of tissue (% IA/g). For $^{225}$Ac, each sample was counted for up to 10 min (24 h after collection when secular equilibrium was reached) using a 150 to 600 keV energy window.

Figure 42A:
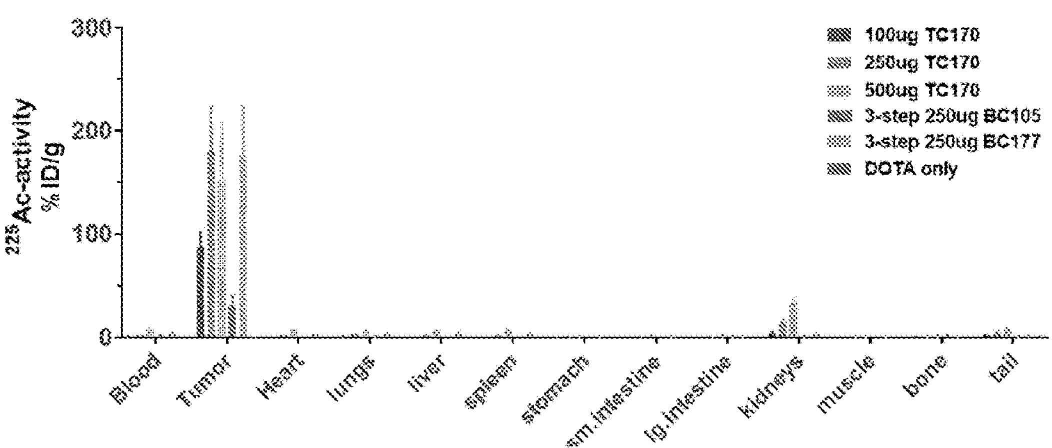
FIG. 42A shows biodistribution of $^{225}$Ac-ABD (1 μCi) in SW1222 xenograft nude mice from distribution study 1.
Figure 42B:
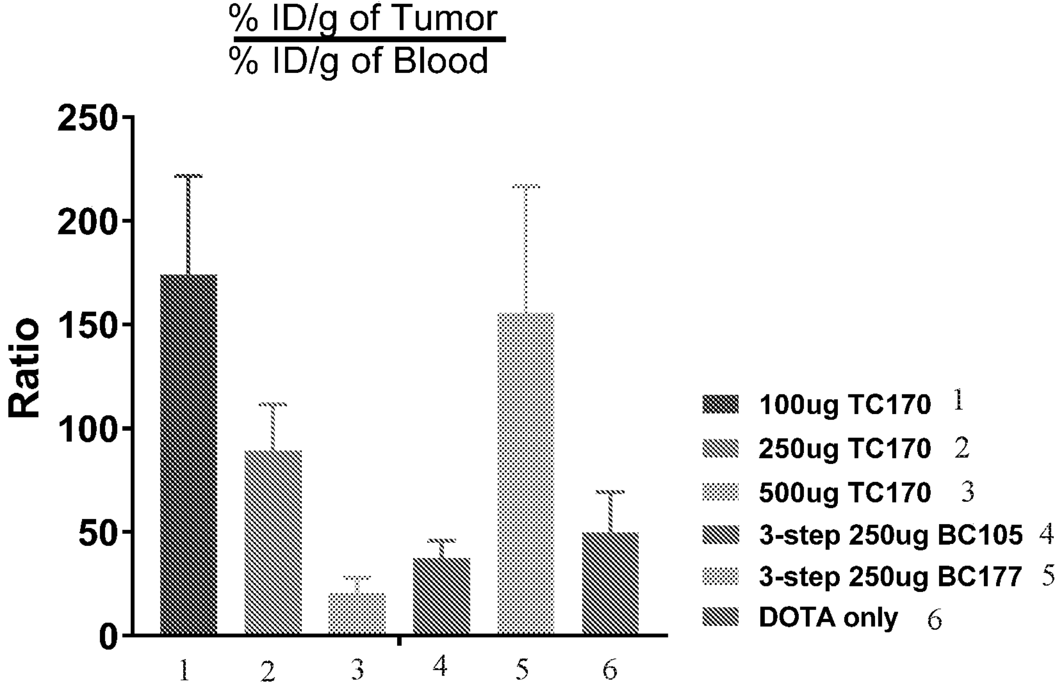
FIG. 42B shows ratio of $^{225}$Ac % ID/g in tumor to blood.

Results. In distribution study-1, biodistribution of $^{225}$Ac-ABD in mice treated with GPA33 SADA (TC170) and GPA33 BsAb-IgG (BC105 and BC177) using SW 1222 xenograft mice were compared side by side (FIGS. 42A-42B). Three different doses of GPA33 SADA (TC170) at 100 μg, 250 μg and 500 μg were used to study dose and $^{225}$Ac-ABD-tissue uptake relationship. In 2-step PRIT protocol for TC170 treatment, antibody was administered first followed by $^{225}$Ac-ABD 48 h later. In 3-step PRIT protocol for BC105 and BC177 treatment, antibody was administered first followed by CA-dextran 24 h later and lastly by 225 Ac-ABD 4 h after CA-dextran injection.

250 μg TC170-treated mice display highest tumor uptake of $^{225}$Ac-ABD compared to 100 μg and 500 μg group. Blood activity for 100 μg, 250 μg, 500 μg TC170 groups are 0.58, 2.00 and 7.55% ID/g respectively. $^{225}$Ac-ABD in kidneys are 4.32, 15.45 and 33.99 for 100 μg, 250 μg, 500 μg TC170 groups respectively. 100 μg TC170 group while having the lowest $^{225}$Ac-activity in blood and kidney, these mice have half the tumor uptake compared to 250 μg. 500 μg TC170 group while having the highest $^{225}$Ac-activity in blood and kidney, these mice show similar tumor uptake as 250 μg group (FIG. 42A).

FIG. 42A shows 6 times higher tumor uptake of $^{225}$Ac in 2-step TC170-treated mice compared to 3-step GPA33 BsAb-IgG (BC105) PRIT. In 2-step TC170 and 3-step BC177 treatment groups, the tumor uptake of $^{225}$Ac-ABD is comparable. However, the blood activity is 2-fold higher in BC177-treated mice at 4.51 compared to TC170 group at 2.00. Conversely, kidney uptake of 225 Ac-ABD is 5-fold lower in BC177-treated mice at 3.09 compared to TC170 group at 15.45.

Figure 43A:
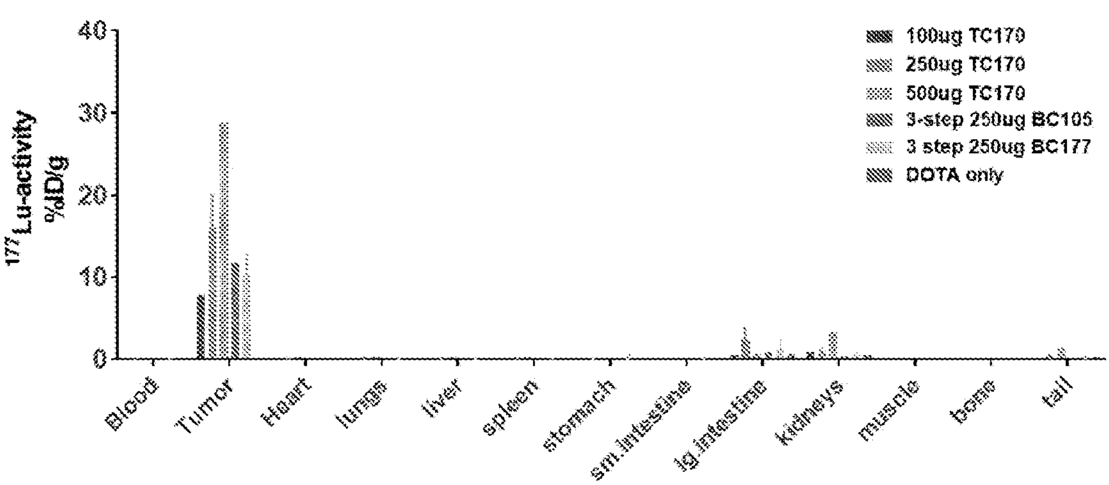
FIG. 43A shows biodistribution of $^{177}$Lu-ABD (500 μCi) in SW1222 xenograft nude mice from distribution study 2.
Figure 43B:
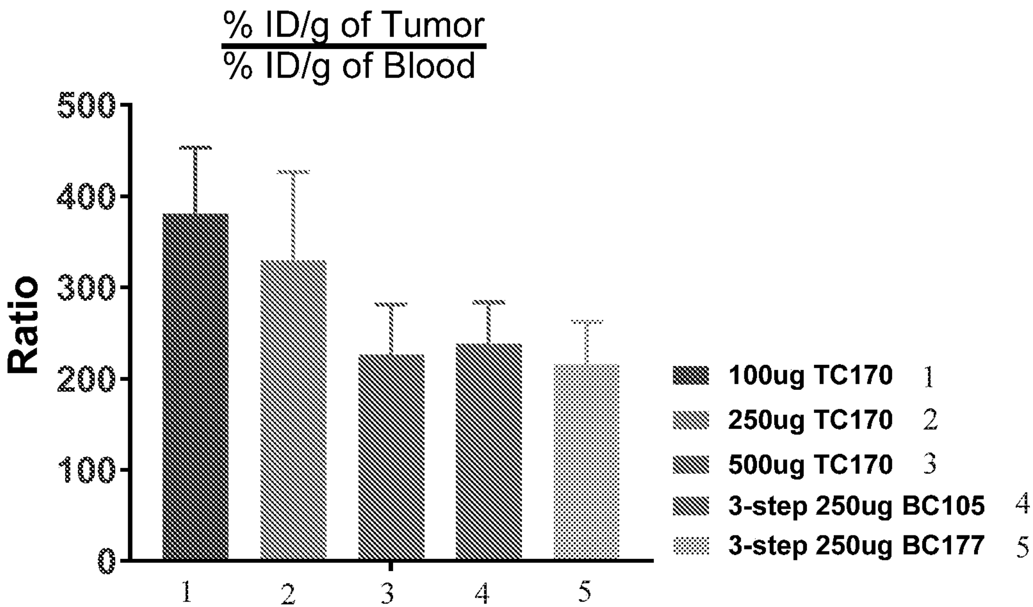
FIG. 43B shows ratio of 177 Lu % ID/g in tumor to blood.

In distribution study-2, the animal study treated with $^{225}$Ac-ABD was repeated with $^{177}$Lu-ABD as radiohapten using identical experiment protocol (FIGS. 43A-43B). 500 μg TC170 group evidently display highest tumor uptake (28.8) of $^{177}$Lu-ABD compared to 100 μg (7.738) and 250 μg (15.94) groups (FIG. 43A). The blood $^{177}$Lu-activity in all 3 groups are below 0.2. This observation contrasts the high blood $^{225}$Ac-activity found in 500 μg TC170 group at 7.55. Kidney uptake of $^{177}$Lu-ABD in 100 μg (0.95), 250 μg (1.07) and 500 μg (3.268) TC170 group suggest that 250 μg dose is more tolerable than 500 μg. Ratio of tumor to kidney $^{177}$Lu-ABD uptake in 100 μg (8.15), 250 μg (14.85) and 500 μg (8.82) TC170 group indicate the optimal dosage at 250 μg.

FIG. 43A shows that there is no difference in tumor uptake of $^{177}$Lu-ABD regardless of the protocols (2-step vs 3-step) and clone difference. The blood $^{177}$Lu-activity in all 3 groups are below 0.1. 2-step 250 μg TC170 treated mice display higher kidney (1.07) and large intestine (2.46) uptake of $^{177}$Lu-ABD than 3-step 250 μg 3-step BC105 (kidney, 0.45 and large intestine, 0.88) and BC177 (kidney, 0.57 and large intestine, 1.38) treated mice.

Figure 44:
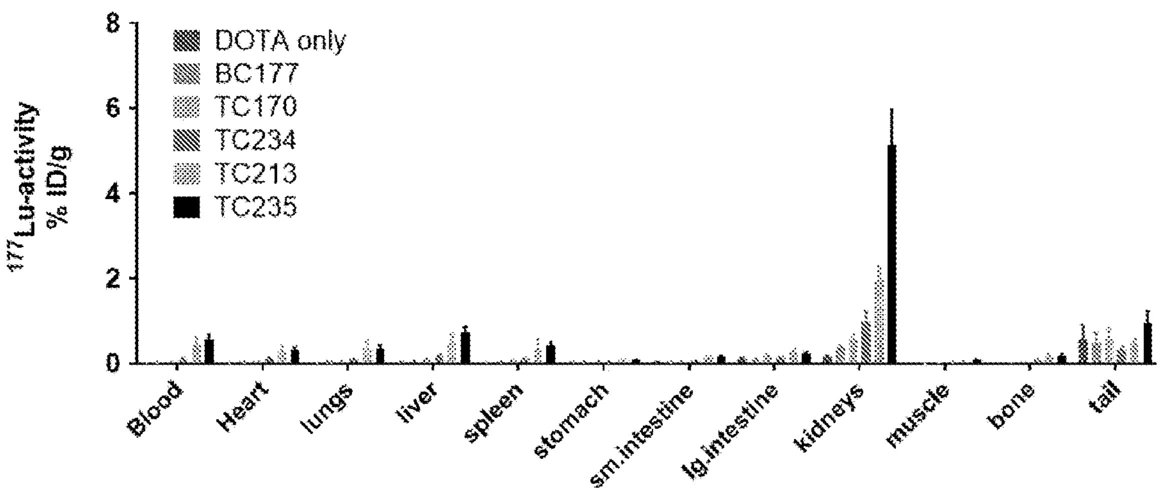
FIG. 44 shows biodistribution of $^{177}$Lu-ABD (1 mCi) in tumor-free nude mice from distribution study 3.

In distribution study-3, ex vivo monitoring of $^{177}$Lu-ABD distribution was conducted in tumor-free nude mice (FIG. 44). Blood $^{177}$Lu-activity is low (<0.58) in all groups. Liver and spleen uptake of $^{177}$Lu-ABD are less than 0.74 and 0.42 respectively in all groups. Kidney retention of $^{177}$Lu-ABD differs among the groups. Kidney uptake of $^{177}$Lu-ABD is low in 3-step BC177 (0.36) and 2-step TC170 (0.58) treated mice where both are below the recommended threshold level of 1% ID/g of $^{177}$Lu-ABD. Mice treated with TC234, a single mutation with estimated pI at 8.03 compared to the parental TC170 pI at 8.46, registered notable increased kidney uptake of $^{177}$Lu-ABD at 1. Mice treated with TC213 and TC235, estimated pI at 7.81 and 7.56 respectively, registered 1.94 and 5.12% ID/g of $^{177}$Lu-ABD in the kidney. These data validate the relationship between antibody p1 and biodistribution in the kidney.

These results demonstrate that the anti-GPA33 immunoglobulin-related compositions of the present technology exhibited potent in vivo cytotoxic activity against one or more GPA33-associated cancers. Accordingly, the immunoglobulin-related compositions of the present technology are useful to treat a GPA33-associated cancer in a subject in need thereof.

Figure 8A:
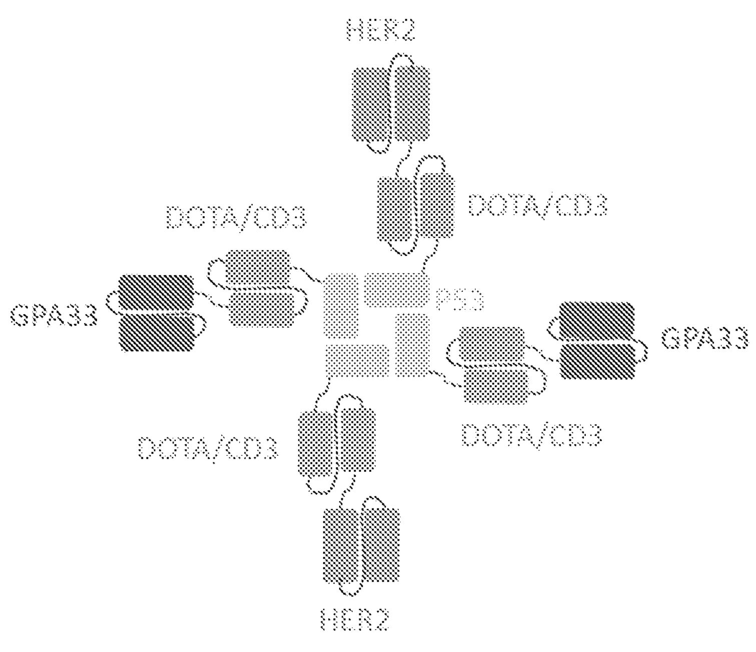
FIG. 8A shows a design of a GPA33×HER2×CD3/DOTA SADA multi-specific antibody.
Figure 8B:
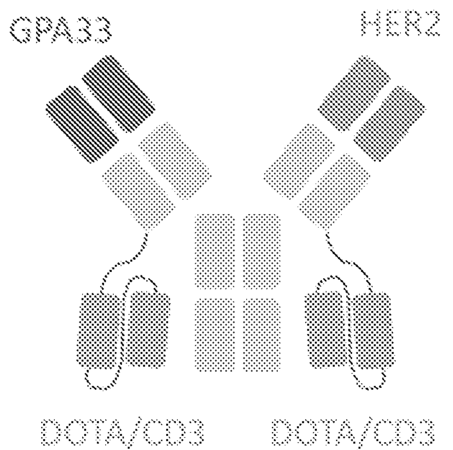
FIG. 8B shows a design of a GPA33×HER2×CD3/DOTA IgG-[L]-scFv multi-specific antibody.

Example 7: Multi-Specific SADA Antibodies Targeting GPA33, HER2 and Radiometal-Bn-DOTA or T-Cells FIGS. 8A-8B illustrate designs for multi-specific antibodies targeting GPA33 and another tumor antigen such as HER2, using both a multi-specific SADA format (FIG. 8A) or a heterodimeric IgG-[L]-scFv (FIG. 8B). These could be used to either improve specificity, targeting only cells that co-express GPA33 and a second tumor antigen, such as HER2 or B7H3, or they could improve targeting of heterogeneous tumors that have lost or downregulated expression of GPA33 but still retain other tumor markers such as HER2 or B7H3. These two designs can be combined with DOTA or CD3 specificities to target radiometal-Bn-DOTA that can deliver radiation or T cells to the targeted tumor sites (TC264-TC281 (FIGS. 24-27), HD152, HD156, HD160, and HD164 (FIGS. 29-32)).

Female nude mice are implanted with SW1222 tumors on day 0 on their right flank. Established tumors are treated with SADA antibodies on day 12 and DOTA[$^{177}$Lu] (1.85 to 18.5 MBq) on day 14. At 24 hours after administration of DOTA[$^{177}$Lu], tissues are excised for gamma scintillation counting (Perkin Elmer).

It is anticipated that the anti-GPA33 immunoglobulin-related compositions of the present technology will exhibit potent in vitro and/or in vivo cytotoxic activity against one or more GPA33-associated cancers. Accordingly, the immunoglobulin-related compositions of the present technology are useful to treat a GPA33-associated cancer in a subject in need thereof.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. An anti-A33 antibody or antigen binding fragment thereof comprising a heavy chain immunoglobulin variable domain ($V_H$) and a light chain immunoglobulin variable domain ($V_L$), wherein: (a) the $V_H$ comprises an amino acid sequence of any one of SEQ ID NOs: 1-3; and (b) the $V_L$ comprises an amino acid sequence of any one of SEQ ID NOs: 4-10.

2. The antibody or antigen binding fragment of claim 1, further comprising a Fc domain of an isotype selected from the group consisting of IgG1, IgG2, IgG3, IgG4, IgA1, IgA2, IgM, IgD, and IgE, optionally wherein the IgG1 comprises an IgG1 constant region comprising one or more amino acid substitutions selected from the group consisting of N297A and K322A; or the IgG4 comprises an IgG4 constant region comprising a S228P mutation; or wherein the antigen binding fragment is selected from the group consisting of Fab, F(ab')$_2$, Fab', scFv, and Fv; or wherein the antibody or antigen binding fragment binds to a GPA33 polypeptide comprising the amino acid sequence of SEQ ID NO: 101; or wherein the antibody is a monoclonal antibody, a chimeric antibody, a humanized antibody, a multi-specific antibody, or a bispecific antibody, optionally wherein the multi-specific antibody or antigen binding fragment binds to T cells, B-cells, myeloid cells, plasma cells, mast-cells, CD3, CD4, CD8, CD20, CD19, CD21, CD23, CD46, CD80, HLA-DR, CD74, CD22, CD14, CD15, CD16, CD123, CD32, CD64, TCR gamma/delta, NKp46, KIR, PD-1, PD-L1, LAG3, CD28, B7H3, STEAP1, HER2, EGFR, CEA, CECAM5, Transferrin receptor, FAP, NKG2D-ligands, TRAIL, FasL, cathepsin G, granzyme, carboxypeptidase, beta-lactamase, DOTA(metal) complex, benzyl-DOTA (metal) complex, proteus-DOTA(metal) complex, NOGADA-proteus-DOTA(metal) complex, Star-DFO (metal) complex, DFO(metal) complex, or a small molecule DOTA hapten; or wherein the antibody lacks α-1,6-fucose modifications.

3. An antibody comprising a heavy chain (HC) amino acid sequence comprising SEQ ID NO: 23, SEQ ID NO: 27, SEQ ID NO: 60, SEQ ID NO: 62, SEQ ID NO: 64, SEQ ID NO: 67, SEQ ID NO: 71, SEQ ID NO: 75, or SEQ ID NO: 79, and a light chain (LC) amino acid sequence comprising SEQ ID NO: 21, SEQ ID NO: 25, SEQ ID NO: 59, SEQ ID NO: 61, SEQ ID NO: 63, SEQ ID NO: 65, SEQ ID NO: 69, SEQ ID NO: 73, or SEQ ID NO: 77; or a first HC amino acid sequence, a second HC amino acid sequence, a first LC amino acid sequence and a second LC amino acid sequence selected from the group consisting of SEQ ID NO: 67, SEQ ID NO: 68, SEQ ID NO: 65 and SEQ ID NO: 66 HD152); SEQ ID NO: 71, SEQ ID NO: 72, SEQ ID NO: 69 and SEQ ID NO: 70 HD156); SEQ ID NO: 75, SEQ ID NO: 76, SEQ ID NO: 73 and SEQ ID NO: 74 HD160); and SEQ ID NO: 79, SEQ ID NO: 80, SEQ ID NO: 77 and SEQ ID NO: 78 HD164), respectively, optionally wherein the antibody is a chimeric antibody, a humanized antibody, a multi-specific antibody, or a bispecific antibody, optionally wherein the multi-specific antibody or antigen binding fragment binds to T cells, B-cells, myeloid cells, plasma cells, mast-cells, CD3, CD4, CD8, CD20, CD19, CD21, CD23, CD46, CD80, HLA-DR, CD74, CD22, CD14, CD15, CD16, CD123, CD32, CD64, TCR gamma/delta, NKp46, KIR, PD-1, PD-L1, LAG3, CD28, B7H3, STEAP1, HER2, EGFR, CEA, CECAM5, Transferrin receptor, FAP, NKG2D-ligands, TRAIL, FasL, cathepsin G, granzyme, carboxypeptidase, beta-lactamase, DOTA(metal) complex, benzyl-DOTA(metal) complex, proteus-DOTA (metal) complex, NOGADA-proteus-DOTA(metal) complex, Star-DFO(metal) complex, DFO(metal) complex, or a small molecule DOTA hapten; or wherein the antibody binds to a GPA33 polypeptide comprising the amino acid sequence of SEQ ID NO: 101.

4. The antibody of claim 3, comprising a HC amino acid sequence and a LC amino acid sequence selected from the group consisting of: SEQ ID NO: 23 and SEQ ID NO: 21 (BC015 (G3A HIL4)); SEQ ID NO: 27 and SEQ ID NO: 25 (BC016 (G3A H3L3)); SEQ ID NO: 60 and SEQ ID NO: 59 (BC369 (G3A HIL4 huOKT3)); SEQ ID NO: 62 and SEQ ID NO: 61 (BC373 (G3A HIL4 huOT3 H2L2)); and SEQ ID NO: 64 and SEQ ID NO: 63 (BC377 (G3A H1L4 huOT3 H2L4)), respectively.

5. A multi-specific antibody or antigen binding fragment of claim 1 comprising an amino acid sequence selected from any one of SEQ ID NOs: 11, 13, 15, 17, 19, or 29-58, optionally wherein the antibody or antigen binding fragment does not cross into gut epithelium or gut lumen when the antibody or antigen binding fragment is intravenously or intraperitoneally administered to a subject.

6. A recombinant nucleic acid sequence encoding the antibody or antigen binding fragment of claim 1, optionally wherein the recombinant nucleic acid sequence is selected from the group consisting of: SEQ ID NOs: 12, 14, 16, 18, 20, 22, 24, 26 and 28.

7. A host cell or vector comprising the recombinant nucleic acid sequence of claim 6.

8. A composition comprising the antibody or antigen binding fragment of claim 1 and a pharmaceutically-acceptable carrier, wherein the antibody or antigen binding fragment is optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

9. A method for treating a GPA33-associated cancer in a subject in need thereof, comprising administering to the subject an effective amount of the antibody or antigen binding fragment of claim 1, optionally wherein the GPA33-associated cancer is colorectal cancer, T cell leukemia, *Pseudomyxoma peritonei*, appendiceal cancer, pancreatic cancer, or gastric cancer; or the antibody or antigen binding fragment is administered to the subject separately, sequentially or simultaneously with an additional therapeutic agent, optionally wherein the additional therapeutic agent is one or more of alkylating agents, platinum agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents, T cells, or an immunomodulating/stimulating antibody.

10. A method for detecting a tumor in a subject in vivo comprising (a) administering to the subject an effective amount of the antibody or antigen binding fragment of claim 1, wherein the antibody or antigen binding fragment is configured to localize to a tumor expressing GPA33 and is labeled with a radioisotope; and (b) detecting the presence of a tumor in the subject by detecting radioactive levels emitted by the antibody or antigen binding fragment that are higher than a reference value optionally wherein the subject is diagnosed with or is suspected of having cancer; or wherein the radioactive levels emitted by the antibody or antigen binding fragment are detected using positron emission tomography or single photon emission computed tomography.

11. The method of claim 10, further comprising administering to the subject an effective amount of an immunoconjugate comprising the antibody or antigen binding fragment conjugated to a radionuclide, optionally wherein the radionuclide is an alpha particle-emitting isotope, a beta particle-emitting isotope, an Auger-emitter, or any combination thereof, optionally wherein the beta particle-emitting isotope is selected from the group consisting of $^{86}$Y, $^{90}$Y, $^{89}$Sr, $^{165}$Dy, $^{186}$Re, $^{188}$Re, $^{177}$Lu, and $^{67}$Cu.

12. A kit comprising the antibody, or antigen binding fragment thereof, of claim 1 and instructions for use, optionally wherein the antibody or antigen binding fragment is coupled to at least one detectable label selected from the group consisting of a radioactive label, a fluorescent label, and a chromogenic label or wherein the kit further comprises a secondary antibody that specifically binds to the antibody or antigen.

13. The multi-specific antibody or antigen binding fragment of claim 1 or a multi-specific antibody or antigen binding fragment comprising an amino acid sequence of SEQ ID NOs: 11, 13, 15, 17, 19, or 29-58, wherein the multi-specific antibody binds to at least a radiolabeled DOTA hapten and a GPA33 antigen.

14. A method for selecting a subject for pretargeted radioimmunotherapy comprising (a) administering to the subject an effective amount of a complex comprising a radiolabeled DOTA hapten and the multi-specific antibody or antigen binding fragment of claim 13, wherein the complex is configured to localize to a GPA33 expressing tumor;

(b) detecting radioactive levels emitted by the complex; and (c) selecting the subject for pretargeted radioimmunotherapy when the radioactive levels emitted by the complex are higher than a reference value.

15. A method for treating cancer in a subject in need thereof or increasing tumor sensitivity to radiation therapy in a subject diagnosed with a GPA33-associated cancer comprising administering to the subject an effective amount of a complex comprising a radiolabeled DOTA hapten and the multi-specific antibody or antigen binding fragment of claim 13, wherein the complex is configured to localize to a GPA33 expressing tumor optionally wherein the subject is human; or the complex is administered intravenously, intramuscularly, intraarterially, intrathecally, intracapsularly, intraorbitally, intradermally, intraperitoneally, transtracheally, subcutaneously, intracerebroventricularly, orally, intratumorally, or intranasally; or the radiolabeled-DOTA hapten comprises an alpha particle-emitting isotope, a beta particle-emitting isotope, or an Auger-emitter; or the radiolabeled-DOTA hapten comprises $^{213}$Bi, $^{211}$ At, $^{225}$ Ac, $^{132}$Dy, $^{212}$Bi, $^{223}$Ra, $^{219}$Rn, $^{215}$Po, $^{211}$Bi, $^{221}$Fr, $^{217}$ At, $^{255}$Fm, $^{86}$Y, $^{90}$Y, $^{89}$Sr, $^{165}$Dy, $^{186}$Re, $^{188}$Re, $^{177}$Lu, $^{67}$Cu, $^{111}$ In, $^{67}$Ga, $^{51}$Cr, $^{58}$Co, $^{99m}$Tc, $^{103m}$Rh, $^{195m}$Pt, $^{119}$Sb, $^{161}$FIO, $^{189m}$Os, $^{192}$Ir, $^{201}$Tl, $^{203}$Pb, $^{68}$Ga, $^{227}$Th, or $^{64}$Cu.

16. A method for treating cancer in a subject in need thereof or increasing tumor sensitivity to radiation therapy in a subject diagnosed with a GPA33-associated cancer comprising (a) administering an effective amount of the multi-specific antibody or antigen binding fragment of claim 13, wherein the multi-specific antibody or antigen binding fragment is configured to localize to a GPA33 expressing tumor; and (b) administering an effective amount of a radiolabeled-DOTA hapten to the subject, wherein the radiolabeled-DOTA hapten is configured to bind to the multi-specific antibody or antigen binding fragment, optionally wherein the method further comprises administering an effective amount of a clearing agent to the subject prior to administration of the radiolabeled-DOTA hapten; or the subject is human; or the radiolabeled-DOTA hapten comprises an alpha particle-emitting isotope, a beta particle-emitting isotope, or an Auger-emitter; or the radiolabeled-DOTA hapten comprises $^{213}$Bi, $^{211}$ At, $^{225}$ Ac, $^{152}$Dy, $^{212}$Bi, $^{223}$Ra, $^{219}$Rn, $^{215}$Po, $^{211}$Bi, $^{221}$Fr, $^{217}$ At, $^{255}$Fm, $^{86}$Y, $^{90}$Y, $^{89}$Sr, $^{165}$Dy, $^{186}$Re, $^{188}$Re, $^{177}$Lu, $^{67}$Cu, $^{111}$ In, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, $^{203}$Pb, $^{68}$Ga, $^{227}$Th, or $^{64}$Cu.

17. The multi-specific antibody or antigen binding fragment of claim 1, wherein the multi-specific antibody binds to at least CD3 and a GPA33 antigen.

18. An ex vivo armed T cell that is coated or complexed with an effective amount of the multi-specific antibody of claim 17, wherein the multi-specific antibody includes a CD3 binding domain, optionally wherein the multi-specific antibody is an immunoglobulin comprising two heavy chains and two light chains, wherein each of the light chains is fused to a single chain variable fragment (scFv), and wherein at least one scFv of the multi-specific antibody comprises the CD3 binding domain.

19. A method for treating a GPA33-associated cancer in a subject in need thereof comprising administering to the subject an effective amount of the ex vivo armed T cell of claim 18.

20. A method for treating a GPA33-associated cancer in a subject in need thereof, comprising administering to the subject an effective amount of a bispecific antibody of claim 1, wherein the bispecific antibody comprises an immunoglobulin, said immunoglobulin comprising two identical heavy chains and two identical light chains, said light chains being a first light chain and a second light chain, wherein the first light chain is fused to a first single chain variable fragment (scFv), via a peptide linker, to create a first light chain fusion polypeptide, and wherein the second light chain is fused to a second scFv, via a peptide linker, to create a second light chain fusion polypeptide, wherein the first scFv is fused to the carboxyl end of the first light chain, and wherein the second scFv is fused to the carboxyl end of the second light chain, wherein the first and second scFv are identical, and wherein the first and second light chain fusion polypeptides are identical and wherein the immunoglobulin binds to GPA33, and the first and second scFvs bind to CD3, optionally wherein the GPA33-associated cancer is colorectal cancer, T cell leukemia, *Pseudomyxoma peritonei*, appendiceal cancer, pancreatic cancer, or gastric cancer; or the bispecific antibody is administered to the subject separately, sequentially or simultaneously with an additional therapeutic agent, optionally wherein the additional therapeutic agent is one or more of alkylating agents, platinum agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents, T cells, or an immuno-modulating/stimulating antibody.

* * * * *

SEQUENCE LISTING

```
<160> NUMBER OF SEQ ID NOS: 116

<210> SEQ ID NO 1
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
```

```
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala
        115


<210> SEQ ID NO 2
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Ser Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala
        115


<210> SEQ ID NO 3
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Ala Asp Ser Val
    50                  55                  60

Lys Gly Arg Phe Thr Ile Ser Arg Asp Ser Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
```

```
            100                 105                 110

Val Thr Val Ser Ala
        115


<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ala Pro Lys Arg Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Trp Ser Tyr Pro Leu
                85                  90                  95

Thr Phe Gly Ser Gly Thr Lys Leu Glu Val Lys
            100                 105


<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Ser Pro Ser Ser Leu Ser Thr Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ala Pro Lys Thr Leu Ile
        35                  40                  45

Tyr Leu Ala Ser Ser Leu Gln Ser Gly Val Pro Ser Arg Phe Ser Gly
    50                  55                  60

Ser Gly Ser Gly Thr Glu Phe Thr Leu Thr Ile Ser Asn Val Gln Pro
65                  70                  75                  80

Glu Asp Phe Ala Asp Tyr Phe Cys Leu Gln His Trp Ser Tyr Pro Leu
                85                  90                  95

Thr Phe Gly Ser Gly Thr Lys Leu Glu Val Lys
            100                 105


<210> SEQ ID NO 6
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6
```

```
Asp Ile Gln Met Thr Gln Ser Pro Ser Ser Leu Ser Thr Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ala Pro Lys Thr Leu Ile
        35                  40                  45

Tyr Leu Ala Ser Asn Arg His Ser Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Trp Ser Tyr Pro Leu
                85                  90                  95

Thr Phe Gly Ser Gly Thr Lys Leu Glu Val Lys
            100                 105


<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ala Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Trp Ser Tyr Pro Leu
                85                  90                  95

Thr Phe Gly Ser Gly Thr Lys Leu Glu Val Lys
            100                 105


<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ala Pro Lys Arg Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80
```

```
Glu Asp Phe Ala Thr Tyr Phe Cys Leu Gln His Trp Ser Tyr Pro Leu
                85                  90                  95

Thr Phe Gly Ser Gly Thr Lys Leu Glu Val Lys
            100                 105


<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ala Pro Lys Arg Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Val Gln Pro
65                  70                  75                  80

Glu Asp Phe Ala Thr Tyr Tyr Cys Leu Gln His Trp Ser Tyr Pro Leu
                85                  90                  95

Thr Phe Gly Ser Gly Thr Lys Leu Glu Val Lys
            100                 105


<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ala Pro Lys Arg Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Asp Tyr Tyr Cys Leu Gln His Trp Ser Tyr Pro Leu
                85                  90                  95

Thr Phe Gly Ser Gly Thr Lys Leu Glu Val Lys
            100                 105


<210> SEQ ID NO 11
<211> LENGTH: 597
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 11

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser His Val Gln Leu Val Glu Ser Gly Gly Gly Leu Val Gln
        275                 280                 285

Pro Gly Gly Ser Leu Arg Leu Ser Cys Ala Ala Ser Gly Phe Ser Leu
    290                 295                 300

Thr Asp Tyr Gly Val His Trp Val Arg Gln Ala Pro Gly Lys Gly Leu
305                 310                 315                 320

Glu Trp Leu Gly Val Ile Trp Ser Gly Gly Gly Thr Ala Tyr Asn Thr
                325                 330                 335

Ala Leu Ile Ser Arg Phe Thr Ile Ser Arg Asp Asn Ser Lys Asn Thr
            340                 345                 350

Leu Tyr Leu Gln Met Asn Ser Leu Arg Ala Glu Asp Thr Ala Val Tyr
        355                 360                 365

Tyr Cys Ala Arg Arg Gly Ser Tyr Pro Tyr Asn Tyr Phe Asp Ala Trp
    370                 375                 380

Gly Cys Gly Thr Leu Val Thr Val Ser Ser Gly Gly Gly Gly Ser Gly
385                 390                 395                 400

Gly Gly Gly Ser Gly Gly Gly Gly Ser Gly Gly Gly Gly Ser Gly Gly
```

```
                405                 410                 415

Gly Gly Ser Gly Gly Gly Gly Ser Gln Ala Val Val Thr Gln Glu Pro
            420                 425                 430

Ser Leu Thr Val Ser Pro Gly Gly Thr Val Thr Leu Thr Cys Gly Ser
        435                 440                 445

Ser Thr Gly Ala Val Thr Ala Ser Asn Tyr Ala Asn Trp Val Gln Gln
    450                 455                 460

Lys Pro Gly Gln Cys Pro Arg Gly Leu Ile Gly Gly His Asn Asn Arg
465                 470                 475                 480

Pro Pro Gly Val Pro Ala Arg Phe Ser Gly Ser Leu Leu Gly Gly Lys
                485                 490                 495

Ala Ala Leu Thr Leu Leu Gly Ala Gln Pro Glu Asp Glu Ala Glu Tyr
            500                 505                 510

Tyr Cys Ala Leu Trp Tyr Ser Asp His Trp Val Ile Gly Gly Gly Thr
        515                 520                 525

Lys Leu Thr Val Leu Gly Thr Pro Leu Gly Asp Thr Thr His Thr Ser
    530                 535                 540

Gly Lys Pro Leu Asp Gly Glu Tyr Phe Thr Leu Gln Ile Arg Gly Arg
545                 550                 555                 560

Glu Arg Phe Glu Met Phe Arg Glu Leu Asn Glu Ala Leu Glu Leu Lys
                565                 570                 575

Asp Ala Gln Ala Gly Lys Glu Pro Gly Gly Ser Gly Gly Ala Pro His
            580                 585                 590

His His His His His
        595


<210> SEQ ID NO 12
<211> LENGTH: 1791
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

gaggtgcagc tggtggagag cggaggaggc ctggtgaagc caggaggcag cctgaggctg     60

tcctgcgccg cctctggatt cgcctttagc acctacgata tgtcctgggt gcgccaggca    120

cctggcaagg gcctggagtg ggtgtctacc atcagctccg gcggcagcta cacatactat    180

gccgactccg tgaagggccg gttcaccatc agccgggata acgccaagaa tagcctgtat    240

ctgcagatga actccctgcg ggccgaggac acagccgtgt actattgtgc ccaaccaca     300

gtggtgccct ttgcctattg gggccagggc accctggtga cagtgagcgc cggcggagga    360

ggctctggag gaggaggcag cggaggcggc ggctccggcg gcggcggctc tggcggcggc    420

ggcagcggag gaggcggctc cgacatccag atgacccaga gcccatctag cctgtccgcc    480

tctgtgggcg atcgggtgac catcacatgc aaggcctccc agaatgtgag aacagtggtg    540

gcctggtacc agcagaagcc cggcaaggcc cctaagaccc tgatctatct ggcctccaac    600

aggcacacag gagtgccatc tcgcttcagc ggctccggct ctggaaccga gtttaccctg    660

acaatctcca atctgcagcc tgaggatttc gccacatact attgtctgca gcactggtct    720

tacccactga cctttggcag cggcacaaag ctggaggtga agcggggcgg agggggatcc    780

ggcggcggag gatctggcgg aggtggaagt gggggaggcg gatctcatgt gcagctggtg    840

gaaagcggag gcggcctggt gcagcctggg ggatctctga gactgtcttg tgccgccagc    900
```

```
ggcttctccc tgaccgatta tggcgtgcac tgggtgcgac aggcccctgg caaaggactg    960

gaatggctgg gagtgatttg gagtggcgga ggcaccgcct acaacaccgc cctgatctcc   1020

cggttcacca tcagccggga caactccaag aacaccctgt acctgcagat gaactccctg   1080

cgggccgagg acaccgctgt gtactactgc gccagacggg gctcctaccc ctacaactac   1140

ttcgacgctt ggggctgcgg caccctcgtg acagtgtcta gcggaggggg aggttctggg   1200

ggcggaggtt caggtggtgg tggttccggg ggtggtggct ctggtggcgg tggttctggc   1260

ggtggcggat ctcaggctgt cgtgacccag gaacccagcc tgactgtgtc tcctggcgga   1320

accgtgaccc tgacctgcgg atcttctacc ggcgctgtga ccgccagcaa ctacgccaat   1380

tgggtgcagc agaaacctgg acagtgccct agaggcctga tcggcggcca caacaacaga   1440

cctccaggcg tgccagcccg gttctctgga tctctgctgg gcggaaaggc cgctctgaca   1500

ctgctgggtg ctcagcctga ggacgaggcc gagtactact gtgccctgtg gtactccgac   1560

cactgggtca tcggaggcgg gaccaagctg accgtgctgg gaacacccct gggagacacc   1620

acacatacta gtgggaaacc tctggatggc gagtacttta ccctgcagat tagaggccgc   1680

gaacgattcg agatgtttcg cgaactgaat gaggccctgg aactgaagga tgctcaggca   1740

ggcaaggagc caggagggtc aggaggagca ccgcaccatc atcatcacca t            1791
```

```
<210> SEQ ID NO 13
<211> LENGTH: 597
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ala Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Trp Ser Tyr Pro Leu
                85                  90                  95

Thr Phe Gly Ser Gly Thr Lys Leu Glu Val Lys Arg Gly Gly Gly Gly
            100                 105                 110

Ser Gly Gly Gly Gly Ser Gly Gly Gly Gly Ser Gly Gly Gly Gly Ser
        115                 120                 125

Gly Gly Gly Gly Ser Gly Gly Gly Gly Ser Glu Val Gln Leu Val Glu
    130                 135                 140

Ser Gly Gly Gly Leu Val Lys Pro Gly Gly Ser Leu Arg Leu Ser Cys
145                 150                 155                 160

Ala Ala Ser Gly Phe Ala Phe Ser Thr Tyr Asp Met Ser Trp Val Arg
                165                 170                 175

Gln Ala Pro Gly Lys Gly Leu Glu Trp Val Ser Thr Ile Ser Ser Gly
            180                 185                 190

Gly Ser Tyr Thr Tyr Tyr Ala Asp Ser Val Lys Gly Arg Phe Thr Ile
        195                 200                 205
```

```
Ser Arg Asp Asn Ala Lys Asn Ser Leu Tyr Leu Gln Met Asn Ser Leu
    210                 215                 220

Arg Ala Glu Asp Thr Ala Val Tyr Tyr Cys Ala Pro Thr Thr Val Val
225                 230                 235                 240

Pro Phe Ala Tyr Trp Gly Gln Gly Thr Leu Val Thr Val Ser Ala Gly
                245                 250                 255

Gly Gly Gly Ser Gly Gly Gly Gly Ser Gly Gly Gly Gly Ser Gly Gly
            260                 265                 270

Gly Gly Ser His Val Gln Leu Val Glu Ser Gly Gly Gly Leu Val Gln
        275                 280                 285

Pro Gly Gly Ser Leu Arg Leu Ser Cys Ala Ala Ser Gly Phe Ser Leu
    290                 295                 300

Thr Asp Tyr Gly Val His Trp Val Arg Gln Ala Pro Gly Lys Gly Leu
305                 310                 315                 320

Glu Trp Leu Gly Val Ile Trp Ser Gly Gly Gly Thr Ala Tyr Asn Thr
                325                 330                 335

Ala Leu Ile Ser Arg Phe Thr Ile Ser Arg Asp Asn Ser Lys Asn Thr
            340                 345                 350

Leu Tyr Leu Gln Met Asn Ser Leu Arg Ala Glu Asp Thr Ala Val Tyr
        355                 360                 365

Tyr Cys Ala Arg Arg Gly Ser Tyr Pro Tyr Asn Tyr Phe Asp Ala Trp
    370                 375                 380

Gly Cys Gly Thr Leu Val Thr Val Ser Ser Gly Gly Gly Gly Ser Gly
385                 390                 395                 400

Gly Gly Gly Ser Gly Gly Gly Gly Ser Gly Gly Gly Gly Ser Gly Gly
                405                 410                 415

Gly Gly Ser Gly Gly Gly Gly Ser Gln Ala Val Val Thr Gln Glu Pro
            420                 425                 430

Ser Leu Thr Val Ser Pro Gly Gly Thr Val Thr Leu Thr Cys Gly Ser
        435                 440                 445

Ser Thr Gly Ala Val Thr Ala Ser Asn Tyr Ala Asn Trp Val Gln Gln
    450                 455                 460

Lys Pro Gly Gln Cys Pro Arg Gly Leu Ile Gly Gly His Asn Asn Arg
465                 470                 475                 480

Pro Pro Gly Val Pro Ala Arg Phe Ser Gly Ser Leu Leu Gly Gly Lys
                485                 490                 495

Ala Ala Leu Thr Leu Leu Gly Ala Gln Pro Glu Asp Glu Ala Glu Tyr
            500                 505                 510

Tyr Cys Ala Leu Trp Tyr Ser Asp His Trp Val Ile Gly Gly Gly Thr
        515                 520                 525

Lys Leu Thr Val Leu Gly Thr Pro Leu Gly Asp Thr Thr His Thr Ser
    530                 535                 540

Gly Lys Pro Leu Asp Gly Glu Tyr Phe Thr Leu Gln Ile Arg Gly Arg
545                 550                 555                 560

Glu Arg Phe Glu Met Phe Arg Glu Leu Asn Glu Ala Leu Glu Leu Lys
                565                 570                 575

Asp Ala Gln Ala Gly Lys Glu Pro Gly Gly Ser Gly Gly Ala Pro His
            580                 585                 590

His His His His His
        595
```

<210> SEQ ID NO 14
<211> LENGTH: 1791

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
gacatccaga tgacccagag cccaagctcc ctgtccgcct ctgtgggcga tagggtgacc     60
atcacatgca aggcctccca gaacgtgaga acagtggtgg cctggtacca gcagaagccc    120
ggcaaggccc ctaagaccct gatctatctg gcctccaaca ggcacacagg agtgccatct    180
cgcttcagcg gctccggctc tggaaccgag tttaccctga caatcagcaa tctgcagcct    240
gaggacttcg ccacatacta ttgtctgcag cactggtctt acccactgac ctttggcagc    300
ggcacaaagc tggaggtgaa gaggggagga ggaggcagcg gcggaggagg ctccggaggc    360
ggcggctctg gcggcggcgg cagcggcggc ggcggctccg gaggaggcgg ctctgaggtg    420
cagctggtgg agagcggagg aggcctggtg aagccaggag gcagcctgag gctgtcctgc    480
gccgcctctg gattcgcctt tagcacctac gacatgtcct gggtgcgcca ggcacctggc    540
aagggcctgg agtgggtgtc caccatctct agcggcggct cttacacata ctatgccgac    600
agcgtgaagg gccggttcac catctccaga gataacgcca agaattctct gtatctgcag    660
atgaatagcc tgcgggccga ggatacagcc gtgtactatt gtgccccaac cacagtggtg    720
ccctttgcct attggggcca gggcaccctg gtgacagtga gcgccggcgg agggggatcc    780
ggcggcggag gatctggcgg aggtggaagt gggggaggcg gatctcatgt gcagctggtg    840
gaaagcggag gcggcctggt gcagcctggg ggatctctga gactgtcttg tgccgccagc    900
ggcttctccc tgaccgatta tggcgtgcac tgggtgcgac aggcccctgg caaaggactg    960
gaatggctgg gagtgatttg gagtggcgga ggcaccgcct acaacaccgc cctgatctcc   1020
cggttcacca tcagccggga caactccaag aacaccctgt acctgcagat gaactccctg   1080
cgggccgagg acaccgctgt gtactactgc gccagacggg gctcctaccc ctacaactac   1140
ttcgacgctt ggggctgcgg caccctcgtg acagtgtcta gcggaggggg aggttctggg   1200
ggcggaggtt caggtggtgg tggttccggg ggtggtggct ctggtggcgg tggttctggc   1260
ggtggcggat ctcaggctgt cgtgacccag gaacccagcc tgactgtgtc tcctggcgga   1320
accgtgaccc tgacctgcgg atcttctacc ggcgctgtga ccgccagcaa ctacgccaat   1380
tgggtgcagc agaaacctgg acagtgccct agaggcctga tcggcggcca caacaacaga   1440
cctccaggcg tgccagcccg gttctctgga tctctgctgg gcggaaaggc cgctctgaca   1500
ctgctgggtg ctcagcctga ggacgaggcc gagtactact gtgccctgtg gtactccgac   1560
cactgggtca tcggaggcgg gaccaagctg accgtgctgg gaacacccct gggagacacc   1620
acacatacta gtgggaaacc tctggatggc gagtacttta ccctgcagat tagaggccgc   1680
gaacgattcg agatgtttcg cgaactgaat gaggccctgg aactgaagga tgctcaggca   1740
ggcaaggagc caggagggtc aggaggagca ccgcaccatc atcatcacca t            1791
```

<210> SEQ ID NO 15
<211> LENGTH: 597
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Ala Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser His Val Gln Leu Val Glu Ser Gly Gly Gly Leu Val Gln
        275                 280                 285

Pro Gly Gly Ser Leu Arg Leu Ser Cys Ala Ala Ser Gly Phe Ser Leu
    290                 295                 300

Thr Asp Tyr Gly Val His Trp Val Arg Gln Ala Pro Gly Lys Gly Leu
305                 310                 315                 320

Glu Trp Leu Gly Val Ile Trp Ser Gly Gly Gly Thr Ala Tyr Asn Thr
                325                 330                 335

Ala Leu Ile Ser Arg Phe Thr Ile Ser Arg Asp Asn Ser Lys Asn Thr
            340                 345                 350

Leu Tyr Leu Gln Met Asn Ser Leu Arg Ala Glu Asp Thr Ala Val Tyr
        355                 360                 365

Tyr Cys Ala Arg Arg Gly Ser Tyr Pro Tyr Asn Tyr Phe Asp Ala Trp
    370                 375                 380

Gly Cys Gly Thr Leu Val Thr Val Ser Ser Gly Gly Gly Gly Ser Gly
385                 390                 395                 400

Gly Gly Gly Ser Gly Gly Gly Gly Ser Gly Gly Gly Gly Ser Gly Gly
                405                 410                 415

Gly Gly Ser Gly Gly Gly Gly Ser Gln Ala Val Val Thr Gln Glu Pro
```

```
            420                 425                 430

Ser Leu Thr Val Ser Pro Gly Gly Thr Val Thr Leu Thr Cys Gly Ser
        435                 440                 445

Ser Thr Gly Ala Val Thr Ala Ser Asn Tyr Ala Asn Trp Val Gln Gln
    450                 455                 460

Lys Pro Gly Gln Cys Pro Arg Gly Leu Ile Gly Gly His Asn Asn Arg
465                 470                 475                 480

Pro Pro Gly Val Pro Ala Arg Phe Ser Gly Ser Leu Leu Gly Gly Lys
                485                 490                 495

Ala Ala Leu Thr Leu Leu Gly Ala Gln Pro Glu Asp Glu Ala Glu Tyr
            500                 505                 510

Tyr Cys Ala Leu Trp Tyr Ser Asp His Trp Val Ile Gly Gly Gly Thr
        515                 520                 525

Lys Leu Thr Val Leu Gly Thr Pro Leu Gly Asp Thr Thr His Thr Ser
    530                 535                 540

Gly Lys Pro Leu Asp Gly Glu Tyr Phe Thr Leu Gln Ile Arg Gly Arg
545                 550                 555                 560

Glu Arg Phe Glu Met Phe Arg Glu Leu Asn Glu Ala Leu Glu Leu Lys
                565                 570                 575

Asp Ala Gln Ala Gly Lys Glu Pro Gly Gly Ser Gly Gly Ala Pro His
            580                 585                 590

His His His His His
        595


<210> SEQ ID NO 16
<211> LENGTH: 1791
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

gaggtgcagc tggtggagtc tggtgggggt ctggtcgatc ctggtggtag tctgaggctg      60

agttgtgccg cttctgggtt tgccttcagc acctacgaca tgtcctgggt gagacaggct     120

ccaggcaagg gcctggagtg ggtgtctacc atcagctccg gcggcagcta cacatactat     180

gctgactccg tgaagggccg gttcaccatc tctagggata acgccgctaa tagcctgtat     240

ctgcagatga actccctgcg cgccgaggat acagccgtgt actattgcgc cccaaccaca     300

gtggtgccct ttgcttattg gggccagggc accctggtga cagtgtccgc cggcggagga     360

ggctctggag gaggaggcag cggtggcggc ggctccggcg gcggcggctc tggcggcggc     420

ggcagcggtg gtggcggctc cgacatccag atgacccagt ccccttctag cctgtccgct     480

tctgtgggcg atcgggtgac catcacatgc aaggcctctc agaatgtgag gacagtggtg     540

gcttggtacc agcagaagcc cggcaaggcc cctaagaccc tgatctatct ggcttctaac     600

agacacacag gagtgcctag ccgcttcagc ggctccggct ctggaaccga gtttaccctg     660

acaatcagca atctgcagcc agaggacttc gccacatact attgtctgca gcactggtct     720

taccccctga cttttgggag cgggactaaa ctggaggtga aacggggcgg agggggatcc     780

ggcggcggag gatctggcgg aggtggaagt gggggaggcg gatctcatgt gcagctggtg     840

gaaagcggag gcggcctggt gcagcctggg ggatctctga gactgtcttg tgccgccagc     900

ggcttctccc tgaccgatta tggcgtgcac tgggtgcgac aggcccctgg caaaggactg     960

gaatggctgg gagtgatttg gagtggcgga ggcaccgcct acaacaccgc cctgatctcc    1020
```

```
cggttcacca tcagccggga caactccaag aacaccctgt acctgcagat gaactccctg   1080

cgggccgagg acaccgctgt gtactactgc gccagacggg gctcctaccc ctacaactac   1140

ttcgacgctt ggggctgcgg caccctcgtg acagtgtcta gcggaggggg aggttctggg   1200

ggcggaggtt caggtggtgg tggttccggg ggtggtggct ctggtggcgg tggttctggc   1260

ggtggcggat ctcaggctgt cgtgacccag gaacccagcc tgactgtgtc tcctggcgga   1320

accgtgaccc tgacctgcgg atcttctacc ggcgctgtga ccgccagcaa ctacgccaat   1380

tgggtgcagc agaaacctgg acagtgccct agaggcctga tcggcggcca caacaacaga   1440

cctccaggcg tgccagcccg gttctctgga tctctgctgg gcggaaaggc cgctctgaca   1500

ctgctgggtg ctcagcctga ggacgaggcc gagtactact gtgccctgtg gtactccgac   1560

cactgggtca tcggaggcgg gaccaagctg accgtgctgg gaacacccct gggagacacc   1620

acacatacta gtgggaaacc tctggatggc gagtacttta ccctgcagat tagaggccgc   1680

gaacgattcg agatgtttcg cgaactgaat gaggccctgg aactgaagga tgctcaggca   1740

ggcaaggagc caggagggtc aggaggagca ccgcaccatc atcatcacca t            1791

<210> SEQ ID NO 17
<211> LENGTH: 597
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220
```

```
Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser His Val Gln Leu Val Glu Ser Gly Gly Gly Leu Val Gln
        275                 280                 285

Pro Gly Gly Ser Leu Arg Leu Ser Cys Ala Ala Ser Gly Phe Ser Leu
    290                 295                 300

Thr Asp Tyr Gly Val His Trp Val Arg Gln Ala Pro Gly Lys Gly Leu
305                 310                 315                 320

Glu Trp Leu Gly Val Ile Trp Ser Gly Gly Gly Thr Ala Tyr Asn Thr
                325                 330                 335

Ala Leu Ile Ser Arg Phe Thr Ile Ser Arg Asp Asn Ser Lys Asn Thr
            340                 345                 350

Leu Tyr Leu Gln Met Asn Ser Leu Arg Ala Glu Asp Thr Ala Val Tyr
        355                 360                 365

Tyr Cys Ala Arg Arg Gly Ser Tyr Pro Tyr Asn Tyr Phe Asp Ala Trp
    370                 375                 380

Gly Cys Gly Thr Leu Val Thr Val Ser Ser Gly Gly Gly Gly Ser Gly
385                 390                 395                 400

Gly Gly Gly Ser Gly Gly Gly Gly Ser Gly Gly Gly Gly Ser Gly Gly
                405                 410                 415

Gly Gly Ser Gly Gly Gly Gly Ser Gln Ala Val Val Thr Gln Glu Pro
            420                 425                 430

Ser Leu Thr Val Ser Pro Gly Gly Thr Val Thr Leu Thr Cys Gly Ser
        435                 440                 445

Ser Thr Gly Ala Val Thr Ala Ser Asn Tyr Ala Asn Trp Val Gln Gln
    450                 455                 460

Lys Pro Gly Gln Cys Pro Arg Gly Leu Ile Gly Gly His Asn Asn Arg
465                 470                 475                 480

Pro Pro Gly Val Pro Ala Arg Phe Ser Gly Ser Leu Leu Gly Gly Lys
                485                 490                 495

Ala Ala Leu Thr Leu Leu Gly Ala Gln Pro Glu Asp Glu Ala Glu Tyr
            500                 505                 510

Tyr Cys Ala Leu Trp Tyr Ser Asp His Trp Val Ile Gly Gly Gly Thr
        515                 520                 525

Lys Leu Thr Val Leu Gly Thr Pro Leu Gly Asp Thr Thr His Thr Ser
    530                 535                 540

Gly Lys Pro Leu Asp Gly Glu Tyr Phe Thr Leu Gln Ile Arg Gly Arg
545                 550                 555                 560

Glu Arg Phe Glu Met Phe Arg Glu Leu Asn Glu Ala Leu Glu Leu Lys
                565                 570                 575

Asp Ala Gln Ala Gly Lys Glu Pro Gly Gly Ser Gly Gly Ala Pro His
            580                 585                 590

His His His His His
        595
```

<210> SEQ ID NO 18
<211> LENGTH: 1791
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 18

```
gaggtgcagc tggtggagag cggaggaggc ctggtggacc ccggaggcag cctgagactg     60
tcctgcgccg cttctggctt cgcctttagc acctacgata tgtcctgggt gcgccaggct    120
cctggcaagg gcctggagtg ggtgtctacc atcagctccg gcggcagcta cacatactat    180
gccgactccg tgaagggccg gttcaccatc tctagggata acgctaagaa tagcctgtat    240
ctgcagatga actccctgcg ggccgaggac acagccgtgt actattgtgc cccaaccaca    300
gtggtgccct ttgcttattg gggccagggc accctggtga cagtgtctgc cggcggagga    360
ggctctggag gaggaggcag cggtggcggc ggctccggcg gcggcggctc tggcggcggc    420
ggcagcggtg gtggcggctc cgacatccag atgacccaga gcccatctag cctgtccgct    480
tctgtgggcg atcgggtgac catcacatgc aaggcctccc agaatgtgag gacagtggtg    540
gcttggtacc agcagaagcc cggcaaggcc cctaagaccc tgatctatct ggcttccaac    600
agacacacag gagtgccctc tcgcttcagc ggctccggct ctggaaccga gtttaccctg    660
acaatctcca atctgcagcc tgaggatttc gccacatact attgtctgca gcactggtct    720
tacccactga cctttggcag cggcacaaag ctggaggtga agcggggcgg aggggggatcc    780
ggcggcggag gatctggcgg aggtggaagt gggggaggcg gatctcatgt gcagctggtg    840
gaaagcggag gcggcctggt gcagcctggg ggatctctga gactgtcttg tgccgccagc    900
ggcttctccc tgaccgatta tggcgtgcac tgggtgcgac aggcccctgg caaaggactg    960
gaatggctgg gagtgatttg gagtggcgga ggcaccgcct acaacaccgc cctgatctcc   1020
cggttcacca tcagccggga caactccaag aacaccctgt acctgcagat gaactccctg   1080
cgggccgagg acaccgctgt gtactactgc gccagacggg gctcctaccc ctacaactac   1140
ttcgacgctt ggggctgcgg caccctcgtg acagtgtcta gcggaggggg aggttctggg   1200
ggcggaggtt caggtggtgg tggttccggg ggtggtggct ctggtggcgg tggttctggc   1260
ggtggcggat ctcaggctgt cgtgacccag gaacccagcc tgactgtgtc tcctggcgga   1320
accgtgaccc tgacctgcgg atcttctacc ggcgctgtga ccgccagcaa ctacgccaat   1380
tgggtgcagc agaaacctgg acagtgccct agaggcctga tcggcggcca caacaacaga   1440
cctccaggcg tgccagcccg gttctctgga tctctgctgg gcggaaaggc cgctctgaca   1500
ctgctgggtg ctcagcctga ggacgaggcc gagtactact gtgccctgtg gtactccgac   1560
cactgggtca tcggaggcgg gaccaagctg accgtgctgg gaacacccct gggagacacc   1620
acacatacta gtgggaaacc tctggatggc gagtacttta ccctgcagat tagaggccgc   1680
gaacgattcg agatgtttcg cgaactgaat gaggccctgg aactgaagga tgctcaggca   1740
ggcaaggagc caggagggtc aggaggagca ccgcaccatc atcatcacca t            1791
```

<210> SEQ ID NO 19
<211> LENGTH: 597
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Glu Val Gln Leu Val Glu Ser Gly Gly Gly Leu Val Asp Pro Gly Gly
1               5                   10                  15
```

```
Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Ala Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Gln Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser His Val Gln Leu Val Glu Ser Gly Gly Gly Leu Val Gln
        275                 280                 285

Pro Gly Gly Ser Leu Arg Leu Ser Cys Ala Ala Ser Gly Phe Ser Leu
    290                 295                 300

Thr Asp Tyr Gly Val His Trp Val Arg Gln Ala Pro Gly Lys Gly Leu
305                 310                 315                 320

Glu Trp Leu Gly Val Ile Trp Ser Gly Gly Gly Thr Ala Tyr Asn Thr
                325                 330                 335

Ala Leu Ile Ser Arg Phe Thr Ile Ser Arg Asp Asn Ser Lys Asn Thr
            340                 345                 350

Leu Tyr Leu Gln Met Asn Ser Leu Arg Ala Glu Asp Thr Ala Val Tyr
        355                 360                 365

Tyr Cys Ala Arg Arg Gly Ser Tyr Pro Tyr Asn Tyr Phe Asp Ala Trp
    370                 375                 380

Gly Cys Gly Thr Leu Val Thr Val Ser Ser Gly Gly Gly Gly Ser Gly
385                 390                 395                 400

Gly Gly Gly Ser Gly Gly Gly Gly Ser Gly Gly Gly Gly Ser Gly Gly
                405                 410                 415

Gly Gly Ser Gly Gly Gly Gly Ser Gln Ala Val Val Thr Gln Glu Pro
            420                 425                 430

Ser Leu Thr Val Ser Pro Gly Gly Thr Val Thr Leu Thr Cys Gly Ser
```

```
        435                 440                 445

Ser Thr Gly Ala Val Thr Ala Ser Asn Tyr Ala Asn Trp Val Gln Gln
    450                 455                 460

Lys Pro Gly Gln Cys Pro Arg Gly Leu Ile Gly Gly His Asn Asn Arg
465                 470                 475                 480

Pro Pro Gly Val Pro Ala Arg Phe Ser Gly Ser Leu Leu Gly Gly Lys
                485                 490                 495

Ala Ala Leu Thr Leu Leu Gly Ala Gln Pro Glu Asp Glu Ala Glu Tyr
            500                 505                 510

Tyr Cys Ala Leu Trp Tyr Ser Asp His Trp Val Ile Gly Gly Gly Thr
        515                 520                 525

Lys Leu Thr Val Leu Gly Thr Pro Leu Gly Asp Thr Thr His Thr Ser
    530                 535                 540

Gly Lys Pro Leu Asp Gly Glu Tyr Phe Thr Leu Gln Ile Arg Gly Arg
545                 550                 555                 560

Glu Arg Phe Glu Met Phe Arg Glu Leu Asn Glu Ala Leu Glu Leu Lys
                565                 570                 575

Asp Ala Gln Ala Gly Lys Glu Pro Gly Gly Ser Gly Gly Ala Pro His
            580                 585                 590

His His His His His
        595


<210> SEQ ID NO 20
<211> LENGTH: 1790
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

gaggtgcagc tggtggagag cggaggaggc ctggtggacc ccggaggcag cctgagactg     60

tcctgcgccg cttctggctt cgcctttagc acctacgata tgtcctgggt gcgccaggct    120

cctggcaagg gcctggagtg ggtgtctacc atcagctccg gcggcagcta cacatactat    180

gccgactccg tgaagggccg gttcaccatc tctagggata acgccgctaa tagcctgtat    240

ctgcagatga actccctgcg ggccgaggac acagccgtgt actattgtgc cccaaccaca    300

gtggtgccct ttgcttattg gggccagggc accctggtga cagtgtctgc cggcggagga    360

ggctctggag gaggaggcag cggtggcggc ggctccggcg gcggcggctc tggcggcggc    420

ggcagcggtg gtggcggctc cgacatccag atgacccaga gcccatctag cctgtccgct    480

tctgtgggcg atcgggtgac catcacatgc aaggcctccc agaatgtgag gacagtggtg    540

gcttggtacc agcagaagcc cggccaggcc cctaagaccc tgatctatct ggcttccaac    600

agacacacag gagtgccctc tcgcttcagc ggctccggct ctggaaccga gtttaccctg    660

acaatctcca atctgcagcc tgaggatttc gccacatact attgtctgca gcactggtct    720

tacccactga cctttggcag cggcacaaag ctggaggtga agcgggcgga gggggatccg    780

gcggcggagg atctggcgga ggtggaagtg gggaggcgg atctcatgtg cagctggtgg    840

aaagcggagg cggcctggtg cagcctgggg gatctctgag actgtcttgt gccgccagcg    900

gcttctccct gaccgattat ggcgtgcact gggtgcgaca ggcccctggc aaaggactgg    960

aatggctggg agtgatttgg agtggcggag gcaccgccta caacaccgcc ctgatctccc   1020

ggttcaccat cagccgggac aactccaaga acaccctgta cctgcagatg aactccctgc   1080
```

```
gggccgagga caccgctgtg tactactgcg ccagacgggg ctcctacccc tacaactact   1140

tcgacgcttg gggctgcggc accctcgtga cagtgtctag cggaggggga ggttctgggg   1200

gcggaggttc aggtggtggt ggttccgggg gtggtggctc tggtggcggt ggttctggcg   1260

gtggcggatc tcaggctgtc gtgacccagg aacccagcct gactgtgtct cctggcggaa   1320

ccgtgaccct gacctgcgga tcttctaccg gcgctgtgac cgccagcaac tacgccaatt   1380

gggtgcagca gaaacctgga cagtgcccta gaggcctgat cggcggccac aacaacagac   1440

ctccaggcgt gccagcccgg ttctctggat ctctgctggg cggaaaggcc gctctgacac   1500

tgctgggtgc tcagcctgag gacgaggccg agtactactg tgccctgtgg tactccgacc   1560

actgggtcat cggaggcggg accaagctga ccgtgctggg aacacccctg ggagacacca   1620

cacatactag tgggaaacct ctggatggcg agtactttac cctgcagatt agaggccgcg   1680

aacgattcga gatgtttcgc gaactgaatg aggccctgga actgaaggat gctcaggcag   1740

gcaaggagcc aggagggtca ggaggagcac cgcaccatca tcatcaccat              1790
```

<210> SEQ ID NO 21
<211> LENGTH: 491
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ala Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Trp Ser Tyr Pro Leu
                85                  90                  95

Thr Phe Gly Ser Gly Thr Lys Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Lys Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Thr Ser Gly Gly Gly Gly Ser Gly Gly
    210                 215                 220

Gly Gly Ser Gly Gly Gly Gly Ser His Val Gln Leu Val Glu Ser Gly
225                 230                 235                 240
```

```
Gly Gly Leu Val Gln Pro Gly Gly Ser Leu Arg Leu Ser Cys Ala Ala
                245                 250                 255

Ser Gly Phe Ser Leu Thr Asp Tyr Gly Val His Trp Val Arg Gln Ala
            260                 265                 270

Pro Gly Lys Gly Leu Glu Trp Leu Gly Val Ile Trp Ser Gly Gly Gly
        275                 280                 285

Thr Ala Tyr Asn Thr Ala Leu Ile Ser Arg Phe Thr Ile Ser Arg Asp
    290                 295                 300

Asn Ser Lys Asn Thr Leu Tyr Leu Gln Met Asn Ser Leu Arg Ala Glu
305                 310                 315                 320

Asp Thr Ala Val Tyr Tyr Cys Ala Arg Arg Gly Ser Tyr Pro Tyr Asn
                325                 330                 335

Tyr Phe Asp Ala Trp Gly Cys Gly Thr Leu Val Thr Val Ser Ser Gly
            340                 345                 350

Gly Gly Gly Ser Gly Gly Gly Gly Ser Gly Gly Gly Gly Ser Gly Gly
        355                 360                 365

Gly Gly Ser Gly Gly Gly Gly Ser Gly Gly Gly Gly Ser Gln Ala Val
    370                 375                 380

Val Thr Gln Glu Pro Ser Leu Thr Val Ser Pro Gly Gly Thr Val Thr
385                 390                 395                 400

Leu Thr Cys Gly Ser Ser Thr Gly Ala Val Thr Ala Ser Asn Tyr Ala
                405                 410                 415

Asn Trp Val Gln Gln Lys Pro Gly Gln Cys Pro Arg Gly Leu Ile Gly
            420                 425                 430

Gly His Asn Asn Arg Pro Pro Gly Val Pro Ala Arg Phe Ser Gly Ser
        435                 440                 445

Leu Leu Gly Gly Lys Ala Ala Leu Thr Leu Leu Gly Ala Gln Pro Glu
    450                 455                 460

Asp Glu Ala Glu Tyr Tyr Cys Ala Leu Trp Tyr Ser Asp His Trp Val
465                 470                 475                 480

Ile Gly Gly Gly Thr Lys Leu Thr Val Leu Gly
                485                 490
```

<210> SEQ ID NO 22
<211> LENGTH: 1470
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
gacatccaga tgacccagag cccatctagc ctgtccgcct ctgtgggcga tcgggtgacc      60

atcacatgca aggcctccca gaatgtgaga acagtggtgg cctggtacca gcagaagccc     120

ggcaaggccc ctaagaccct gatctatctg gcctccaaca ggcacacagg agtgccatct     180

cgcttcagcg gctccggctc tggaaccgag tttaccctga caatctccaa tctgcagcct     240

gaggatttcg ccacatacta ttgtctgcag cactggtctt acccactgac ctttggcagc     300

ggcacaaagc tggaggtgaa gagaaccgtg gccgctccct ccgtgttcat cttcccacct     360

tccgacgagc agctgaagtc cggcaccgct tctgtcgtgt gcctgctgaa caacttctac     420

ccccgcgagg ccaaggtgca gtggaaggtg gacaacgccc tgcagtccgg caactcccag     480

gaatccgtga ccgagcagga ctccaaggac agcacctaca gcctgtcctc taccctgacc     540

ctgtccaagg ccgactacga gaagcacaag gtgtacgcct gcgaagtgac ccaccagggc     600
```

```
ctgtctagcc ccgtgaccaa gtctttcaac cggggcgagt gcactagtgg cggcggagga    660

tctggcggag gtggaagtgg gggaggcgga tctcatgtgc agctggtgga aagcggaggc    720

ggcctggtgc agcctggggg atctctgaga ctgtcttgtg ccgccagcgg cttctccctg    780

accgattatg gcgtgcactg ggtgcgacag gcccctggca aaggactgga atggctggga    840

gtgatttgga gtggcggagg caccgcctac aacaccgccc tgatctcccg gttcaccatc    900

agccgggaca actccaagaa caccctgtac ctgcagatga actccctgcg ggccgaggac    960

accgctgtgt actactgcgc cagacggggc tcctacccct acaactactt cgacgcttgg   1020

ggctgcggca ccctcgtgac agtgtctagc ggagggggag gttctggggg cggaggttca   1080

ggtggtggtg gttccggggg tggtggctct ggtggcggtg gttctggcgg tggcggatct   1140

caggctgtcg tgacccagga acccagcctg actgtgtctc ctggcggaac cgtgaccctg   1200

acctgcggat cttctaccgg cgctgtgacc gccagcaact acgccaattg ggtgcagcag   1260

aaacctggac agtgccctag aggcctgatc ggcggccaca acaacagacc tccaggcgtg   1320

ccagcccggt tctctggatc tctgctgggc ggaaaggccg ctctgacact gctgggtgct   1380

cagcctgagg acgaggccga gtactactgt gccctgtggt actccgacca ctgggtcatc   1440

ggaggcggga ccaagctgac cgtgctggga                                    1470
```

<210> SEQ ID NO 23
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
```

```
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

```
<210> SEQ ID NO 24
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

gaggtgcagc tggtggaatc tggcggcgga ctcgtgaagc ctggcggctc tctgagactg      60

tcttgtgccg cctctggctt cgccttctcc acctacgaca tgtcctgggt gcgacaggcc     120

cctggcaaga gactggaatg ggtggccaca atctcctccg gcggctccta cacctactac     180

ctggactctg tgaagggccg gttcaccatc tcccgggaca acgccaagaa ctccctgtac     240

ctgcagatga acagcctgcg ggccgaggac accgccgtgt actattgtgc tcccaccacc     300

gtggtgccct tcgcctattg gggacagggc accctcgtga ccgtgtcctc tgcttctacc     360

aagggcccat cggtcttccc cctggcaccc tcctccaaga gcacctctgg gggcacagcg     420

gccctgggct gcctggtcaa ggactacttc cccgaaccgg tgacggtgtc gtggaactca     480

ggcgccctga ccagcggcgt gcacaccttc ccggccgtcc tacagtcctc aggactctac     540

tccctcagca gcgtggtgac cgtgccctcc agcagcttgg gcacccagac ctacatctgc     600

aacgtgaatc acaagcccag caacaccaag gtggacaaga gagttgagcc caaatcttgt     660
```

```
gacaaaactc acacatgccc accgtgccca gcacctgaac tcctgggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacgc cagcacgtac    900

cgtgtggtca gcgtcctcac cgtcctgcac caggactggc tgaatggcaa ggagtacaag    960

tgcaaggtct ccaacaaagc cctcccagcc cccatcgaga aaaccatctc caaagccaaa   1020

gggcagcccc gagaaccaca ggtgtacacc ctgcccccat cccgggatga gctgaccaag   1080

aaccaggtca gcctgacctg cctggtcaaa ggcttctatc ccagcgacat cgccgtggag   1140

tgggagagca atgggcagcc ggagaacaac tacaagacca cgcctcccgt gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtaa a                                              1341
```

<210> SEQ ID NO 25
<211> LENGTH: 490
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Asp Ile Gln Met Thr Gln Ser Pro Ser Ser Leu Ser Thr Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ala Pro Lys Thr Leu Ile
        35                  40                  45

Tyr Leu Ala Ser Asn Arg His Ser Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Trp Ser Tyr Pro Leu
                85                  90                  95

Thr Phe Gly Ser Gly Thr Lys Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Gly Ser Gly Gly Gly
    210                 215                 220

Gly Ser Gly Gly Gly Gly Ser His Val Gln Leu Val Glu Ser Gly Gly
```

```
225                 230                 235                 240

Gly Leu Val Gln Pro Gly Gly Ser Leu Arg Leu Ser Cys Ala Ala Ser
                245                 250                 255

Gly Phe Ser Leu Thr Asp Tyr Gly Val His Trp Val Arg Gln Ala Pro
            260                 265                 270

Gly Lys Gly Leu Glu Trp Leu Gly Val Ile Trp Ser Gly Gly Gly Thr
        275                 280                 285

Ala Tyr Asn Thr Ala Leu Ile Ser Arg Phe Thr Ile Ser Arg Asp Asn
    290                 295                 300

Ser Lys Asn Thr Leu Tyr Leu Gln Met Asn Ser Leu Arg Ala Glu Asp
305                 310                 315                 320

Thr Ala Val Tyr Tyr Cys Ala Arg Arg Gly Ser Tyr Pro Tyr Asn Tyr
                325                 330                 335

Phe Asp Ala Trp Gly Cys Gly Thr Leu Val Thr Val Ser Ser Gly Gly
            340                 345                 350

Gly Gly Ser Gly Gly Gly Gly Ser Gly Gly Gly Gly Ser Gly Gly Gly
        355                 360                 365

Gly Ser Gly Gly Gly Gly Ser Gly Gly Gly Gly Ser Gln Ala Val Val
    370                 375                 380

Thr Gln Glu Pro Ser Leu Thr Val Ser Pro Gly Gly Thr Val Thr Leu
385                 390                 395                 400

Thr Cys Gly Ser Ser Thr Gly Ala Val Thr Ala Ser Asn Tyr Ala Asn
                405                 410                 415

Trp Val Gln Gln Lys Pro Gly Gln Cys Pro Arg Gly Leu Ile Gly Gly
            420                 425                 430

His Asn Asn Arg Pro Pro Gly Val Pro Ala Arg Phe Ser Gly Ser Leu
        435                 440                 445

Leu Gly Gly Lys Ala Ala Leu Thr Leu Leu Gly Ala Gln Pro Glu Asp
    450                 455                 460

Glu Ala Glu Tyr Tyr Cys Ala Leu Trp Tyr Ser Asp His Trp Val Ile
465                 470                 475                 480

Gly Gly Gly Thr Lys Leu Thr Val Leu Gly
                485                 490


<210> SEQ ID NO 26
<211> LENGTH: 1470
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

gacatccaga tgacccagag ccctagctcc ctgtctacaa gcgtgggcga tagggtgacc     60

atcacatgca aggcctccca gaacgtgaga accgtggtgg cctggtacca gcagaagccc    120

ggcaaggccc ctaagacact gatctatctg gcctccaaca ggcactctgg agtgcccagc    180

agattctccg gctctggcag cggcaccgag tttaccctga caatctctaa tctgcagcca    240

gaggacttcg ccacatacta ttgtctgcag cactggtcct accccctgac ctttggctct    300

ggcacaaagc tggaggtgaa gagaaccgtg gccgctccct ccgtgttcat cttcccacct    360

tccgacgagc agctgaagtc cggcaccgct tctgtcgtgt gcctgctgaa caacttctac    420

ccccgcgagg ccaaggtgca gtggaaggtg gacaacgccc tgcagtccgg caactcccag    480

gaatccgtga ccgagcagga ctccaaggac agcacctaca gcctgtcctc taccctgacc    540
```

```
ctgtccaagg ccgactacga gaagcacaag gtgtacgcct gcgaagtgac ccaccagggc    600

ctgtctagcc ccgtgaccaa gtctttcaac cggggcgagt gcactagtgg cggcggagga    660

tctggcggag gtggaagtgg gggaggcgga tctcatgtgc agctggtgga aagcggaggc    720

ggcctggtgc agcctggggg atctctgaga ctgtcttgtg ccgccagcgg cttctccctg    780

accgattatg gcgtgcactg ggtgcgacag gcccctggca aaggactgga atggctggga    840

gtgatttgga gtggcggagg caccgcctac aacaccgccc tgatctcccg gttcaccatc    900

agccgggaca actccaagaa caccctgtac ctgcagatga actccctgcg ggccgaggac    960

accgctgtgt actactgcgc cagacggggc tcctacccct acaactactt cgacgcttgg   1020

ggctgcggca ccctcgtgac agtgtctagc ggagggggag gttctggggg cggaggttca   1080

ggtggtggtg gttccggggg tggtggctct ggtggcggtg gttctggcgg tggcggatct   1140

caggctgtcg tgacccagga acccagcctg actgtgtctc ctggcggaac cgtgaccctg   1200

acctgcggat cttctaccgg cgctgtgacc gccagcaact acgccaattg ggtgcagcag   1260

aaacctggac agtgccctag aggcctgatc ggcggccaca acaacagacc tccaggcgtg   1320

ccagcccggt tctctggatc tctgctgggc ggaaaggccg ctctgacact gctgggtgct   1380

cagcctgagg acgaggccga gtactactgt gccctgtggt actccgacca ctgggtcatc   1440

ggaggcggga ccaagctgac cgtgctggga                                    1470
```

```
<210> SEQ ID NO 27
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Ala Asp Ser Val
    50                  55                  60

Lys Gly Arg Phe Thr Ile Ser Arg Asp Ser Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

```
Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 28
<211> LENGTH: 1341
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
gaggtgcagc tggtggagtc cggaggaggc ctggtgaagc caggaggctc cctgaggctg      60

tcttgcgccg ccagcggatt cgccttttcc acctacgaca tgtcttgggt gcgccaggca     120

ccaggcaagg gcctggagtg ggtggcaacc atcagctccg gaggcagcta cacatactat     180

gccgactccg tgaagggccg gttcaccatc agccgggaca gcgccaagaa ctctctgtat     240

ctgcagatga atagcctgcg ggccgaggat acagccgtgt actattgtgc ccccaccaca     300

gtggtgcctt ttgcctattg gggccagggc accctggtga cagtgtctgc cgcttctacc     360

aagggcccat cggtcttccc cctggcaccc tcctccaaga gcacctctgg gggcacagcg     420

gccctgggct gcctggtcaa ggactacttc cccgaaccgg tgacggtgtc gtggaactca     480

ggcgccctga ccagcggcgt gcacaccttc ccggccgtcc tacagtcctc aggactctac     540

tccctcagca gcgtggtgac cgtgccctcc agcagcttgg gcacccagac ctacatctgc     600
```

```
aacgtgaatc acaagcccag caacaccaag gtggacaaga gagttgagcc caaatcttgt    660

gacaaaactc acacatgccc accgtgccca gcacctgaac tcctgggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacgc cagcacgtac    900

cgtgtggtca gcgtcctcac cgtcctgcac caggactggc tgaatggcaa ggagtacaag    960

tgcaaggtct ccaacaaagc cctcccagcc cccatcgaga aaaccatctc caaagccaaa   1020

gggcagcccc gagaaccaca ggtgtacacc ctgcccccat cccgggatga gctgaccaag   1080

aaccaggtca gcctgacctg cctggtcaaa ggcttctatc ccagcgacat cgccgtggag   1140

tgggagagca atgggcagcc ggagaacaac tacaagacca cgcctcccgt gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtaa a                                             1341


<210> SEQ ID NO 29
<211> LENGTH: 594
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220
```

```
Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Gln Val Gln Leu Val Gln Ser Gly Gly Gly Val Val Gln
        275                 280                 285

Pro Gly Arg Ser Leu Arg Leu Ser Cys Lys Ala Ser Gly Tyr Thr Phe
    290                 295                 300

Thr Arg Tyr Thr Met His Trp Val Arg Gln Ala Pro Gly Lys Cys Leu
305                 310                 315                 320

Glu Trp Ile Gly Tyr Ile Asn Pro Ser Arg Gly Tyr Thr Asn Tyr Asn
                325                 330                 335

Gln Lys Phe Lys Asp Arg Phe Thr Ile Ser Arg Asp Asn Ser Lys Asn
            340                 345                 350

Thr Ala Phe Leu Gln Met Asp Ser Leu Arg Pro Glu Asp Thr Gly Val
        355                 360                 365

Tyr Phe Cys Ala Arg Tyr Tyr Asp Asp His Tyr Ser Leu Asp Tyr Trp
    370                 375                 380

Gly Gln Gly Thr Pro Val Thr Val Ser Ser Gly Gly Gly Gly Ser Gly
385                 390                 395                 400

Gly Gly Gly Ser Gly Gly Gly Gly Ser Gly Gly Gly Gly Ser Gly Gly
                405                 410                 415

Gly Gly Ser Gly Gly Gly Gly Ser Asp Ile Gln Met Thr Gln Ser Pro
            420                 425                 430

Ser Ser Leu Ser Ala Ser Val Gly Asp Arg Val Thr Ile Thr Cys Ser
        435                 440                 445

Ala Ser Ser Ser Val Ser Tyr Met Asn Trp Tyr Gln Gln Thr Pro Gly
    450                 455                 460

Lys Ala Pro Lys Arg Trp Ile Tyr Asp Thr Ser Lys Leu Ala Ser Gly
465                 470                 475                 480

Val Pro Ser Arg Phe Ser Gly Ser Gly Ser Gly Thr Asp Tyr Thr Phe
                485                 490                 495

Thr Ile Ser Ser Leu Gln Pro Glu Asp Ile Ala Thr Tyr Tyr Cys Gln
            500                 505                 510

Gln Trp Ser Ser Asn Pro Phe Thr Phe Gly Cys Gly Thr Lys Leu Gln
        515                 520                 525

Ile Thr Arg Thr Pro Leu Gly Asp Thr Thr His Thr Ser Gly Lys Pro
    530                 535                 540

Leu Asp Gly Glu Tyr Phe Thr Leu Gln Ile Arg Gly Arg Glu Arg Phe
545                 550                 555                 560

Glu Met Phe Arg Glu Leu Asn Glu Ala Leu Glu Leu Lys Asp Ala Gln
                565                 570                 575

Ala Gly Lys Glu Pro Gly Gly Ser Gly Gly Ala Pro His His His His
            580                 585                 590

His His
```

<210> SEQ ID NO 30
<211> LENGTH: 594
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Gln Val Gln Leu Val Gln Ser Gly Gly Gly Val Val Gln
        275                 280                 285

Pro Gly Arg Ser Leu Arg Leu Ser Cys Lys Ala Ser Gly Tyr Thr Phe
    290                 295                 300

Thr Arg Tyr Thr Met His Trp Val Arg Gln Ala Pro Gly Lys Cys Leu
305                 310                 315                 320

Glu Trp Ile Gly Tyr Ile Asn Pro Ser Arg Gly Tyr Thr Asn Tyr Asn
                325                 330                 335

Gln Lys Phe Lys Asp Arg Phe Thr Ile Ser Arg Asp Asn Ser Lys Asn
            340                 345                 350

Thr Ala Phe Leu Gln Met Asp Ser Leu Arg Pro Glu Asp Thr Gly Val
        355                 360                 365

Tyr Phe Cys Ala Arg Tyr Tyr Asp Asp His Tyr Ser Leu Asp Tyr Trp
    370                 375                 380

Gly Gln Gly Thr Pro Val Thr Val Ser Ser Gly Gly Gly Gly Ser Gly
385                 390                 395                 400

Gly Gly Gly Ser Gly Gly Gly Gly Ser Gly Gly Gly Gly Ser Gly Gly
```

```
                405                 410                 415

Gly Gly Ser Gly Gly Gly Gly Ser Asp Ile Gln Met Thr Gln Ser Pro
            420                 425                 430

Ser Ser Leu Ser Ala Ser Val Gly Asp Arg Val Thr Ile Thr Cys Ser
        435                 440                 445

Ala Ser Ser Ser Val Ser Tyr Met Asn Trp Tyr Gln Gln Thr Pro Gly
    450                 455                 460

Lys Ala Pro Lys Arg Trp Ile Tyr Asp Thr Ser Lys Leu Ala Ser Gly
465                 470                 475                 480

Val Pro Ser Arg Phe Ser Gly Ser Gly Ser Gly Thr Asp Tyr Thr Phe
                485                 490                 495

Thr Ile Ser Ser Leu Gln Pro Glu Asp Ile Ala Thr Tyr Tyr Cys Gln
            500                 505                 510

Gln Trp Ser Ser Asn Pro Phe Thr Phe Gly Cys Gly Thr Lys Leu Gln
        515                 520                 525

Ile Thr Arg Thr Pro Leu Gly Asp Thr Thr His Thr Ser Gly Lys Pro
    530                 535                 540

Leu Asp Gly Glu Tyr Phe Thr Leu Gln Ile Arg Gly Arg Glu Arg Phe
545                 550                 555                 560

Glu Met Phe Arg Glu Leu Asn Glu Ala Leu Glu Leu Lys Asp Ala Gln
                565                 570                 575

Ala Gly Lys Glu Pro Gly Gly Ser Gly Gly Ala Pro His His His His
            580                 585                 590

His His


<210> SEQ ID NO 31
<211> LENGTH: 594
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Ala Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
```

```
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Gln Val Gln Leu Val Gln Ser Gly Gly Gly Val Val Gln
        275                 280                 285

Pro Gly Arg Ser Leu Arg Leu Ser Cys Lys Ala Ser Gly Tyr Thr Phe
    290                 295                 300

Thr Arg Tyr Thr Met His Trp Val Arg Gln Ala Pro Gly Lys Cys Leu
305                 310                 315                 320

Glu Trp Ile Gly Tyr Ile Asn Pro Ser Arg Gly Tyr Thr Asn Tyr Asn
                325                 330                 335

Gln Lys Phe Lys Asp Arg Phe Thr Ile Ser Arg Asp Asn Ser Lys Asn
            340                 345                 350

Thr Ala Phe Leu Gln Met Asp Ser Leu Arg Pro Glu Asp Thr Gly Val
        355                 360                 365

Tyr Phe Cys Ala Arg Tyr Tyr Asp Asp His Tyr Ser Leu Asp Tyr Trp
    370                 375                 380

Gly Gln Gly Thr Pro Val Thr Val Ser Ser Gly Gly Gly Gly Ser Gly
385                 390                 395                 400

Gly Gly Gly Ser Gly Gly Gly Gly Ser Gly Gly Gly Gly Ser Gly Gly
                405                 410                 415

Gly Gly Ser Gly Gly Gly Gly Ser Asp Ile Gln Met Thr Gln Ser Pro
            420                 425                 430

Ser Ser Leu Ser Ala Ser Val Gly Asp Arg Val Thr Ile Thr Cys Ser
        435                 440                 445

Ala Ser Ser Ser Val Ser Tyr Met Asn Trp Tyr Gln Gln Thr Pro Gly
    450                 455                 460

Lys Ala Pro Lys Arg Trp Ile Tyr Asp Thr Ser Lys Leu Ala Ser Gly
465                 470                 475                 480

Val Pro Ser Arg Phe Ser Gly Ser Gly Ser Gly Thr Asp Tyr Thr Phe
                485                 490                 495

Thr Ile Ser Ser Leu Gln Pro Glu Asp Ile Ala Thr Tyr Tyr Cys Gln
            500                 505                 510

Gln Trp Ser Ser Asn Pro Phe Thr Phe Gly Cys Gly Thr Lys Leu Gln
        515                 520                 525

Ile Thr Arg Thr Pro Leu Gly Asp Thr Thr His Thr Ser Gly Lys Pro
    530                 535                 540

Leu Asp Gly Glu Tyr Phe Thr Leu Gln Ile Arg Gly Arg Glu Arg Phe
545                 550                 555                 560

Glu Met Phe Arg Glu Leu Asn Glu Ala Leu Glu Leu Lys Asp Ala Gln
                565                 570                 575

Ala Gly Lys Glu Pro Gly Gly Ser Gly Gly Ala Pro His His His His
            580                 585                 590
```

```
His His


<210> SEQ ID NO 32
<211> LENGTH: 594
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Ala Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Gln Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Gln Val Gln Leu Val Gln Ser Gly Gly Gly Val Val Gln
        275                 280                 285

Pro Gly Arg Ser Leu Arg Leu Ser Cys Lys Ala Ser Gly Tyr Thr Phe
    290                 295                 300

Thr Arg Tyr Thr Met His Trp Val Arg Gln Ala Pro Gly Lys Cys Leu
305                 310                 315                 320

Glu Trp Ile Gly Tyr Ile Asn Pro Ser Arg Gly Tyr Thr Asn Tyr Asn
                325                 330                 335

Gln Lys Phe Lys Asp Arg Phe Thr Ile Ser Arg Asp Asn Ser Lys Asn
            340                 345                 350
```

Thr Ala Phe Leu Gln Met Asp Ser Leu Arg Pro Glu Asp Thr Gly Val
355 360 365

Tyr Phe Cys Ala Arg Tyr Tyr Asp Asp His Tyr Ser Leu Asp Tyr Trp
370 375 380

Gly Gln Gly Thr Pro Val Thr Val Ser Ser Gly Gly Gly Gly Ser Gly
385 390 395 400

Gly Gly Gly Ser Gly Gly Gly Gly Ser Gly Gly Gly Gly Ser Gly Gly
405 410 415

Gly Gly Ser Gly Gly Gly Gly Ser Asp Ile Gln Met Thr Gln Ser Pro
420 425 430

Ser Ser Leu Ser Ala Ser Val Gly Asp Arg Val Thr Ile Thr Cys Ser
435 440 445

Ala Ser Ser Ser Val Ser Tyr Met Asn Trp Tyr Gln Gln Thr Pro Gly
450 455 460

Lys Ala Pro Lys Arg Trp Ile Tyr Asp Thr Ser Lys Leu Ala Ser Gly
465 470 475 480

Val Pro Ser Arg Phe Ser Gly Ser Gly Ser Gly Thr Asp Tyr Thr Phe
485 490 495

Thr Ile Ser Ser Leu Gln Pro Glu Asp Ile Ala Thr Tyr Tyr Cys Gln
500 505 510

Gln Trp Ser Ser Asn Pro Phe Thr Phe Gly Cys Gly Thr Lys Leu Gln
515 520 525

Ile Thr Arg Thr Pro Leu Gly Asp Thr Thr His Thr Ser Gly Lys Pro
530 535 540

Leu Asp Gly Glu Tyr Phe Thr Leu Gln Ile Arg Gly Arg Glu Arg Phe
545 550 555 560

Glu Met Phe Arg Glu Leu Asn Glu Ala Leu Glu Leu Lys Asp Ala Gln
565 570 575

Ala Gly Lys Glu Pro Gly Gly Ser Gly Gly Ala Pro His His His His
580 585 590

His His

<210> SEQ ID NO 33
<211> LENGTH: 594
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

Glu Val Gln Leu Val Glu Ser Gly Gly Gly Leu Val Lys Pro Gly Gly
1 5 10 15

Ser Leu Arg Leu Ser Cys Ala Ala Ser Gly Phe Ala Phe Ser Thr Tyr
20 25 30

Asp Met Ser Trp Val Arg Gln Ala Pro Gly Lys Gly Leu Glu Trp Val
35 40 45

Ser Thr Ile Ser Ser Gly Gly Ser Tyr Thr Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Pro Thr Thr Val Val Pro Phe Ala Tyr Trp Gly Gln Gly Thr Leu
100 105 110

```
Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Gln Val Gln Leu Gln Gln Ser Gly Ala Glu Val Ala Lys
        275                 280                 285

Pro Gly Ala Ser Val Lys Val Ser Cys Lys Ala Ser Gly Tyr Thr Phe
    290                 295                 300

Thr Arg Tyr Thr Met His Trp Val Arg Gln Ala Pro Gly Gln Gly Leu
305                 310                 315                 320

Glu Trp Met Gly Tyr Ile Asn Pro Ser Arg Gly Tyr Thr Asn Tyr Asn
                325                 330                 335

Gln Lys Phe Lys Asp Arg Ala Thr Leu Thr Arg Asp Lys Ser Ile Ser
            340                 345                 350

Thr Ala Tyr Met Glu Leu Ser Arg Leu Arg Ser Asp Asp Thr Ala Val
        355                 360                 365

Tyr Tyr Cys Ala Arg Tyr Tyr Asp Asp His Tyr Ser Leu Asp Tyr Trp
    370                 375                 380

Gly Gln Gly Thr Thr Leu Thr Val Ser Ser Gly Gly Gly Gly Ser Gly
385                 390                 395                 400

Gly Gly Gly Ser Gly Gly Gly Gly Ser Gly Gly Gly Gly Ser Gly Gly
                405                 410                 415

Gly Gly Ser Gly Gly Gly Gly Ser Asp Ile Gln Met Thr Gln Ser Pro
            420                 425                 430

Ser Ser Leu Ser Ala Ser Val Gly Asp Arg Val Thr Met Thr Cys Ser
        435                 440                 445

Ala Ser Ser Ser Val Ser Tyr Met Asn Trp Tyr Gln Gln Lys Pro Gly
    450                 455                 460

Lys Ala Pro Lys Leu Leu Ile Tyr Asp Thr Ser Lys Leu Ala Ser Gly
465                 470                 475                 480

Val Pro Ser Arg Phe Ser Gly Ser Gly Ser Gly Thr Asp Phe Thr Leu
                485                 490                 495

Thr Ile Ser Ser Met Gln Pro Glu Asp Phe Ala Thr Tyr Tyr Cys Gln
            500                 505                 510

Gln Trp Ser Ser Asn Pro Phe Thr Phe Gly Ser Gly Thr Lys Leu Glu
        515                 520                 525
```

```
Ile Asn Arg Thr Pro Leu Gly Asp Thr Thr His Thr Ser Gly Lys Pro
    530                 535                 540

Leu Asp Gly Glu Tyr Phe Thr Leu Gln Ile Arg Gly Arg Glu Arg Phe
545                 550                 555                 560

Glu Met Phe Arg Glu Leu Asn Glu Ala Leu Glu Leu Lys Asp Ala Gln
                565                 570                 575

Ala Gly Lys Glu Pro Gly Gly Ser Gly Gly Ala Pro His His His His
            580                 585                 590

His His


<210> SEQ ID NO 34
<211> LENGTH: 594
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Gln Val Gln Leu Gln Gln Ser Gly Ala Glu Val Ala Lys
        275                 280                 285
```

```
Pro Gly Ala Ser Val Lys Val Ser Cys Lys Ala Ser Gly Tyr Thr Phe
    290                 295                 300

Thr Arg Tyr Thr Met His Trp Val Arg Gln Ala Pro Gly Gln Gly Leu
305                 310                 315                 320

Glu Trp Met Gly Tyr Ile Asn Pro Ser Arg Gly Tyr Thr Asn Tyr Asn
                325                 330                 335

Gln Lys Phe Lys Asp Arg Ala Thr Leu Thr Arg Asp Lys Ser Ile Ser
            340                 345                 350

Thr Ala Tyr Met Glu Leu Ser Arg Leu Arg Ser Asp Asp Thr Ala Val
        355                 360                 365

Tyr Tyr Cys Ala Arg Tyr Tyr Asp Asp His Tyr Ser Leu Asp Tyr Trp
    370                 375                 380

Gly Gln Gly Thr Thr Leu Thr Val Ser Ser Gly Gly Gly Gly Ser Gly
385                 390                 395                 400

Gly Gly Gly Ser Gly Gly Gly Gly Ser Gly Gly Gly Gly Ser Gly Gly
                405                 410                 415

Gly Gly Ser Gly Gly Gly Gly Ser Asp Ile Gln Met Thr Gln Ser Pro
            420                 425                 430

Ser Ser Leu Ser Ala Ser Val Gly Asp Arg Val Thr Met Thr Cys Ser
        435                 440                 445

Ala Ser Ser Ser Val Ser Tyr Met Asn Trp Tyr Gln Gln Lys Pro Gly
    450                 455                 460

Lys Ala Pro Lys Leu Leu Ile Tyr Asp Thr Ser Lys Leu Ala Ser Gly
465                 470                 475                 480

Val Pro Ser Arg Phe Ser Gly Ser Gly Ser Gly Thr Asp Phe Thr Leu
                485                 490                 495

Thr Ile Ser Ser Met Gln Pro Glu Asp Phe Ala Thr Tyr Tyr Cys Gln
            500                 505                 510

Gln Trp Ser Ser Asn Pro Phe Thr Phe Gly Ser Gly Thr Lys Leu Glu
        515                 520                 525

Ile Asn Arg Thr Pro Leu Gly Asp Thr Thr His Thr Ser Gly Lys Pro
    530                 535                 540

Leu Asp Gly Glu Tyr Phe Thr Leu Gln Ile Arg Gly Arg Glu Arg Phe
545                 550                 555                 560

Glu Met Phe Arg Glu Leu Asn Glu Ala Leu Glu Leu Lys Asp Ala Gln
                565                 570                 575

Ala Gly Lys Glu Pro Gly Gly Ser Gly Gly Ala Pro His His His His
            580                 585                 590

His His
```

```
<210> SEQ ID NO 35
<211> LENGTH: 594
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45
```

-continued

```
Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Ala Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Gln Val Gln Leu Gln Gln Ser Gly Ala Glu Val Ala Lys
        275                 280                 285

Pro Gly Ala Ser Val Lys Val Ser Cys Lys Ala Ser Gly Tyr Thr Phe
    290                 295                 300

Thr Arg Tyr Thr Met His Trp Val Arg Gln Ala Pro Gly Gln Gly Leu
305                 310                 315                 320

Glu Trp Met Gly Tyr Ile Asn Pro Ser Arg Gly Tyr Thr Asn Tyr Asn
                325                 330                 335

Gln Lys Phe Lys Asp Arg Ala Thr Leu Thr Arg Asp Lys Ser Ile Ser
            340                 345                 350

Thr Ala Tyr Met Glu Leu Ser Arg Leu Arg Ser Asp Asp Thr Ala Val
        355                 360                 365

Tyr Tyr Cys Ala Arg Tyr Tyr Asp Asp His Tyr Ser Leu Asp Tyr Trp
    370                 375                 380

Gly Gln Gly Thr Thr Leu Thr Val Ser Ser Gly Gly Gly Gly Ser Gly
385                 390                 395                 400

Gly Gly Gly Ser Gly Gly Gly Gly Ser Gly Gly Gly Gly Ser Gly Gly
                405                 410                 415

Gly Gly Ser Gly Gly Gly Gly Ser Asp Ile Gln Met Thr Gln Ser Pro
            420                 425                 430

Ser Ser Leu Ser Ala Ser Val Gly Asp Arg Val Thr Met Thr Cys Ser
        435                 440                 445

Ala Ser Ser Ser Val Ser Tyr Met Asn Trp Tyr Gln Gln Lys Pro Gly
    450                 455                 460

Lys Ala Pro Lys Leu Leu Ile Tyr Asp Thr Ser Lys Leu Ala Ser Gly
```

```
465                 470                 475                 480

Val Pro Ser Arg Phe Ser Gly Ser Gly Ser Gly Thr Asp Phe Thr Leu
                485                 490                 495

Thr Ile Ser Ser Met Gln Pro Glu Asp Phe Ala Thr Tyr Tyr Cys Gln
            500                 505                 510

Gln Trp Ser Ser Asn Pro Phe Thr Phe Gly Ser Gly Thr Lys Leu Glu
        515                 520                 525

Ile Asn Arg Thr Pro Leu Gly Asp Thr Thr His Thr Ser Gly Lys Pro
    530                 535                 540

Leu Asp Gly Glu Tyr Phe Thr Leu Gln Ile Arg Gly Arg Glu Arg Phe
545                 550                 555                 560

Glu Met Phe Arg Glu Leu Asn Glu Ala Leu Glu Leu Lys Asp Ala Gln
                565                 570                 575

Ala Gly Lys Glu Pro Gly Gly Ser Gly Gly Ala Pro His His His His
            580                 585                 590

His His


<210> SEQ ID NO 36
<211> LENGTH: 594
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Ala Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Gln Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
```

```
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Gln Val Gln Leu Gln Gln Ser Gly Ala Glu Val Ala Lys
        275                 280                 285

Pro Gly Ala Ser Val Lys Val Ser Cys Lys Ala Ser Gly Tyr Thr Phe
    290                 295                 300

Thr Arg Tyr Thr Met His Trp Val Arg Gln Ala Pro Gly Gln Gly Leu
305                 310                 315                 320

Glu Trp Met Gly Tyr Ile Asn Pro Ser Arg Gly Tyr Thr Asn Tyr Asn
                325                 330                 335

Gln Lys Phe Lys Asp Arg Ala Thr Leu Thr Arg Asp Lys Ser Ile Ser
            340                 345                 350

Thr Ala Tyr Met Glu Leu Ser Arg Leu Arg Ser Asp Asp Thr Ala Val
        355                 360                 365

Tyr Tyr Cys Ala Arg Tyr Tyr Asp Asp His Tyr Ser Leu Asp Tyr Trp
    370                 375                 380

Gly Gln Gly Thr Thr Leu Thr Val Ser Ser Gly Gly Gly Gly Ser Gly
385                 390                 395                 400

Gly Gly Gly Ser Gly Gly Gly Gly Ser Gly Gly Gly Gly Ser Gly Gly
                405                 410                 415

Gly Gly Ser Gly Gly Gly Gly Ser Asp Ile Gln Met Thr Gln Ser Pro
            420                 425                 430

Ser Ser Leu Ser Ala Ser Val Gly Asp Arg Val Thr Met Thr Cys Ser
        435                 440                 445

Ala Ser Ser Ser Val Ser Tyr Met Asn Trp Tyr Gln Gln Lys Pro Gly
    450                 455                 460

Lys Ala Pro Lys Leu Leu Ile Tyr Asp Thr Ser Lys Leu Ala Ser Gly
465                 470                 475                 480

Val Pro Ser Arg Phe Ser Gly Ser Gly Ser Gly Thr Asp Phe Thr Leu
                485                 490                 495

Thr Ile Ser Ser Met Gln Pro Glu Asp Phe Ala Thr Tyr Tyr Cys Gln
            500                 505                 510

Gln Trp Ser Ser Asn Pro Phe Thr Phe Gly Ser Gly Thr Lys Leu Glu
        515                 520                 525

Ile Asn Arg Thr Pro Leu Gly Asp Thr Thr His Thr Ser Gly Lys Pro
    530                 535                 540

Leu Asp Gly Glu Tyr Phe Thr Leu Gln Ile Arg Gly Arg Glu Arg Phe
545                 550                 555                 560

Glu Met Phe Arg Glu Leu Asn Glu Ala Leu Glu Leu Lys Asp Ala Gln
                565                 570                 575

Ala Gly Lys Glu Pro Gly Gly Ser Gly Gly Ala Pro His His His His
            580                 585                 590

His His
```

<210> SEQ ID NO 37
<211> LENGTH: 594
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Gln Val Gln Leu Gln Gln Ser Gly Ala Glu Val Ala Lys
        275                 280                 285

Pro Gly Ala Ser Val Lys Val Ser Cys Lys Ala Ser Gly Tyr Thr Phe
    290                 295                 300

Thr Arg Tyr Thr Met His Trp Val Arg Gln Ala Pro Gly Gln Gly Leu
305                 310                 315                 320

Glu Trp Met Gly Tyr Ile Asn Pro Ser Arg Gly Tyr Thr Asn Tyr Asn
                325                 330                 335

Gln Lys Phe Lys Asp Arg Ala Thr Leu Thr Arg Asp Lys Ser Ile Ser
            340                 345                 350

Thr Ala Tyr Met Glu Leu Ser Arg Leu Arg Ser Asp Asp Thr Ala Val
        355                 360                 365

Tyr Tyr Cys Ala Arg Tyr Tyr Asp Asp His Tyr Ser Leu Asp Tyr Trp
    370                 375                 380

Gly Gln Gly Thr Thr Leu Thr Val Ser Ser Gly Gly Gly Gly Ser Gly
385                 390                 395                 400

Gly Gly Gly Ser Gly Gly Gly Gly Ser Gly Gly Gly Gly Ser Gly Gly
                405                 410                 415
```

```
Gly Gly Ser Gly Gly Gly Gly Ser Asp Ile Gln Met Thr Gln Ser Pro
            420                 425                 430

Ser Ser Leu Ser Ala Ser Val Gly Asp Arg Val Thr Ile Thr Cys Ser
        435                 440                 445

Ala Ser Ser Ser Val Ser Tyr Met Asn Trp Tyr Gln Gln Lys Pro Gly
    450                 455                 460

Lys Ala Pro Lys Arg Trp Ile Tyr Asp Thr Ser Lys Leu Ala Ser Gly
465                 470                 475                 480

Val Pro Ser Arg Phe Ser Gly Ser Gly Ser Gly Thr Asp Phe Thr Leu
                485                 490                 495

Thr Ile Ser Ser Leu Gln Pro Glu Asp Phe Ala Thr Tyr Tyr Cys Gln
            500                 505                 510

Gln Trp Ser Ser Asn Pro Phe Thr Phe Gly Ser Gly Thr Lys Leu Glu
        515                 520                 525

Ile Asn Arg Thr Pro Leu Gly Asp Thr Thr His Thr Ser Gly Lys Pro
    530                 535                 540

Leu Asp Gly Glu Tyr Phe Thr Leu Gln Ile Arg Gly Arg Glu Arg Phe
545                 550                 555                 560

Glu Met Phe Arg Glu Leu Asn Glu Ala Leu Glu Leu Lys Asp Ala Gln
                565                 570                 575

Ala Gly Lys Glu Pro Gly Gly Ser Gly Gly Ala Pro His His His His
            580                 585                 590

His His


<210> SEQ ID NO 38
<211> LENGTH: 594
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175
```

```
Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Gln Val Gln Leu Gln Gln Ser Gly Ala Glu Val Ala Lys
        275                 280                 285

Pro Gly Ala Ser Val Lys Val Ser Cys Lys Ala Ser Gly Tyr Thr Phe
    290                 295                 300

Thr Arg Tyr Thr Met His Trp Val Arg Gln Ala Pro Gly Gln Gly Leu
305                 310                 315                 320

Glu Trp Met Gly Tyr Ile Asn Pro Ser Arg Gly Tyr Thr Asn Tyr Asn
                325                 330                 335

Gln Lys Phe Lys Asp Arg Ala Thr Leu Thr Arg Asp Lys Ser Ile Ser
            340                 345                 350

Thr Ala Tyr Met Glu Leu Ser Arg Leu Arg Ser Asp Asp Thr Ala Val
        355                 360                 365

Tyr Tyr Cys Ala Arg Tyr Tyr Asp Asp His Tyr Ser Leu Asp Tyr Trp
    370                 375                 380

Gly Gln Gly Thr Thr Leu Thr Val Ser Ser Gly Gly Gly Gly Ser Gly
385                 390                 395                 400

Gly Gly Gly Ser Gly Gly Gly Gly Ser Gly Gly Gly Gly Ser Gly Gly
                405                 410                 415

Gly Gly Ser Gly Gly Gly Gly Ser Asp Ile Gln Met Thr Gln Ser Pro
            420                 425                 430

Ser Ser Leu Ser Ala Ser Val Gly Asp Arg Val Thr Ile Thr Cys Ser
        435                 440                 445

Ala Ser Ser Ser Val Ser Tyr Met Asn Trp Tyr Gln Gln Lys Pro Gly
    450                 455                 460

Lys Ala Pro Lys Arg Trp Ile Tyr Asp Thr Ser Lys Leu Ala Ser Gly
465                 470                 475                 480

Val Pro Ser Arg Phe Ser Gly Ser Gly Ser Gly Thr Asp Phe Thr Leu
                485                 490                 495

Thr Ile Ser Ser Leu Gln Pro Glu Asp Phe Ala Thr Tyr Tyr Cys Gln
            500                 505                 510

Gln Trp Ser Ser Asn Pro Phe Thr Phe Gly Ser Gly Thr Lys Leu Glu
        515                 520                 525

Ile Asn Arg Thr Pro Leu Gly Asp Thr Thr His Thr Ser Gly Lys Pro
    530                 535                 540

Leu Asp Gly Glu Tyr Phe Thr Leu Gln Ile Arg Gly Arg Glu Arg Phe
545                 550                 555                 560

Glu Met Phe Arg Glu Leu Asn Glu Ala Leu Glu Leu Lys Asp Ala Gln
                565                 570                 575

Ala Gly Lys Glu Pro Gly Gly Ser Gly Gly Ala Pro His His His His
            580                 585                 590
```

His His

<210> SEQ ID NO 39
<211> LENGTH: 594
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Ala Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Gln Val Gln Leu Gln Gln Ser Gly Ala Glu Val Ala Lys
        275                 280                 285

Pro Gly Ala Ser Val Lys Val Ser Cys Lys Ala Ser Gly Tyr Thr Phe
    290                 295                 300

Thr Arg Tyr Thr Met His Trp Val Arg Gln Ala Pro Gly Gln Gly Leu
305                 310                 315                 320

Glu Trp Met Gly Tyr Ile Asn Pro Ser Arg Gly Tyr Thr Asn Tyr Asn
                325                 330                 335

Gln Lys Phe Lys Asp Arg Ala Thr Leu Thr Arg Asp Lys Ser Ile Ser
            340                 345                 350
```

```
Thr Ala Tyr Met Glu Leu Ser Arg Leu Arg Ser Asp Asp Thr Ala Val
        355                 360                 365

Tyr Tyr Cys Ala Arg Tyr Tyr Asp Asp His Tyr Ser Leu Asp Tyr Trp
    370                 375                 380

Gly Gln Gly Thr Thr Leu Thr Val Ser Ser Gly Gly Gly Gly Ser Gly
385                 390                 395                 400

Gly Gly Gly Ser Gly Gly Gly Gly Ser Gly Gly Gly Gly Ser Gly Gly
                405                 410                 415

Gly Gly Ser Gly Gly Gly Gly Ser Asp Ile Gln Met Thr Gln Ser Pro
            420                 425                 430

Ser Ser Leu Ser Ala Ser Val Gly Asp Arg Val Thr Ile Thr Cys Ser
        435                 440                 445

Ala Ser Ser Ser Val Ser Tyr Met Asn Trp Tyr Gln Gln Lys Pro Gly
    450                 455                 460

Lys Ala Pro Lys Arg Trp Ile Tyr Asp Thr Ser Lys Leu Ala Ser Gly
465                 470                 475                 480

Val Pro Ser Arg Phe Ser Gly Ser Gly Ser Gly Thr Asp Phe Thr Leu
                485                 490                 495

Thr Ile Ser Ser Leu Gln Pro Glu Asp Phe Ala Thr Tyr Tyr Cys Gln
            500                 505                 510

Gln Trp Ser Ser Asn Pro Phe Thr Phe Gly Ser Gly Thr Lys Leu Glu
        515                 520                 525

Ile Asn Arg Thr Pro Leu Gly Asp Thr Thr His Thr Ser Gly Lys Pro
    530                 535                 540

Leu Asp Gly Glu Tyr Phe Thr Leu Gln Ile Arg Gly Arg Glu Arg Phe
545                 550                 555                 560

Glu Met Phe Arg Glu Leu Asn Glu Ala Leu Glu Leu Lys Asp Ala Gln
                565                 570                 575

Ala Gly Lys Glu Pro Gly Gly Ser Gly Gly Ala Pro His His His His
            580                 585                 590

His His


<210> SEQ ID NO 40
<211> LENGTH: 594
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Ala Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110
```

```
Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Gln Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Gln Val Gln Leu Gln Gln Ser Gly Ala Glu Val Ala Lys
        275                 280                 285

Pro Gly Ala Ser Val Lys Val Ser Cys Lys Ala Ser Gly Tyr Thr Phe
    290                 295                 300

Thr Arg Tyr Thr Met His Trp Val Arg Gln Ala Pro Gly Gln Gly Leu
305                 310                 315                 320

Glu Trp Met Gly Tyr Ile Asn Pro Ser Arg Gly Tyr Thr Asn Tyr Asn
                325                 330                 335

Gln Lys Phe Lys Asp Arg Ala Thr Leu Thr Arg Asp Lys Ser Ile Ser
            340                 345                 350

Thr Ala Tyr Met Glu Leu Ser Arg Leu Arg Ser Asp Asp Thr Ala Val
        355                 360                 365

Tyr Tyr Cys Ala Arg Tyr Tyr Asp Asp His Tyr Ser Leu Asp Tyr Trp
    370                 375                 380

Gly Gln Gly Thr Thr Leu Thr Val Ser Ser Gly Gly Gly Gly Ser Gly
385                 390                 395                 400

Gly Gly Gly Ser Gly Gly Gly Gly Ser Gly Gly Gly Gly Ser Gly Gly
                405                 410                 415

Gly Gly Ser Gly Gly Gly Gly Ser Asp Ile Gln Met Thr Gln Ser Pro
            420                 425                 430

Ser Ser Leu Ser Ala Ser Val Gly Asp Arg Val Thr Ile Thr Cys Ser
        435                 440                 445

Ala Ser Ser Ser Val Ser Tyr Met Asn Trp Tyr Gln Gln Lys Pro Gly
    450                 455                 460

Lys Ala Pro Lys Arg Trp Ile Tyr Asp Thr Ser Lys Leu Ala Ser Gly
465                 470                 475                 480

Val Pro Ser Arg Phe Ser Gly Ser Gly Ser Gly Thr Asp Phe Thr Leu
                485                 490                 495

Thr Ile Ser Ser Leu Gln Pro Glu Asp Phe Ala Thr Tyr Tyr Cys Gln
            500                 505                 510

Gln Trp Ser Ser Asn Pro Phe Thr Phe Gly Ser Gly Thr Lys Leu Glu
        515                 520                 525

Ile Asn Arg Thr Pro Leu Gly Asp Thr Thr His Thr Ser Gly Lys Pro
```

```
    530                 535                 540

Leu Asp Gly Glu Tyr Phe Thr Leu Gln Ile Arg Gly Arg Glu Arg Phe
545                 550                 555                 560

Glu Met Phe Arg Glu Leu Asn Glu Ala Leu Glu Leu Lys Asp Ala Gln
                565                 570                 575

Ala Gly Lys Glu Pro Gly Gly Ser Gly Gly Ala Pro His His His His
            580                 585                 590

His His


<210> SEQ ID NO 41
<211> LENGTH: 875
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Asp Ile Gln Met Thr Gln Ser Pro Ser Ser Leu Ser Ala
        275                 280                 285

Ser Val Gly Asp Arg Val Thr Ile Thr Cys Arg Ala Ser Gln Asp Val
```

```
    290                 295                 300

Asn Thr Ala Val Ala Trp Tyr Gln Gln Lys Pro Gly Lys Ala Pro Lys
305                 310                 315                 320

Leu Leu Ile Tyr Ser Ala Ser Phe Leu Tyr Ser Gly Val Pro Ser Arg
                325                 330                 335

Phe Ser Gly Ser Arg Ser Gly Thr Asp Phe Thr Leu Thr Ile Ser Ser
            340                 345                 350

Leu Gln Pro Glu Asp Phe Ala Thr Tyr Tyr Cys Gln Gln His Tyr Thr
        355                 360                 365

Thr Pro Pro Thr Phe Gly Gln Gly Thr Lys Val Glu Ile Lys Arg Gly
    370                 375                 380

Gly Gly Gly Ser Gly Gly Gly Gly Ser Gly Gly Gly Gly Ser Gly Gly
385                 390                 395                 400

Gly Gly Ser Gly Gly Gly Gly Ser Gly Gly Gly Gly Ser Glu Val Gln
                405                 410                 415

Leu Val Glu Ser Gly Gly Gly Leu Val Gln Pro Gly Gly Ser Leu Arg
            420                 425                 430

Leu Ser Cys Ala Ala Ser Gly Phe Asn Ile Lys Asp Thr Tyr Ile His
        435                 440                 445

Trp Val Arg Gln Ala Pro Gly Lys Gly Leu Glu Trp Val Ala Arg Ile
    450                 455                 460

Tyr Pro Thr Asn Gly Tyr Thr Arg Tyr Ala Asp Ser Val Lys Gly Arg
465                 470                 475                 480

Phe Thr Ile Ser Ala Asp Thr Ser Lys Asn Thr Ala Tyr Leu Gln Met
                485                 490                 495

Asn Ser Leu Arg Ala Glu Asp Thr Ala Val Tyr Tyr Cys Ser Arg Trp
            500                 505                 510

Gly Gly Asp Gly Phe Tyr Ala Met Asp Tyr Trp Gly Gln Gly Thr Leu
        515                 520                 525

Val Thr Val Ser Ser Gly Gly Gly Gly Ser Gly Gly Gly Gly Ser Gly
    530                 535                 540

Gly Gly Gly Ser Gly Gly Gly Gly Ser His Val Gln Leu Val Glu Ser
545                 550                 555                 560

Gly Gly Gly Leu Val Gln Pro Gly Gly Ser Leu Arg Leu Ser Cys Ala
                565                 570                 575

Ala Ser Gly Phe Ser Leu Thr Asp Tyr Gly Val His Trp Val Arg Gln
            580                 585                 590

Ala Pro Gly Lys Gly Leu Glu Trp Leu Gly Val Ile Trp Ser Gly Gly
        595                 600                 605

Gly Thr Ala Tyr Asn Thr Ala Leu Ile Ser Arg Phe Thr Ile Ser Arg
    610                 615                 620

Asp Asn Ser Lys Asn Thr Leu Tyr Leu Gln Met Asn Ser Leu Arg Ala
625                 630                 635                 640

Glu Asp Thr Ala Val Tyr Tyr Cys Ala Arg Arg Gly Ser Tyr Pro Tyr
                645                 650                 655

Asn Tyr Phe Asp Ala Trp Gly Cys Gly Thr Leu Val Thr Val Ser Ser
            660                 665                 670

Gly Gly Gly Gly Ser Gly Gly Gly Gly Ser Gly Gly Gly Gly Ser Gly
        675                 680                 685

Gly Gly Gly Ser Gly Gly Gly Gly Ser Gly Gly Gly Gly Ser Gln Ala
    690                 695                 700

Val Val Thr Gln Glu Pro Ser Leu Thr Val Ser Pro Gly Gly Thr Val
705                 710                 715                 720
```

```
Thr Leu Thr Cys Gly Ser Ser Thr Gly Ala Val Thr Ala Ser Asn Tyr
                725                 730                 735

Ala Asn Trp Val Gln Gln Lys Pro Gly Gln Cys Pro Arg Gly Leu Ile
            740                 745                 750

Gly Gly His Asn Asn Arg Pro Pro Gly Val Pro Ala Arg Phe Ser Gly
        755                 760                 765

Ser Leu Leu Gly Gly Lys Ala Ala Leu Thr Leu Leu Gly Ala Gln Pro
    770                 775                 780

Glu Asp Glu Ala Glu Tyr Tyr Cys Ala Leu Trp Tyr Ser Asp His Trp
785                 790                 795                 800

Val Ile Gly Gly Gly Thr Lys Leu Thr Val Leu Gly Thr Pro Leu Gly
                805                 810                 815

Asp Thr Thr His Thr Ser Gly Lys Pro Leu Asp Gly Glu Tyr Phe Thr
            820                 825                 830

Leu Gln Ile Arg Gly Arg Glu Arg Phe Glu Met Phe Arg Glu Leu Asn
        835                 840                 845

Glu Ala Leu Glu Leu Lys Asp Ala Gln Ala Gly Lys Glu Pro Gly Gly
    850                 855                 860

Ser Gly Gly Ala Pro His His His His His His
865                 870                 875


<210> SEQ ID NO 42
<211> LENGTH: 875
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
```

```
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Asp Ile Gln Met Thr Gln Ser Pro Ser Ser Leu Ser Ala
        275                 280                 285

Ser Val Gly Asp Arg Val Thr Ile Thr Cys Arg Ala Ser Gln Asp Val
    290                 295                 300

Asn Thr Ala Val Ala Trp Tyr Gln Gln Lys Pro Gly Lys Ala Pro Lys
305                 310                 315                 320

Leu Leu Ile Tyr Ser Ala Ser Phe Leu Tyr Ser Gly Val Pro Ser Arg
                325                 330                 335

Phe Ser Gly Ser Arg Ser Gly Thr Asp Phe Thr Leu Thr Ile Ser Ser
            340                 345                 350

Leu Gln Pro Glu Asp Phe Ala Thr Tyr Tyr Cys Gln Gln His Tyr Thr
        355                 360                 365

Thr Pro Pro Thr Phe Gly Gln Gly Thr Lys Val Glu Ile Lys Arg Gly
    370                 375                 380

Gly Gly Gly Ser Gly Gly Gly Gly Ser Gly Gly Gly Gly Ser Gly Gly
385                 390                 395                 400

Gly Gly Ser Gly Gly Gly Gly Ser Gly Gly Gly Gly Ser Glu Val Gln
                405                 410                 415

Leu Val Glu Ser Gly Gly Gly Leu Val Gln Pro Gly Gly Ser Leu Arg
            420                 425                 430

Leu Ser Cys Ala Ala Ser Gly Phe Asn Ile Lys Asp Thr Tyr Ile His
        435                 440                 445

Trp Val Arg Gln Ala Pro Gly Lys Gly Leu Glu Trp Val Ala Arg Ile
    450                 455                 460

Tyr Pro Thr Asn Gly Tyr Thr Arg Tyr Ala Asp Ser Val Lys Gly Arg
465                 470                 475                 480

Phe Thr Ile Ser Ala Asp Thr Ser Lys Asn Thr Ala Tyr Leu Gln Met
                485                 490                 495

Asn Ser Leu Arg Ala Glu Asp Thr Ala Val Tyr Tyr Cys Ser Arg Trp
            500                 505                 510

Gly Gly Asp Gly Phe Tyr Ala Met Asp Tyr Trp Gly Gln Gly Thr Leu
        515                 520                 525

Val Thr Val Ser Ser Gly Gly Gly Gly Ser Gly Gly Gly Gly Ser Gly
    530                 535                 540

Gly Gly Gly Ser Gly Gly Gly Gly Ser His Val Gln Leu Val Glu Ser
545                 550                 555                 560

Gly Gly Gly Leu Val Gln Pro Gly Gly Ser Leu Arg Leu Ser Cys Ala
                565                 570                 575

Ala Ser Gly Phe Ser Leu Thr Asp Tyr Gly Val His Trp Val Arg Gln
            580                 585                 590

Ala Pro Gly Lys Gly Leu Glu Trp Leu Gly Val Ile Trp Ser Gly Gly
        595                 600                 605

Gly Thr Ala Tyr Asn Thr Ala Leu Ile Ser Arg Phe Thr Ile Ser Arg
    610                 615                 620
```

```
Asp Asn Ser Lys Asn Thr Leu Tyr Leu Gln Met Asn Ser Leu Arg Ala
625                 630                 635                 640

Glu Asp Thr Ala Val Tyr Tyr Cys Ala Arg Arg Gly Ser Tyr Pro Tyr
                645                 650                 655

Asn Tyr Phe Asp Ala Trp Gly Cys Gly Thr Leu Val Thr Val Ser Ser
            660                 665                 670

Gly Gly Gly Gly Ser Gly Gly Gly Gly Ser Gly Gly Gly Gly Ser Gly
        675                 680                 685

Gly Gly Gly Ser Gly Gly Gly Gly Ser Gly Gly Gly Gly Ser Gln Ala
    690                 695                 700

Val Val Thr Gln Glu Pro Ser Leu Thr Val Ser Pro Gly Gly Thr Val
705                 710                 715                 720

Thr Leu Thr Cys Gly Ser Ser Thr Gly Ala Val Thr Ala Ser Asn Tyr
                725                 730                 735

Ala Asn Trp Val Gln Gln Lys Pro Gly Gln Cys Pro Arg Gly Leu Ile
            740                 745                 750

Gly Gly His Asn Asn Arg Pro Pro Gly Val Pro Ala Arg Phe Ser Gly
        755                 760                 765

Ser Leu Leu Gly Gly Lys Ala Ala Leu Thr Leu Leu Gly Ala Gln Pro
    770                 775                 780

Glu Asp Glu Ala Glu Tyr Tyr Cys Ala Leu Trp Tyr Ser Asp His Trp
785                 790                 795                 800

Val Ile Gly Gly Gly Thr Lys Leu Thr Val Leu Gly Thr Pro Leu Gly
                805                 810                 815

Asp Thr Thr His Thr Ser Gly Lys Pro Leu Asp Gly Glu Tyr Phe Thr
            820                 825                 830

Leu Gln Ile Arg Gly Arg Glu Arg Phe Glu Met Phe Arg Glu Leu Asn
        835                 840                 845

Glu Ala Leu Glu Leu Lys Asp Ala Gln Ala Gly Lys Glu Pro Gly Gly
    850                 855                 860

Ser Gly Gly Ala Pro His His His His His His
865                 870                 875


<210> SEQ ID NO 43
<211> LENGTH: 875
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Ala Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
```

```
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Asp Ile Gln Met Thr Gln Ser Pro Ser Ser Leu Ser Ala
        275                 280                 285

Ser Val Gly Asp Arg Val Thr Ile Thr Cys Arg Ala Ser Gln Asp Val
    290                 295                 300

Asn Thr Ala Val Ala Trp Tyr Gln Gln Lys Pro Gly Lys Ala Pro Lys
305                 310                 315                 320

Leu Leu Ile Tyr Ser Ala Ser Phe Leu Tyr Ser Gly Val Pro Ser Arg
                325                 330                 335

Phe Ser Gly Ser Arg Ser Gly Thr Asp Phe Thr Leu Thr Ile Ser Ser
            340                 345                 350

Leu Gln Pro Glu Asp Phe Ala Thr Tyr Tyr Cys Gln Gln His Tyr Thr
        355                 360                 365

Thr Pro Pro Thr Phe Gly Gln Gly Thr Lys Val Glu Ile Lys Arg Gly
    370                 375                 380

Gly Gly Gly Ser Gly Gly Gly Gly Ser Gly Gly Gly Gly Ser Gly Gly
385                 390                 395                 400

Gly Gly Ser Gly Gly Gly Gly Ser Gly Gly Gly Gly Ser Glu Val Gln
                405                 410                 415

Leu Val Glu Ser Gly Gly Gly Leu Val Gln Pro Gly Gly Ser Leu Arg
            420                 425                 430

Leu Ser Cys Ala Ala Ser Gly Phe Asn Ile Lys Asp Thr Tyr Ile His
        435                 440                 445

Trp Val Arg Gln Ala Pro Gly Lys Gly Leu Glu Trp Val Ala Arg Ile
    450                 455                 460

Tyr Pro Thr Asn Gly Tyr Thr Arg Tyr Ala Asp Ser Val Lys Gly Arg
465                 470                 475                 480

Phe Thr Ile Ser Ala Asp Thr Ser Lys Asn Thr Ala Tyr Leu Gln Met
                485                 490                 495

Asn Ser Leu Arg Ala Glu Asp Thr Ala Val Tyr Tyr Cys Ser Arg Trp
            500                 505                 510

Gly Gly Asp Gly Phe Tyr Ala Met Asp Tyr Trp Gly Gln Gly Thr Leu
        515                 520                 525
```

Val Thr Val Ser Ser Gly Gly Gly Gly Ser Gly Gly Gly Gly Ser Gly
530 535 540

Gly Gly Gly Ser Gly Gly Gly Gly Ser His Val Gln Leu Val Glu Ser
545 550 555 560

Gly Gly Gly Leu Val Gln Pro Gly Gly Ser Leu Arg Leu Ser Cys Ala
565 570 575

Ala Ser Gly Phe Ser Leu Thr Asp Tyr Gly Val His Trp Val Arg Gln
580 585 590

Ala Pro Gly Lys Gly Leu Glu Trp Leu Gly Val Ile Trp Ser Gly Gly
595 600 605

Gly Thr Ala Tyr Asn Thr Ala Leu Ile Ser Arg Phe Thr Ile Ser Arg
610 615 620

Asp Asn Ser Lys Asn Thr Leu Tyr Leu Gln Met Asn Ser Leu Arg Ala
625 630 635 640

Glu Asp Thr Ala Val Tyr Tyr Cys Ala Arg Arg Gly Ser Tyr Pro Tyr
645 650 655

Asn Tyr Phe Asp Ala Trp Gly Cys Gly Thr Leu Val Thr Val Ser Ser
660 665 670

Gly Gly Gly Gly Ser Gly Gly Gly Gly Ser Gly Gly Gly Gly Ser Gly
675 680 685

Gly Gly Gly Ser Gly Gly Gly Gly Ser Gly Gly Gly Gly Ser Gln Ala
690 695 700

Val Val Thr Gln Glu Pro Ser Leu Thr Val Ser Pro Gly Gly Thr Val
705 710 715 720

Thr Leu Thr Cys Gly Ser Ser Thr Gly Ala Val Thr Ala Ser Asn Tyr
725 730 735

Ala Asn Trp Val Gln Gln Lys Pro Gly Gln Cys Pro Arg Gly Leu Ile
740 745 750

Gly Gly His Asn Asn Arg Pro Pro Gly Val Pro Ala Arg Phe Ser Gly
755 760 765

Ser Leu Leu Gly Gly Lys Ala Ala Leu Thr Leu Leu Gly Ala Gln Pro
770 775 780

Glu Asp Glu Ala Glu Tyr Tyr Cys Ala Leu Trp Tyr Ser Asp His Trp
785 790 795 800

Val Ile Gly Gly Gly Thr Lys Leu Thr Val Leu Gly Thr Pro Leu Gly
805 810 815

Asp Thr Thr His Thr Ser Gly Lys Pro Leu Asp Gly Glu Tyr Phe Thr
820 825 830

Leu Gln Ile Arg Gly Arg Glu Arg Phe Glu Met Phe Arg Glu Leu Asn
835 840 845

Glu Ala Leu Glu Leu Lys Asp Ala Gln Ala Gly Lys Glu Pro Gly Gly
850 855 860

Ser Gly Gly Ala Pro His His His His His His
865 870 875

<210> SEQ ID NO 44
<211> LENGTH: 875
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

Glu Val Gln Leu Val Glu Ser Gly Gly Gly Leu Val Asp Pro Gly Gly

-continued

```
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Ala Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Gln Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Asp Ile Gln Met Thr Gln Ser Pro Ser Ser Leu Ser Ala
        275                 280                 285

Ser Val Gly Asp Arg Val Thr Ile Thr Cys Arg Ala Ser Gln Asp Val
    290                 295                 300

Asn Thr Ala Val Ala Trp Tyr Gln Gln Lys Pro Gly Lys Ala Pro Lys
305                 310                 315                 320

Leu Leu Ile Tyr Ser Ala Ser Phe Leu Tyr Ser Gly Val Pro Ser Arg
                325                 330                 335

Phe Ser Gly Ser Arg Ser Gly Thr Asp Phe Thr Leu Thr Ile Ser Ser
            340                 345                 350

Leu Gln Pro Glu Asp Phe Ala Thr Tyr Tyr Cys Gln Gln His Tyr Thr
        355                 360                 365

Thr Pro Pro Thr Phe Gly Gln Gly Thr Lys Val Glu Ile Lys Arg Gly
    370                 375                 380

Gly Gly Gly Ser Gly Gly Gly Gly Ser Gly Gly Gly Gly Ser Gly Gly
385                 390                 395                 400

Gly Gly Ser Gly Gly Gly Gly Ser Gly Gly Gly Gly Ser Glu Val Gln
                405                 410                 415

Leu Val Glu Ser Gly Gly Gly Leu Val Gln Pro Gly Gly Ser Leu Arg
            420                 425                 430
```

```
Leu Ser Cys Ala Ala Ser Gly Phe Asn Ile Lys Asp Thr Tyr Ile His
        435                 440                 445

Trp Val Arg Gln Ala Pro Gly Lys Gly Leu Glu Trp Val Ala Arg Ile
    450                 455                 460

Tyr Pro Thr Asn Gly Tyr Thr Arg Tyr Ala Asp Ser Val Lys Gly Arg
465                 470                 475                 480

Phe Thr Ile Ser Ala Asp Thr Ser Lys Asn Thr Ala Tyr Leu Gln Met
                485                 490                 495

Asn Ser Leu Arg Ala Glu Asp Thr Ala Val Tyr Tyr Cys Ser Arg Trp
            500                 505                 510

Gly Gly Asp Gly Phe Tyr Ala Met Asp Tyr Trp Gly Gln Gly Thr Leu
        515                 520                 525

Val Thr Val Ser Ser Gly Gly Gly Gly Ser Gly Gly Gly Gly Ser Gly
    530                 535                 540

Gly Gly Gly Ser Gly Gly Gly Gly Ser His Val Gln Leu Val Glu Ser
545                 550                 555                 560

Gly Gly Gly Leu Val Gln Pro Gly Gly Ser Leu Arg Leu Ser Cys Ala
                565                 570                 575

Ala Ser Gly Phe Ser Leu Thr Asp Tyr Gly Val His Trp Val Arg Gln
            580                 585                 590

Ala Pro Gly Lys Gly Leu Glu Trp Leu Gly Val Ile Trp Ser Gly Gly
        595                 600                 605

Gly Thr Ala Tyr Asn Thr Ala Leu Ile Ser Arg Phe Thr Ile Ser Arg
    610                 615                 620

Asp Asn Ser Lys Asn Thr Leu Tyr Leu Gln Met Asn Ser Leu Arg Ala
625                 630                 635                 640

Glu Asp Thr Ala Val Tyr Tyr Cys Ala Arg Arg Gly Ser Tyr Pro Tyr
                645                 650                 655

Asn Tyr Phe Asp Ala Trp Gly Cys Gly Thr Leu Val Thr Val Ser Ser
            660                 665                 670

Gly Gly Gly Gly Ser Gly Gly Gly Gly Ser Gly Gly Gly Gly Ser Gly
        675                 680                 685

Gly Gly Gly Ser Gly Gly Gly Gly Ser Gly Gly Gly Gly Ser Gln Ala
    690                 695                 700

Val Val Thr Gln Glu Pro Ser Leu Thr Val Ser Pro Gly Gly Thr Val
705                 710                 715                 720

Thr Leu Thr Cys Gly Ser Ser Thr Gly Ala Val Thr Ala Ser Asn Tyr
                725                 730                 735

Ala Asn Trp Val Gln Gln Lys Pro Gly Gln Cys Pro Arg Gly Leu Ile
            740                 745                 750

Gly Gly His Asn Asn Arg Pro Pro Gly Val Pro Ala Arg Phe Ser Gly
        755                 760                 765

Ser Leu Leu Gly Gly Lys Ala Ala Leu Thr Leu Leu Gly Ala Gln Pro
    770                 775                 780

Glu Asp Glu Ala Glu Tyr Tyr Cys Ala Leu Trp Tyr Ser Asp His Trp
785                 790                 795                 800

Val Ile Gly Gly Gly Thr Lys Leu Thr Val Leu Gly Thr Pro Leu Gly
                805                 810                 815

Asp Thr Thr His Thr Ser Gly Lys Pro Leu Asp Gly Glu Tyr Phe Thr
            820                 825                 830

Leu Gln Ile Arg Gly Arg Glu Arg Phe Glu Met Phe Arg Glu Leu Asn
        835                 840                 845
```

```
Glu Ala Leu Glu Leu Lys Asp Ala Gln Ala Gly Lys Glu Pro Gly Gly
    850                 855                 860

Ser Gly Gly Ala Pro His His His His His His
865                 870                 875


<210> SEQ ID NO 45
<211> LENGTH: 872
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Asp Ile Gln Met Thr Gln Ser Pro Ser Ser Leu Ser Ala
        275                 280                 285

Ser Val Gly Asp Arg Val Thr Ile Thr Cys Arg Ala Ser Gln Asp Val
    290                 295                 300

Asn Thr Ala Val Ala Trp Tyr Gln Gln Lys Pro Gly Lys Ala Pro Lys
305                 310                 315                 320

Leu Leu Ile Tyr Ser Ala Ser Phe Leu Tyr Ser Gly Val Pro Ser Arg
                325                 330                 335
```

```
Phe Ser Gly Ser Arg Ser Gly Thr Asp Phe Thr Leu Thr Ile Ser Ser
            340                 345                 350

Leu Gln Pro Glu Asp Phe Ala Thr Tyr Tyr Cys Gln Gln His Tyr Thr
        355                 360                 365

Thr Pro Pro Thr Phe Gly Gln Gly Thr Lys Val Glu Ile Lys Arg Gly
    370                 375                 380

Gly Gly Gly Ser Gly Gly Gly Gly Ser Gly Gly Gly Gly Ser Gly Gly
385                 390                 395                 400

Gly Gly Ser Gly Gly Gly Gly Ser Gly Gly Gly Gly Ser Glu Val Gln
                405                 410                 415

Leu Val Glu Ser Gly Gly Gly Leu Val Gln Pro Gly Gly Ser Leu Arg
            420                 425                 430

Leu Ser Cys Ala Ala Ser Gly Phe Asn Ile Lys Asp Thr Tyr Ile His
        435                 440                 445

Trp Val Arg Gln Ala Pro Gly Lys Gly Leu Glu Trp Val Ala Arg Ile
    450                 455                 460

Tyr Pro Thr Asn Gly Tyr Thr Arg Tyr Ala Asp Ser Val Lys Gly Arg
465                 470                 475                 480

Phe Thr Ile Ser Ala Asp Thr Ser Lys Asn Thr Ala Tyr Leu Gln Met
                485                 490                 495

Asn Ser Leu Arg Ala Glu Asp Thr Ala Val Tyr Tyr Cys Ser Arg Trp
            500                 505                 510

Gly Gly Asp Gly Phe Tyr Ala Met Asp Tyr Trp Gly Gln Gly Thr Leu
        515                 520                 525

Val Thr Val Ser Ser Gly Gly Gly Gly Ser Gly Gly Gly Gly Ser Gly
    530                 535                 540

Gly Gly Gly Ser Gly Gly Gly Gly Ser Gln Val Gln Leu Val Gln Ser
545                 550                 555                 560

Gly Gly Gly Val Val Gln Pro Gly Arg Ser Leu Arg Leu Ser Cys Lys
                565                 570                 575

Ala Ser Gly Tyr Thr Phe Thr Arg Tyr Thr Met His Trp Val Arg Gln
            580                 585                 590

Ala Pro Gly Lys Cys Leu Glu Trp Ile Gly Tyr Ile Asn Pro Ser Arg
        595                 600                 605

Gly Tyr Thr Asn Tyr Asn Gln Lys Phe Lys Asp Arg Phe Thr Ile Ser
    610                 615                 620

Arg Asp Asn Ser Lys Asn Thr Ala Phe Leu Gln Met Asp Ser Leu Arg
625                 630                 635                 640

Pro Glu Asp Thr Gly Val Tyr Phe Cys Ala Arg Tyr Tyr Asp Asp His
                645                 650                 655

Tyr Ser Leu Asp Tyr Trp Gly Gln Gly Thr Pro Val Thr Val Ser Ser
            660                 665                 670

Gly Gly Gly Gly Ser Gly Gly Gly Gly Ser Gly Gly Gly Gly Ser Gly
        675                 680                 685

Gly Gly Gly Ser Gly Gly Gly Gly Ser Gly Gly Gly Gly Ser Asp Ile
    690                 695                 700

Gln Met Thr Gln Ser Pro Ser Ser Leu Ser Ala Ser Val Gly Asp Arg
705                 710                 715                 720

Val Thr Ile Thr Cys Ser Ala Ser Ser Ser Val Ser Tyr Met Asn Trp
                725                 730                 735

Tyr Gln Gln Thr Pro Gly Lys Ala Pro Lys Arg Trp Ile Tyr Asp Thr
            740                 745                 750
```

```
Ser Lys Leu Ala Ser Gly Val Pro Ser Arg Phe Ser Gly Ser Gly Ser
        755                 760                 765

Gly Thr Asp Tyr Thr Phe Thr Ile Ser Ser Leu Gln Pro Glu Asp Ile
    770                 775                 780

Ala Thr Tyr Tyr Cys Gln Gln Trp Ser Ser Asn Pro Phe Thr Phe Gly
785                 790                 795                 800

Cys Gly Thr Lys Leu Gln Ile Thr Arg Thr Pro Leu Gly Asp Thr Thr
                805                 810                 815

His Thr Ser Gly Lys Pro Leu Asp Gly Glu Tyr Phe Thr Leu Gln Ile
            820                 825                 830

Arg Gly Arg Glu Arg Phe Glu Met Phe Arg Glu Leu Asn Glu Ala Leu
        835                 840                 845

Glu Leu Lys Asp Ala Gln Ala Gly Lys Glu Pro Gly Gly Ser Gly Gly
    850                 855                 860

Ala Pro His His His His His His
865                 870


<210> SEQ ID NO 46
<211> LENGTH: 872
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240
```

```
Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Asp Ile Gln Met Thr Gln Ser Pro Ser Ser Leu Ser Ala
        275                 280                 285

Ser Val Gly Asp Arg Val Thr Ile Thr Cys Arg Ala Ser Gln Asp Val
    290                 295                 300

Asn Thr Ala Val Ala Trp Tyr Gln Gln Lys Pro Gly Lys Ala Pro Lys
305                 310                 315                 320

Leu Leu Ile Tyr Ser Ala Ser Phe Leu Tyr Ser Gly Val Pro Ser Arg
                325                 330                 335

Phe Ser Gly Ser Arg Ser Gly Thr Asp Phe Thr Leu Thr Ile Ser Ser
            340                 345                 350

Leu Gln Pro Glu Asp Phe Ala Thr Tyr Tyr Cys Gln Gln His Tyr Thr
        355                 360                 365

Thr Pro Pro Thr Phe Gly Gln Gly Thr Lys Val Glu Ile Lys Arg Gly
    370                 375                 380

Gly Gly Gly Ser Gly Gly Gly Gly Ser Gly Gly Gly Gly Ser Gly Gly
385                 390                 395                 400

Gly Gly Ser Gly Gly Gly Gly Ser Gly Gly Gly Gly Ser Glu Val Gln
                405                 410                 415

Leu Val Glu Ser Gly Gly Gly Leu Val Gln Pro Gly Gly Ser Leu Arg
            420                 425                 430

Leu Ser Cys Ala Ala Ser Gly Phe Asn Ile Lys Asp Thr Tyr Ile His
        435                 440                 445

Trp Val Arg Gln Ala Pro Gly Lys Gly Leu Glu Trp Val Ala Arg Ile
    450                 455                 460

Tyr Pro Thr Asn Gly Tyr Thr Arg Tyr Ala Asp Ser Val Lys Gly Arg
465                 470                 475                 480

Phe Thr Ile Ser Ala Asp Thr Ser Lys Asn Thr Ala Tyr Leu Gln Met
                485                 490                 495

Asn Ser Leu Arg Ala Glu Asp Thr Ala Val Tyr Tyr Cys Ser Arg Trp
            500                 505                 510

Gly Gly Asp Gly Phe Tyr Ala Met Asp Tyr Trp Gly Gln Gly Thr Leu
        515                 520                 525

Val Thr Val Ser Ser Gly Gly Gly Gly Ser Gly Gly Gly Gly Ser Gly
    530                 535                 540

Gly Gly Gly Ser Gly Gly Gly Gly Ser Gln Val Gln Leu Val Gln Ser
545                 550                 555                 560

Gly Gly Gly Val Val Gln Pro Gly Arg Ser Leu Arg Leu Ser Cys Lys
                565                 570                 575

Ala Ser Gly Tyr Thr Phe Thr Arg Tyr Thr Met His Trp Val Arg Gln
            580                 585                 590

Ala Pro Gly Lys Cys Leu Glu Trp Ile Gly Tyr Ile Asn Pro Ser Arg
        595                 600                 605

Gly Tyr Thr Asn Tyr Asn Gln Lys Phe Lys Asp Arg Phe Thr Ile Ser
    610                 615                 620

Arg Asp Asn Ser Lys Asn Thr Ala Phe Leu Gln Met Asp Ser Leu Arg
625                 630                 635                 640

Pro Glu Asp Thr Gly Val Tyr Phe Cys Ala Arg Tyr Tyr Asp Asp His
                645                 650                 655
```

```
Tyr Ser Leu Asp Tyr Trp Gly Gln Gly Thr Pro Val Thr Val Ser Ser
            660                 665                 670

Gly Gly Gly Gly Ser Gly Gly Gly Gly Ser Gly Gly Gly Gly Ser Gly
        675                 680                 685

Gly Gly Gly Ser Gly Gly Gly Gly Ser Gly Gly Gly Gly Ser Asp Ile
    690                 695                 700

Gln Met Thr Gln Ser Pro Ser Ser Leu Ser Ala Ser Val Gly Asp Arg
705                 710                 715                 720

Val Thr Ile Thr Cys Ser Ala Ser Ser Ser Val Ser Tyr Met Asn Trp
                725                 730                 735

Tyr Gln Gln Thr Pro Gly Lys Ala Pro Lys Arg Trp Ile Tyr Asp Thr
            740                 745                 750

Ser Lys Leu Ala Ser Gly Val Pro Ser Arg Phe Ser Gly Ser Gly Ser
        755                 760                 765

Gly Thr Asp Tyr Thr Phe Thr Ile Ser Ser Leu Gln Pro Glu Asp Ile
    770                 775                 780

Ala Thr Tyr Tyr Cys Gln Gln Trp Ser Ser Asn Pro Phe Thr Phe Gly
785                 790                 795                 800

Cys Gly Thr Lys Leu Gln Ile Thr Arg Thr Pro Leu Gly Asp Thr Thr
                805                 810                 815

His Thr Ser Gly Lys Pro Leu Asp Gly Glu Tyr Phe Thr Leu Gln Ile
            820                 825                 830

Arg Gly Arg Glu Arg Phe Glu Met Phe Arg Glu Leu Asn Glu Ala Leu
        835                 840                 845

Glu Leu Lys Asp Ala Gln Ala Gly Lys Glu Pro Gly Gly Ser Gly Gly
    850                 855                 860

Ala Pro His His His His His His
865                 870
```

<210> SEQ ID NO 47
<211> LENGTH: 594
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

```
Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Ala Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140
```

```
Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Gln Val Gln Leu Val Gln Ser Gly Gly Gly Val Val Gln
        275                 280                 285

Pro Gly Arg Ser Leu Arg Leu Ser Cys Lys Ala Ser Gly Tyr Thr Phe
    290                 295                 300

Thr Arg Tyr Thr Met His Trp Val Arg Gln Ala Pro Gly Lys Cys Leu
305                 310                 315                 320

Glu Trp Ile Gly Tyr Ile Asn Pro Ser Arg Gly Tyr Thr Asn Tyr Asn
                325                 330                 335

Gln Lys Phe Lys Asp Arg Phe Thr Ile Ser Arg Asp Asn Ser Lys Asn
            340                 345                 350

Thr Ala Phe Leu Gln Met Asp Ser Leu Arg Pro Glu Asp Thr Gly Val
        355                 360                 365

Tyr Phe Cys Ala Arg Tyr Tyr Asp Asp His Tyr Ser Leu Asp Tyr Trp
    370                 375                 380

Gly Gln Gly Thr Pro Val Thr Val Ser Ser Gly Gly Gly Gly Ser Gly
385                 390                 395                 400

Gly Gly Gly Ser Gly Gly Gly Gly Ser Gly Gly Gly Gly Ser Gly Gly
                405                 410                 415

Gly Gly Ser Gly Gly Gly Gly Ser Asp Ile Gln Met Thr Gln Ser Pro
            420                 425                 430

Ser Ser Leu Ser Ala Ser Val Gly Asp Arg Val Thr Ile Thr Cys Ser
        435                 440                 445

Ala Ser Ser Ser Val Ser Tyr Met Asn Trp Tyr Gln Gln Thr Pro Gly
    450                 455                 460

Lys Ala Pro Lys Arg Trp Ile Tyr Asp Thr Ser Lys Leu Ala Ser Gly
465                 470                 475                 480

Val Pro Ser Arg Phe Ser Gly Ser Gly Ser Gly Thr Asp Tyr Thr Phe
                485                 490                 495

Thr Ile Ser Ser Leu Gln Pro Glu Asp Ile Ala Thr Tyr Tyr Cys Gln
            500                 505                 510

Gln Trp Ser Ser Asn Pro Phe Thr Phe Gly Cys Gly Thr Lys Leu Gln
        515                 520                 525

Ile Thr Arg Thr Pro Leu Gly Asp Thr Thr His Thr Ser Gly Lys Pro
    530                 535                 540

Leu Asp Gly Glu Tyr Phe Thr Leu Gln Ile Arg Gly Arg Glu Arg Phe
545                 550                 555                 560
```

```
Glu Met Phe Arg Glu Leu Asn Glu Ala Leu Glu Leu Lys Asp Ala Gln
                565                 570                 575

Ala Gly Lys Glu Pro Gly Gly Ser Gly Gly Ala Pro His His His His
            580                 585                 590

His His


<210> SEQ ID NO 48
<211> LENGTH: 872
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Ala Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Gln Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Asp Ile Gln Met Thr Gln Ser Pro Ser Ser Leu Ser Ala
        275                 280                 285

Ser Val Gly Asp Arg Val Thr Ile Thr Cys Arg Ala Ser Gln Asp Val
    290                 295                 300

Asn Thr Ala Val Ala Trp Tyr Gln Gln Lys Pro Gly Lys Ala Pro Lys
305                 310                 315                 320
```

```
Leu Leu Ile Tyr Ser Ala Ser Phe Leu Tyr Ser Gly Val Pro Ser Arg
                325                 330                 335

Phe Ser Gly Ser Arg Ser Gly Thr Asp Phe Thr Leu Thr Ile Ser Ser
            340                 345                 350

Leu Gln Pro Glu Asp Phe Ala Thr Tyr Tyr Cys Gln Gln His Tyr Thr
        355                 360                 365

Thr Pro Pro Thr Phe Gly Gln Gly Thr Lys Val Glu Ile Lys Arg Gly
    370                 375                 380

Gly Gly Gly Ser Gly Gly Gly Gly Ser Gly Gly Gly Gly Ser Gly Gly
385                 390                 395                 400

Gly Gly Ser Gly Gly Gly Gly Ser Gly Gly Gly Gly Ser Glu Val Gln
                405                 410                 415

Leu Val Glu Ser Gly Gly Gly Leu Val Gln Pro Gly Gly Ser Leu Arg
            420                 425                 430

Leu Ser Cys Ala Ala Ser Gly Phe Asn Ile Lys Asp Thr Tyr Ile His
        435                 440                 445

Trp Val Arg Gln Ala Pro Gly Lys Gly Leu Glu Trp Val Ala Arg Ile
    450                 455                 460

Tyr Pro Thr Asn Gly Tyr Thr Arg Tyr Ala Asp Ser Val Lys Gly Arg
465                 470                 475                 480

Phe Thr Ile Ser Ala Asp Thr Ser Lys Asn Thr Ala Tyr Leu Gln Met
                485                 490                 495

Asn Ser Leu Arg Ala Glu Asp Thr Ala Val Tyr Tyr Cys Ser Arg Trp
            500                 505                 510

Gly Gly Asp Gly Phe Tyr Ala Met Asp Tyr Trp Gly Gln Gly Thr Leu
        515                 520                 525

Val Thr Val Ser Ser Gly Gly Gly Gly Ser Gly Gly Gly Gly Ser Gly
    530                 535                 540

Gly Gly Gly Ser Gly Gly Gly Gly Ser Gln Val Gln Leu Val Gln Ser
545                 550                 555                 560

Gly Gly Gly Val Val Gln Pro Gly Arg Ser Leu Arg Leu Ser Cys Lys
                565                 570                 575

Ala Ser Gly Tyr Thr Phe Thr Arg Tyr Thr Met His Trp Val Arg Gln
            580                 585                 590

Ala Pro Gly Lys Cys Leu Glu Trp Ile Gly Tyr Ile Asn Pro Ser Arg
        595                 600                 605

Gly Tyr Thr Asn Tyr Asn Gln Lys Phe Lys Asp Arg Phe Thr Ile Ser
    610                 615                 620

Arg Asp Asn Ser Lys Asn Thr Ala Phe Leu Gln Met Asp Ser Leu Arg
625                 630                 635                 640

Pro Glu Asp Thr Gly Val Tyr Phe Cys Ala Arg Tyr Tyr Asp Asp His
                645                 650                 655

Tyr Ser Leu Asp Tyr Trp Gly Gln Gly Thr Pro Val Thr Val Ser Ser
            660                 665                 670

Gly Gly Gly Gly Ser Gly Gly Gly Gly Ser Gly Gly Gly Gly Ser Gly
        675                 680                 685

Gly Gly Gly Ser Gly Gly Gly Gly Ser Gly Gly Gly Gly Ser Asp Ile
    690                 695                 700

Gln Met Thr Gln Ser Pro Ser Ser Leu Ser Ala Ser Val Gly Asp Arg
705                 710                 715                 720

Val Thr Ile Thr Cys Ser Ala Ser Ser Ser Val Ser Tyr Met Asn Trp
                725                 730                 735

Tyr Gln Gln Thr Pro Gly Lys Ala Pro Lys Arg Trp Ile Tyr Asp Thr
```

```
            740                 745                 750

Ser Lys Leu Ala Ser Gly Val Pro Ser Arg Phe Ser Gly Ser Gly Ser
        755                 760                 765

Gly Thr Asp Tyr Thr Phe Thr Ile Ser Ser Leu Gln Pro Glu Asp Ile
    770                 775                 780

Ala Thr Tyr Tyr Cys Gln Gln Trp Ser Ser Asn Pro Phe Thr Phe Gly
785                 790                 795                 800

Cys Gly Thr Lys Leu Gln Ile Thr Arg Thr Pro Leu Gly Asp Thr Thr
                805                 810                 815

His Thr Ser Gly Lys Pro Leu Asp Gly Glu Tyr Phe Thr Leu Gln Ile
            820                 825                 830

Arg Gly Arg Glu Arg Phe Glu Met Phe Arg Glu Leu Asn Glu Ala Leu
        835                 840                 845

Glu Leu Lys Asp Ala Gln Ala Gly Lys Glu Pro Gly Gly Ser Gly Gly
    850                 855                 860

Ala Pro His His His His His His
865                 870


<210> SEQ ID NO 49
<211> LENGTH: 872
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220
```

```
Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Asp Ile Gln Met Thr Gln Ser Pro Ser Ser Leu Ser Ala
        275                 280                 285

Ser Val Gly Asp Arg Val Thr Ile Thr Cys Arg Ala Ser Gln Asp Val
    290                 295                 300

Asn Thr Ala Val Ala Trp Tyr Gln Gln Lys Pro Gly Lys Ala Pro Lys
305                 310                 315                 320

Leu Leu Ile Tyr Ser Ala Ser Phe Leu Tyr Ser Gly Val Pro Ser Arg
                325                 330                 335

Phe Ser Gly Ser Arg Ser Gly Thr Asp Phe Thr Leu Thr Ile Ser Ser
            340                 345                 350

Leu Gln Pro Glu Asp Phe Ala Thr Tyr Tyr Cys Gln Gln His Tyr Thr
        355                 360                 365

Thr Pro Pro Thr Phe Gly Gln Gly Thr Lys Val Glu Ile Lys Arg Gly
    370                 375                 380

Gly Gly Gly Ser Gly Gly Gly Gly Ser Gly Gly Gly Gly Ser Gly Gly
385                 390                 395                 400

Gly Gly Ser Gly Gly Gly Gly Ser Gly Gly Gly Gly Ser Glu Val Gln
                405                 410                 415

Leu Val Glu Ser Gly Gly Gly Leu Val Gln Pro Gly Gly Ser Leu Arg
            420                 425                 430

Leu Ser Cys Ala Ala Ser Gly Phe Asn Ile Lys Asp Thr Tyr Ile His
        435                 440                 445

Trp Val Arg Gln Ala Pro Gly Lys Gly Leu Glu Trp Val Ala Arg Ile
    450                 455                 460

Tyr Pro Thr Asn Gly Tyr Thr Arg Tyr Ala Asp Ser Val Lys Gly Arg
465                 470                 475                 480

Phe Thr Ile Ser Ala Asp Thr Ser Lys Asn Thr Ala Tyr Leu Gln Met
                485                 490                 495

Asn Ser Leu Arg Ala Glu Asp Thr Ala Val Tyr Tyr Cys Ser Arg Trp
            500                 505                 510

Gly Gly Asp Gly Phe Tyr Ala Met Asp Tyr Trp Gly Gln Gly Thr Leu
        515                 520                 525

Val Thr Val Ser Ser Gly Gly Gly Gly Ser Gly Gly Gly Gly Ser Gly
    530                 535                 540

Gly Gly Gly Ser Gly Gly Gly Gly Ser Gln Val Gln Leu Gln Gln Ser
545                 550                 555                 560

Gly Ala Glu Val Ala Lys Pro Gly Ala Ser Val Lys Val Ser Cys Lys
                565                 570                 575

Ala Ser Gly Tyr Thr Phe Thr Arg Tyr Thr Met His Trp Val Arg Gln
            580                 585                 590

Ala Pro Gly Gln Gly Leu Glu Trp Met Gly Tyr Ile Asn Pro Ser Arg
        595                 600                 605

Gly Tyr Thr Asn Tyr Asn Gln Lys Phe Lys Asp Arg Ala Thr Leu Thr
    610                 615                 620

Arg Asp Lys Ser Ile Ser Thr Ala Tyr Met Glu Leu Ser Arg Leu Arg
625                 630                 635                 640

Ser Asp Asp Thr Ala Val Tyr Tyr Cys Ala Arg Tyr Tyr Asp Asp His
```

```
                645                 650                 655

Tyr Ser Leu Asp Tyr Trp Gly Gln Gly Thr Thr Leu Thr Val Ser Ser
            660                 665                 670

Gly Gly Gly Gly Ser Gly Gly Gly Gly Ser Gly Gly Gly Gly Ser Gly
        675                 680                 685

Gly Gly Gly Ser Gly Gly Gly Gly Ser Gly Gly Gly Gly Ser Asp Ile
    690                 695                 700

Gln Met Thr Gln Ser Pro Ser Ser Leu Ser Ala Ser Val Gly Asp Arg
705                 710                 715                 720

Val Thr Met Thr Cys Ser Ala Ser Ser Ser Val Ser Tyr Met Asn Trp
                725                 730                 735

Tyr Gln Gln Lys Pro Gly Lys Ala Pro Lys Leu Leu Ile Tyr Asp Thr
            740                 745                 750

Ser Lys Leu Ala Ser Gly Val Pro Ser Arg Phe Ser Gly Ser Gly Ser
        755                 760                 765

Gly Thr Asp Phe Thr Leu Thr Ile Ser Ser Met Gln Pro Glu Asp Phe
    770                 775                 780

Ala Thr Tyr Tyr Cys Gln Gln Trp Ser Ser Asn Pro Phe Thr Phe Gly
785                 790                 795                 800

Ser Gly Thr Lys Leu Glu Ile Asn Arg Thr Pro Leu Gly Asp Thr Thr
                805                 810                 815

His Thr Ser Gly Lys Pro Leu Asp Gly Glu Tyr Phe Thr Leu Gln Ile
            820                 825                 830

Arg Gly Arg Glu Arg Phe Glu Met Phe Arg Glu Leu Asn Glu Ala Leu
        835                 840                 845

Glu Leu Lys Asp Ala Gln Ala Gly Lys Glu Pro Gly Gly Ser Gly Gly
    850                 855                 860

Ala Pro His His His His His His
865                 870


<210> SEQ ID NO 50
<211> LENGTH: 872
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125
```

```
Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Asp Ile Gln Met Thr Gln Ser Pro Ser Ser Leu Ser Ala
        275                 280                 285

Ser Val Gly Asp Arg Val Thr Ile Thr Cys Arg Ala Ser Gln Asp Val
    290                 295                 300

Asn Thr Ala Val Ala Trp Tyr Gln Gln Lys Pro Gly Lys Ala Pro Lys
305                 310                 315                 320

Leu Leu Ile Tyr Ser Ala Ser Phe Leu Tyr Ser Gly Val Pro Ser Arg
                325                 330                 335

Phe Ser Gly Ser Arg Ser Gly Thr Asp Phe Thr Leu Thr Ile Ser Ser
            340                 345                 350

Leu Gln Pro Glu Asp Phe Ala Thr Tyr Tyr Cys Gln Gln His Tyr Thr
        355                 360                 365

Thr Pro Pro Thr Phe Gly Gln Gly Thr Lys Val Glu Ile Lys Arg Gly
    370                 375                 380

Gly Gly Gly Ser Gly Gly Gly Gly Ser Gly Gly Gly Gly Ser Gly Gly
385                 390                 395                 400

Gly Gly Ser Gly Gly Gly Gly Ser Gly Gly Gly Gly Ser Glu Val Gln
                405                 410                 415

Leu Val Glu Ser Gly Gly Gly Leu Val Gln Pro Gly Gly Ser Leu Arg
            420                 425                 430

Leu Ser Cys Ala Ala Ser Gly Phe Asn Ile Lys Asp Thr Tyr Ile His
        435                 440                 445

Trp Val Arg Gln Ala Pro Gly Lys Gly Leu Glu Trp Val Ala Arg Ile
    450                 455                 460

Tyr Pro Thr Asn Gly Tyr Thr Arg Tyr Ala Asp Ser Val Lys Gly Arg
465                 470                 475                 480

Phe Thr Ile Ser Ala Asp Thr Ser Lys Asn Thr Ala Tyr Leu Gln Met
                485                 490                 495

Asn Ser Leu Arg Ala Glu Asp Thr Ala Val Tyr Tyr Cys Ser Arg Trp
            500                 505                 510

Gly Gly Asp Gly Phe Tyr Ala Met Asp Tyr Trp Gly Gln Gly Thr Leu
        515                 520                 525

Val Thr Val Ser Ser Gly Gly Gly Gly Ser Gly Gly Gly Gly Ser Gly
    530                 535                 540

Gly Gly Gly Ser Gly Gly Gly Gly Ser Gln Val Gln Leu Gln Gln Ser
```

```
545                 550                 555                 560

Gly Ala Glu Val Ala Lys Pro Gly Ala Ser Val Lys Val Ser Cys Lys
                565                 570                 575

Ala Ser Gly Tyr Thr Phe Thr Arg Tyr Thr Met His Trp Val Arg Gln
            580                 585                 590

Ala Pro Gly Gln Gly Leu Glu Trp Met Gly Tyr Ile Asn Pro Ser Arg
        595                 600                 605

Gly Tyr Thr Asn Tyr Asn Gln Lys Phe Lys Asp Arg Ala Thr Leu Thr
    610                 615                 620

Arg Asp Lys Ser Ile Ser Thr Ala Tyr Met Glu Leu Ser Arg Leu Arg
625                 630                 635                 640

Ser Asp Asp Thr Ala Val Tyr Tyr Cys Ala Arg Tyr Tyr Asp Asp His
                645                 650                 655

Tyr Ser Leu Asp Tyr Trp Gly Gln Gly Thr Thr Leu Thr Val Ser Ser
            660                 665                 670

Gly Gly Gly Gly Ser Gly Gly Gly Gly Ser Gly Gly Gly Gly Ser Gly
        675                 680                 685

Gly Gly Gly Ser Gly Gly Gly Gly Ser Gly Gly Gly Gly Ser Asp Ile
    690                 695                 700

Gln Met Thr Gln Ser Pro Ser Ser Leu Ser Ala Ser Val Gly Asp Arg
705                 710                 715                 720

Val Thr Met Thr Cys Ser Ala Ser Ser Ser Val Ser Tyr Met Asn Trp
                725                 730                 735

Tyr Gln Gln Lys Pro Gly Lys Ala Pro Lys Leu Leu Ile Tyr Asp Thr
            740                 745                 750

Ser Lys Leu Ala Ser Gly Val Pro Ser Arg Phe Ser Gly Ser Gly Ser
        755                 760                 765

Gly Thr Asp Phe Thr Leu Thr Ile Ser Ser Met Gln Pro Glu Asp Phe
    770                 775                 780

Ala Thr Tyr Tyr Cys Gln Gln Trp Ser Ser Asn Pro Phe Thr Phe Gly
785                 790                 795                 800

Ser Gly Thr Lys Leu Glu Ile Asn Arg Thr Pro Leu Gly Asp Thr Thr
                805                 810                 815

His Thr Ser Gly Lys Pro Leu Asp Gly Glu Tyr Phe Thr Leu Gln Ile
            820                 825                 830

Arg Gly Arg Glu Arg Phe Glu Met Phe Arg Glu Leu Asn Glu Ala Leu
        835                 840                 845

Glu Leu Lys Asp Ala Gln Ala Gly Lys Glu Pro Gly Gly Ser Gly Gly
    850                 855                 860

Ala Pro His His His His His His
865                 870


<210> SEQ ID NO 51
<211> LENGTH: 872
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30
```

```
Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Ala Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Asp Ile Gln Met Thr Gln Ser Pro Ser Ser Leu Ser Ala
        275                 280                 285

Ser Val Gly Asp Arg Val Thr Ile Thr Cys Arg Ala Ser Gln Asp Val
    290                 295                 300

Asn Thr Ala Val Ala Trp Tyr Gln Gln Lys Pro Gly Lys Ala Pro Lys
305                 310                 315                 320

Leu Leu Ile Tyr Ser Ala Ser Phe Leu Tyr Ser Gly Val Pro Ser Arg
                325                 330                 335

Phe Ser Gly Ser Arg Ser Gly Thr Asp Phe Thr Leu Thr Ile Ser Ser
            340                 345                 350

Leu Gln Pro Glu Asp Phe Ala Thr Tyr Tyr Cys Gln Gln His Tyr Thr
        355                 360                 365

Thr Pro Pro Thr Phe Gly Gln Gly Thr Lys Val Glu Ile Lys Arg Gly
    370                 375                 380

Gly Gly Gly Ser Gly Gly Gly Gly Ser Gly Gly Gly Gly Ser Gly Gly
385                 390                 395                 400

Gly Gly Ser Gly Gly Gly Gly Ser Gly Gly Gly Gly Ser Glu Val Gln
                405                 410                 415

Leu Val Glu Ser Gly Gly Gly Leu Val Gln Pro Gly Gly Ser Leu Arg
            420                 425                 430

Leu Ser Cys Ala Ala Ser Gly Phe Asn Ile Lys Asp Thr Tyr Ile His
        435                 440                 445

Trp Val Arg Gln Ala Pro Gly Lys Gly Leu Glu Trp Val Ala Arg Ile
```

```
    450                 455                 460

Tyr Pro Thr Asn Gly Tyr Thr Arg Tyr Ala Asp Ser Val Lys Gly Arg
465                 470                 475                 480

Phe Thr Ile Ser Ala Asp Thr Ser Lys Asn Thr Ala Tyr Leu Gln Met
                485                 490                 495

Asn Ser Leu Arg Ala Glu Asp Thr Ala Val Tyr Tyr Cys Ser Arg Trp
            500                 505                 510

Gly Gly Asp Gly Phe Tyr Ala Met Asp Tyr Trp Gly Gln Gly Thr Leu
        515                 520                 525

Val Thr Val Ser Ser Gly Gly Gly Gly Ser Gly Gly Gly Gly Ser Gly
    530                 535                 540

Gly Gly Gly Ser Gly Gly Gly Gly Ser Gln Val Gln Leu Gln Gln Ser
545                 550                 555                 560

Gly Ala Glu Val Ala Lys Pro Gly Ala Ser Val Lys Val Ser Cys Lys
                565                 570                 575

Ala Ser Gly Tyr Thr Phe Thr Arg Tyr Thr Met His Trp Val Arg Gln
            580                 585                 590

Ala Pro Gly Gln Gly Leu Glu Trp Met Gly Tyr Ile Asn Pro Ser Arg
        595                 600                 605

Gly Tyr Thr Asn Tyr Asn Gln Lys Phe Lys Asp Arg Ala Thr Leu Thr
    610                 615                 620

Arg Asp Lys Ser Ile Ser Thr Ala Tyr Met Glu Leu Ser Arg Leu Arg
625                 630                 635                 640

Ser Asp Asp Thr Ala Val Tyr Tyr Cys Ala Arg Tyr Tyr Asp Asp His
                645                 650                 655

Tyr Ser Leu Asp Tyr Trp Gly Gln Gly Thr Thr Leu Thr Val Ser Ser
            660                 665                 670

Gly Gly Gly Gly Ser Gly Gly Gly Gly Ser Gly Gly Gly Gly Ser Gly
        675                 680                 685

Gly Gly Gly Ser Gly Gly Gly Gly Ser Gly Gly Gly Gly Ser Asp Ile
    690                 695                 700

Gln Met Thr Gln Ser Pro Ser Ser Leu Ser Ala Ser Val Gly Asp Arg
705                 710                 715                 720

Val Thr Met Thr Cys Ser Ala Ser Ser Ser Val Ser Tyr Met Asn Trp
                725                 730                 735

Tyr Gln Gln Lys Pro Gly Lys Ala Pro Lys Leu Leu Ile Tyr Asp Thr
            740                 745                 750

Ser Lys Leu Ala Ser Gly Val Pro Ser Arg Phe Ser Gly Ser Gly Ser
        755                 760                 765

Gly Thr Asp Phe Thr Leu Thr Ile Ser Ser Met Gln Pro Glu Asp Phe
    770                 775                 780

Ala Thr Tyr Tyr Cys Gln Gln Trp Ser Ser Asn Pro Phe Thr Phe Gly
785                 790                 795                 800

Ser Gly Thr Lys Leu Glu Ile Asn Arg Thr Pro Leu Gly Asp Thr Thr
                805                 810                 815

His Thr Ser Gly Lys Pro Leu Asp Gly Glu Tyr Phe Thr Leu Gln Ile
            820                 825                 830

Arg Gly Arg Glu Arg Phe Glu Met Phe Arg Glu Leu Asn Glu Ala Leu
        835                 840                 845

Glu Leu Lys Asp Ala Gln Ala Gly Lys Glu Pro Gly Gly Ser Gly Gly
    850                 855                 860

Ala Pro His His His His His His
865                 870
```

<210> SEQ ID NO 52
<211> LENGTH: 872
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

```
Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Ala Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Gln Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Asp Ile Gln Met Thr Gln Ser Pro Ser Ser Leu Ser Ala
        275                 280                 285

Ser Val Gly Asp Arg Val Thr Ile Thr Cys Arg Ala Ser Gln Asp Val
    290                 295                 300

Asn Thr Ala Val Ala Trp Tyr Gln Gln Lys Pro Gly Lys Ala Pro Lys
305                 310                 315                 320

Leu Leu Ile Tyr Ser Ala Ser Phe Leu Tyr Ser Gly Val Pro Ser Arg
                325                 330                 335

Phe Ser Gly Ser Arg Ser Gly Thr Asp Phe Thr Leu Thr Ile Ser Ser
            340                 345                 350

Leu Gln Pro Glu Asp Phe Ala Thr Tyr Tyr Cys Gln Gln His Tyr Thr
```

```
        355                 360                 365

Thr Pro Pro Thr Phe Gly Gln Gly Thr Lys Val Glu Ile Lys Arg Gly
    370                 375                 380

Gly Gly Gly Ser Gly Gly Gly Gly Ser Gly Gly Gly Gly Ser Gly Gly
385                 390                 395                 400

Gly Gly Ser Gly Gly Gly Gly Ser Gly Gly Gly Gly Ser Glu Val Gln
                405                 410                 415

Leu Val Glu Ser Gly Gly Gly Leu Val Gln Pro Gly Gly Ser Leu Arg
            420                 425                 430

Leu Ser Cys Ala Ala Ser Gly Phe Asn Ile Lys Asp Thr Tyr Ile His
        435                 440                 445

Trp Val Arg Gln Ala Pro Gly Lys Gly Leu Glu Trp Val Ala Arg Ile
    450                 455                 460

Tyr Pro Thr Asn Gly Tyr Thr Arg Tyr Ala Asp Ser Val Lys Gly Arg
465                 470                 475                 480

Phe Thr Ile Ser Ala Asp Thr Ser Lys Asn Thr Ala Tyr Leu Gln Met
                485                 490                 495

Asn Ser Leu Arg Ala Glu Asp Thr Ala Val Tyr Tyr Cys Ser Arg Trp
            500                 505                 510

Gly Gly Asp Gly Phe Tyr Ala Met Asp Tyr Trp Gly Gln Gly Thr Leu
        515                 520                 525

Val Thr Val Ser Ser Gly Gly Gly Gly Ser Gly Gly Gly Gly Ser Gly
    530                 535                 540

Gly Gly Gly Ser Gly Gly Gly Gly Ser Gln Val Gln Leu Gln Gln Ser
545                 550                 555                 560

Gly Ala Glu Val Ala Lys Pro Gly Ala Ser Val Lys Val Ser Cys Lys
                565                 570                 575

Ala Ser Gly Tyr Thr Phe Thr Arg Tyr Thr Met His Trp Val Arg Gln
            580                 585                 590

Ala Pro Gly Gln Gly Leu Glu Trp Met Gly Tyr Ile Asn Pro Ser Arg
        595                 600                 605

Gly Tyr Thr Asn Tyr Asn Gln Lys Phe Lys Asp Arg Ala Thr Leu Thr
    610                 615                 620

Arg Asp Lys Ser Ile Ser Thr Ala Tyr Met Glu Leu Ser Arg Leu Arg
625                 630                 635                 640

Ser Asp Asp Thr Ala Val Tyr Tyr Cys Ala Arg Tyr Tyr Asp Asp His
                645                 650                 655

Tyr Ser Leu Asp Tyr Trp Gly Gln Gly Thr Thr Leu Thr Val Ser Ser
            660                 665                 670

Gly Gly Gly Gly Ser Gly Gly Gly Gly Ser Gly Gly Gly Gly Ser Gly
        675                 680                 685

Gly Gly Gly Ser Gly Gly Gly Gly Ser Gly Gly Gly Gly Ser Asp Ile
    690                 695                 700

Gln Met Thr Gln Ser Pro Ser Ser Leu Ser Ala Ser Val Gly Asp Arg
705                 710                 715                 720

Val Thr Met Thr Cys Ser Ala Ser Ser Ser Val Ser Tyr Met Asn Trp
                725                 730                 735

Tyr Gln Gln Lys Pro Gly Lys Ala Pro Lys Leu Leu Ile Tyr Asp Thr
            740                 745                 750

Ser Lys Leu Ala Ser Gly Val Pro Ser Arg Phe Ser Gly Ser Gly Ser
        755                 760                 765

Gly Thr Asp Phe Thr Leu Thr Ile Ser Ser Met Gln Pro Glu Asp Phe
    770                 775                 780
```

Ala Thr Tyr Tyr Cys Gln Gln Trp Ser Ser Asn Pro Phe Thr Phe Gly
785 790 795 800

Ser Gly Thr Lys Leu Glu Ile Asn Arg Thr Pro Leu Gly Asp Thr Thr
805 810 815

His Thr Ser Gly Lys Pro Leu Asp Gly Glu Tyr Phe Thr Leu Gln Ile
820 825 830

Arg Gly Arg Glu Arg Phe Glu Met Phe Arg Glu Leu Asn Glu Ala Leu
835 840 845

Glu Leu Lys Asp Ala Gln Ala Gly Lys Glu Pro Gly Gly Ser Gly Gly
850 855 860

Ala Pro His His His His His His
865 870

<210> SEQ ID NO 53
<211> LENGTH: 872
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

Glu Val Gln Leu Val Glu Ser Gly Gly Gly Leu Val Lys Pro Gly Gly
1 5 10 15

Ser Leu Arg Leu Ser Cys Ala Ala Ser Gly Phe Ala Phe Ser Thr Tyr
20 25 30

Asp Met Ser Trp Val Arg Gln Ala Pro Gly Lys Gly Leu Glu Trp Val
35 40 45

Ser Thr Ile Ser Ser Gly Gly Ser Tyr Thr Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Pro Thr Thr Val Val Pro Phe Ala Tyr Trp Gly Gln Gly Thr Leu
100 105 110

Val Thr Val Ser Ala Gly Gly Gly Gly Ser Gly Gly Gly Gly Ser Gly
115 120 125

Gly Gly Gly Ser Gly Gly Gly Gly Ser Gly Gly Gly Gly Ser Gly Gly
130 135 140

Gly Gly Ser Asp Ile Gln Met Thr Gln Ser Pro Ser Ser Leu Ser Ala
145 150 155 160

Ser Val Gly Asp Arg Val Thr Ile Thr Cys Lys Ala Ser Gln Asn Val
165 170 175

Arg Thr Val Val Ala Trp Tyr Gln Gln Lys Pro Gly Lys Ala Pro Lys
180 185 190

Thr Leu Ile Tyr Leu Ala Ser Asn Arg His Thr Gly Val Pro Ser Arg
195 200 205

Phe Ser Gly Ser Gly Ser Gly Thr Glu Phe Thr Leu Thr Ile Ser Asn
210 215 220

Leu Gln Pro Glu Asp Phe Ala Thr Tyr Tyr Cys Leu Gln His Trp Ser
225 230 235 240

Tyr Pro Leu Thr Phe Gly Ser Gly Thr Lys Leu Glu Val Lys Arg Gly
245 250 255

Gly Gly Gly Ser Gly Gly Gly Gly Ser Gly Gly Gly Gly Ser Gly Gly

```
            260                 265                 270

Gly Gly Ser Asp Ile Gln Met Thr Gln Ser Pro Ser Ser Leu Ser Ala
        275                 280                 285

Ser Val Gly Asp Arg Val Thr Ile Thr Cys Arg Ala Ser Gln Asp Val
    290                 295                 300

Asn Thr Ala Val Ala Trp Tyr Gln Gln Lys Pro Gly Lys Ala Pro Lys
305                 310                 315                 320

Leu Leu Ile Tyr Ser Ala Ser Phe Leu Tyr Ser Gly Val Pro Ser Arg
                325                 330                 335

Phe Ser Gly Ser Arg Ser Gly Thr Asp Phe Thr Leu Thr Ile Ser Ser
            340                 345                 350

Leu Gln Pro Glu Asp Phe Ala Thr Tyr Tyr Cys Gln Gln His Tyr Thr
        355                 360                 365

Thr Pro Pro Thr Phe Gly Gln Gly Thr Lys Val Glu Ile Lys Arg Gly
    370                 375                 380

Gly Gly Gly Ser Gly Gly Gly Gly Ser Gly Gly Gly Gly Ser Gly Gly
385                 390                 395                 400

Gly Gly Ser Gly Gly Gly Gly Ser Gly Gly Gly Gly Ser Glu Val Gln
                405                 410                 415

Leu Val Glu Ser Gly Gly Gly Leu Val Gln Pro Gly Gly Ser Leu Arg
            420                 425                 430

Leu Ser Cys Ala Ala Ser Gly Phe Asn Ile Lys Asp Thr Tyr Ile His
        435                 440                 445

Trp Val Arg Gln Ala Pro Gly Lys Gly Leu Glu Trp Val Ala Arg Ile
    450                 455                 460

Tyr Pro Thr Asn Gly Tyr Thr Arg Tyr Ala Asp Ser Val Lys Gly Arg
465                 470                 475                 480

Phe Thr Ile Ser Ala Asp Thr Ser Lys Asn Thr Ala Tyr Leu Gln Met
                485                 490                 495

Asn Ser Leu Arg Ala Glu Asp Thr Ala Val Tyr Tyr Cys Ser Arg Trp
            500                 505                 510

Gly Gly Asp Gly Phe Tyr Ala Met Asp Tyr Trp Gly Gln Gly Thr Leu
        515                 520                 525

Val Thr Val Ser Ser Gly Gly Gly Gly Ser Gly Gly Gly Gly Ser Gly
    530                 535                 540

Gly Gly Gly Ser Gly Gly Gly Gly Ser Gln Val Gln Leu Gln Gln Ser
545                 550                 555                 560

Gly Ala Glu Val Ala Lys Pro Gly Ala Ser Val Lys Val Ser Cys Lys
                565                 570                 575

Ala Ser Gly Tyr Thr Phe Thr Arg Tyr Thr Met His Trp Val Arg Gln
            580                 585                 590

Ala Pro Gly Gln Gly Leu Glu Trp Met Gly Tyr Ile Asn Pro Ser Arg
        595                 600                 605

Gly Tyr Thr Asn Tyr Asn Gln Lys Phe Lys Asp Arg Ala Thr Leu Thr
    610                 615                 620

Arg Asp Lys Ser Ile Ser Thr Ala Tyr Met Glu Leu Ser Arg Leu Arg
625                 630                 635                 640

Ser Asp Asp Thr Ala Val Tyr Tyr Cys Ala Arg Tyr Tyr Asp Asp His
                645                 650                 655

Tyr Ser Leu Asp Tyr Trp Gly Gln Gly Thr Thr Leu Thr Val Ser Ser
            660                 665                 670

Gly Gly Gly Gly Ser Gly Gly Gly Gly Ser Gly Gly Gly Gly Ser Gly
        675                 680                 685
```

```
Gly Gly Gly Ser Gly Gly Gly Gly Ser Gly Gly Gly Gly Ser Asp Ile
    690                 695                 700

Gln Met Thr Gln Ser Pro Ser Ser Leu Ser Ala Ser Val Gly Asp Arg
705                 710                 715                 720

Val Thr Ile Thr Cys Ser Ala Ser Ser Ser Val Ser Tyr Met Asn Trp
                725                 730                 735

Tyr Gln Gln Lys Pro Gly Lys Ala Pro Lys Arg Trp Ile Tyr Asp Thr
            740                 745                 750

Ser Lys Leu Ala Ser Gly Val Pro Ser Arg Phe Ser Gly Ser Gly Ser
        755                 760                 765

Gly Thr Asp Phe Thr Leu Thr Ile Ser Ser Leu Gln Pro Glu Asp Phe
    770                 775                 780

Ala Thr Tyr Tyr Cys Gln Gln Trp Ser Ser Asn Pro Phe Thr Phe Gly
785                 790                 795                 800

Ser Gly Thr Lys Leu Glu Ile Asn Arg Thr Pro Leu Gly Asp Thr Thr
                805                 810                 815

His Thr Ser Gly Lys Pro Leu Asp Gly Glu Tyr Phe Thr Leu Gln Ile
            820                 825                 830

Arg Gly Arg Glu Arg Phe Glu Met Phe Arg Glu Leu Asn Glu Ala Leu
        835                 840                 845

Glu Leu Lys Asp Ala Gln Ala Gly Lys Glu Pro Gly Gly Ser Gly Gly
    850                 855                 860

Ala Pro His His His His His His
865                 870


<210> SEQ ID NO 54
<211> LENGTH: 872
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
```

```
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Asp Ile Gln Met Thr Gln Ser Pro Ser Ser Leu Ser Ala
        275                 280                 285

Ser Val Gly Asp Arg Val Thr Ile Thr Cys Arg Ala Ser Gln Asp Val
    290                 295                 300

Asn Thr Ala Val Ala Trp Tyr Gln Gln Lys Pro Gly Lys Ala Pro Lys
305                 310                 315                 320

Leu Leu Ile Tyr Ser Ala Ser Phe Leu Tyr Ser Gly Val Pro Ser Arg
                325                 330                 335

Phe Ser Gly Ser Arg Ser Gly Thr Asp Phe Thr Leu Thr Ile Ser Ser
            340                 345                 350

Leu Gln Pro Glu Asp Phe Ala Thr Tyr Tyr Cys Gln Gln His Tyr Thr
        355                 360                 365

Thr Pro Pro Thr Phe Gly Gln Gly Thr Lys Val Glu Ile Lys Arg Gly
    370                 375                 380

Gly Gly Gly Ser Gly Gly Gly Gly Ser Gly Gly Gly Gly Ser Gly Gly
385                 390                 395                 400

Gly Gly Ser Gly Gly Gly Gly Ser Gly Gly Gly Gly Ser Glu Val Gln
                405                 410                 415

Leu Val Glu Ser Gly Gly Gly Leu Val Gln Pro Gly Gly Ser Leu Arg
            420                 425                 430

Leu Ser Cys Ala Ala Ser Gly Phe Asn Ile Lys Asp Thr Tyr Ile His
        435                 440                 445

Trp Val Arg Gln Ala Pro Gly Lys Gly Leu Glu Trp Val Ala Arg Ile
    450                 455                 460

Tyr Pro Thr Asn Gly Tyr Thr Arg Tyr Ala Asp Ser Val Lys Gly Arg
465                 470                 475                 480

Phe Thr Ile Ser Ala Asp Thr Ser Lys Asn Thr Ala Tyr Leu Gln Met
                485                 490                 495

Asn Ser Leu Arg Ala Glu Asp Thr Ala Val Tyr Tyr Cys Ser Arg Trp
            500                 505                 510

Gly Gly Asp Gly Phe Tyr Ala Met Asp Tyr Trp Gly Gln Gly Thr Leu
        515                 520                 525

Val Thr Val Ser Ser Gly Gly Gly Gly Ser Gly Gly Gly Gly Ser Gly
    530                 535                 540

Gly Gly Gly Ser Gly Gly Gly Gly Ser Gln Val Gln Leu Gln Gln Ser
545                 550                 555                 560

Gly Ala Glu Val Ala Lys Pro Gly Ala Ser Val Lys Val Ser Cys Lys
                565                 570                 575

Ala Ser Gly Tyr Thr Phe Thr Arg Tyr Thr Met His Trp Val Arg Gln
            580                 585                 590
```

Ala Pro Gly Gln Gly Leu Glu Trp Met Gly Tyr Ile Asn Pro Ser Arg
595 600 605

Gly Tyr Thr Asn Tyr Asn Gln Lys Phe Lys Asp Arg Ala Thr Leu Thr
610 615 620

Arg Asp Lys Ser Ile Ser Thr Ala Tyr Met Glu Leu Ser Arg Leu Arg
625 630 635 640

Ser Asp Asp Thr Ala Val Tyr Tyr Cys Ala Arg Tyr Tyr Asp Asp His
645 650 655

Tyr Ser Leu Asp Tyr Trp Gly Gln Gly Thr Thr Leu Thr Val Ser Ser
660 665 670

Gly Gly Gly Gly Ser Gly Gly Gly Gly Ser Gly Gly Gly Gly Ser Gly
675 680 685

Gly Gly Gly Ser Gly Gly Gly Gly Ser Gly Gly Gly Gly Ser Asp Ile
690 695 700

Gln Met Thr Gln Ser Pro Ser Ser Leu Ser Ala Ser Val Gly Asp Arg
705 710 715 720

Val Thr Ile Thr Cys Ser Ala Ser Ser Ser Val Ser Tyr Met Asn Trp
725 730 735

Tyr Gln Gln Lys Pro Gly Lys Ala Pro Lys Arg Trp Ile Tyr Asp Thr
740 745 750

Ser Lys Leu Ala Ser Gly Val Pro Ser Arg Phe Ser Gly Ser Gly Ser
755 760 765

Gly Thr Asp Phe Thr Leu Thr Ile Ser Ser Leu Gln Pro Glu Asp Phe
770 775 780

Ala Thr Tyr Tyr Cys Gln Gln Trp Ser Ser Asn Pro Phe Thr Phe Gly
785 790 795 800

Ser Gly Thr Lys Leu Glu Ile Asn Arg Thr Pro Leu Gly Asp Thr Thr
805 810 815

His Thr Ser Gly Lys Pro Leu Asp Gly Glu Tyr Phe Thr Leu Gln Ile
820 825 830

Arg Gly Arg Glu Arg Phe Glu Met Phe Arg Glu Leu Asn Glu Ala Leu
835 840 845

Glu Leu Lys Asp Ala Gln Ala Gly Lys Glu Pro Gly Gly Ser Gly Gly
850 855 860

Ala Pro His His His His His His
865 870

<210> SEQ ID NO 55
<211> LENGTH: 872
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

Glu Val Gln Leu Val Glu Ser Gly Gly Gly Leu Val Asp Pro Gly Gly
1 5 10 15

Ser Leu Arg Leu Ser Cys Ala Ala Ser Gly Phe Ala Phe Ser Thr Tyr
20 25 30

Asp Met Ser Trp Val Arg Gln Ala Pro Gly Lys Gly Leu Glu Trp Val
35 40 45

Ser Thr Ile Ser Ser Gly Gly Ser Tyr Thr Tyr Tyr Ala Asp Ser Val
50 55 60

Lys Gly Arg Phe Thr Ile Ser Arg Asp Asn Ala Ala Asn Ser Leu Tyr

```
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Asp Ile Gln Met Thr Gln Ser Pro Ser Ser Leu Ser Ala
        275                 280                 285

Ser Val Gly Asp Arg Val Thr Ile Thr Cys Arg Ala Ser Gln Asp Val
    290                 295                 300

Asn Thr Ala Val Ala Trp Tyr Gln Gln Lys Pro Gly Lys Ala Pro Lys
305                 310                 315                 320

Leu Leu Ile Tyr Ser Ala Ser Phe Leu Tyr Ser Gly Val Pro Ser Arg
                325                 330                 335

Phe Ser Gly Ser Arg Ser Gly Thr Asp Phe Thr Leu Thr Ile Ser Ser
            340                 345                 350

Leu Gln Pro Glu Asp Phe Ala Thr Tyr Tyr Cys Gln Gln His Tyr Thr
        355                 360                 365

Thr Pro Pro Thr Phe Gly Gln Gly Thr Lys Val Glu Ile Lys Arg Gly
    370                 375                 380

Gly Gly Gly Ser Gly Gly Gly Gly Ser Gly Gly Gly Gly Ser Gly Gly
385                 390                 395                 400

Gly Gly Ser Gly Gly Gly Gly Ser Gly Gly Gly Gly Ser Glu Val Gln
                405                 410                 415

Leu Val Glu Ser Gly Gly Gly Leu Val Gln Pro Gly Gly Ser Leu Arg
            420                 425                 430

Leu Ser Cys Ala Ala Ser Gly Phe Asn Ile Lys Asp Thr Tyr Ile His
        435                 440                 445

Trp Val Arg Gln Ala Pro Gly Lys Gly Leu Glu Trp Val Ala Arg Ile
    450                 455                 460

Tyr Pro Thr Asn Gly Tyr Thr Arg Tyr Ala Asp Ser Val Lys Gly Arg
465                 470                 475                 480

Phe Thr Ile Ser Ala Asp Thr Ser Lys Asn Thr Ala Tyr Leu Gln Met
                485                 490                 495
```

```
Asn Ser Leu Arg Ala Glu Asp Thr Ala Val Tyr Tyr Cys Ser Arg Trp
            500                 505                 510

Gly Gly Asp Gly Phe Tyr Ala Met Asp Tyr Trp Gly Gln Gly Thr Leu
        515                 520                 525

Val Thr Val Ser Ser Gly Gly Gly Gly Ser Gly Gly Gly Gly Ser Gly
    530                 535                 540

Gly Gly Gly Ser Gly Gly Gly Gly Ser Gln Val Gln Leu Gln Gln Ser
545                 550                 555                 560

Gly Ala Glu Val Ala Lys Pro Gly Ala Ser Val Lys Val Ser Cys Lys
                565                 570                 575

Ala Ser Gly Tyr Thr Phe Thr Arg Tyr Thr Met His Trp Val Arg Gln
            580                 585                 590

Ala Pro Gly Gln Gly Leu Glu Trp Met Gly Tyr Ile Asn Pro Ser Arg
        595                 600                 605

Gly Tyr Thr Asn Tyr Asn Gln Lys Phe Lys Asp Arg Ala Thr Leu Thr
    610                 615                 620

Arg Asp Lys Ser Ile Ser Thr Ala Tyr Met Glu Leu Ser Arg Leu Arg
625                 630                 635                 640

Ser Asp Asp Thr Ala Val Tyr Tyr Cys Ala Arg Tyr Tyr Asp Asp His
                645                 650                 655

Tyr Ser Leu Asp Tyr Trp Gly Gln Gly Thr Thr Leu Thr Val Ser Ser
            660                 665                 670

Gly Gly Gly Gly Ser Gly Gly Gly Gly Ser Gly Gly Gly Gly Ser Gly
        675                 680                 685

Gly Gly Gly Ser Gly Gly Gly Gly Ser Gly Gly Gly Gly Ser Asp Ile
    690                 695                 700

Gln Met Thr Gln Ser Pro Ser Ser Leu Ser Ala Ser Val Gly Asp Arg
705                 710                 715                 720

Val Thr Ile Thr Cys Ser Ala Ser Ser Ser Val Ser Tyr Met Asn Trp
                725                 730                 735

Tyr Gln Gln Lys Pro Gly Lys Ala Pro Lys Arg Trp Ile Tyr Asp Thr
            740                 745                 750

Ser Lys Leu Ala Ser Gly Val Pro Ser Arg Phe Ser Gly Ser Gly Ser
        755                 760                 765

Gly Thr Asp Phe Thr Leu Thr Ile Ser Ser Leu Gln Pro Glu Asp Phe
    770                 775                 780

Ala Thr Tyr Tyr Cys Gln Gln Trp Ser Ser Asn Pro Phe Thr Phe Gly
785                 790                 795                 800

Ser Gly Thr Lys Leu Glu Ile Asn Arg Thr Pro Leu Gly Asp Thr Thr
                805                 810                 815

His Thr Ser Gly Lys Pro Leu Asp Gly Glu Tyr Phe Thr Leu Gln Ile
            820                 825                 830

Arg Gly Arg Glu Arg Phe Glu Met Phe Arg Glu Leu Asn Glu Ala Leu
        835                 840                 845

Glu Leu Lys Asp Ala Gln Ala Gly Lys Glu Pro Gly Gly Ser Gly Gly
    850                 855                 860

Ala Pro His His His His His His
865                 870
```

<210> SEQ ID NO 56
<211> LENGTH: 872
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 56

Glu Val Gln Leu Val Glu Ser Gly Gly Gly Leu Val Asp Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Ala Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Gln Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Asp Ile Gln Met Thr Gln Ser Pro Ser Ser Leu Ser Ala
        275                 280                 285

Ser Val Gly Asp Arg Val Thr Ile Thr Cys Arg Ala Ser Gln Asp Val
    290                 295                 300

Asn Thr Ala Val Ala Trp Tyr Gln Gln Lys Pro Gly Lys Ala Pro Lys
305                 310                 315                 320

Leu Leu Ile Tyr Ser Ala Ser Phe Leu Tyr Ser Gly Val Pro Ser Arg
                325                 330                 335

Phe Ser Gly Ser Arg Ser Gly Thr Asp Phe Thr Leu Thr Ile Ser Ser
            340                 345                 350

Leu Gln Pro Glu Asp Phe Ala Thr Tyr Tyr Cys Gln Gln His Tyr Thr
        355                 360                 365

Thr Pro Pro Thr Phe Gly Gln Gly Thr Lys Val Glu Ile Lys Arg Gly
    370                 375                 380

Gly Gly Gly Ser Gly Gly Gly Gly Ser Gly Gly Gly Gly Ser Gly Gly
385                 390                 395                 400
```

```
Gly Gly Ser Gly Gly Gly Gly Ser Gly Gly Gly Gly Ser Glu Val Gln
                405                 410                 415

Leu Val Glu Ser Gly Gly Gly Leu Val Gln Pro Gly Gly Ser Leu Arg
            420                 425                 430

Leu Ser Cys Ala Ala Ser Gly Phe Asn Ile Lys Asp Thr Tyr Ile His
        435                 440                 445

Trp Val Arg Gln Ala Pro Gly Lys Gly Leu Glu Trp Val Ala Arg Ile
    450                 455                 460

Tyr Pro Thr Asn Gly Tyr Thr Arg Tyr Ala Asp Ser Val Lys Gly Arg
465                 470                 475                 480

Phe Thr Ile Ser Ala Asp Thr Ser Lys Asn Thr Ala Tyr Leu Gln Met
                485                 490                 495

Asn Ser Leu Arg Ala Glu Asp Thr Ala Val Tyr Tyr Cys Ser Arg Trp
            500                 505                 510

Gly Gly Asp Gly Phe Tyr Ala Met Asp Tyr Trp Gly Gln Gly Thr Leu
        515                 520                 525

Val Thr Val Ser Ser Gly Gly Gly Gly Ser Gly Gly Gly Gly Ser Gly
    530                 535                 540

Gly Gly Gly Ser Gly Gly Gly Gly Ser Gln Val Gln Leu Gln Gln Ser
545                 550                 555                 560

Gly Ala Glu Val Ala Lys Pro Gly Ala Ser Val Lys Val Ser Cys Lys
                565                 570                 575

Ala Ser Gly Tyr Thr Phe Thr Arg Tyr Thr Met His Trp Val Arg Gln
            580                 585                 590

Ala Pro Gly Gln Gly Leu Glu Trp Met Gly Tyr Ile Asn Pro Ser Arg
        595                 600                 605

Gly Tyr Thr Asn Tyr Asn Gln Lys Phe Lys Asp Arg Ala Thr Leu Thr
    610                 615                 620

Arg Asp Lys Ser Ile Ser Thr Ala Tyr Met Glu Leu Ser Arg Leu Arg
625                 630                 635                 640

Ser Asp Asp Thr Ala Val Tyr Tyr Cys Ala Arg Tyr Tyr Asp Asp His
                645                 650                 655

Tyr Ser Leu Asp Tyr Trp Gly Gln Gly Thr Thr Leu Thr Val Ser Ser
            660                 665                 670

Gly Gly Gly Gly Ser Gly Gly Gly Gly Ser Gly Gly Gly Gly Ser Gly
        675                 680                 685

Gly Gly Gly Ser Gly Gly Gly Gly Ser Gly Gly Gly Gly Ser Asp Ile
    690                 695                 700

Gln Met Thr Gln Ser Pro Ser Ser Leu Ser Ala Ser Val Gly Asp Arg
705                 710                 715                 720

Val Thr Ile Thr Cys Ser Ala Ser Ser Ser Val Ser Tyr Met Asn Trp
                725                 730                 735

Tyr Gln Gln Lys Pro Gly Lys Ala Pro Lys Arg Trp Ile Tyr Asp Thr
            740                 745                 750

Ser Lys Leu Ala Ser Gly Val Pro Ser Arg Phe Ser Gly Ser Gly Ser
        755                 760                 765

Gly Thr Asp Phe Thr Leu Thr Ile Ser Ser Leu Gln Pro Glu Asp Phe
    770                 775                 780

Ala Thr Tyr Tyr Cys Gln Gln Trp Ser Ser Asn Pro Phe Thr Phe Gly
785                 790                 795                 800

Ser Gly Thr Lys Leu Glu Ile Asn Arg Thr Pro Leu Gly Asp Thr Thr
                805                 810                 815
```

```
His Thr Ser Gly Lys Pro Leu Asp Gly Glu Tyr Phe Thr Leu Gln Ile
            820                 825                 830

Arg Gly Arg Glu Arg Phe Glu Met Phe Arg Glu Leu Asn Glu Ala Leu
        835                 840                 845

Glu Leu Lys Asp Ala Gln Ala Gly Lys Glu Pro Gly Gly Ser Gly Gly
    850                 855                 860

Ala Pro His His His His His His
865                 870


<210> SEQ ID NO 57
<211> LENGTH: 873
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Glu Ile Val Met Thr Gln Ser Pro Ala Thr Leu Ser Val
        275                 280                 285

Ser Pro Gly Glu Arg Val Thr Leu Ser Cys Arg Ala Ser Gln Ser Ile
    290                 295                 300
```

```
Ser Asp Tyr Leu Tyr Trp Tyr Gln Gln Lys Ser His Glu Ser Pro Arg
305                 310                 315                 320

Leu Leu Ile Lys Tyr Ala Ser Gln Ser Ile Ser Gly Ile Pro Ala Arg
                325                 330                 335

Phe Ser Gly Ser Gly Ser Gly Ser Glu Phe Thr Leu Thr Ile Asn Ser
            340                 345                 350

Val Glu Pro Glu Asp Val Gly Val Tyr Tyr Cys Gln Asn Gly His Ser
        355                 360                 365

Phe Pro Leu Thr Phe Gly Gln Gly Thr Lys Leu Glu Leu Lys Arg Gly
    370                 375                 380

Gly Gly Gly Ser Gly Gly Gly Gly Ser Gly Gly Gly Gly Ser Gly Gly
385                 390                 395                 400

Gly Gly Ser Gly Gly Gly Gly Ser Gly Gly Gly Gly Ser Gln Val Gln
                405                 410                 415

Leu Val Gln Ser Gly Ala Glu Val Val Lys Pro Gly Ala Ser Val Lys
            420                 425                 430

Leu Ser Cys Lys Thr Ser Gly Tyr Thr Phe Thr Asn Tyr Asp Ile Asn
        435                 440                 445

Trp Val Arg Gln Arg Pro Gly Gln Gly Leu Glu Trp Ile Gly Trp Ile
    450                 455                 460

Phe Pro Gly Asp Asp Ser Thr Gln Tyr Asn Glu Lys Phe Lys Gly Lys
465                 470                 475                 480

Ala Thr Leu Thr Thr Asp Thr Ser Thr Ser Thr Ala Tyr Met Glu Leu
                485                 490                 495

Ser Ser Leu Arg Ser Glu Asp Thr Ala Val Tyr Phe Cys Ala Arg Gln
            500                 505                 510

Thr Thr Gly Thr Trp Phe Ala Tyr Trp Gly Gln Gly Thr Leu Val Thr
        515                 520                 525

Val Ser Ser Gly Gly Gly Gly Ser Gly Gly Gly Gly Ser Gly Gly Gly
    530                 535                 540

Gly Ser Gly Gly Gly Gly Ser His Val Gln Leu Val Glu Ser Gly Gly
545                 550                 555                 560

Gly Leu Val Gln Pro Gly Gly Ser Leu Arg Leu Ser Cys Ala Ala Ser
                565                 570                 575

Gly Phe Ser Leu Thr Asp Tyr Gly Val His Trp Val Arg Gln Ala Pro
            580                 585                 590

Gly Lys Gly Leu Glu Trp Leu Gly Val Ile Trp Ser Gly Gly Gly Thr
        595                 600                 605

Ala Tyr Asn Thr Ala Leu Ile Ser Arg Phe Thr Ile Ser Arg Asp Asn
    610                 615                 620

Ser Lys Asn Thr Leu Tyr Leu Gln Met Asn Ser Leu Arg Ala Glu Asp
625                 630                 635                 640

Thr Ala Val Tyr Tyr Cys Ala Arg Arg Gly Ser Tyr Pro Tyr Asn Tyr
                645                 650                 655

Phe Asp Ala Trp Gly Cys Gly Thr Leu Val Thr Val Ser Ser Gly Gly
            660                 665                 670

Gly Gly Ser Gly Gly Gly Gly Ser Gly Gly Gly Gly Ser Gly Gly Gly
        675                 680                 685

Gly Ser Gly Gly Gly Gly Ser Gly Gly Gly Gly Ser Gln Ala Val Val
    690                 695                 700

Thr Gln Glu Pro Ser Leu Thr Val Ser Pro Gly Gly Thr Val Thr Leu
705                 710                 715                 720
```

```
Thr Cys Gly Ser Ser Thr Gly Ala Val Thr Ala Ser Asn Tyr Ala Asn
            725                 730                 735

Trp Val Gln Gln Lys Pro Gly Gln Cys Pro Arg Gly Leu Ile Gly Gly
            740                 745                 750

His Asn Asn Arg Pro Pro Gly Val Pro Ala Arg Phe Ser Gly Ser Leu
        755                 760                 765

Leu Gly Gly Lys Ala Ala Leu Thr Leu Leu Gly Ala Gln Pro Glu Asp
    770                 775                 780

Glu Ala Glu Tyr Tyr Cys Ala Leu Trp Tyr Ser Asp His Trp Val Ile
785                 790                 795                 800

Gly Gly Gly Thr Lys Leu Thr Val Leu Gly Thr Pro Leu Gly Asp Thr
                805                 810                 815

Thr His Thr Ser Gly Lys Pro Leu Asp Gly Glu Tyr Phe Thr Leu Gln
            820                 825                 830

Ile Arg Gly Arg Glu Arg Phe Glu Met Phe Arg Glu Leu Asn Glu Ala
        835                 840                 845

Leu Glu Leu Lys Asp Ala Gln Ala Gly Lys Glu Pro Gly Gly Ser Gly
    850                 855                 860

Gly Ala Pro His His His His His His
865                 870


<210> SEQ ID NO 58
<211> LENGTH: 870
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ala Pro Lys
            180                 185                 190

Thr Leu Ile Tyr Leu Ala Ser Asn Arg His Thr Gly Val Pro Ser Arg
        195                 200                 205
```

```
Phe Ser Gly Ser Gly Ser Gly Thr Glu Phe Thr Leu Thr Ile Ser Asn
    210                 215                 220

Leu Gln Pro Glu Asp Phe Ala Thr Tyr Tyr Cys Leu Gln His Trp Ser
225                 230                 235                 240

Tyr Pro Leu Thr Phe Gly Ser Gly Thr Lys Leu Glu Val Lys Arg Gly
                245                 250                 255

Gly Gly Gly Ser Gly Gly Gly Gly Ser Gly Gly Gly Gly Ser Gly Gly
            260                 265                 270

Gly Gly Ser Glu Ile Val Met Thr Gln Ser Pro Ala Thr Leu Ser Val
        275                 280                 285

Ser Pro Gly Glu Arg Val Thr Leu Ser Cys Arg Ala Ser Gln Ser Ile
    290                 295                 300

Ser Asp Tyr Leu Tyr Trp Tyr Gln Gln Lys Ser His Glu Ser Pro Arg
305                 310                 315                 320

Leu Leu Ile Lys Tyr Ala Ser Gln Ser Ile Ser Gly Ile Pro Ala Arg
                325                 330                 335

Phe Ser Gly Ser Gly Ser Gly Ser Glu Phe Thr Leu Thr Ile Asn Ser
            340                 345                 350

Val Glu Pro Glu Asp Val Gly Val Tyr Tyr Cys Gln Asn Gly His Ser
        355                 360                 365

Phe Pro Leu Thr Phe Gly Gln Gly Thr Lys Leu Glu Leu Lys Arg Gly
    370                 375                 380

Gly Gly Gly Ser Gly Gly Gly Gly Ser Gly Gly Gly Gly Ser Gly Gly
385                 390                 395                 400

Gly Gly Ser Gly Gly Gly Gly Ser Gly Gly Gly Gly Ser Gln Val Gln
                405                 410                 415

Leu Val Gln Ser Gly Ala Glu Val Val Lys Pro Gly Ala Ser Val Lys
            420                 425                 430

Leu Ser Cys Lys Thr Ser Gly Tyr Thr Phe Thr Asn Tyr Asp Ile Asn
        435                 440                 445

Trp Val Arg Gln Arg Pro Gly Gln Gly Leu Glu Trp Ile Gly Trp Ile
    450                 455                 460

Phe Pro Gly Asp Asp Ser Thr Gln Tyr Asn Glu Lys Phe Lys Gly Lys
465                 470                 475                 480

Ala Thr Leu Thr Thr Asp Thr Ser Thr Ser Thr Ala Tyr Met Glu Leu
                485                 490                 495

Ser Ser Leu Arg Ser Glu Asp Thr Ala Val Tyr Phe Cys Ala Arg Gln
            500                 505                 510

Thr Thr Gly Thr Trp Phe Ala Tyr Trp Gly Gln Gly Thr Leu Val Thr
        515                 520                 525

Val Ser Ser Gly Gly Gly Gly Ser Gly Gly Gly Gly Ser Gly Gly Gly
    530                 535                 540

Gly Ser Gly Gly Gly Gly Ser Gln Val Gln Leu Gln Gln Ser Gly Ala
545                 550                 555                 560

Glu Val Ala Lys Pro Gly Ala Ser Val Lys Val Ser Cys Lys Ala Ser
                565                 570                 575

Gly Tyr Thr Phe Thr Arg Tyr Thr Met His Trp Val Arg Gln Ala Pro
            580                 585                 590

Gly Gln Gly Leu Glu Trp Met Gly Tyr Ile Asn Pro Ser Arg Gly Tyr
        595                 600                 605

Thr Asn Tyr Asn Gln Lys Phe Lys Asp Arg Ala Thr Leu Thr Arg Asp
    610                 615                 620
```

```
Lys Ser Ile Ser Thr Ala Tyr Met Glu Leu Ser Arg Leu Arg Ser Asp
625                 630                 635                 640

Asp Thr Ala Val Tyr Tyr Cys Ala Arg Tyr Tyr Asp Asp His Tyr Ser
                645                 650                 655

Leu Asp Tyr Trp Gly Gln Gly Thr Thr Leu Thr Val Ser Ser Gly Gly
            660                 665                 670

Gly Gly Ser Gly Gly Gly Gly Ser Gly Gly Gly Gly Ser Gly Gly Gly
        675                 680                 685

Gly Ser Gly Gly Gly Gly Ser Gly Gly Gly Gly Ser Asp Ile Gln Met
    690                 695                 700

Thr Gln Ser Pro Ser Ser Leu Ser Ala Ser Val Gly Asp Arg Val Thr
705                 710                 715                 720

Ile Thr Cys Ser Ala Ser Ser Ser Val Ser Tyr Met Asn Trp Tyr Gln
                725                 730                 735

Gln Lys Pro Gly Lys Ala Pro Lys Arg Trp Ile Tyr Asp Thr Ser Lys
            740                 745                 750

Leu Ala Ser Gly Val Pro Ser Arg Phe Ser Gly Ser Gly Ser Gly Thr
        755                 760                 765

Asp Phe Thr Leu Thr Ile Ser Ser Leu Gln Pro Glu Asp Phe Ala Thr
    770                 775                 780

Tyr Tyr Cys Gln Gln Trp Ser Ser Asn Pro Phe Thr Phe Gly Ser Gly
785                 790                 795                 800

Thr Lys Leu Glu Ile Asn Arg Thr Pro Leu Gly Asp Thr Thr His Thr
                805                 810                 815

Ser Gly Lys Pro Leu Asp Gly Glu Tyr Phe Thr Leu Gln Ile Arg Gly
            820                 825                 830

Arg Glu Arg Phe Glu Met Phe Arg Glu Leu Asn Glu Ala Leu Glu Leu
        835                 840                 845

Lys Asp Ala Gln Ala Gly Lys Glu Pro Gly Gly Ser Gly Gly Ala Pro
    850                 855                 860

His His His His His His
865                 870
```

```
<210> SEQ ID NO 59
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ala Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Trp Ser Tyr Pro Leu
                85                  90                  95

Thr Phe Gly Ser Gly Thr Lys Leu Glu Val Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Lys Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Thr Ser Gly Gly Gly Gly Ser Gly Gly
    210                 215                 220

Gly Gly Ser Gly Gly Gly Gly Ser Gln Val Gln Leu Val Gln Ser Gly
225                 230                 235                 240

Gly Gly Val Val Gln Pro Gly Arg Ser Leu Arg Leu Ser Cys Lys Ala
                245                 250                 255

Ser Gly Tyr Thr Phe Thr Arg Tyr Thr Met His Trp Val Arg Gln Ala
            260                 265                 270

Pro Gly Lys Cys Leu Glu Trp Ile Gly Tyr Ile Asn Pro Ser Arg Gly
        275                 280                 285

Tyr Thr Asn Tyr Asn Gln Lys Phe Lys Asp Arg Phe Thr Ile Ser Arg
    290                 295                 300

Asp Asn Ser Lys Asn Thr Ala Phe Leu Gln Met Asp Ser Leu Arg Pro
305                 310                 315                 320

Glu Asp Thr Gly Val Tyr Phe Cys Ala Arg Tyr Tyr Asp Asp His Tyr
                325                 330                 335

Ser Leu Asp Tyr Trp Gly Gln Gly Thr Pro Val Thr Val Ser Ser Gly
            340                 345                 350

Gly Gly Gly Ser Gly Gly Gly Gly Ser Gly Gly Gly Gly Ser Gly Gly
        355                 360                 365

Gly Gly Ser Gly Gly Gly Gly Ser Gly Gly Gly Gly Ser Asp Ile Gln
    370                 375                 380

Met Thr Gln Ser Pro Ser Ser Leu Ser Ala Ser Val Gly Asp Arg Val
385                 390                 395                 400

Thr Ile Thr Cys Ser Ala Ser Ser Ser Val Ser Tyr Met Asn Trp Tyr
                405                 410                 415

Gln Gln Thr Pro Gly Lys Ala Pro Lys Arg Trp Ile Tyr Asp Thr Ser
            420                 425                 430

Lys Leu Ala Ser Gly Val Pro Ser Arg Phe Ser Gly Ser Gly Ser Gly
        435                 440                 445

Thr Asp Tyr Thr Phe Thr Ile Ser Ser Leu Gln Pro Glu Asp Ile Ala
    450                 455                 460

Thr Tyr Tyr Cys Gln Gln Trp Ser Ser Asn Pro Phe Thr Phe Gly Cys
465                 470                 475                 480

Gly Thr Lys Leu Gln Ile Thr Arg
                485
```

```
<210> SEQ ID NO 60
<211> LENGTH: 447
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 60

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

```
Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 61
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ala Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Trp Ser Tyr Pro Leu
                85                  90                  95

Thr Phe Gly Ser Gly Thr Lys Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Lys Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Thr Ser Gly Gly Gly Gly Ser Gly Gly
    210                 215                 220

Gly Gly Ser Gly Gly Gly Gly Ser Gln Val Gln Leu Gln Gln Ser Gly
225                 230                 235                 240

Ala Glu Val Ala Lys Pro Gly Ala Ser Val Lys Val Ser Cys Lys Ala
                245                 250                 255

Ser Gly Tyr Thr Phe Thr Arg Tyr Thr Met His Trp Val Arg Gln Ala
            260                 265                 270

Pro Gly Gln Gly Leu Glu Trp Met Gly Tyr Ile Asn Pro Ser Arg Gly
        275                 280                 285

Tyr Thr Asn Tyr Asn Gln Lys Phe Lys Asp Arg Ala Thr Leu Thr Arg
    290                 295                 300

Asp Lys Ser Ile Ser Thr Ala Tyr Met Glu Leu Ser Arg Leu Arg Ser
```

```
305                 310                 315                 320

Asp Asp Thr Ala Val Tyr Tyr Cys Ala Arg Tyr Tyr Asp Asp His Tyr
                325                 330                 335

Ser Leu Asp Tyr Trp Gly Gln Gly Thr Thr Leu Thr Val Ser Ser Gly
            340                 345                 350

Gly Gly Gly Ser Gly Gly Gly Gly Ser Gly Gly Gly Gly Ser Gly Gly
        355                 360                 365

Gly Gly Ser Gly Gly Gly Gly Ser Gly Gly Gly Gly Ser Asp Ile Gln
    370                 375                 380

Met Thr Gln Ser Pro Ser Ser Leu Ser Ala Ser Val Gly Asp Arg Val
385                 390                 395                 400

Thr Met Thr Cys Ser Ala Ser Ser Ser Val Ser Tyr Met Asn Trp Tyr
                405                 410                 415

Gln Gln Lys Pro Gly Lys Ala Pro Lys Leu Leu Ile Tyr Asp Thr Ser
            420                 425                 430

Lys Leu Ala Ser Gly Val Pro Ser Arg Phe Ser Gly Ser Gly Ser Gly
        435                 440                 445

Thr Asp Phe Thr Leu Thr Ile Ser Ser Met Gln Pro Glu Asp Phe Ala
    450                 455                 460

Thr Tyr Tyr Cys Gln Gln Trp Ser Ser Asn Pro Phe Thr Phe Gly Ser
465                 470                 475                 480

Gly Thr Lys Leu Glu Ile Asn Arg
                485


<210> SEQ ID NO 62
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

```
Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 63
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ala Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Trp Ser Tyr Pro Leu
                85                  90                  95
```

```
Thr Phe Gly Ser Gly Thr Lys Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Lys Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Thr Ser Gly Gly Gly Gly Ser Gly Gly
    210                 215                 220

Gly Gly Ser Gly Gly Gly Gly Ser Gln Val Gln Leu Gln Gln Ser Gly
225                 230                 235                 240

Ala Glu Val Ala Lys Pro Gly Ala Ser Val Lys Val Ser Cys Lys Ala
                245                 250                 255

Ser Gly Tyr Thr Phe Thr Arg Tyr Thr Met His Trp Val Arg Gln Ala
            260                 265                 270

Pro Gly Gln Gly Leu Glu Trp Met Gly Tyr Ile Asn Pro Ser Arg Gly
        275                 280                 285

Tyr Thr Asn Tyr Asn Gln Lys Phe Lys Asp Arg Ala Thr Leu Thr Arg
    290                 295                 300

Asp Lys Ser Ile Ser Thr Ala Tyr Met Glu Leu Ser Arg Leu Arg Ser
305                 310                 315                 320

Asp Asp Thr Ala Val Tyr Tyr Cys Ala Arg Tyr Tyr Asp Asp His Tyr
                325                 330                 335

Ser Leu Asp Tyr Trp Gly Gln Gly Thr Thr Leu Thr Val Ser Ser Gly
            340                 345                 350

Gly Gly Gly Ser Gly Gly Gly Gly Ser Gly Gly Gly Gly Ser Gly Gly
        355                 360                 365

Gly Gly Ser Gly Gly Gly Gly Ser Gly Gly Gly Gly Ser Asp Ile Gln
    370                 375                 380

Met Thr Gln Ser Pro Ser Ser Leu Ser Ala Ser Val Gly Asp Arg Val
385                 390                 395                 400

Thr Ile Thr Cys Ser Ala Ser Ser Ser Val Ser Tyr Met Asn Trp Tyr
                405                 410                 415

Gln Gln Lys Pro Gly Lys Ala Pro Lys Arg Trp Ile Tyr Asp Thr Ser
            420                 425                 430

Lys Leu Ala Ser Gly Val Pro Ser Arg Phe Ser Gly Ser Gly Ser Gly
        435                 440                 445

Thr Asp Phe Thr Leu Thr Ile Ser Ser Leu Gln Pro Glu Asp Phe Ala
    450                 455                 460

Thr Tyr Tyr Cys Gln Gln Trp Ser Ser Asn Pro Phe Thr Phe Gly Ser
465                 470                 475                 480

Gly Thr Lys Leu Glu Ile Asn Arg
                485
```

<210> SEQ ID NO 64
<211> LENGTH: 447

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

```
Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 65
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ala Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Trp Ser Tyr Pro Leu
                85                  90                  95

Thr Phe Gly Ser Gly Thr Lys Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Lys Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Thr Ser Gly Gly Gly Ser Gly Gly
    210                 215                 220

Gly Gly Ser Gly Gly Gly Gly Ser His Val Gln Leu Val Glu Ser Gly
225                 230                 235                 240

Gly Gly Leu Val Gln Pro Gly Gly Ser Leu Arg Leu Ser Cys Ala Ala
                245                 250                 255

Ser Gly Phe Ser Leu Thr Asp Tyr Gly Val His Trp Val Arg Gln Ala
            260                 265                 270

Pro Gly Lys Gly Leu Glu Trp Leu Gly Val Ile Trp Ser Gly Gly Gly
        275                 280                 285

Thr Ala Tyr Asn Thr Ala Leu Ile Ser Arg Phe Thr Ile Ser Arg Asp
```

```
    290                 295                 300

Asn Ser Lys Asn Thr Leu Tyr Leu Gln Met Asn Ser Leu Arg Ala Glu
305                 310                 315                 320

Asp Thr Ala Val Tyr Tyr Cys Ala Arg Arg Gly Ser Tyr Pro Tyr Asn
                325                 330                 335

Tyr Phe Asp Ala Trp Gly Cys Gly Thr Leu Val Thr Val Ser Ser Gly
            340                 345                 350

Gly Gly Gly Ser Gly Gly Gly Gly Ser Gly Gly Gly Gly Ser Gly Gly
        355                 360                 365

Gly Gly Ser Gly Gly Gly Gly Ser Gly Gly Gly Gly Ser Gln Ala Val
    370                 375                 380

Val Thr Gln Glu Pro Ser Leu Thr Val Ser Pro Gly Gly Thr Val Thr
385                 390                 395                 400

Leu Thr Cys Gly Ser Ser Thr Gly Ala Val Thr Ala Ser Asn Tyr Ala
                405                 410                 415

Asn Trp Val Gln Gln Lys Pro Gly Gln Cys Pro Arg Gly Leu Ile Gly
            420                 425                 430

Gly His Asn Asn Arg Pro Pro Gly Val Pro Ala Arg Phe Ser Gly Ser
        435                 440                 445

Leu Leu Gly Gly Lys Ala Ala Leu Thr Leu Leu Gly Ala Gln Pro Glu
    450                 455                 460

Asp Glu Ala Glu Tyr Tyr Cys Ala Leu Trp Tyr Ser Asp His Trp Val
465                 470                 475                 480

Ile Gly Gly Gly Thr Lys Leu Thr Val Leu Gly
                485                 490


<210> SEQ ID NO 66
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Gly Ser Gly Gly Gly
    210                 215                 220

Gly Ser Gly Gly Gly Gly Ser His Val Gln Leu Val Glu Ser Gly Gly
225                 230                 235                 240

Gly Leu Val Gln Pro Gly Gly Ser Leu Arg Leu Ser Cys Ala Ala Ser
                245                 250                 255

Gly Phe Ser Leu Thr Asp Tyr Gly Val His Trp Val Arg Gln Ala Pro
            260                 265                 270

Gly Lys Gly Leu Glu Trp Leu Gly Val Ile Trp Ser Gly Gly Gly Thr
        275                 280                 285

Ala Tyr Asn Thr Ala Leu Ile Ser Arg Phe Thr Ile Ser Arg Asp Asn
    290                 295                 300

Ser Lys Asn Thr Leu Tyr Leu Gln Met Asn Ser Leu Arg Ala Glu Asp
305                 310                 315                 320

Thr Ala Val Tyr Tyr Cys Ala Arg Arg Gly Ser Tyr Pro Tyr Asn Tyr
                325                 330                 335

Phe Asp Ala Trp Gly Cys Gly Thr Leu Val Thr Val Ser Ser Gly Gly
            340                 345                 350

Gly Gly Ser Gly Gly Gly Gly Ser Gly Gly Gly Gly Ser Gly Gly Gly
        355                 360                 365

Gly Ser Gly Gly Gly Gly Ser Gly Gly Gly Gly Ser Gln Ala Val Val
    370                 375                 380

Thr Gln Glu Pro Ser Leu Thr Val Ser Pro Gly Gly Thr Val Thr Leu
385                 390                 395                 400

Thr Cys Gly Ser Ser Thr Gly Ala Val Thr Ala Ser Asn Tyr Ala Asn
                405                 410                 415

Trp Val Gln Gln Lys Pro Gly Gln Cys Pro Arg Gly Leu Ile Gly Gly
            420                 425                 430

His Asn Asn Arg Pro Pro Gly Val Pro Ala Arg Phe Ser Gly Ser Leu
        435                 440                 445

Leu Gly Gly Lys Ala Ala Leu Thr Leu Leu Gly Ala Gln Pro Glu Asp
    450                 455                 460

Glu Ala Glu Tyr Tyr Cys Ala Leu Trp Tyr Ser Asp His Trp Val Ile
465                 470                 475                 480

Gly Gly Gly Thr Lys Leu Thr Val Leu Gly
                485                 490


<210> SEQ ID NO 67
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30
```

```
Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Leu Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 68
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Ala Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 69
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ala Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Trp Ser Tyr Pro Leu
                85                  90                  95

Thr Phe Gly Ser Gly Thr Lys Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Lys Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Thr Ser Gly Gly Gly Gly Ser Gly Gly
    210                 215                 220

Gly Gly Ser Gly Gly Gly Gly Ser Gln Val Gln Leu Val Gln Ser Gly
225                 230                 235                 240

Gly Gly Val Val Gln Pro Gly Arg Ser Leu Arg Leu Ser Cys Lys Ala
                245                 250                 255

Ser Gly Tyr Thr Phe Thr Arg Tyr Thr Met His Trp Val Arg Gln Ala
```

```
            260                 265                 270

Pro Gly Lys Cys Leu Glu Trp Ile Gly Tyr Ile Asn Pro Ser Arg Gly
        275                 280                 285

Tyr Thr Asn Tyr Asn Gln Lys Phe Lys Asp Arg Phe Thr Ile Ser Arg
    290                 295                 300

Asp Asn Ser Lys Asn Thr Ala Phe Leu Gln Met Asp Ser Leu Arg Pro
305                 310                 315                 320

Glu Asp Thr Gly Val Tyr Phe Cys Ala Arg Tyr Tyr Asp Asp His Tyr
                325                 330                 335

Ser Leu Asp Tyr Trp Gly Gln Gly Thr Pro Val Thr Val Ser Ser Gly
            340                 345                 350

Gly Gly Gly Ser Gly Gly Gly Gly Ser Gly Gly Gly Gly Ser Gly Gly
        355                 360                 365

Gly Gly Ser Gly Gly Gly Gly Ser Gly Gly Gly Gly Ser Asp Ile Gln
    370                 375                 380

Met Thr Gln Ser Pro Ser Ser Leu Ser Ala Ser Val Gly Asp Arg Val
385                 390                 395                 400

Thr Ile Thr Cys Ser Ala Ser Ser Ser Val Ser Tyr Met Asn Trp Tyr
                405                 410                 415

Gln Gln Thr Pro Gly Lys Ala Pro Lys Arg Trp Ile Tyr Asp Thr Ser
            420                 425                 430

Lys Leu Ala Ser Gly Val Pro Ser Arg Phe Ser Gly Ser Gly Ser Gly
        435                 440                 445

Thr Asp Tyr Thr Phe Thr Ile Ser Ser Leu Gln Pro Glu Asp Ile Ala
    450                 455                 460

Thr Tyr Tyr Cys Gln Gln Trp Ser Ser Asn Pro Phe Thr Phe Gly Cys
465                 470                 475                 480

Gly Thr Lys Leu Gln Ile Thr Arg
                485


<210> SEQ ID NO 70
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Gly Ser Gly Gly Gly
    210                 215                 220

Gly Ser Gly Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
                245                 250                 255

Gly Tyr Thr Phe Thr Arg Tyr Thr Met His Trp Val Arg Gln Ala Pro
            260                 265                 270

Gly Lys Cys Leu Glu Trp Ile Gly Tyr Ile Asn Pro Ser Arg Gly Tyr
        275                 280                 285

Thr Asn Tyr Asn Gln Lys Phe Lys Asp Arg Phe Thr Ile Ser Arg Asp
    290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
                325                 330                 335

Leu Asp Tyr Trp Gly Gln Gly Thr Pro Val Thr Val Ser Ser Gly Gly
            340                 345                 350

Gly Gly Ser Gly Gly Gly Gly Ser Gly Gly Gly Gly Ser Gly Gly Gly
        355                 360                 365

Gly Ser Gly Gly Gly Gly Ser Gly Gly Gly Gly Ser Asp Ile Gln Met
    370                 375                 380

Thr Gln Ser Pro Ser Ser Leu Ser Ala Ser Val Gly Asp Arg Val Thr
385                 390                 395                 400

Ile Thr Cys Ser Ala Ser Ser Ser Val Ser Tyr Met Asn Trp Tyr Gln
                405                 410                 415

Gln Thr Pro Gly Lys Ala Pro Lys Arg Trp Ile Tyr Asp Thr Ser Lys
            420                 425                 430

Leu Ala Ser Gly Val Pro Ser Arg Phe Ser Gly Ser Gly Ser Gly Thr
        435                 440                 445

Asp Tyr Thr Phe Thr Ile Ser Ser Leu Gln Pro Glu Asp Ile Ala Thr
    450                 455                 460

Tyr Tyr Cys Gln Gln Trp Ser Ser Asn Pro Phe Thr Phe Gly Cys Gly
465                 470                 475                 480

Thr Lys Leu Gln Ile Thr Arg
                485
```

```
<210> SEQ ID NO 71
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71
```

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Leu Leu Tyr Ser Lys Leu Thr Val Asp Lys Ser Arg
                405                 410                 415
```

```
Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 72
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Ala Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 73
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ala Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Trp Ser Tyr Pro Leu
                85                  90                  95

Thr Phe Gly Ser Gly Thr Lys Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Lys Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Thr Ser Gly Gly Gly Gly Ser Gly Gly
    210                 215                 220

Gly Gly Ser Gly Gly Gly Gly Ser Gln Val Gln Leu Gln Gln Ser Gly
```

```
225                 230                 235                 240

Ala Glu Val Ala Lys Pro Gly Ala Ser Val Lys Val Ser Cys Lys Ala
                245                 250                 255

Ser Gly Tyr Thr Phe Thr Arg Tyr Thr Met His Trp Val Arg Gln Ala
            260                 265                 270

Pro Gly Gln Gly Leu Glu Trp Met Gly Tyr Ile Asn Pro Ser Arg Gly
        275                 280                 285

Tyr Thr Asn Tyr Asn Gln Lys Phe Lys Asp Arg Ala Thr Leu Thr Arg
    290                 295                 300

Asp Lys Ser Ile Ser Thr Ala Tyr Met Glu Leu Ser Arg Leu Arg Ser
305                 310                 315                 320

Asp Asp Thr Ala Val Tyr Tyr Cys Ala Arg Tyr Tyr Asp Asp His Tyr
                325                 330                 335

Ser Leu Asp Tyr Trp Gly Gln Gly Thr Thr Leu Thr Val Ser Ser Gly
            340                 345                 350

Gly Gly Gly Ser Gly Gly Gly Gly Ser Gly Gly Gly Gly Ser Gly Gly
        355                 360                 365

Gly Gly Ser Gly Gly Gly Gly Ser Gly Gly Gly Gly Ser Asp Ile Gln
    370                 375                 380

Met Thr Gln Ser Pro Ser Ser Leu Ser Ala Ser Val Gly Asp Arg Val
385                 390                 395                 400

Thr Met Thr Cys Ser Ala Ser Ser Ser Val Ser Tyr Met Asn Trp Tyr
                405                 410                 415

Gln Gln Lys Pro Gly Lys Ala Pro Lys Leu Leu Ile Tyr Asp Thr Ser
            420                 425                 430

Lys Leu Ala Ser Gly Val Pro Ser Arg Phe Ser Gly Ser Gly Ser Gly
        435                 440                 445

Thr Asp Phe Thr Leu Thr Ile Ser Ser Met Gln Pro Glu Asp Phe Ala
    450                 455                 460

Thr Tyr Tyr Cys Gln Gln Trp Ser Ser Asn Pro Phe Thr Phe Gly Ser
465                 470                 475                 480

Gly Thr Lys Leu Glu Ile Asn Arg
                485


<210> SEQ ID NO 74
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95
```

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Gly Ser Gly Gly Gly
    210                 215                 220

Gly Ser Gly Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
                245                 250                 255

Gly Tyr Thr Phe Thr Arg Tyr Thr Met His Trp Val Arg Gln Ala Pro
            260                 265                 270

Gly Lys Cys Leu Glu Trp Ile Gly Tyr Ile Asn Pro Ser Arg Gly Tyr
        275                 280                 285

Thr Asn Tyr Asn Gln Lys Phe Lys Asp Arg Phe Thr Ile Ser Arg Asp
    290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
                325                 330                 335

Leu Asp Tyr Trp Gly Gln Gly Thr Pro Val Thr Val Ser Ser Gly Gly
            340                 345                 350

Gly Gly Ser Gly Gly Gly Gly Ser Gly Gly Gly Gly Ser Gly Gly Gly
        355                 360                 365

Gly Ser Gly Gly Gly Gly Ser Gly Gly Gly Gly Ser Asp Ile Gln Met
    370                 375                 380

Thr Gln Ser Pro Ser Ser Leu Ser Ala Ser Val Gly Asp Arg Val Thr
385                 390                 395                 400

Ile Thr Cys Ser Ala Ser Ser Ser Val Ser Tyr Met Asn Trp Tyr Gln
                405                 410                 415

Gln Thr Pro Gly Lys Ala Pro Lys Arg Trp Ile Tyr Asp Thr Ser Lys
            420                 425                 430

Leu Ala Ser Gly Val Pro Ser Arg Phe Ser Gly Ser Gly Ser Gly Thr
        435                 440                 445

Asp Tyr Thr Phe Thr Ile Ser Ser Leu Gln Pro Glu Asp Ile Ala Thr
    450                 455                 460

Tyr Tyr Cys Gln Gln Trp Ser Ser Asn Pro Phe Thr Phe Gly Cys Gly
465                 470                 475                 480

Thr Lys Leu Gln Ile Thr Arg
                485
```

<210> SEQ ID NO 75
<211> LENGTH: 447
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 75

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

```
Gly Gln Pro Glu Asn Asn Tyr Lys Thr Thr Pro Pro Val Leu Asp Ser
385                 390                 395                 400

Asp Gly Ser Phe Leu Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 76
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Ala Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 77
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ala Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Trp Ser Tyr Pro Leu
                85                  90                  95

Thr Phe Gly Ser Gly Thr Lys Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Lys Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
```

```
        195                 200                 205

Ser Phe Asn Arg Gly Glu Cys Thr Ser Gly Gly Gly Gly Ser Gly Gly
    210                 215                 220

Gly Gly Ser Gly Gly Gly Gly Ser Gln Val Gln Leu Gln Gln Ser Gly
225                 230                 235                 240

Ala Glu Val Ala Lys Pro Gly Ala Ser Val Lys Val Ser Cys Lys Ala
                245                 250                 255

Ser Gly Tyr Thr Phe Thr Arg Tyr Thr Met His Trp Val Arg Gln Ala
            260                 265                 270

Pro Gly Gln Gly Leu Glu Trp Met Gly Tyr Ile Asn Pro Ser Arg Gly
        275                 280                 285

Tyr Thr Asn Tyr Asn Gln Lys Phe Lys Asp Arg Ala Thr Leu Thr Arg
    290                 295                 300

Asp Lys Ser Ile Ser Thr Ala Tyr Met Glu Leu Ser Arg Leu Arg Ser
305                 310                 315                 320

Asp Asp Thr Ala Val Tyr Tyr Cys Ala Arg Tyr Tyr Asp Asp His Tyr
                325                 330                 335

Ser Leu Asp Tyr Trp Gly Gln Gly Thr Thr Leu Thr Val Ser Ser Gly
            340                 345                 350

Gly Gly Gly Ser Gly Gly Gly Gly Ser Gly Gly Gly Gly Ser Gly Gly
        355                 360                 365

Gly Gly Ser Gly Gly Gly Gly Ser Gly Gly Gly Gly Ser Asp Ile Gln
    370                 375                 380

Met Thr Gln Ser Pro Ser Ser Leu Ser Ala Ser Val Gly Asp Arg Val
385                 390                 395                 400

Thr Ile Thr Cys Ser Ala Ser Ser Ser Val Ser Tyr Met Asn Trp Tyr
                405                 410                 415

Gln Gln Lys Pro Gly Lys Ala Pro Lys Arg Trp Ile Tyr Asp Thr Ser
            420                 425                 430

Lys Leu Ala Ser Gly Val Pro Ser Arg Phe Ser Gly Ser Gly Ser Gly
        435                 440                 445

Thr Asp Phe Thr Leu Thr Ile Ser Ser Leu Gln Pro Glu Asp Phe Ala
    450                 455                 460

Thr Tyr Tyr Cys Gln Gln Trp Ser Ser Asn Pro Phe Thr Phe Gly Ser
465                 470                 475                 480

Gly Thr Lys Leu Glu Ile Asn Arg
                485


<210> SEQ ID NO 78
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60
```

```
Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Gly Ser Gly Gly Gly
    210                 215                 220

Gly Ser Gly Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
                245                 250                 255

Gly Tyr Thr Phe Thr Arg Tyr Thr Met His Trp Val Arg Gln Ala Pro
            260                 265                 270

Gly Lys Cys Leu Glu Trp Ile Gly Tyr Ile Asn Pro Ser Arg Gly Tyr
        275                 280                 285

Thr Asn Tyr Asn Gln Lys Phe Lys Asp Arg Phe Thr Ile Ser Arg Asp
    290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
                325                 330                 335

Leu Asp Tyr Trp Gly Gln Gly Thr Pro Val Thr Val Ser Ser Gly Gly
            340                 345                 350

Gly Gly Ser Gly Gly Gly Gly Ser Gly Gly Gly Gly Ser Gly Gly Gly
        355                 360                 365

Gly Ser Gly Gly Gly Gly Ser Gly Gly Gly Gly Ser Asp Ile Gln Met
    370                 375                 380

Thr Gln Ser Pro Ser Ser Leu Ser Ala Ser Val Gly Asp Arg Val Thr
385                 390                 395                 400

Ile Thr Cys Ser Ala Ser Ser Ser Val Ser Tyr Met Asn Trp Tyr Gln
                405                 410                 415

Gln Thr Pro Gly Lys Ala Pro Lys Arg Trp Ile Tyr Asp Thr Ser Lys
            420                 425                 430

Leu Ala Ser Gly Val Pro Ser Arg Phe Ser Gly Ser Gly Ser Gly Thr
        435                 440                 445

Asp Tyr Thr Phe Thr Ile Ser Ser Leu Gln Pro Glu Asp Ile Ala Thr
    450                 455                 460

Tyr Tyr Cys Gln Gln Trp Ser Ser Asn Pro Phe Thr Phe Gly Cys Gly
465                 470                 475                 480

Thr Lys Leu Gln Ile Thr Arg
```

485

<210> SEQ ID NO 79
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 79

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350
```

```
Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Leu Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 80
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Ala Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 81
<211> LENGTH: 384
<212> TYPE: PRT
<213> ORGANISM: Homo sapiens

<400> SEQUENCE: 81

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
```

```
            180                 185                 190

Val Gly Ser Asp Leu Lys Asp Ala His Leu Thr Trp Glu Val Ala Gly
        195                 200                 205

Lys Val Pro Thr Gly Gly Val Glu Glu Gly Leu Leu Glu Arg His Ser
    210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
                245                 250                 255

Pro Pro Gln Arg Leu Met Ala Leu Arg Glu Pro Ala Ala Gln Ala Pro
            260                 265                 270

Val Lys Leu Ser Leu Asn Leu Leu Ala Ser Ser Asp Pro Pro Glu Ala
        275                 280                 285

Ala Ser Trp Leu Leu Cys Glu Val Ser Gly Phe Ser Pro Pro Asn Ile
    290                 295                 300

Leu Leu Met Trp Leu Glu Asp Gln Arg Glu Val Asn Thr Ser Gly Phe
305                 310                 315                 320

Ala Pro Ala Arg Pro Pro Pro Gln Pro Gly Ser Thr Thr Phe Trp Ala
                325                 330                 335

Trp Ser Val Leu Arg Val Pro Ala Pro Pro Ser Pro Gln Pro Ala Thr
            340                 345                 350

Tyr Thr Cys Val Val Ser His Glu Asp Ser Arg Thr Leu Leu Asn Ala
        355                 360                 365

Ser Arg Ser Leu Glu Val Ser Tyr Val Thr Asp His Gly Pro Met Lys
    370                 375                 380


<210> SEQ ID NO 82
<211> LENGTH: 330
<212> TYPE: PRT
<213> ORGANISM: Homo sapiens

<400> SEQUENCE: 82

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 83
<211> LENGTH: 326
<212> TYPE: PRT
<213> ORGANISM: Homo sapiens

<400> SEQUENCE: 83

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220
```

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 84
<211> LENGTH: 377
<212> TYPE: PRT
<213> ORGANISM: Homo sapiens

<400> SEQUENCE: 84

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln

```
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375


<210> SEQ ID NO 85
<211> LENGTH: 452
<212> TYPE: PRT
<213> ORGANISM: Homo sapiens

<400> SEQUENCE: 85

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255
```

```
Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
    290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
    370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
                405                 410                 415

Glu Ala Leu Pro Asn Arg Val Thr Glu Arg Thr Val Asp Lys Ser Thr
            420                 425                 430

Gly Lys Pro Thr Leu Tyr Asn Val Ser Leu Val Met Ser Asp Thr Ala
        435                 440                 445

Gly Thr Cys Tyr
    450


<210> SEQ ID NO 86
<211> LENGTH: 327
<212> TYPE: PRT
<213> ORGANISM: Homo sapiens

<400> SEQUENCE: 86

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 87
<211> LENGTH: 353
<212> TYPE: PRT
<213> ORGANISM: Homo sapiens

<400> SEQUENCE: 87

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
```

```
    210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr


<210> SEQ ID NO 88
<211> LENGTH: 340
<212> TYPE: PRT
<213> ORGANISM: Homo sapiens

<400> SEQUENCE: 88

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
```

225 230 235 240

Gly Phe Ser Pro Lys Asp Val Leu Val Arg Trp Leu Gln Gly Ser Gln
245 250 255

Glu Leu Pro Arg Glu Lys Tyr Leu Thr Trp Ala Ser Arg Gln Glu Pro
260 265 270

Ser Gln Gly Thr Thr Thr Phe Ala Val Thr Ser Ile Leu Arg Val Ala
275 280 285

Ala Glu Asp Trp Lys Lys Gly Asp Thr Phe Ser Cys Met Val Gly His
290 295 300

Glu Ala Leu Pro Leu Ala Phe Thr Gln Lys Thr Ile Asp Arg Met Ala
305 310 315 320

Gly Lys Pro Thr His Val Asn Val Ser Val Val Met Ala Glu Val Asp
325 330 335

Gly Thr Cys Tyr
340

<210> SEQ ID NO 89
<211> LENGTH: 106
<212> TYPE: PRT
<213> ORGANISM: Homo sapiens

<400> SEQUENCE: 89

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

Pro Arg Glu Ala Lys Val Gln Trp Lys Val Asp Asn Ala Leu Gln Ser
35 40 45

Gly Asn Ser Gln Glu Ser Val Thr Glu Gln Asp Ser Lys Asp Ser Thr
50 55 60

Tyr Ser Leu Ser Ser Thr Leu Thr Leu Ser Lys Ala Asp Tyr Glu Lys
65 70 75 80

His Lys Val Tyr Ala Cys Glu Val Thr His Gln Gly Leu Ser Ser Pro
85 90 95

Val Thr Lys Ser Phe Asn Arg Gly Glu Cys
100 105

<210> SEQ ID NO 90
<211> LENGTH: 39
<212> TYPE: PRT
<213> ORGANISM: Homo sapiens

<400> SEQUENCE: 90

Lys Pro Leu Asp Gly Glu Tyr Phe Thr Leu Gln Ile Arg Gly Arg Glu
1 5 10 15

Arg Phe Glu Met Phe Arg Glu Leu Asn Glu Ala Leu Glu Leu Lys Asp
20 25 30

Ala Gln Ala Gly Lys Glu Pro
35

<210> SEQ ID NO 91
<211> LENGTH: 57
<212> TYPE: PRT
<213> ORGANISM: Homo sapiens

<400> SEQUENCE: 91

Arg Ser Pro Asp Asp Glu Leu Leu Tyr Leu Pro Val Arg Gly Arg Glu
1 5 10 15

```
Thr Tyr Glu Met Leu Leu Lys Ile Lys Glu Ser Leu Glu Leu Met Gln
            20                  25                  30

Tyr Leu Pro Gln His Thr Ile Glu Thr Tyr Arg Gln Gln Gln Gln Gln
        35                  40                  45

Gln His Gln His Leu Leu Gln Lys Gln
    50                  55


<210> SEQ ID NO 92
<211> LENGTH: 52
<212> TYPE: PRT
<213> ORGANISM: Homo sapiens

<400> SEQUENCE: 92

Arg His Gly Asp Glu Asp Thr Tyr Tyr Leu Gln Val Arg Gly Arg Glu
1               5                   10                  15

Asn Phe Glu Ile Leu Met Lys Leu Lys Glu Ser Leu Glu Leu Met Glu
            20                  25                  30

Leu Val Pro Gln Pro Leu Val Asp Ser Tyr Arg Gln Gln Gln Gln Leu
        35                  40                  45

Leu Gln Arg Pro
    50


<210> SEQ ID NO 93
<211> LENGTH: 27
<212> TYPE: PRT
<213> ORGANISM: Homo sapiens

<400> SEQUENCE: 93

Gln Ala Ile Lys Lys Glu Leu Thr Gln Ile Lys Gln Lys Val Asp Ser
1               5                   10                  15

Leu Leu Glu Asn Leu Glu Lys Ile Glu Lys Glu
            20                  25


<210> SEQ ID NO 94
<211> LENGTH: 54
<212> TYPE: PRT
<213> ORGANISM: Homo sapiens

<400> SEQUENCE: 94

Ser Thr Arg Arg Ile Leu Gly Leu Ala Ile Glu Ser Gln Asp Ala Gly
1               5                   10                  15

Ile Lys Thr Ile Thr Met Leu Asp Glu Gln Lys Glu Gln Leu Asn Arg
            20                  25                  30

Ile Glu Glu Gly Leu Asp Gln Ile Asn Lys Asp Met Arg Glu Thr Glu
        35                  40                  45

Lys Thr Leu Thr Glu Leu
    50


<210> SEQ ID NO 95
<211> LENGTH: 97
<212> TYPE: PRT
<213> ORGANISM: Homo sapiens

<400> SEQUENCE: 95

Met Cys Gly Ala Pro Ser Ala Thr Gln Pro Ala Thr Ala Glu Thr Gln
1               5                   10                  15

His Ile Ala Asp Gln Val Arg Ser Gln Leu Glu Glu Lys Glu Asn Lys
            20                  25                  30

Lys Phe Pro Val Phe Lys Ala Val Ser Phe Lys Ser Gln Val Val Ala
```

```
        35                  40                  45

Gly Thr Asn Tyr Phe Ile Lys Val His Val Gly Asp Glu Asp Phe Val
    50                  55                  60

His Leu Arg Val Phe Gln Ser Leu Pro His Glu Asn Lys Pro Leu Thr
65                  70                  75                  80

Leu Ser Asn Tyr Gln Thr Asn Lys Ala Lys His Asp Glu Leu Thr Tyr
                85                  90                  95

Phe


<210> SEQ ID NO 96
<211> LENGTH: 30
<212> TYPE: PRT
<213> ORGANISM: Homo sapiens

<400> SEQUENCE: 96

Asp Glu Ile Ser Met Met Gly Arg Val Val Lys Val Glu Lys Gln Val
1               5                   10                  15

Gln Ser Ile Glu His Lys Leu Asp Leu Leu Leu Gly Phe Tyr
            20                  25                  30


<210> SEQ ID NO 97
<211> LENGTH: 60
<212> TYPE: PRT
<213> ORGANISM: Homo sapiens

<400> SEQUENCE: 97

Thr Val Ala Glu Ala Lys Arg Gln Ala Ala Glu Asp Ala Leu Ala Val
1               5                   10                  15

Ile Asn Gln Gln Glu Asp Ser Ser Glu Ser Cys Trp Asn Cys Gly Arg
            20                  25                  30

Lys Ala Ser Glu Thr Cys Ser Gly Cys Asn Thr Ala Arg Tyr Cys Gly
        35                  40                  45

Ser Phe Cys Gln His Lys Asp Trp Glu Lys His His
    50                  55                  60


<210> SEQ ID NO 98
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Gln Met Thr Gln Ser Pro Ser Ser Leu Ser Val Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Leu Ala Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln His Trp Ser Tyr Pro Leu
                85                  90                  95

Thr Phe Gly Gln Gly Thr Lys Val Glu Val Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Ala Ser His Val Lys Leu Gln Glu Ser Gly Pro Gly Leu Val Gln Pro
225                 230                 235                 240

Ser Gln Ser Leu Ser Leu Thr Cys Thr Val Ser Gly Phe Ser Leu Thr
                245                 250                 255

Asp Tyr Gly Val His Trp Val Arg Gln Ser Pro Gly Lys Gly Leu Glu
            260                 265                 270

Trp Leu Gly Val Ile Trp Ser Gly Gly Gly Thr Ala Tyr Asn Thr Ala
        275                 280                 285

Leu Ile Ser Arg Leu Asn Ile Tyr Arg Asp Asn Ser Lys Asn Gln Val
    290                 295                 300

Phe Leu Glu Met Asn Ser Leu Gln Ala Glu Asp Thr Ala Met Tyr Tyr
305                 310                 315                 320

Cys Ala Arg Arg Gly Ser Tyr Pro Tyr Asn Tyr Phe Asp Ala Trp Gly
                325                 330                 335

Cys Gly Thr Thr Val Thr Val Ser Ser Gly Gly Gly Gly Ser Gly Gly
            340                 345                 350

Gly Gly Ser Gly Gly Gly Gly Ser Gln Ala Val Val Ile Gln Glu Ser
        355                 360                 365

Ala Leu Thr Thr Pro Pro Gly Glu Thr Val Thr Leu Thr Cys Gly Ser
    370                 375                 380

Ser Thr Gly Ala Val Thr Ala Ser Asn Tyr Ala Asn Trp Val Gln Glu
385                 390                 395                 400

Lys Pro Asp His Cys Phe Thr Gly Leu Ile Gly Gly His Asn Asn Arg
                405                 410                 415

Pro Pro Gly Val Pro Ala Arg Phe Ser Gly Ser Leu Ile Gly Asp Lys
            420                 425                 430

Ala Ala Leu Thr Ile Ala Gly Thr Gln Thr Glu Asp Glu Ala Ile Tyr
        435                 440                 445

Phe Cys Ala Leu Trp Tyr Ser Asp His Trp Val Ile Gly Gly Gly Thr
    450                 455                 460

Arg Leu Thr Val Leu Gly
465                 470
```

<210> SEQ ID NO 99
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 99

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Ser Ser Lys Asn Thr Leu Tyr
65                  70                  75                  80

Leu Gln Met Asn Ser Leu Gln Ala Glu Asp Ser Ala Ile Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415
```

```
Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 100
<211> LENGTH: 319
<212> TYPE: PRT
<213> ORGANISM: Homo sapiens

<400> SEQUENCE: 100

Met Val Gly Lys Met Trp Pro Val Leu Trp Thr Leu Cys Ala Val Arg
1               5                   10                  15

Val Thr Val Asp Ala Ile Ser Val Glu Thr Pro Gln Asp Val Leu Arg
            20                  25                  30

Ala Ser Gln Gly Lys Ser Val Thr Leu Pro Cys Thr Tyr His Thr Ser
        35                  40                  45

Thr Ser Ser Arg Glu Gly Leu Ile Gln Trp Asp Lys Leu Leu Leu Thr
    50                  55                  60

His Thr Glu Arg Val Val Ile Trp Pro Phe Ser Asn Lys Asn Tyr Ile
65                  70                  75                  80

His Gly Glu Leu Tyr Lys Asn Arg Val Ser Ile Ser Asn Asn Ala Glu
                85                  90                  95

Gln Ser Asp Ala Ser Ile Thr Ile Asp Gln Leu Thr Met Ala Asp Asn
            100                 105                 110

Gly Thr Tyr Glu Cys Ser Val Ser Leu Met Ser Asp Leu Glu Gly Asn
        115                 120                 125

Thr Lys Ser Arg Val Arg Leu Leu Val Leu Val Pro Pro Ser Lys Pro
    130                 135                 140

Glu Cys Gly Ile Glu Gly Glu Thr Ile Ile Gly Asn Asn Ile Gln Leu
145                 150                 155                 160

Thr Cys Gln Ser Lys Glu Gly Ser Pro Thr Pro Gln Tyr Ser Trp Lys
                165                 170                 175

Arg Tyr Asn Ile Leu Asn Gln Glu Gln Pro Leu Ala Gln Pro Ala Ser
            180                 185                 190

Gly Gln Pro Val Ser Leu Lys Asn Ile Ser Thr Asp Thr Ser Gly Tyr
        195                 200                 205

Tyr Ile Cys Thr Ser Ser Asn Glu Glu Gly Thr Gln Phe Cys Asn Ile
    210                 215                 220

Thr Val Ala Val Arg Ser Pro Ser Met Asn Val Ala Leu Tyr Val Gly
225                 230                 235                 240

Ile Ala Val Gly Val Val Ala Ala Leu Ile Ile Ile Gly Ile Ile Ile
                245                 250                 255

Tyr Cys Cys Cys Cys Arg Gly Lys Asp Asp Asn Thr Glu Asp Lys Glu
            260                 265                 270

Asp Ala Arg Pro Asn Arg Glu Ala Tyr Glu Glu Pro Pro Glu Gln Leu
        275                 280                 285

Arg Glu Leu Ser Arg Glu Arg Glu Glu Glu Asp Asp Tyr Arg Gln Glu
    290                 295                 300

Glu Gln Arg Ser Thr Gly Arg Glu Ser Pro Asp His Leu Asp Gln
305                 310                 315


<210> SEQ ID NO 101
<211> LENGTH: 214
<212> TYPE: PRT
<213> ORGANISM: Homo sapiens
```

<400> SEQUENCE: 101

```
Ile Ser Val Glu Thr Pro Gln Asp Val Leu Arg Ala Ser Gln Gly Lys
1               5                   10                  15

Ser Val Thr Leu Pro Cys Thr Tyr His Thr Ser Thr Ser Ser Arg Glu
            20                  25                  30

Gly Leu Ile Gln Trp Asp Lys Leu Leu Leu Thr His Thr Glu Arg Val
        35                  40                  45

Val Ile Trp Pro Phe Ser Asn Lys Asn Tyr Ile His Gly Glu Leu Tyr
    50                  55                  60

Lys Asn Arg Val Ser Ile Ser Asn Asn Ala Glu Gln Ser Asp Ala Ser
65                  70                  75                  80

Ile Thr Ile Asp Gln Leu Thr Met Ala Asp Asn Gly Thr Tyr Glu Cys
                85                  90                  95

Ser Val Ser Leu Met Ser Asp Leu Glu Gly Asn Thr Lys Ser Arg Val
            100                 105                 110

Arg Leu Leu Val Leu Val Pro Pro Ser Lys Pro Glu Cys Gly Ile Glu
        115                 120                 125

Gly Glu Thr Ile Ile Gly Asn Asn Ile Gln Leu Thr Cys Gln Ser Lys
    130                 135                 140

Glu Gly Ser Pro Thr Pro Gln Tyr Ser Trp Lys Arg Tyr Asn Ile Leu
145                 150                 155                 160

Asn Gln Glu Gln Pro Leu Ala Gln Pro Ala Ser Gly Gln Pro Val Ser
                165                 170                 175

Leu Lys Asn Ile Ser Thr Asp Thr Ser Gly Tyr Tyr Ile Cys Thr Ser
            180                 185                 190

Ser Asn Glu Glu Gly Thr Gln Phe Cys Asn Ile Thr Val Ala Val Arg
        195                 200                 205

Ser Pro Ser Met Asn Val
    210
```

<210> SEQ ID NO 102
<211> LENGTH: 490
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 102

```
Asp Ile Gln Met Thr Gln Ser Gln Ser Ser Leu Ser Thr Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ser Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Val Gln Pro
65                  70                  75                  80

Glu Asp Phe Ala Asp Tyr Phe Cys Leu Gln His Trp Ser Tyr Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Gly Ser Gly Gly Gly
    210                 215                 220

Gly Ser Gly Gly Gly Gly Ser His Val Gln Leu Val Glu Ser Gly Gly
225                 230                 235                 240

Gly Leu Val Gln Pro Gly Gly Ser Leu Arg Leu Ser Cys Ala Ala Ser
                245                 250                 255

Gly Phe Ser Leu Thr Asp Tyr Gly Val His Trp Val Arg Gln Ala Pro
            260                 265                 270

Gly Lys Gly Leu Glu Trp Leu Gly Val Ile Trp Ser Gly Gly Gly Thr
        275                 280                 285

Ala Tyr Asn Thr Ala Leu Ile Ser Arg Phe Thr Ile Ser Arg Asp Asn
    290                 295                 300

Ser Lys Asn Thr Leu Tyr Leu Gln Met Asn Ser Leu Arg Ala Glu Asp
305                 310                 315                 320

Thr Ala Val Tyr Tyr Cys Ala Arg Arg Gly Ser Tyr Pro Tyr Asn Tyr
                325                 330                 335

Phe Asp Ala Trp Gly Cys Gly Thr Leu Val Thr Val Ser Ser Gly Gly
            340                 345                 350

Gly Gly Ser Gly Gly Gly Gly Ser Gly Gly Gly Gly Ser Gly Gly Gly
        355                 360                 365

Gly Ser Gly Gly Gly Gly Ser Gly Gly Gly Gly Ser Gln Ala Val Val
    370                 375                 380

Thr Gln Glu Pro Ser Leu Thr Val Ser Pro Gly Gly Thr Val Thr Leu
385                 390                 395                 400

Thr Cys Gly Ser Ser Thr Gly Ala Val Thr Ala Ser Asn Tyr Ala Asn
                405                 410                 415

Trp Val Gln Gln Lys Pro Gly Gln Cys Pro Arg Gly Leu Ile Gly Gly
            420                 425                 430

His Asn Asn Arg Pro Pro Gly Val Pro Ala Arg Phe Ser Gly Ser Leu
        435                 440                 445

Leu Gly Gly Lys Ala Ala Leu Thr Leu Leu Gly Ala Gln Pro Glu Asp
    450                 455                 460

Glu Ala Glu Tyr Tyr Cys Ala Leu Trp Tyr Ser Asp His Trp Val Ile
465                 470                 475                 480

Gly Gly Gly Thr Lys Leu Thr Val Leu Gly
                485                 490
```

<210> SEQ ID NO 103
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 103

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Arg Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415
```

```
Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 104
<211> LENGTH: 597
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Arg Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Gln Ser Ser Leu Ser Thr
145                 150                 155                 160

Ser Val Gly Asp Arg Val Thr Ile Thr Cys Lys Ala Ser Gln Asn Val
                165                 170                 175

Arg Thr Val Val Ala Trp Tyr Gln Gln Lys Pro Gly Lys Ser Pro Lys
            180                 185                 190

Thr Leu Ile Tyr Leu Ala Ser Asn Arg His Thr Gly Val Pro Ser Arg
        195                 200                 205

Phe Ser Gly Ser Gly Ser Gly Thr Glu Phe Thr Leu Thr Ile Ser Asn
    210                 215                 220

Val Gln Pro Glu Asp Phe Ala Asp Tyr Phe Cys Leu Gln His Trp Ser
225                 230                 235                 240

Tyr Pro Leu Thr Phe Gly Ser Gly Thr Lys Leu Glu Ile Lys Arg Gly
                245                 250                 255

Gly Gly Gly Ser Gly Gly Gly Gly Ser Gly Gly Gly Gly Ser Gly Gly
            260                 265                 270

Gly Gly Ser His Val Gln Leu Val Glu Ser Gly Gly Gly Leu Val Gln
        275                 280                 285

Pro Gly Gly Ser Leu Arg Leu Ser Cys Ala Ala Ser Gly Phe Ser Leu
    290                 295                 300

Thr Asp Tyr Gly Val His Trp Val Arg Gln Ala Pro Gly Lys Gly Leu
305                 310                 315                 320

Glu Trp Leu Gly Val Ile Trp Ser Gly Gly Gly Thr Ala Tyr Asn Thr
```

```
                325                 330                 335

Ala Leu Ile Ser Arg Phe Thr Ile Ser Arg Asp Asn Ser Lys Asn Thr
            340                 345                 350

Leu Tyr Leu Gln Met Asn Ser Leu Arg Ala Glu Asp Thr Ala Val Tyr
        355                 360                 365

Tyr Cys Ala Arg Arg Gly Ser Tyr Pro Tyr Asn Tyr Phe Asp Ala Trp
    370                 375                 380

Gly Cys Gly Thr Leu Val Thr Val Ser Ser Gly Gly Gly Gly Ser Gly
385                 390                 395                 400

Gly Gly Gly Ser Gly Gly Gly Gly Ser Gly Gly Gly Gly Ser Gly Gly
                405                 410                 415

Gly Gly Ser Gly Gly Gly Gly Ser Gln Ala Val Val Thr Gln Glu Pro
            420                 425                 430

Ser Leu Thr Val Ser Pro Gly Gly Thr Val Thr Leu Thr Cys Gly Ser
        435                 440                 445

Ser Thr Gly Ala Val Thr Ala Ser Asn Tyr Ala Asn Trp Val Gln Gln
    450                 455                 460

Lys Pro Gly Gln Cys Pro Arg Gly Leu Ile Gly Gly His Asn Asn Arg
465                 470                 475                 480

Pro Pro Gly Val Pro Ala Arg Phe Ser Gly Ser Leu Leu Gly Gly Lys
                485                 490                 495

Ala Ala Leu Thr Leu Leu Gly Ala Gln Pro Glu Asp Glu Ala Glu Tyr
            500                 505                 510

Tyr Cys Ala Leu Trp Tyr Ser Asp His Trp Val Ile Gly Gly Gly Thr
        515                 520                 525

Lys Leu Thr Val Leu Gly Thr Pro Leu Gly Asp Thr Thr His Thr Ser
    530                 535                 540

Gly Lys Pro Leu Asp Gly Glu Tyr Phe Thr Leu Gln Ile Arg Gly Arg
545                 550                 555                 560

Glu Arg Phe Glu Met Phe Arg Glu Leu Asn Glu Ala Leu Glu Leu Lys
                565                 570                 575

Asp Ala Gln Ala Gly Lys Glu Pro Gly Gly Ser Gly Gly Ala Pro His
            580                 585                 590

His His His His His
        595


<210> SEQ ID NO 105
<211> LENGTH: 597
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Asp Ile Gln Met Thr Gln Ser Gln Ser Ser Leu Ser Thr Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ser Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Val Gln Pro
65                  70                  75                  80
```

```
Glu Asp Phe Ala Asp Tyr Phe Cys Leu Gln His Trp Ser Tyr Pro Leu
                85                  90                  95

Thr Phe Gly Ser Gly Thr Lys Leu Glu Ile Lys Arg Gly Gly Gly Gly
            100                 105                 110

Ser Gly Gly Gly Gly Ser Gly Gly Gly Gly Ser Gly Gly Gly Gly Ser
        115                 120                 125

Gly Gly Gly Gly Ser Gly Gly Gly Gly Ser Glu Val Gln Leu Val Glu
    130                 135                 140

Ser Gly Gly Gly Leu Val Lys Pro Gly Gly Ser Leu Arg Leu Ser Cys
145                 150                 155                 160

Ala Ala Ser Gly Phe Ala Phe Ser Thr Tyr Asp Met Ser Trp Val Arg
                165                 170                 175

Gln Ala Pro Gly Lys Arg Leu Glu Trp Val Ala Thr Ile Ser Ser Gly
            180                 185                 190

Gly Ser Tyr Thr Tyr Tyr Leu Asp Ser Val Lys Gly Arg Phe Thr Ile
        195                 200                 205

Ser Arg Asp Asn Ala Lys Asn Ser Leu Tyr Leu Gln Met Asn Ser Leu
    210                 215                 220

Arg Ala Glu Asp Thr Ala Val Tyr Tyr Cys Ala Pro Thr Thr Val Val
225                 230                 235                 240

Pro Phe Ala Tyr Trp Gly Gln Gly Thr Leu Val Thr Val Ser Ser Gly
                245                 250                 255

Gly Gly Gly Ser Gly Gly Gly Gly Ser Gly Gly Gly Gly Ser Gly Gly
            260                 265                 270

Gly Gly Ser His Val Gln Leu Val Glu Ser Gly Gly Gly Leu Val Gln
        275                 280                 285

Pro Gly Gly Ser Leu Arg Leu Ser Cys Ala Ala Ser Gly Phe Ser Leu
    290                 295                 300

Thr Asp Tyr Gly Val His Trp Val Arg Gln Ala Pro Gly Lys Gly Leu
305                 310                 315                 320

Glu Trp Leu Gly Val Ile Trp Ser Gly Gly Gly Thr Ala Tyr Asn Thr
                325                 330                 335

Ala Leu Ile Ser Arg Phe Thr Ile Ser Arg Asp Asn Ser Lys Asn Thr
            340                 345                 350

Leu Tyr Leu Gln Met Asn Ser Leu Arg Ala Glu Asp Thr Ala Val Tyr
        355                 360                 365

Tyr Cys Ala Arg Arg Gly Ser Tyr Pro Tyr Asn Tyr Phe Asp Ala Trp
    370                 375                 380

Gly Cys Gly Thr Leu Val Thr Val Ser Ser Gly Gly Gly Gly Ser Gly
385                 390                 395                 400

Gly Gly Gly Ser Gly Gly Gly Gly Ser Gly Gly Gly Gly Ser Gly Gly
                405                 410                 415

Gly Gly Ser Gly Gly Gly Gly Ser Gln Ala Val Val Thr Gln Glu Pro
            420                 425                 430

Ser Leu Thr Val Ser Pro Gly Gly Thr Val Thr Leu Thr Cys Gly Ser
        435                 440                 445

Ser Thr Gly Ala Val Thr Ala Ser Asn Tyr Ala Asn Trp Val Gln Gln
    450                 455                 460

Lys Pro Gly Gln Cys Pro Arg Gly Leu Ile Gly Gly His Asn Asn Arg
465                 470                 475                 480

Pro Pro Gly Val Pro Ala Arg Phe Ser Gly Ser Leu Leu Gly Gly Lys
                485                 490                 495

Ala Ala Leu Thr Leu Leu Gly Ala Gln Pro Glu Asp Glu Ala Glu Tyr
```

```
            500                 505                 510

Tyr Cys Ala Leu Trp Tyr Ser Asp His Trp Val Ile Gly Gly Gly Thr
        515                 520                 525

Lys Leu Thr Val Leu Gly Thr Pro Leu Gly Asp Thr Thr His Thr Ser
    530                 535                 540

Gly Lys Pro Leu Asp Gly Glu Tyr Phe Thr Leu Gln Ile Arg Gly Arg
545                 550                 555                 560

Glu Arg Phe Glu Met Phe Arg Glu Leu Asn Glu Ala Leu Glu Leu Lys
                565                 570                 575

Asp Ala Gln Ala Gly Lys Glu Pro Gly Gly Ser Gly Gly Ala Pro His
            580                 585                 590

His His His His His
        595


<210> SEQ ID NO 106
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Thr Tyr
            20                  25                  30

Asp Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Ser Ala Arg Asn Thr Leu Tyr
65                  70                  75                  80

Leu Gln Met Ser Ser Leu Arg Ser Glu Asp Thr Ala Leu Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala
        115


<210> SEQ ID NO 107
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Val
            20                  25                  30

Val Ala Trp Tyr Gln Gln Lys Pro Gly Gln Ser Pro Lys Thr Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
```

```
65                  70                  75                  80

Glu Asp Leu Ala Asp Tyr Phe Cys Leu Gln His Trp Ser Tyr Pro Leu
                85                  90                  95

Thr Phe Gly Ser Gly Thr Lys Leu Glu Val Lys
            100                 105


<210> SEQ ID NO 108
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30


<210> SEQ ID NO 109
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Gly Gly Gly Ser Gly Gly Gly Gly Ser Gly Gly Gly Gly Ser Gly
1               5                   10                  15

Gly Gly Gly Ser
            20


<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Thr Pro Leu Gly Asp Thr Thr His Thr
1               5


<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Gly Gly Gly Ser Gly Gly Gly Gly Ser Gly Gly Gly Gly Ser
1               5                   10                  15


<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: See specification as filed for detailed
      description of substitutions and preferred embodiments

<400> SEQUENCE: 112

Gly Gly Gly Gly Ser
1               5


<210> SEQ ID NO 113
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Gly Gly Gly Ser
1               5


<210> SEQ ID NO 114
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 114

His His His His His His
1               5


<210> SEQ ID NO 115
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(75)
<223> OTHER INFORMATION: This sequence may encompass 1-15 "Gly Gly Gly
      Gly Ser" repeating units
<220> FEATURE:
<223> OTHER INFORMATION: See specification as filed for detailed
      description of substitutions and preferred embodiments

<400> SEQUENCE: 115

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser
65                  70                  75


<210> SEQ ID NO 116
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: SITE
<222> LOCATION: (1)..(150)
<223> OTHER INFORMATION: This sequence may encompass 1-20, 25, or 30
      "Gly Gly Gly Gly Ser" repeating units
<220> FEATURE:
<223> OTHER INFORMATION: See specification as filed for detailed
      description of substitutions and preferred embodiments

<400> SEQUENCE: 116

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser Gly Gly Gly Gly Ser Gly Gly Gly Gly Ser Gly Gly
            100                 105                 110

Gly Gly Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser
145                 150
```